(12) United States Patent
Sharma et al.

(10) Patent No.: US 11,135,078 B2
(45) Date of Patent: Oct. 5, 2021

(54) INTRAGASTRIC DEVICE FOR TREATING OBESITY

(71) Applicant: SynerZ Medical, Inc., Newark, DE (US)

(72) Inventors: Virender K. Sharma, Paradise Valley, AZ (US); Raghuveer Basude, Fremont, CA (US)

(73) Assignee: SynerZ Medical, Inc., Newark, DE (US)

( * ) Notice: Subject to any disclaimer, the term of this patent is extended or adjusted under 35 U.S.C. 154(b) by 193 days.

(21) Appl. No.: 15/988,080

(22) Filed: May 24, 2018

(65) Prior Publication Data

US 2018/0263803 A1    Sep. 20, 2018

Related U.S. Application Data

(60) Division of application No. 15/134,288, filed on Apr. 20, 2016, now Pat. No. 10,010,439, which is a (Continued)

(51) Int. Cl.
*A61F 5/00* (2006.01)
*A61F 2/04* (2013.01)
(Continued)

(52) U.S. Cl.
CPC .............. *A61F 5/0076* (2013.01); *A61F 2/04* (2013.01); *A61F 5/0013* (2013.01);
(Continued)

(58) Field of Classification Search
CPC ........ A61F 5/0013; A61F 5/0073; A61F 2/04; A61F 5/0076; A61F 5/0079;
(Continued)

(56) References Cited

U.S. PATENT DOCUMENTS

| 1,899,781 A | 2/1933 | Twiss |
| 2,464,933 A | 3/1949 | Kaslow |

(Continued)

FOREIGN PATENT DOCUMENTS

| AU | 2010271294 A1 | 2/2012 |
| AU | 2011203951 A1 | 7/2012 |

(Continued)

OTHER PUBLICATIONS

US 8,668,662 B2, 03/2014, Levine (withdrawn)

(Continued)

*Primary Examiner* — Richard G Louis

(57) ABSTRACT

An intragastric device including (1) a first wire mesh structure having a pre-deployment shape, a post-deployment shape greater than the pre-deployment state, and one or more openings on an upper portion of the first wire mesh structure that are configured to permit food to enter the device, (2) a second wire mesh structure having a pre-deployment shape a post-deployment shape greater than the pre-deployment state, and one or more openings on a lower portion of the second wire mesh structure that are configured to permit food to exit the device. A sleeve may be coupled to the lower portion of the wire mesh structure. An anti-migration collar may interconnect the wire mesh structure and the sleeve. In use, food enters the upper portion of the first wire mesh structure, passes through both wire mesh structures, and then exits the lower portion of the second wire mesh structure.

20 Claims, 107 Drawing Sheets

Related U.S. Application Data continuation-in-part of application No. 14/862,706, filed on Sep. 23, 2015, now Pat. No. 10,420,665, which is a continuation-in-part of application No. 14/214,609, filed on Mar. 14, 2014, now Pat. No. 9,526,648, which is a continuation-in-part of application No. 14/096,505, filed on Dec. 4, 2013, now Pat. No. 10,413,436, which is a continuation of application No. 12/814,481, filed on Jun. 13, 2010, now Pat. No. 8,628,554.

(60) Provisional application No. 62/158,406, filed on May 7, 2015, provisional application No. 62/054,230, filed on Sep. 23, 2014, provisional application No. 61/884,981, filed on Sep. 30, 2013, provisional application No. 61/782,564, filed on Mar. 14, 2013.

(51) Int. Cl.
| | |
|---|---|
| *A61M 25/01* | (2006.01) |
| *A61M 25/09* | (2006.01) |
| *A61F 2/915* | (2013.01) |
| *A61B 6/12* | (2006.01) |
| *A61M 25/00* | (2006.01) |
| *A61B 17/12* | (2006.01) |
| *A61B 17/00* | (2006.01) |

(52) U.S. Cl.
CPC .......... *A61F 5/0036* (2013.01); *A61F 5/0073* (2013.01); *A61F 5/0079* (2013.01); *A61F 5/0089* (2013.01); *A61M 25/0108* (2013.01); *A61M 25/0136* (2013.01); *A61M 25/09* (2013.01); *A61B 6/12* (2013.01); *A61B 17/12036* (2013.01); *A61B 17/12172* (2013.01); *A61B 2017/00818* (2013.01); *A61B 2017/1205* (2013.01); *A61F 2002/045* (2013.01); *A61F 2002/9155* (2013.01); *A61F 2220/0016* (2013.01); *A61F 2230/0067* (2013.01); *A61F 2230/0071* (2013.01); *A61M 25/0054* (2013.01); *A61M 25/0068* (2013.01); *A61M 2025/0004* (2013.01)

(58) Field of Classification Search
CPC .................. A61F 5/0036; A61F 5/0089; A61F 2230/0067; A61F 2002/045; A61F 2220/0016; A61F 2230/0071; A61F 2202/9155; A61M 25/0108; A61M 25/0136; A61M 25/09; A61M 25/0068; A61M 25/0054; A61M 2025/0004; A61B 17/12036; A61B 17/12172; A61B 2017/1205; A61B 2017/00818; A61B 6/12; D10B 2509/06; D04C 1/06
See application file for complete search history.

(56) References Cited

U.S. PATENT DOCUMENTS

| | | |
|---|---|---|
| 3,780,740 A | 12/1973 | Rhea |
| 4,133,315 A | 1/1979 | Berman et al. |
| 4,134,405 A | 1/1979 | Smit |
| 4,246,893 A | 1/1981 | Berson |
| 4,270,542 A | 6/1981 | Plumley |
| 4,279,251 A | 7/1981 | Ruesch |
| 4,315,509 A | 2/1982 | Smit |
| 4,403,604 A | 9/1983 | Wilkinson et al. |
| 4,416,267 A | 11/1983 | Garren et al. |
| 4,441,215 A | 4/1984 | Kaster |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,738,667 A | 4/1988 | Galloway |
| 4,763,653 A | 8/1988 | Rockey |
| 4,767,627 A | 8/1988 | Caldwell et al. |
| 4,823,808 A | 4/1989 | Clegg et al. |
| 4,846,836 A | 7/1989 | Reich |
| 4,878,905 A | 11/1989 | Blass |
| 4,899,747 A | 2/1990 | Garren et al. |
| 4,913,141 A | 4/1990 | Hillstead |
| 5,035,706 A | 7/1991 | Giantureo et al. |
| 5,037,387 A | 8/1991 | Quinn et al. |
| 5,041,126 A | 8/1991 | Gianturco |
| 5,057,091 A | 10/1991 | Andersen |
| 5,104,399 A | 4/1992 | Lazarus |
| 5,152,756 A | 10/1992 | Quinn et al. |
| 5,163,952 A | 11/1992 | Froix |
| 5,188,104 A | 2/1993 | Wernicke et al. |
| 5,211,658 A | 5/1993 | Clouse |
| 5,234,454 A | 8/1993 | Bangs |
| 5,236,423 A | 8/1993 | Mix et al. |
| 5,246,456 A | 9/1993 | Wilkinson |
| 5,259,399 A | 11/1993 | Brown |
| 5,279,553 A | 1/1994 | Winkler et al. |
| 5,282,824 A | 2/1994 | Gianturco |
| 5,290,217 A | 3/1994 | Campos |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,327,914 A | 7/1994 | Shlain |
| 5,345,949 A | 9/1994 | Shlain |
| 5,364,353 A | 11/1994 | Corfitsen et al. |
| 5,387,235 A | 2/1995 | Chuter |
| 5,401,241 A | 3/1995 | Delany |
| 5,405,377 A | 4/1995 | Cragg |
| 5,405,378 A | 4/1995 | Strecker |
| 5,423,872 A | 6/1995 | Cigaina |
| 5,432,872 A | 6/1995 | Cigaina |
| 5,443,498 A | 8/1995 | Fontaine |
| 5,456,713 A | 10/1995 | Chuter |
| 5,480,423 A | 1/1996 | Ravenscroft et al. |
| 5,507,767 A | 4/1996 | Maeda et al. |
| 5,507,771 A | 4/1996 | Gianturco |
| 5,514,176 A | 5/1996 | Bosley, Jr. |
| 5,536,274 A | 7/1996 | Neuss |
| 5,562,697 A | 10/1996 | Christiansen |
| 5,569,219 A | 10/1996 | Hakki et al. |
| 5,593,434 A | 1/1997 | Williams |
| 5,611,787 A | 3/1997 | Demeter et al. |
| 5,624,430 A | 4/1997 | Eton et al. |
| 5,630,797 A | 5/1997 | Diedrich et al. |
| 5,637,699 A | 6/1997 | Dorn |
| 5,653,743 A | 8/1997 | Martin |
| 5,658,322 A | 8/1997 | Fleming |
| 5,662,713 A | 9/1997 | Andersen et al. |
| 5,665,064 A | 9/1997 | Bodicky et al. |
| 5,668,263 A | 9/1997 | Hoyer |
| 5,674,241 A | 10/1997 | Bley et al. |
| 5,690,692 A | 11/1997 | Fleming |
| 5,693,084 A | 12/1997 | Chuter |
| 5,700,272 A | 12/1997 | Gordon et al. |
| 5,709,657 A | 1/1998 | Zimmon |
| 5,713,910 A | 2/1998 | Gordon et al. |
| 5,715,832 A | 2/1998 | Koblish et al. |
| 5,720,776 A | 2/1998 | Chuter et al. |
| 5,733,325 A | 3/1998 | Robinson et al. |
| 5,741,277 A | 4/1998 | Gordon et al. |
| 5,741,279 A | 4/1998 | Gordon et al. |
| 5,749,918 A | 5/1998 | Hogendijk et al. |
| 5,755,777 A | 5/1998 | Chuter |
| 5,771,903 A | 6/1998 | Jakobsson et al. |
| 5,800,456 A | 9/1998 | Maeda et al. |
| 5,800,526 A | 9/1998 | Anderson et al. |
| 5,817,466 A | 10/1998 | Hoyer |

(56) References Cited

U.S. PATENT DOCUMENTS

| | | | |
|---|---|---|---|
| 5,820,584 | A | 10/1998 | Crabb |
| 5,830,229 | A | 11/1998 | Konya et al. |
| 5,835,897 | A | 11/1998 | Dang |
| 5,843,164 | A | 12/1998 | Frantzen et al. |
| 5,861,036 | A | 1/1999 | Godin |
| 5,868,141 | A | 2/1999 | Ellias |
| 5,876,445 | A | 3/1999 | Andersen et al. |
| 5,887,594 | A | 3/1999 | Locicero, III |
| 5,891,845 | A | 4/1999 | Myers |
| 5,922,019 | A | 7/1999 | Hankh et al. |
| 5,955,579 | A | 9/1999 | Leonard |
| 5,965,396 | A | 10/1999 | Pan |
| 5,993,483 | A | 11/1999 | Gianotti |
| 6,027,508 | A | 2/2000 | Ren et al. |
| 6,048,351 | A | 4/2000 | Gordon et al. |
| 6,087,129 | A | 7/2000 | Newgard |
| 6,099,552 | A | 8/2000 | Adams |
| 6,102,922 | A | 8/2000 | Jakobsson et al. |
| 6,113,609 | A | 9/2000 | Adams |
| 6,117,911 | A | 9/2000 | Grainger |
| 6,132,471 | A | 10/2000 | Johlin, Jr. |
| 6,146,416 | A | 11/2000 | Andersen et al. |
| 6,159,238 | A | 12/2000 | Killion et al. |
| 6,180,082 | B1 | 1/2001 | Watering |
| 6,183,461 | B1 | 2/2001 | Matsuura et al. |
| 6,184,254 | B1 | 2/2001 | Bokoski |
| 6,200,336 | B1 | 3/2001 | Pavcnik et al. |
| 6,200,600 | B1 | 3/2001 | Rashid |
| 6,241,738 | B1 | 6/2001 | Dereume |
| 6,245,761 | B1 | 6/2001 | Britton |
| 6,251,132 | B1 | 6/2001 | Ravenscroft et al. |
| 6,254,642 | B1 | 7/2001 | Taylor |
| 6,258,120 | B1 | 7/2001 | McKenzie et al. |
| 6,264,700 | B1 | 7/2001 | Kilcoyne et al. |
| 6,302,891 | B1 | 10/2001 | Nadal |
| 6,302,917 | B1 | 10/2001 | Dua et al. |
| 6,303,637 | B1 | 10/2001 | Bao |
| 6,322,538 | B1 | 11/2001 | Elbert et al. |
| 6,331,190 | B1 | 12/2001 | Shokoohi et al. |
| 6,332,877 | B1 | 12/2001 | Michels |
| 6,364,868 | B1 | 4/2002 | Ikeguchi |
| 6,370,511 | B1 | 4/2002 | Dang |
| 6,387,114 | B2 | 5/2002 | Adams |
| 6,406,840 | B1 | 6/2002 | Li |
| 6,410,587 | B1 | 6/2002 | Grainger |
| 6,424,864 | B1 | 7/2002 | Matsuura |
| 6,450,989 | B2 | 9/2002 | Dubrul et al. |
| 6,454,785 | B2 | 9/2002 | De Hoyos Garza |
| 6,485,409 | B1 | 11/2002 | Voloshin et al. |
| 6,494,888 | B1 | 12/2002 | Laufer |
| 6,503,264 | B1 | 1/2003 | Birk |
| 6,508,833 | B2 | 1/2003 | Pavcnik et al. |
| 6,524,335 | B1 | 2/2003 | Hartley et al. |
| 6,524,336 | B1 | 2/2003 | Papazolgou et al. |
| 6,530,951 | B1 | 3/2003 | Bates et al. |
| 6,531,491 | B1 | 3/2003 | Kania |
| 6,534,524 | B1 | 3/2003 | Kania |
| 6,537,247 | B2 | 3/2003 | Shannon |
| 6,540,789 | B1 | 4/2003 | Silverman et al. |
| 6,544,291 | B2 | 4/2003 | Taylor |
| 6,547,801 | B1 | 4/2003 | Dargent et al. |
| 6,558,400 | B2 | 5/2003 | Deem et al. |
| 6,558,429 | B2 | 5/2003 | Taylor |
| 6,565,597 | B1 | 5/2003 | Fearnot et al. |
| 6,571,127 | B1 | 5/2003 | Ben-Haim |
| 6,572,627 | B2 | 6/2003 | Gabbay |
| 6,572,629 | B2 | 6/2003 | Kalloo et al. |
| 6,575,896 | B2 | 6/2003 | Silverman et al. |
| 6,589,213 | B2 | 7/2003 | Reydel |
| 6,589,275 | B1 | 7/2003 | Ivancev et al. |
| 6,596,023 | B1 | 7/2003 | Nunez et al. |
| 6,623,518 | B2 | 9/2003 | Thompson et al. |
| 6,630,123 | B1 | 10/2003 | Waitering |
| 6,635,079 | B2 | 10/2003 | Unsworth et al. |
| 6,656,194 | B1 | 12/2003 | Gannoe et al. |
| 6,663,639 | B1 | 12/2003 | Laufer et al. |
| 6,666,848 | B2 | 12/2003 | Stone |
| 6,675,809 | B2 | 1/2004 | Stack et al. |
| 6,676,692 | B2 | 1/2004 | Rabkin et al. |
| 6,685,962 | B2 | 2/2004 | Friedman et al. |
| 6,695,875 | B2 | 2/2004 | Stelter et al. |
| 6,696,575 | B2 | 2/2004 | Schmidt |
| 6,699,263 | B2 | 3/2004 | Cope |
| 6,733,512 | B2 | 5/2004 | McGhan |
| 6,734,208 | B2 | 5/2004 | Grainger |
| 6,740,121 | B2 | 5/2004 | Geitz |
| 6,743,198 | B1 | 6/2004 | Tihon |
| 6,755,869 | B2 | 6/2004 | Geitz |
| 6,761,733 | B2 | 7/2004 | Chobotov et al. |
| 6,764,518 | B2 | 7/2004 | Godin |
| 6,773,440 | B2 | 8/2004 | Gannoe et al. |
| 6,773,441 | B1 | 8/2004 | Laufer |
| 6,776,791 | B1 | 8/2004 | Stallings et al. |
| 6,776,999 | B1 | 8/2004 | Krumme |
| 6,802,846 | B2 | 10/2004 | Hauschild et al. |
| 6,802,868 | B2 | 10/2004 | Silverman et al. |
| 6,844,349 | B2 | 1/2005 | Kath |
| 6,845,776 | B2 | 1/2005 | Stack et al. |
| 6,855,153 | B2 | 2/2005 | Saadat |
| 6,884,890 | B2 | 4/2005 | Kania |
| 6,890,924 | B2 | 5/2005 | Kath |
| 6,891,044 | B2 | 5/2005 | Kania |
| 6,911,198 | B2 | 6/2005 | Shachar |
| 6,932,838 | B2 | 8/2005 | Schwartz et al. |
| 6,939,370 | B2 | 9/2005 | Hartley et al. |
| 6,947,792 | B2 | 9/2005 | Ben-Haim |
| 6,950,707 | B2 | 9/2005 | Whitehurst |
| 6,994,095 | B2 | 2/2006 | Burnett |
| 7,019,147 | B1 | 3/2006 | Barth |
| 7,025,791 | B2 | 4/2006 | Levine et al. |
| 7,033,373 | B2 | 4/2006 | De et al. |
| 7,033,384 | B2 | 4/2006 | Gannoe et al. |
| 7,037,344 | B2 | 5/2006 | Kagan et al. |
| 7,041,120 | B2 | 5/2006 | Li et al. |
| 7,044,979 | B2 | 5/2006 | Silverman et al. |
| 7,056,305 | B2 | 6/2006 | Garza Alvarez |
| 7,060,080 | B2 | 6/2006 | Bachmann |
| 7,063,860 | B2 | 6/2006 | Chancellor |
| 7,066,945 | B2 | 6/2006 | Hashiba et al. |
| 7,071,337 | B2 | 7/2006 | Kath |
| 7,083,629 | B2 | 8/2006 | Weller |
| 7,084,171 | B2 | 8/2006 | Grainger |
| 7,090,699 | B2 | 8/2006 | Geitz |
| 7,097,665 | B2 | 8/2006 | Stack et al. |
| 7,111,627 | B2 | 9/2006 | Stack et al. |
| 7,120,497 | B2 | 10/2006 | Ben-Haim |
| 7,121,283 | B2 | 10/2006 | Stack et al. |
| 7,122,058 | B2 | 10/2006 | Levine et al. |
| 7,128,750 | B1 | 10/2006 | Stergiopulos |
| 7,141,581 | B2 | 11/2006 | Bender |
| 7,141,587 | B2 | 11/2006 | Kania |
| 7,145,008 | B2 | 12/2006 | Kath |
| 7,146,984 | B2 | 12/2006 | Stack et al. |
| 7,148,380 | B2 | 12/2006 | Wang |
| 7,152,607 | B2 | 12/2006 | Stack et al. |
| 7,153,314 | B2 | 12/2006 | Laufer |
| 7,172,613 | B2 | 2/2007 | Wazne |
| 7,189,750 | B2 | 3/2007 | Assaf |
| 7,196,093 | B2 | 3/2007 | Yuan |
| 7,208,499 | B2 | 4/2007 | Kath |
| 7,211,114 | B2 | 5/2007 | Bessler |
| 7,220,284 | B2 | 5/2007 | Kagan et al. |
| 7,221,978 | B2 | 5/2007 | Ben-Haim |
| 7,230,098 | B2 | 6/2007 | Cui |
| 7,235,562 | B2 | 6/2007 | Kath |
| 7,238,191 | B2 | 7/2007 | Bachmann |
| 7,267,694 | B2 | 9/2007 | Levine et al. |
| 7,271,262 | B2 | 9/2007 | LaGreca |
| 7,273,451 | B2 | 9/2007 | Sekine et al. |
| 7,288,099 | B2 | 10/2007 | Deem et al. |
| 7,288,101 | B2 | 10/2007 | Deem et al. |
| 7,306,614 | B2 | 12/2007 | Weller |
| 7,309,858 | B2 | 12/2007 | Pappin |
| 7,314,443 | B2 | 1/2008 | Jordan et al. |

(56) References Cited

U.S. PATENT DOCUMENTS

| | | |
|---|---|---|
| 7,316,716 B2 | 1/2008 | Egan |
| 7,320,696 B2 | 1/2008 | Gazi et al. |
| 7,329,285 B2 | 2/2008 | Levine et al. |
| 7,330,747 B2 | 2/2008 | Maier |
| 7,330,753 B2 | 2/2008 | Policker |
| 7,332,493 B2 | 2/2008 | Kath |
| 7,332,513 B2 | 2/2008 | Assaf |
| 7,335,210 B2 | 2/2008 | Smit |
| 7,335,646 B2 | 2/2008 | Kieffer |
| 7,338,433 B2 | 3/2008 | Coe |
| 7,347,868 B2 | 3/2008 | Burnett et al. |
| 7,347,875 B2 | 3/2008 | Levine et al. |
| 7,354,454 B2 | 4/2008 | Stack et al. |
| 7,364,591 B2 | 4/2008 | Silverman et al. |
| 7,368,577 B2 | 5/2008 | Assaf |
| 7,371,862 B2 | 5/2008 | Vanotti |
| 7,410,988 B2 | 8/2008 | Dickson, Jr. |
| 7,416,685 B2 | 8/2008 | Freeman |
| 7,427,415 B2 | 9/2008 | Scharp et al. |
| 7,435,739 B2 | 10/2008 | Chen |
| 7,462,487 B2 | 12/2008 | Tsao |
| 7,468,355 B2 | 12/2008 | Hamdi |
| 7,476,256 B2 | 1/2009 | Meade et al. |
| 7,483,746 B2 | 1/2009 | Lee et al. |
| 7,498,445 B2 | 3/2009 | Assaf |
| 7,503,922 B2 | 3/2009 | Deem et al. |
| 7,510,559 B2 | 3/2009 | Deem et al. |
| 7,511,070 B2 | 3/2009 | Grainger |
| 7,513,914 B2 | 4/2009 | Schurr |
| 7,530,985 B2 | 5/2009 | Takemoto et al. |
| 7,547,312 B2 | 6/2009 | Bauman et al. |
| 7,579,477 B2 | 8/2009 | Assaf |
| 7,582,313 B2 | 9/2009 | Faustman |
| 7,585,869 B2 | 9/2009 | Bhattacharya |
| 7,594,926 B2 | 9/2009 | Linder et al. |
| 7,601,525 B2 | 10/2009 | Batich |
| 7,604,649 B2 | 10/2009 | McGuckin et al. |
| 7,608,114 B2 | 10/2009 | Levine et al. |
| 7,620,454 B2 | 11/2009 | Dinsmoor |
| 7,620,560 B2 | 11/2009 | Dang |
| 7,625,939 B2 | 12/2009 | Heiser |
| 7,628,821 B2 | 12/2009 | Stack et al. |
| 7,628,988 B2 | 12/2009 | Faustman |
| 7,637,905 B2 | 12/2009 | Saadat et al. |
| 7,637,919 B2 | 12/2009 | Ishikawa et al. |
| 7,654,951 B2 | 2/2010 | Ishikawa |
| 7,662,929 B2 | 2/2010 | Brown |
| 7,674,396 B2 | 3/2010 | Sterling |
| 7,674,457 B2 | 3/2010 | Borlongan |
| 7,678,068 B2 | 3/2010 | Levine et al. |
| 7,682,330 B2 | 3/2010 | Meade et al. |
| 7,691,152 B2 | 4/2010 | Silverman et al. |
| 7,695,446 B2 | 4/2010 | Levine et al. |
| 7,696,213 B2 | 4/2010 | Cheng |
| 7,699,863 B2 | 4/2010 | Marco et al. |
| 7,725,333 B2 | 5/2010 | Dang |
| 7,727,143 B2 | 6/2010 | Birk et al. |
| 7,731,757 B2 | 6/2010 | Taylor et al. |
| 7,736,373 B2 | 6/2010 | Laufer |
| 7,741,336 B2 | 6/2010 | Kath |
| 7,742,818 B2 | 6/2010 | Dinsmoor |
| 7,749,254 B2 | 7/2010 | Sobelman et al. |
| 7,758,535 B2 | 7/2010 | Levine et al. |
| 7,765,008 B2 | 7/2010 | Ben-Haim |
| 7,766,861 B2 | 8/2010 | Levine et al. |
| 7,766,973 B2 | 8/2010 | Levine et al. |
| 7,771,382 B2 | 8/2010 | Levine et al. |
| 7,774,216 B2 | 8/2010 | Dang |
| 7,780,590 B2 | 8/2010 | Birk et al. |
| 7,794,447 B2 | 9/2010 | Dann et al. |
| 7,795,290 B2 | 9/2010 | Dickson, Jr. |
| 7,798,954 B2 | 9/2010 | Birk et al. |
| 7,799,088 B2 | 9/2010 | Geitz |
| 7,803,177 B2 | 9/2010 | Hartley et al. |
| 7,803,195 B2 | 9/2010 | Levy |
| 7,811,298 B2 | 10/2010 | Birk |
| 7,811,299 B2 | 10/2010 | Bachmann et al. |
| 7,815,589 B2 | 10/2010 | Meade et al. |
| 7,815,591 B2 | 10/2010 | Levine et al. |
| 7,819,836 B2 | 10/2010 | Levine et al. |
| 7,833,280 B2 | 11/2010 | Stack et al. |
| 7,837,643 B2 | 11/2010 | Levine et al. |
| 7,837,669 B2 | 11/2010 | Dann et al. |
| 7,838,524 B2 | 11/2010 | Lee |
| 7,840,269 B2 | 11/2010 | Policker |
| 7,846,138 B2 | 12/2010 | Dann et al. |
| 7,850,704 B2 | 12/2010 | Burnett |
| 7,862,574 B2 | 1/2011 | Deem |
| 7,867,283 B2 | 1/2011 | Krueger et al. |
| 7,881,797 B2 | 2/2011 | Griffin et al. |
| 7,883,524 B2 | 2/2011 | Chen |
| 7,892,214 B2 | 2/2011 | Kagan et al. |
| 7,892,827 B2 | 2/2011 | Matschiner |
| 7,901,419 B2 | 3/2011 | Bachmann et al. |
| 7,909,838 B2 | 3/2011 | Deem |
| 7,922,684 B2 | 4/2011 | Weitzner et al. |
| 7,928,109 B2 | 4/2011 | Luzzio |
| 7,935,073 B2 | 5/2011 | Levine et al. |
| 7,945,323 B2 | 5/2011 | Jaax et al. |
| 7,959,552 B2 | 6/2011 | Jordan et al. |
| 7,959,640 B2 | 6/2011 | Kantsevoy et al. |
| 7,960,345 B2 | 6/2011 | Kim |
| 7,966,071 B2 | 6/2011 | Ben-Haim |
| 7,968,575 B2 | 6/2011 | Assaf |
| 7,972,346 B2 | 7/2011 | Bachmann et al. |
| 7,976,488 B2 | 7/2011 | Levine et al. |
| 7,979,290 B2 | 7/2011 | Dang |
| 7,981,162 B2 | 7/2011 | Stack et al. |
| 7,981,163 B2 | 7/2011 | Meade et al. |
| 7,985,844 B2 | 7/2011 | Brown |
| 7,998,220 B2 | 8/2011 | Murphy |
| 7,998,966 B2 | 8/2011 | Bearss |
| 8,002,731 B2 | 8/2011 | Weitzner et al. |
| 8,003,806 B2 | 8/2011 | Bloxham |
| 8,006,701 B2 | 8/2011 | Bilotti |
| 8,007,507 B2 | 8/2011 | Waller |
| 8,008,449 B2 | 8/2011 | Korman |
| 8,012,135 B2 | 9/2011 | Dann et al. |
| 8,012,140 B1 | 9/2011 | Kagan et al. |
| 8,012,162 B2 | 9/2011 | Bachmann |
| 8,012,966 B2 | 9/2011 | Tang |
| 8,021,693 B2 | 9/2011 | Faustman |
| 8,043,206 B2 | 10/2011 | Birk |
| 8,043,248 B2 | 10/2011 | Pasricha |
| 8,048,169 B2 | 11/2011 | Burnett et al. |
| 8,048,170 B2 | 11/2011 | Silverman et al. |
| 8,057,420 B2 | 11/2011 | Meade et al. |
| 8,057,494 B2 | 11/2011 | Laufer |
| 8,062,656 B2 | 11/2011 | Oh-Lee |
| 8,066,689 B2 | 11/2011 | Mitelberg et al. |
| 8,070,743 B2 | 12/2011 | Kagan et al. |
| 8,070,824 B2 | 12/2011 | Burnett et al. |
| 8,075,577 B2 | 12/2011 | Deem |
| 8,079,974 B2 | 12/2011 | Stergiopulos |
| 8,080,022 B2 | 12/2011 | Deem |
| 8,080,025 B2 | 12/2011 | Deem |
| 8,084,457 B2 | 12/2011 | Choidas |
| 8,084,484 B2 | 12/2011 | Frank |
| 8,092,482 B2 | 1/2012 | Gannoe et al. |
| 8,095,219 B2 | 1/2012 | Lee et al. |
| 8,096,966 B2 | 1/2012 | Levine et al. |
| 8,105,392 B2 | 1/2012 | Durgin |
| 8,106,197 B2 | 1/2012 | Cui |
| 8,109,895 B2 | 2/2012 | Williams et al. |
| 8,114,045 B2 | 2/2012 | Surti |
| 8,114,893 B2 | 2/2012 | Baell |
| 8,116,883 B2 | 2/2012 | Williams |
| 8,118,774 B2 | 2/2012 | Dann et al. |
| 8,121,869 B2 | 2/2012 | Dang |
| 8,123,765 B2 | 2/2012 | Deem |
| 8,123,766 B2 | 2/2012 | Bauman et al. |
| 8,123,767 B2 | 2/2012 | Bauman et al. |
| 8,134,010 B2 | 3/2012 | Assaf |
| 8,137,301 B2 | 3/2012 | Levine et al. |

(56) References Cited

U.S. PATENT DOCUMENTS

| | | |
|---|---|---|
| 8,137,662 B2 | 3/2012 | Freeman |
| 8,142,469 B2 | 3/2012 | Sosnowski et al. |
| 8,142,514 B2 | 3/2012 | Geitz |
| 8,147,561 B2 | 4/2012 | Binmoeller |
| 8,162,871 B2 | 4/2012 | Levine et al. |
| 8,173,129 B2 | 5/2012 | Faustman |
| 8,177,853 B2 | 5/2012 | Stack et al. |
| 8,182,441 B2 | 5/2012 | Swain et al. |
| 8,182,459 B2 | 5/2012 | Dann et al. |
| 8,182,543 B2 | 5/2012 | Schurr |
| 8,187,289 B2 | 5/2012 | Tacchino |
| 2,014,854 A1 | 6/2012 | Freeman |
| 8,207,166 B2 | 6/2012 | Lee |
| 8,211,186 B2 | 7/2012 | Belhe et al. |
| 8,216,266 B2 | 7/2012 | Hively |
| 8,216,268 B2 | 7/2012 | Haller et al. |
| 8,219,201 B2 | 7/2012 | Ben-Haim |
| 8,226,593 B2 | 7/2012 | Graham |
| 8,226,602 B2 | 7/2012 | Quijana et al. |
| 8,232,273 B2 | 7/2012 | Baell |
| 8,236,023 B2 | 8/2012 | Birk et al. |
| 8,247,411 B2 | 8/2012 | Luzzio |
| 8,252,816 B2 | 8/2012 | Frank |
| 8,268,821 B2 | 9/2012 | Nadeson |
| 8,273,755 B2 | 9/2012 | Cheng |
| 8,277,468 B2 | 10/2012 | Laufer |
| 8,282,598 B2 | 10/2012 | Belhe et al. |
| 8,282,666 B2 | 10/2012 | Birk |
| 8,290,582 B2 | 10/2012 | Lin |
| 8,292,800 B2 | 10/2012 | Stone et al. |
| 8,296,165 B2 | 10/2012 | Dang |
| 8,299,022 B2 | 10/2012 | Dong |
| 8,303,669 B2 | 11/2012 | Meade et al. |
| 8,308,630 B2 | 11/2012 | Birk et al. |
| 8,308,813 B2 | 11/2012 | Krueger et al. |
| 8,317,677 B2 | 11/2012 | Bertolote et al. |
| 8,323,180 B2 | 12/2012 | Birk et al. |
| 8,323,229 B2 | 12/2012 | Shin |
| 8,334,263 B2 | 12/2012 | Nadeson |
| 8,337,567 B2 | 12/2012 | Stack et al. |
| 8,337,829 B2 | 12/2012 | Freeman |
| 8,357,501 B2 | 1/2013 | Jackson |
| 8,362,251 B2 | 1/2013 | Tang |
| 8,366,602 B2 | 2/2013 | Birk et al. |
| 8,376,929 B2 | 2/2013 | Birk et al. |
| 8,377,081 B2 | 2/2013 | Bachmann et al. |
| 8,382,780 B2 | 2/2013 | Birk |
| 3,007,934 A1 | 3/2013 | Eickhoff |
| 8,398,654 B2 | 3/2013 | Franklin et al. |
| 8,399,223 B2 | 3/2013 | Park |
| 8,403,877 B2 | 3/2013 | Priplata et al. |
| 8,409,221 B2 | 4/2013 | Franklin et al. |
| 8,409,226 B2 | 4/2013 | Kantsevoy et al. |
| 8,414,559 B2 | 4/2013 | Gross |
| 8,425,451 B2 | 4/2013 | Levine et al. |
| 8,430,894 B2 | 4/2013 | Brooks |
| 8,430,895 B2 | 4/2013 | Brooks |
| 8,431,597 B2 | 4/2013 | Munchhof |
| 8,436,011 B2 | 5/2013 | Bellevergue |
| 8,440,822 B2 | 5/2013 | Luzzio |
| 8,465,447 B2 | 6/2013 | Krueger et al. |
| 8,470,815 B2 | 6/2013 | SaulnierSholler |
| 8,475,401 B2 | 7/2013 | Priplata et al. |
| 8,486,153 B2 | 7/2013 | Levine et al. |
| 8,491,472 B2 | 7/2013 | Mitelberg et al. |
| 8,491,519 B2 | 7/2013 | Chin |
| 8,496,931 B2 | 7/2013 | Pogue |
| 8,506,517 B2 | 8/2013 | Stergiopulos |
| 8,506,532 B2 | 8/2013 | Olroyd et al. |
| 8,507,274 B2 | 8/2013 | Melton |
| 8,515,542 B2 | 8/2013 | Jaax et al. |
| 8,517,915 B2 | 8/2013 | Perron et al. |
| 8,518,970 B2 | 8/2013 | Baell |
| 8,529,943 B2 | 9/2013 | Kliger |
| 8,556,918 B2 | 10/2013 | Bauman et al. |
| 8,556,925 B2 | 10/2013 | Makower et al. |
| 8,556,934 B2 | 10/2013 | Godin |
| 8,568,488 B2 | 10/2013 | Stack et al. |
| 8,579,988 B2 | 11/2013 | Burnett et al. |
| 8,585,628 B2 | 11/2013 | Harris |
| 8,585,753 B2 | 11/2013 | Scanlon |
| 8,585,771 B2 | 11/2013 | Binmoeller et al. |
| 8,591,452 B2 | 11/2013 | Priplata et al. |
| 8,591,533 B2 | 11/2013 | Needleman |
| 8,591,598 B2 | 11/2013 | Silverman et al. |
| 8,597,224 B2 | 12/2013 | Vargas |
| 8,603,186 B2 | 12/2013 | Binmoeller |
| 8,613,749 B2 | 12/2013 | Deem et al. |
| 8,623,893 B2 | 1/2014 | Lassalle |
| 8,628,554 B2 | 1/2014 | Sharma |
| 8,628,583 B2 | 1/2014 | Meade et al. |
| 8,633,204 B2 | 1/2014 | Cheng |
| 8,636,683 B2 | 1/2014 | Chin et al. |
| 8,636,751 B2 | 1/2014 | Albrecht |
| 8,642,623 B2 | 2/2014 | Frank |
| 8,652,083 B2 | 2/2014 | Weitzner et al. |
| 8,657,885 B2 | 2/2014 | Burnett et al. |
| 8,663,301 B2 | 3/2014 | Riina et al. |
| 8,663,338 B2 | 3/2014 | Burnett et al. |
| 8,678,993 B2 | 3/2014 | Stroumpoulis |
| 8,679,137 B2 | 3/2014 | Bauman et al. |
| 8,683,881 B2 | 4/2014 | Bouasaysys et al. |
| 8,691,271 B2 | 4/2014 | Burnett et al. |
| 8,698,373 B2 | 4/2014 | Augarten et al. |
| 8,702,641 B2 | 4/2014 | Belhe et al. |
| 8,702,642 B2 | 4/2014 | Belhe et al. |
| 8,708,979 B2 | 4/2014 | Honaryar et al. |
| 8,715,158 B2 | 5/2014 | Honaryar et al. |
| 8,725,435 B2 | 5/2014 | Snow et al. |
| 8,753,369 B2 | 6/2014 | Murature et al. |
| 8,758,221 B2 | 6/2014 | Snow et al. |
| 8,764,624 B2 | 7/2014 | Snow et al. |
| 8,771,219 B2 | 7/2014 | Meade et al. |
| 8,795,301 B2 | 8/2014 | Burnett et al. |
| 8,801,597 B2 | 8/2014 | Franklin et al. |
| 8,801,647 B2 | 8/2014 | Melanson et al. |
| 8,808,270 B2 | 8/2014 | Dann et al. |
| 8,821,373 B2 | 9/2014 | Schwab et al. |
| 8,821,429 B2 | 9/2014 | Vargas |
| 8,821,430 B2 | 9/2014 | Stergiopulos |
| 8,821,521 B2 | 9/2014 | Burnett |
| 8,821,584 B2 | 9/2014 | Burnett et al. |
| 8,834,405 B2 | 9/2014 | Meade et al. |
| 8,834,553 B2 | 9/2014 | Melanson et al. |
| 8,840,541 B2 | 9/2014 | Snow et al. |
| 8,840,679 B2 | 9/2014 | Durgin |
| 8,840,952 B2 | 9/2014 | Ashby et al. |
| 8,845,513 B2 | 9/2014 | Coe |
| 8,845,672 B2 | 9/2014 | Alverdy |
| 8,858,421 B2 | 10/2014 | Honaryar |
| 8,864,840 B2 | 10/2014 | Dominguez et al. |
| 8,870,806 B2 | 10/2014 | Levine et al. |
| 8,870,966 B2 | 10/2014 | Schwab et al. |
| 8,876,694 B2 | 11/2014 | Honaryar et al. |
| 8,882,655 B2 | 11/2014 | Nitka et al. |
| 8,882,698 B2 | 11/2014 | Levine et al. |
| 8,882,728 B2 | 11/2014 | Harders et al. |
| 8,882,798 B2 | 11/2014 | Schwab et al. |
| 8,888,732 B2 | 11/2014 | Raven et al. |
| 8,888,797 B2 | 11/2014 | Burnett et al. |
| 8,894,568 B2 | 11/2014 | Kwok et al. |
| 8,900,117 B2 | 12/2014 | Birk |
| 8,900,118 B2 | 12/2014 | Birk et al. |
| 8,905,915 B2 | 12/2014 | Birk |
| 8,905,916 B2 | 12/2014 | Jacobs et al. |
| 8,920,358 B2 | 12/2014 | Levine et al. |
| 8,920,447 B2 | 12/2014 | Dominguez |
| 8,932,247 B2 | 1/2015 | Stergiopulos |
| 8,939,888 B2 | 1/2015 | Augarten et al. |
| 8,956,318 B2 | 2/2015 | Miller et al. |
| 8,956,380 B2 | 2/2015 | Dominguez et al. |
| 8,961,393 B2 | 2/2015 | Rion et al. |
| 8,961,394 B2 | 2/2015 | Honaryar et al. |
| 8,968,177 B2 | 3/2015 | Silverman et al. |

(56) References Cited

U.S. PATENT DOCUMENTS

| | | |
|---|---|---|
| 8,968,270 B2 | 3/2015 | Kagan et al. |
| 8,979,735 B2 | 3/2015 | Augarten |
| 8,992,415 B2 | 3/2015 | Deuel et al. |
| 8,992,559 B2 | 3/2015 | Weitzner et al. |
| 9,017,358 B2 | 4/2015 | Schwab et al. |
| 9,023,062 B2 | 5/2015 | Franklin et al. |
| 9,023,063 B2 | 5/2015 | Franklin et al. |
| 9,028,394 B2 | 5/2015 | Honaryar et al. |
| 9,039,649 B2 | 5/2015 | Neisz et al. |
| 9,044,298 B2 | 6/2015 | Franklin et al. |
| 9,044,300 B2 | 6/2015 | Belhe et al. |
| 9,050,165 B2 | 6/2015 | Perron |
| 9,050,168 B2 | 6/2015 | Neisz et al. |
| 9,050,174 B2 | 6/2015 | Pecor et al. |
| 9,060,844 B2 | 6/2015 | Kagan et al. |
| 9,066,780 B2 | 6/2015 | Weber |
| 9,072,579 B2 | 7/2015 | Birk et al. |
| 9,084,669 B2 | 7/2015 | Meade et al. |
| 9,089,395 B2 | 7/2015 | Honaryar |
| 9,095,405 B2 | 8/2015 | Babkes et al. |
| 9,095,416 B2 | 8/2015 | Meade et al. |
| 9,526,648 B2 | 12/2016 | Sharma |
| 10,010,439 B2 | 7/2018 | Sharma et al. |
| 10,413,436 B2 | 9/2019 | Sharma |
| 10,420,665 B2 | 9/2019 | Sharma et al. |
| 10,512,557 B2 | 12/2019 | Sharma |
| 10,779,980 B2 | 9/2020 | Sharma et al. |
| 2001/0011543 A1 | 8/2001 | Forsell |
| 2002/0006962 A1 | 1/2002 | Wang |
| 2002/0071857 A1 | 6/2002 | Kararli |
| 2002/0091439 A1 | 7/2002 | Baker et al. |
| 2002/0137086 A1 | 9/2002 | Olek |
| 2002/0143387 A1 | 10/2002 | Soetikno et al. |
| 2002/0155100 A1 | 10/2002 | Kieffer |
| 2002/0165572 A1 | 11/2002 | Saadat |
| 2002/0165738 A1 | 11/2002 | Dang |
| 2002/0169165 A1 | 11/2002 | Kath |
| 2002/0173987 A1 | 11/2002 | Dang |
| 2002/0173988 A1 | 11/2002 | Dang |
| 2002/0173989 A1 | 11/2002 | Dang |
| 2002/0173992 A1 | 11/2002 | Dang |
| 2002/0183768 A1 | 12/2002 | Deem |
| 2002/0193816 A1 | 12/2002 | Laufer |
| 2002/0193828 A1 | 12/2002 | Griffin et al. |
| 2002/0197656 A1 | 12/2002 | Li |
| 2003/0018299 A1 | 1/2003 | Stone |
| 2003/0040804 A1 | 2/2003 | Stack |
| 2003/0040808 A1 | 2/2003 | Stack et al. |
| 2003/0050684 A1 | 3/2003 | Abrams et al. |
| 2003/0053985 A1 | 3/2003 | Shachar |
| 2003/0055465 A1 | 3/2003 | Ben-Haim |
| 2003/0055466 A1 | 3/2003 | Ben-Haim |
| 2003/0055467 A1 | 3/2003 | Ben-Haim |
| 2003/0064970 A1 | 4/2003 | Grainger |
| 2003/0065359 A1 | 4/2003 | Weller |
| 2003/0066987 A1 | 4/2003 | Schmidt |
| 2003/0086975 A1 | 5/2003 | Ringeisen |
| 2003/0108597 A1 | 6/2003 | Chancellor |
| 2003/0109892 A1 | 6/2003 | Deem |
| 2003/0109935 A1 | 6/2003 | Geitz |
| 2003/0120265 A1 | 6/2003 | Deem |
| 2003/0153905 A1 | 8/2003 | Edwards |
| 2003/0158217 A1 | 8/2003 | Kath |
| 2003/0171261 A1 | 9/2003 | Livingston |
| 2003/0171386 A1 | 9/2003 | Connell |
| 2003/0190368 A1 | 10/2003 | Stoughton |
| 2003/0191476 A1 | 10/2003 | Smit |
| 2003/0191492 A1 | 10/2003 | Gellman et al. |
| 2003/0199989 A1* | 10/2003 | Stack .................. A61F 5/0076 623/23.65 |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0232752 A1 | 12/2003 | Freeman |
| 2004/0024386 A1 | 2/2004 | Deem |
| 2004/0028658 A1 | 2/2004 | Faustman |
| 2004/0039350 A1 | 2/2004 | McKittrick |
| 2004/0039452 A1 | 2/2004 | Bessler |
| 2004/0044357 A1* | 3/2004 | Gannoe .................. A61F 5/003 606/194 |
| 2004/0045045 A1 | 3/2004 | Mather |
| 2004/0062778 A1 | 4/2004 | Shefer |
| 2004/0073278 A1 | 4/2004 | Pachys |
| 2004/0087876 A1 | 5/2004 | Eskuri |
| 2004/0092892 A1 | 5/2004 | Kagan et al. |
| 2004/0097428 A1 | 5/2004 | Hamdi |
| 2004/0106892 A1 | 6/2004 | Stone |
| 2004/0107004 A1 | 6/2004 | Levine et al. |
| 2004/0117031 A1 | 6/2004 | Stack |
| 2004/0122452 A1 | 6/2004 | Deem |
| 2004/0122453 A1 | 6/2004 | Deem |
| 2004/0122456 A1 | 6/2004 | Saadat et al. |
| 2004/0127800 A1 | 7/2004 | Kimball |
| 2004/0133147 A1 | 7/2004 | Woo |
| 2004/0138529 A1 | 7/2004 | Wiltshire et al. |
| 2004/0138760 A1 | 7/2004 | Schurr |
| 2004/0143342 A1 | 7/2004 | Stack et al. |
| 2004/0147816 A1 | 7/2004 | Policker |
| 2004/0147871 A1 | 7/2004 | Burnett |
| 2004/0148034 A1 | 7/2004 | Kagan |
| 2004/0158331 A1 | 8/2004 | Stack |
| 2004/0170631 A1 | 9/2004 | Yacoby-Zeevi |
| 2004/0171634 A1 | 9/2004 | Kania |
| 2004/0172143 A1 | 9/2004 | Geitz |
| 2004/0180086 A1 | 9/2004 | Ramtoola et al. |
| 2004/0181242 A1 | 9/2004 | Stack |
| 2004/0192598 A1 | 9/2004 | Kragie |
| 2004/0193184 A1 | 9/2004 | Laufer |
| 2004/0204429 A1 | 10/2004 | Yuan |
| 2004/0220177 A1 | 11/2004 | Kath |
| 2004/0220248 A1 | 11/2004 | Kania |
| 2004/0220682 A1 | 11/2004 | Levine et al. |
| 2004/0225191 A1 | 11/2004 | Sekine |
| 2004/0236381 A1 | 11/2004 | Dinsmoor |
| 2004/0236382 A1 | 11/2004 | Dinsmoor |
| 2004/0242604 A1 | 12/2004 | Bhattacharya |
| 2004/0243152 A1 | 12/2004 | Taylor et al. |
| 2004/0254204 A1 | 12/2004 | Kath |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0009840 A1 | 1/2005 | Cui |
| 2005/0020667 A1 | 1/2005 | Grainger |
| 2005/0037999 A1 | 2/2005 | LaGreca |
| 2005/0038097 A1 | 2/2005 | Bender |
| 2005/0055039 A1 | 3/2005 | Burnett et al. |
| 2005/0075354 A1 | 4/2005 | Li |
| 2005/0085923 A1 | 4/2005 | Levine et al. |
| 2005/0089577 A1 | 4/2005 | Yokoyama et al. |
| 2005/0101011 A1 | 5/2005 | Tsao |
| 2005/0101618 A1 | 5/2005 | Connell |
| 2005/0124599 A1 | 6/2005 | Kath |
| 2005/0124662 A1 | 6/2005 | Kania |
| 2005/0125020 A1 | 6/2005 | Meade et al. |
| 2005/0125075 A1 | 6/2005 | Meade |
| 2005/0130994 A1 | 6/2005 | Chen |
| 2005/0143765 A1 | 6/2005 | Bachmann |
| 2005/0143766 A1 | 6/2005 | Bachmann |
| 2005/0158288 A1 | 7/2005 | Faustman |
| 2005/0159435 A1 | 7/2005 | Kath |
| 2005/0159769 A1 | 7/2005 | Alverdy |
| 2005/0164388 A1 | 7/2005 | Son |
| 2005/0169902 A1 | 8/2005 | Borlongan |
| 2005/0171556 A1 | 8/2005 | Murphy |
| 2005/0192614 A1* | 9/2005 | Binmoeller ........... A61M 25/04 606/191 |
| 2005/0196423 A1 | 9/2005 | Batich |
| 2005/0197714 A1 | 9/2005 | Sayet |
| 2005/0251182 A1 | 11/2005 | Bachmann |
| 2005/0256111 A1 | 11/2005 | Kath |
| 2005/0256125 A1 | 11/2005 | Kath |
| 2005/0256144 A1 | 11/2005 | Kath |
| 2005/0256587 A1 | 11/2005 | Egan |
| 2005/0267595 A1 | 12/2005 | Chen et al. |

(56) References Cited

U.S. PATENT DOCUMENTS

| | | |
|---|---|---|
| 2005/0273060 A1 | 12/2005 | Levy et al. |
| 2006/0002899 A1 | 1/2006 | Rice |
| 2006/0009858 A1 | 1/2006 | Levine et al. |
| 2006/0015125 A1 | 1/2006 | Swain |
| 2006/0015151 A1 | 1/2006 | Aldrich |
| 2006/0020278 A1 | 1/2006 | Burnett et al. |
| 2006/0025799 A1 | 2/2006 | Basu |
| 2006/0052416 A1 | 3/2006 | Dickson |
| 2006/0064120 A1 | 3/2006 | Levine |
| 2006/0069138 A1 | 3/2006 | Assaf |
| 2006/0069139 A1 | 3/2006 | Assaf |
| 2006/0069400 A1 | 3/2006 | Burnett |
| 2006/0074073 A1 | 4/2006 | Steinfeldt |
| 2006/0078993 A1 | 4/2006 | Phan |
| 2006/0084696 A1 | 4/2006 | Grainger |
| 2006/0089571 A1 | 4/2006 | Gertner |
| 2006/0089627 A1 | 4/2006 | Burnett |
| 2006/0105454 A1 | 5/2006 | Son |
| 2006/0116383 A1 | 6/2006 | Bloxham |
| 2006/0127437 A1 | 6/2006 | Kennedy |
| 2006/0134109 A1 | 6/2006 | Gaitanaris |
| 2006/0134186 A1 | 6/2006 | Carlton |
| 2006/0142731 A1 | 6/2006 | Brooks |
| 2006/0142787 A1 | 6/2006 | Weller |
| 2006/0161187 A1 | 7/2006 | Levine et al. |
| 2006/0161265 A1 | 7/2006 | Levine et al. |
| 2006/0183718 A1 | 8/2006 | Assaf |
| 2006/0183912 A1 | 8/2006 | Assaf |
| 2006/0183913 A1 | 8/2006 | Assaf |
| 2006/0228775 A1 | 10/2006 | Collier |
| 2006/0241130 A1 | 10/2006 | Keinan |
| 2006/0241748 A1 | 10/2006 | Lee |
| 2006/0271088 A1 | 11/2006 | Alfrhan |
| 2006/0276713 A1 | 12/2006 | Maier |
| 2007/0003610 A1 | 1/2007 | Chancellor |
| 2007/0021382 A1 | 1/2007 | Assaf |
| 2007/0021988 A1 | 1/2007 | Dang |
| 2007/0027548 A1 | 2/2007 | Levine et al. |
| 2007/0032879 A1 | 2/2007 | Levine et al. |
| 2007/0037883 A1 | 2/2007 | Dusting |
| 2007/0060940 A1 | 3/2007 | Brazzini et al. |
| 2007/0072874 A1 | 3/2007 | Cui |
| 2007/0072885 A1 | 3/2007 | Bhattacharya |
| 2007/0078435 A1 | 4/2007 | Stone |
| 2007/0083224 A1 | 4/2007 | Hively |
| 2007/0083271 A1 | 4/2007 | Levine et al. |
| 2007/0088389 A1 | 4/2007 | Dunkin |
| 2007/0100367 A1 | 5/2007 | Quijano et al. |
| 2007/0100368 A1 | 5/2007 | Quijano et al. |
| 2007/0104754 A1 | 5/2007 | Sterling |
| 2007/0105861 A1 | 5/2007 | Lee |
| 2007/0112020 A1 | 5/2007 | Vanotti |
| 2007/0118158 A1 | 5/2007 | Deem |
| 2007/0118159 A1 | 5/2007 | Deem |
| 2007/0118168 A1 | 5/2007 | Lointier et al. |
| 2007/0135335 A1 | 6/2007 | Collier |
| 2007/0135825 A1 | 6/2007 | Binmoeller |
| 2007/0135829 A1 | 6/2007 | Paganon |
| 2007/0135831 A1 | 6/2007 | Burnett |
| 2007/0148129 A1 | 6/2007 | Shortman |
| 2007/0149994 A1 | 6/2007 | Sosnowski et al. |
| 2007/0156248 A1 | 7/2007 | Marco et al. |
| 2007/0167963 A1 | 7/2007 | Deem |
| 2007/0173881 A1 | 7/2007 | Birk et al. |
| 2007/0178160 A1 | 8/2007 | Burnett |
| 2007/0185176 A1 | 8/2007 | VanGelder |
| 2007/0185540 A1 | 8/2007 | Ben-Haim |
| 2007/0191344 A1 | 8/2007 | Choidas |
| 2007/0198039 A1 | 8/2007 | Jones et al. |
| 2007/0198074 A1 | 8/2007 | Dann |
| 2007/0207186 A1 | 9/2007 | Scanlon |
| 2007/0210018 A1 | 9/2007 | Wallwiener et al. |
| 2007/0213740 A1 | 9/2007 | Deem |
| 2007/0213748 A1 | 9/2007 | Deem |
| 2007/0219570 A1 | 9/2007 | Deem |
| 2007/0250083 A1 | 10/2007 | Deem |
| 2007/0250132 A1 | 10/2007 | Burnett |
| 2007/0255379 A1 | 11/2007 | Williams |
| 2007/0265598 A1 | 11/2007 | Karasik |
| 2007/0265709 A1 | 11/2007 | Rajan et al. |
| 2007/0275902 A1 | 11/2007 | Gonda |
| 2007/0275962 A1 | 11/2007 | Koul |
| 2007/0276428 A1 | 11/2007 | Haller et al. |
| 2007/0282349 A1 | 12/2007 | Deem |
| 2007/0282452 A1 | 12/2007 | Weitzner |
| 2007/0282453 A1 | 12/2007 | Weitzner |
| 2007/0286856 A1 | 12/2007 | Brown |
| 2007/0293716 A1 | 12/2007 | Baker et al. |
| 2007/0293885 A1 | 12/2007 | Binmoeller |
| 2007/0299320 A1 | 12/2007 | Policker |
| 2008/0021742 A1 | 1/2008 | Dang |
| 2008/0026072 A1 | 1/2008 | Nakayama et al. |
| 2008/0027469 A1 | 1/2008 | Bachmann |
| 2008/0039463 A1 | 2/2008 | Nadeson |
| 2008/0051849 A1 | 2/2008 | Ben-Haim |
| 2008/0058887 A1 | 3/2008 | Griffin et al. |
| 2008/0058889 A1 | 3/2008 | Ben-Haim |
| 2008/0058891 A1 | 3/2008 | Ben-Haim |
| 2008/0059231 A1 | 3/2008 | Dang |
| 2008/0065136 A1 | 3/2008 | Young |
| 2008/0065421 A1 | 3/2008 | Dang |
| 2008/0071383 A1 | 3/2008 | Levine |
| 2008/0090801 A1 | 4/2008 | Cheng |
| 2008/0097466 A1 | 4/2008 | Levine et al. |
| 2008/0097513 A1 | 4/2008 | Kaji |
| 2008/0097788 A1 | 4/2008 | Dang |
| 2008/0120734 A1 | 5/2008 | Kieffer |
| 2008/0154129 A1 | 6/2008 | Mizunuma |
| 2008/0161838 A1 | 7/2008 | DArcangelo |
| 2008/0175828 A1 | 7/2008 | Freeman |
| 2008/0187575 A1 | 8/2008 | Klebl |
| 2008/0194574 A1 | 8/2008 | Eikhoff |
| 2008/0194596 A1 | 8/2008 | Letrent |
| 2008/0195226 A1 | 8/2008 | Williams |
| 2008/0207677 A1 | 8/2008 | Muller |
| 2008/0208241 A1 | 8/2008 | Weiner et al. |
| 2008/0208355 A1 | 8/2008 | Stack |
| 2008/0208356 A1 | 8/2008 | Stack et al. |
| 2008/0208357 A1 | 8/2008 | Melanson et al. |
| 2008/0214545 A1 | 9/2008 | Lee |
| 2008/0221595 A1 | 9/2008 | Surti |
| 2008/0228030 A1 | 9/2008 | Godin |
| 2008/0228066 A1 | 9/2008 | Waitzman |
| 2008/0233163 A1 | 9/2008 | Assaf |
| 2008/0234718 A1 | 9/2008 | Paganon et al. |
| 2008/0234834 A1 | 9/2008 | Meade et al. |
| 2008/0243071 A1 | 10/2008 | Quijano |
| 2008/0243166 A1 | 10/2008 | Paganon et al. |
| 2008/0243167 A1 | 10/2008 | Paganon et al. |
| 2008/0249533 A1 | 10/2008 | Godin |
| 2008/0249635 A1 | 10/2008 | Weitzner et al. |
| 2008/0255587 A1 | 10/2008 | Cully |
| 2008/0255594 A1 | 10/2008 | Cully et al. |
| 2008/0255678 A1 | 10/2008 | Cully et al. |
| 2008/0260797 A1 | 10/2008 | Oh-Lee |
| 2008/0261258 A1 | 10/2008 | Smith |
| 2008/0262529 A1 | 10/2008 | Jacques |
| 2008/0269289 A1 | 10/2008 | Frank |
| 2008/0269555 A1 | 10/2008 | Paganon et al. |
| 2008/0281257 A1 | 11/2008 | Waller |
| 2008/0281375 A1 | 11/2008 | Chen |
| 2008/0293618 A1 | 11/2008 | Heiser |
| 2008/0293733 A1 | 11/2008 | Bearss |
| 2008/0300234 A1 | 12/2008 | Kath |
| 2008/0302855 A1 | 12/2008 | Bilotti |
| 2008/0319471 A1* | 12/2008 | Sosnowski ............ A61M 25/09 606/192 |
| 2009/0005867 A1 | 1/2009 | Lefranc et al. |
| 2009/0012544 A1 | 1/2009 | Thompson et al. |
| 2009/0042785 A1 | 2/2009 | Matschiner |
| 2009/0048313 A1 | 2/2009 | Dickson |
| 2009/0053182 A1 | 2/2009 | Ichim |
| 2009/0054395 A1 | 2/2009 | Luzzio |
| 2009/0062401 A1 | 3/2009 | Odermatt |

(56) References Cited

U.S. PATENT DOCUMENTS

| | | |
|---|---|---|
| 2009/0088676 A1 | 4/2009 | Murata |
| 2009/0093839 A1 | 4/2009 | Kelleher |
| 2009/0105562 A1 | 4/2009 | Chiou |
| 2009/0111805 A1 | 4/2009 | Morris |
| 2009/0138094 A1 | 5/2009 | Schurr |
| 2009/0142413 A1 | 6/2009 | Allen |
| 2009/0149849 A1 | 6/2009 | Lin |
| 2009/0156590 A1 | 6/2009 | Frank |
| 2009/0164028 A1 | 6/2009 | Chen |
| 2009/0171383 A1 | 7/2009 | Cole |
| 2009/0178153 A1 | 7/2009 | Gaitanaris |
| 2009/0182303 A1 | 7/2009 | Walak |
| 2009/0182424 A1 | 7/2009 | Marco et al. |
| 2009/0187197 A1 | 7/2009 | Roeber et al. |
| 2009/0187200 A1 | 7/2009 | Burnett et al. |
| 2009/0187201 A1 | 7/2009 | Burnett et al. |
| 2009/0196912 A1 | 8/2009 | Eickhoff |
| 2009/0198254 A1 | 8/2009 | Laufer |
| 2009/0214474 A1 | 8/2009 | Jennings |
| 2009/0216262 A1 | 8/2009 | Burnett et al. |
| 2009/0217401 A1 | 8/2009 | Korman |
| 2009/0226907 A1 | 9/2009 | Nice |
| 2009/0227641 A1 | 9/2009 | Bhattacharya |
| 2009/0259240 A1 | 10/2009 | Graham |
| 2009/0264345 A1 | 10/2009 | McAlpine |
| 2009/0275511 A1 | 11/2009 | Dong |
| 2009/0276055 A1 | 11/2009 | Harris et al. |
| 2009/0287231 A1 | 11/2009 | Brooks |
| 2009/0299486 A1 | 12/2009 | Shohat et al. |
| 2009/0299487 A1 | 12/2009 | Stack et al. |
| 2009/0306186 A1 | 12/2009 | Jackson |
| 2009/0317374 A1 | 12/2009 | Park |
| 2010/0004239 A1 | 1/2010 | Tang |
| 2010/0016353 A1 | 1/2010 | Henne |
| 2010/0029615 A1 | 2/2010 | Munchhof |
| 2010/0036481 A1 | 2/2010 | Dubrul et al. |
| 2010/0048471 A1 | 2/2010 | Kim |
| 2010/0049224 A1 | 2/2010 | Vargas |
| 2010/0068177 A1 | 3/2010 | Faustman |
| 2010/0114150 A1 | 5/2010 | Magal |
| 2010/0121371 A1 | 5/2010 | Brooks |
| 2010/0136114 A1 | 6/2010 | Mao |
| 2010/0137279 A1 | 6/2010 | Cheng |
| 2010/0145301 A1 | 6/2010 | Magal |
| 2010/0150893 A1 | 6/2010 | Faustman |
| 2010/0152765 A1 | 6/2010 | Haley |
| 2010/0158896 A1 | 6/2010 | Brown |
| 2010/0158902 A1 | 6/2010 | Pogue |
| 2010/0168563 A1 | 7/2010 | Braver |
| 2010/0179584 A1 | 7/2010 | Carpenter et al. |
| 2010/0190782 A1 | 7/2010 | Baell |
| 2010/0204093 A1 | 8/2010 | Kaushal |
| 2010/0204221 A1 | 8/2010 | Vankayalapati |
| 2010/0204688 A1 | 8/2010 | Hoey |
| 2010/0209488 A1 | 8/2010 | Wrasidlo |
| 2010/0210622 A1 | 8/2010 | Baell |
| 2010/0221233 A1 | 9/2010 | Borlongan |
| 2010/0222381 A1 | 9/2010 | Vankayalapati |
| 2010/0234435 A1 | 9/2010 | Bhattacharya |
| 2010/0234886 A1 | 9/2010 | Godin |
| 2010/0235197 A1 | 9/2010 | Dang |
| 2010/0247691 A1 | 9/2010 | Kim |
| 2010/0249822 A1* | 9/2010 | Nihalani ............... A61F 5/0033 606/191 |
| 2010/0249825 A1 | 9/2010 | Nihalani |
| 2010/0255087 A1 | 10/2010 | Coulter |
| 2010/0256654 A1 | 10/2010 | Pasricha |
| 2010/0256775 A1 | 10/2010 | Belhe et al. |
| 2010/0261162 A1 | 10/2010 | Nice |
| 2010/0266675 A1 | 10/2010 | Gerwick |
| 2010/0268260 A1 | 10/2010 | Riina et al. |
| 2010/0286628 A1 | 11/2010 | Gross |
| 2010/0286660 A1 | 11/2010 | Gross |
| 2010/0298631 A1 | 11/2010 | Stack et al. |
| 2010/0298741 A1 | 11/2010 | Gross |
| 2010/0305590 A1 | 12/2010 | Holmes et al. |
| 2010/0324572 A1 | 12/2010 | Needleman |
| 2010/0324928 A1 | 12/2010 | Deng |
| 2011/0004146 A1 | 1/2011 | Priplata |
| 2011/0004320 A1 | 1/2011 | Priplata |
| 2011/0009801 A1 | 1/2011 | Blaeser |
| 2011/0040230 A1 | 2/2011 | Laufer |
| 2011/0040232 A1 | 2/2011 | Magal |
| 2011/0066175 A1 | 3/2011 | Gross |
| 2011/0068143 A1 | 3/2011 | Laufer |
| 2011/0082535 A1 | 4/2011 | Shin |
| 2011/0092482 A1 | 4/2011 | Nadeson |
| 2011/0097280 A1 | 4/2011 | Dees |
| 2011/0098730 A1 | 4/2011 | Kelleher |
| 2011/0118650 A1 | 5/2011 | Nihalani |
| 2011/0124643 A1 | 5/2011 | Bellevergue et al. |
| 2011/0125211 A1 | 5/2011 | Griffin |
| 2011/0130775 A1 | 6/2011 | Tacchino |
| 2011/0136809 A1 | 6/2011 | Lee |
| 2011/0137428 A1 | 6/2011 | Terliuc |
| 2011/0142905 A1 | 6/2011 | Bar-Shalom |
| 2011/0152608 A1 | 6/2011 | Bachmann |
| 2011/0152899 A1 | 6/2011 | Deem |
| 2011/0166120 A1 | 7/2011 | Luzzio |
| 2011/0172585 A1 | 7/2011 | Weitzner et al. |
| 2011/0185439 A1 | 7/2011 | Gaitanaris |
| 2011/0190905 A1 | 8/2011 | Behan |
| 2011/0206760 A1 | 8/2011 | Kliger |
| 2011/0213469 A1* | 9/2011 | Chin ................... A61F 5/0076 623/23.65 |
| 2011/0214189 A1 | 9/2011 | Gaitanaris |
| 2011/0218143 A1 | 9/2011 | Kaushal |
| 2011/0218563 A1 | 9/2011 | Brooks |
| 2011/0245752 A1 | 10/2011 | Levine et al. |
| 2011/0256123 A1 | 10/2011 | Ilan |
| 2011/0257580 A1 | 10/2011 | Meade et al. |
| 2011/0263504 A1 | 10/2011 | Cerami |
| 2011/0269772 A1 | 11/2011 | Bearss |
| 2011/0270405 A1 | 11/2011 | Geitz et al. |
| 2011/0270410 A1 | 11/2011 | Stack et al. |
| 2011/0275891 A1 | 11/2011 | Sherri |
| 2011/0276091 A1 | 11/2011 | Melanson et al. |
| 2011/0288080 A1 | 11/2011 | SaulnierSholler |
| 2011/0295054 A1 | 12/2011 | Aldridge |
| 2011/0295055 A1 | 12/2011 | Albrecht |
| 2011/0295151 A1 | 12/2011 | Bakos |
| 2011/0295286 A1 | 12/2011 | Harris |
| 2011/0301156 A1 | 12/2011 | Frank |
| 2011/0301353 A1 | 12/2011 | Tang |
| 2011/0307075 A1 | 12/2011 | Sharma |
| 2011/0320219 A1 | 12/2011 | Deng |
| 2012/0003204 A1 | 1/2012 | Park |
| 2012/0003634 A1 | 1/2012 | Frumkin |
| 2012/0004676 A1 | 1/2012 | Vargas |
| 2012/0029550 A1 | 2/2012 | Forsell |
| 2012/0029635 A1 | 2/2012 | Schoenhoeffer et al. |
| 2012/0041465 A1 | 2/2012 | Shalon |
| 2012/0046718 A1 | 2/2012 | Singh |
| 2012/0058107 A1 | 3/2012 | Tang |
| 2012/0059431 A1 | 3/2012 | Williams |
| 2012/0065571 A1 | 3/2012 | Thompson et al. |
| 2012/0083819 A1 | 4/2012 | Wang |
| 2012/0087910 A1 | 4/2012 | Trieu |
| 2012/0088300 A1 | 4/2012 | Melton |
| 2012/0088967 A1 | 4/2012 | Laufer |
| 2012/0089170 A1 | 4/2012 | Dominguez |
| 2012/0095384 A1 | 4/2012 | Babkes et al. |
| 2012/0095385 A1 | 4/2012 | Dominguez et al. |
| 2012/0095483 A1 | 4/2012 | Babkes et al. |
| 2012/0095494 A1 | 4/2012 | Dominguez |
| 2012/0095495 A1 | 4/2012 | Babkes |
| 2012/0095497 A1 | 4/2012 | Babkes et al. |
| 2012/0108590 A1 | 5/2012 | Birtalan |
| 2012/0110682 A1 | 5/2012 | Mather |
| 2012/0116286 A1 | 5/2012 | Williams et al. |
| 2012/0121594 A1 | 5/2012 | Smith |
| 2012/0142760 A1 | 6/2012 | Kieffer |
| 2012/0157470 A1 | 6/2012 | Catron |
| 2012/0157495 A1 | 6/2012 | Munchhof |

(56) References Cited

U.S. PATENT DOCUMENTS

| | | |
|---|---|---|
| 2012/0158026 A1 | 6/2012 | Behan |
| 2012/0179086 A1 | 7/2012 | Shank et al. |
| 2012/0184541 A1 | 7/2012 | Baell |
| 2012/0184893 A1 | 7/2012 | Thompson et al. |
| 2012/0184967 A1 | 7/2012 | Levine et al. |
| 2012/0208786 A1 | 8/2012 | Lyles |
| 2012/0209400 A1 | 8/2012 | Schurr |
| 2012/0213731 A1 | 8/2012 | Faustman |
| 2012/0214848 A1 | 8/2012 | Zhang |
| 2012/0215152 A1 | 8/2012 | Levine et al. |
| 2012/0232460 A1 | 9/2012 | Raven |
| 2012/0232577 A1 | 9/2012 | Birk |
| 2012/0245087 A1 | 9/2012 | Jackson |
| 2012/0245553 A1 | 9/2012 | Raven |
| 2012/0253259 A1 | 10/2012 | Belhe et al. |
| 2012/0253260 A1 | 10/2012 | Belhe et al. |
| 2012/0253529 A1 | 10/2012 | Carlson et al. |
| 2012/0258126 A1 | 10/2012 | Scholler |
| 2012/0263781 A1 | 10/2012 | Chancellor |
| 2012/0271217 A1 | 10/2012 | Stack et al. |
| 2012/0277210 A1 | 11/2012 | Catron |
| 2012/0277271 A1 | 11/2012 | Nadeson |
| 2012/0296365 A1 | 11/2012 | Nguyen |
| 2012/0301475 A1 | 11/2012 | Shemesh |
| 2012/0302602 A1 | 11/2012 | Frank |
| 2012/0309775 A1 | 12/2012 | Cheng |
| 2013/0005724 A1 | 1/2013 | Lassalle |
| 2013/0005964 A1 | 1/2013 | Luzzio |
| 2013/0006382 A1 | 1/2013 | Behan |
| 2013/0006672 A1 | 1/2013 | Dang |
| 2013/0011332 A1 | 1/2013 | Boyden |
| 2013/0013084 A1 | 1/2013 | Birk |
| 2013/0030350 A1 | 1/2013 | Albrecht et al. |
| 2013/0030351 A1 | 1/2013 | Belhe et al. |
| 2013/0034844 A1 | 2/2013 | Boyle |
| 2013/0035576 A1 | 2/2013 | OGrady |
| 2013/0041424 A1 | 2/2013 | Neisz |
| 2013/0071466 A1 | 3/2013 | Chancellor |
| 2013/0079329 A1 | 3/2013 | Hood |
| 2013/0079603 A1 | 3/2013 | Vargas |
| 2013/0133091 A1 | 5/2013 | Korman |
| 2013/0156726 A1 | 6/2013 | Ichim |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0177527 A1 | 7/2013 | Imran |
| 2013/0177550 A1 | 7/2013 | Imran |
| 2013/0178472 A1 | 7/2013 | Bellevergue |
| 2013/0189240 A1 | 7/2013 | Cho |
| 2013/0189353 A1 | 7/2013 | Imran |
| 2013/0190675 A1 | 7/2013 | Sandoski |
| 2013/0195970 A1 | 8/2013 | Imran |
| 2013/0197421 A1 | 8/2013 | Sharvit |
| 2013/0204208 A1 | 8/2013 | Olson |
| 2013/0210800 A1 | 8/2013 | Nair |
| 2013/0218289 A1 | 8/2013 | Gao et al. |
| 2013/0245068 A1 | 9/2013 | Kwon |
| 2013/0247233 A1 | 9/2013 | Gaitanaris |
| 2013/0253408 A1 | 9/2013 | Krueger |
| 2013/0273061 A1 | 10/2013 | Huang |
| 2013/0274659 A1 | 10/2013 | Imran |
| 2013/0274789 A1 | 10/2013 | Brook |
| 2013/0281911 A1 | 10/2013 | Babkes et al. |
| 2013/0289139 A1 | 10/2013 | Radford |
| 2013/0289466 A1 | 10/2013 | Babkes et al. |
| 2013/0296764 A1 | 11/2013 | Stack et al. |
| 2013/0296913 A1 | 11/2013 | Foote |
| 2013/0310727 A1 | 11/2013 | Stack et al. |
| 2013/0310833 A1 | 11/2013 | Brown |
| 2013/0324902 A1 | 12/2013 | Miller et al. |
| 2013/0324906 A1 | 12/2013 | Neisz |
| 2013/0324907 A1 | 12/2013 | Huntley et al. |
| 2013/0331359 A1 | 12/2013 | Yun |
| 2013/0331383 A1 | 12/2013 | SaulnierSholler |
| 2013/0331759 A1 | 12/2013 | Neisz |
| 2013/0337563 A1 | 12/2013 | Phan |
| 2013/0338741 A1 | 12/2013 | Singh |
| 2013/0344173 A1 | 12/2013 | Fogelman |
| 2013/0345670 A1 | 12/2013 | Rajagopalan |
| 2014/0004175 A1 | 1/2014 | Kliger |
| 2014/0005190 A1 | 1/2014 | Baell |
| 2014/0018719 A1 | 1/2014 | Chamorro |
| 2014/0024114 A1 | 1/2014 | Melton |
| 2014/0024991 A1 | 1/2014 | Chin |
| 2014/0039250 A1 | 2/2014 | Bachmann |
| 2014/0044641 A1 | 2/2014 | Toporik |
| 2014/0044736 A1 | 2/2014 | Hammers |
| 2014/0045815 A1 | 2/2014 | Hood |
| 2014/0051645 A1 | 2/2014 | Matschiner |
| 2014/0081416 A1 | 3/2014 | Clerc et al. |
| 2014/0094734 A1 | 4/2014 | Stack et al. |
| 2014/0121585 A1 | 5/2014 | Baker |
| 2014/0142720 A1 | 5/2014 | Stack et al. |
| 2014/0180188 A1 | 6/2014 | Chin et al. |
| 2014/0180192 A1 | 6/2014 | Ortiz et al. |
| 2014/0194806 A1 | 7/2014 | Belhe et al. |
| 2014/0194917 A1 | 7/2014 | Sharma |
| 2014/0200502 A1 | 7/2014 | Belhe et al. |
| 2014/0213960 A1 | 7/2014 | Belhe et al. |
| 2014/0221899 A1 | 8/2014 | Vargas |
| 2014/0243992 A1 | 8/2014 | Walsh et al. |
| 2014/0276336 A1 | 9/2014 | Sharma |
| 2015/0196412 A1 | 7/2015 | Roselauf |
| 2015/0196419 A1* | 7/2015 | Roselauf ............... A61F 5/0076 604/8 |
| 2016/0095733 A1 | 4/2016 | Sharma et al. |
| 2017/0312111 A1 | 11/2017 | Sharma et al. |
| 2019/0365552 A1 | 12/2019 | Sharma |
| 2020/0015990 A1 | 1/2020 | Sharma et al. |

FOREIGN PATENT DOCUMENTS

| | | |
|---|---|---|
| AU | 2012211067 A1 | 8/2013 |
| AU | 2010232570 B2 | 11/2013 |
| AU | 2014200766 A1 | 3/2014 |
| AU | 2012315575 A1 | 4/2014 |
| CA | 2756991 A1 | 10/2010 |
| CN | 1575155 A | 2/2005 |
| CN | 1713870 A | 12/2005 |
| CN | 2756991 Y | 2/2006 |
| CN | 102014763 A | 4/2011 |
| CN | 102387762 A | 3/2012 |
| CN | 102470038 A | 5/2012 |
| CN | 102824239 A | 12/2012 |
| CN | 103635212 A | 3/2014 |
| CN | 105263439 A | 1/2016 |
| EP | 0278937 B1 | 10/1993 |
| EP | 0480667 B1 | 3/1996 |
| EP | 0774571 A1 | 5/1997 |
| EP | 0754017 B1 | 6/2002 |
| EP | 0843538 B1 | 6/2002 |
| EP | 1420730 A2 | 5/2004 |
| EP | 1492477 A1 | 1/2005 |
| EP | 1492478 A1 | 1/2005 |
| EP | 2451411 A2 | 5/2012 |
| EP | 2521513 A1 | 11/2012 |
| EP | 2667910 A2 | 12/2013 |
| EP | 2413849 B1 | 7/2014 |
| EP | 2760502 A1 | 8/2014 |
| JP | 04-212348 A | 8/1992 |
| JP | 2005-500127 A | 1/2005 |
| JP | 2010-523262 A | 7/2010 |
| JP | 2011-152425 A | 8/2011 |
| JP | 2012-522595 A | 9/2012 |
| KR | 10-1065368 B1 | 9/2011 |

(56) References Cited

FOREIGN PATENT DOCUMENTS

| | | |
|---|---|---|
| KR | 2012-0008492 A | 1/2012 |
| WO | 88/00027 A1 | 1/1988 |
| WO | 91/01117 A1 | 2/1991 |
| WO | 94/01165 A1 | 1/1994 |
| WO | 00/12027 A1 | 3/2000 |
| WO | 00/32137 A1 | 6/2000 |
| WO | 00/42949 A2 | 7/2000 |
| WO | 01/45485 A2 | 6/2001 |
| WO | 01/49359 A1 | 7/2001 |
| WO | 02/96327 A2 | 12/2002 |
| WO | 03/17882 A2 | 3/2003 |
| WO | 03/86246 A1 | 10/2003 |
| WO | 03/86247 A1 | 10/2003 |
| WO | 03/86360 A1 | 10/2003 |
| WO | 03/94784 A2 | 11/2003 |
| WO | 03/94785 A1 | 11/2003 |
| WO | 2004/049982 A2 | 6/2004 |
| WO | 2004/064680 A1 | 8/2004 |
| WO | 2004/069331 A2 | 8/2004 |
| WO | 2004/069332 A1 | 8/2004 |
| WO | 20041064685 A1 | 8/2004 |
| WO | 2004/087014 A2 | 10/2004 |
| WO | 2004/087233 A2 | 10/2004 |
| WO | 2006/064503 A2 | 6/2006 |
| WO | 2007/007339 A2 | 1/2007 |
| WO | 2007/072469 A2 | 6/2007 |
| WO | 2008/023374 A2 | 2/2008 |
| WO | 2008/112894 A1 | 9/2008 |
| WO | 2008/121409 A1 | 10/2008 |
| WO | 2008/121831 A1 | 10/2008 |
| WO | 2008/154450 A1 | 12/2008 |
| WO | 2010/115011 A1 | 10/2010 |
| WO | 2010/128495 A1 | 11/2010 |
| WO | 2011/006098 A2 | 1/2011 |
| WO | 2011/085234 A1 | 7/2011 |
| WO | 2011/159271 A1 | 12/2011 |
| WO | 2012/068377 A1 | 5/2012 |
| WO | 2012/103531 A2 | 8/2012 |
| WO | 2013/049779 A1 | 4/2013 |
| WO | 2014/113483 A1 | 7/2014 |
| WO | 2014/153267 A2 | 9/2014 |
| WO | 2015/071496 A1 | 5/2015 |
| WO | 2016/049149 A2 | 3/2016 |
| WO | 2017/132676 A1 | 8/2017 |
| WO | WO201713266 | 8/2017 |

OTHER PUBLICATIONS

International Preliminary Report on Patentability received for PCT Patent Application No. PCT/US2014/029846, dated Sep. 24, 2015, 16 pages.
International Preliminary Report on Patentability received for PCT Patent Application No. PCT/US2015/051668, dated Apr. 6, 2017, 10 pages.
International Preliminary Report on Patentability received for PCT Patent Application No. PCT/US2016/028509, dated Apr. 5, 2018, 7 pages.
International Preliminary Report on Patentability received for PCT Patent Application No. PCT/US2017/029571, dated Nov. 8, 2018, 12 pages.
International Search Report—Application No. PCT/US2017/029571 dated Sep. 11, 2017.
International Search Report and Written Opinion received for PCT Patent Application No. PCT/US2016/028509, dated Aug. 12, 2016, 8 pages.
International Search Report for PCT/US2015/051668, dated Apr. 19, 2016.
International Written Opinion received for PCT Patent Application No. PCT/US2014/029846, dated Apr. 2, 2015, 14 pages.
International Written Opinion received for PCT Patent Application No. PCT/US2015/051668, dated Apr. 19, 2016, 8 pages.
International Written Opinion received for PCT Patent Application No. PCT/US2017/029571, dated Sep. 11, 2017, 10 pages.
Klausner et al., "Expandable gastroretentive dosage forms", Journal of Controlled Release 90:143-162 (2003).
Sun et al., "Intestinal electric stimulation decreases fat absorption in rats: Therapeutic potential for obesity", Obes Res. Aug. 2004; 12(8):1235-42.

\* cited by examiner

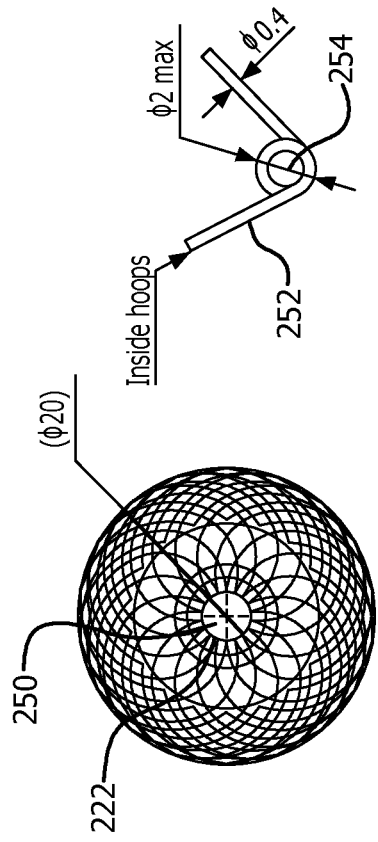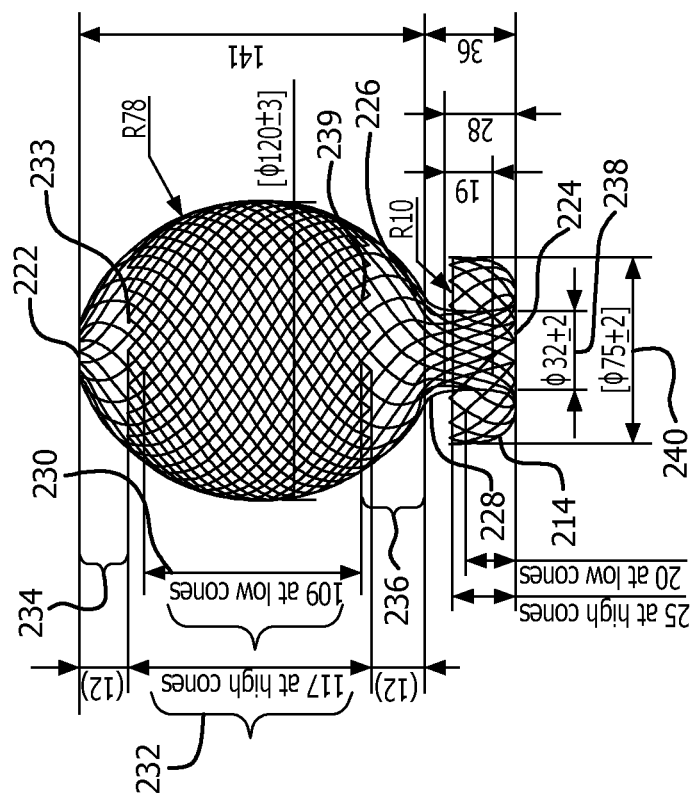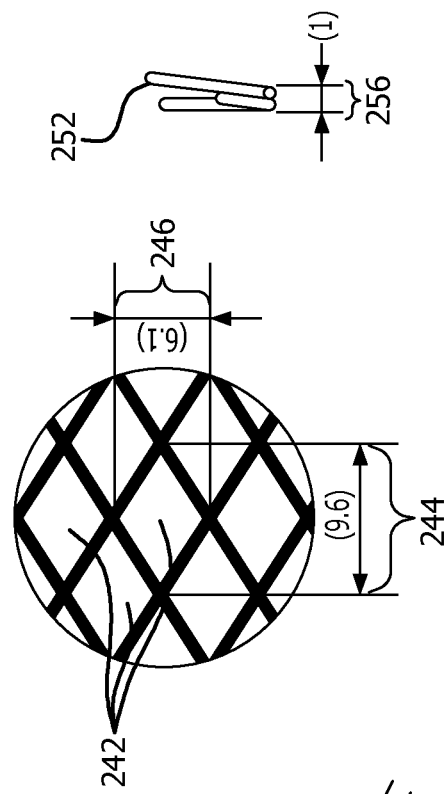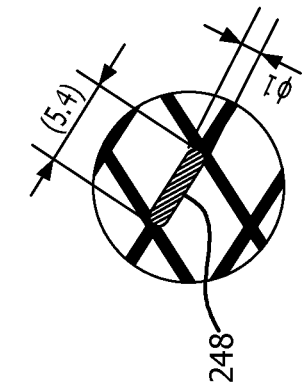

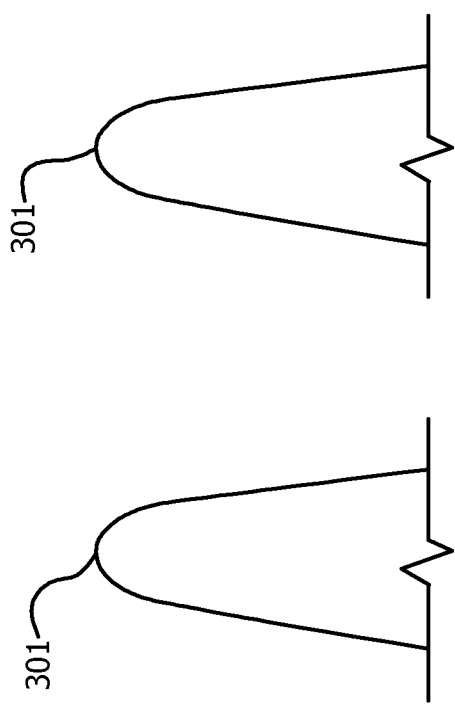
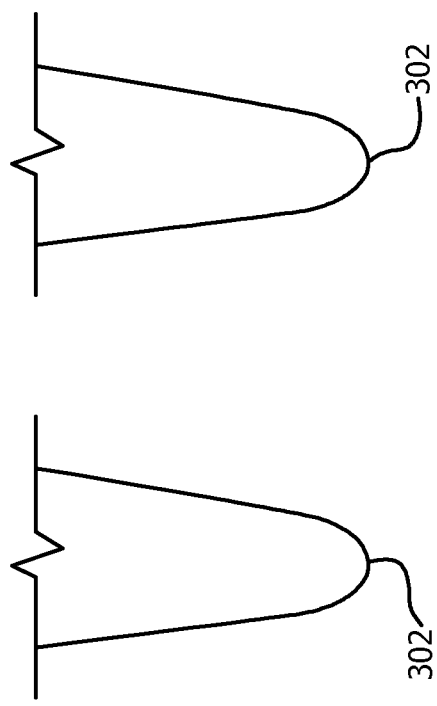
FIG. 3A
FIG. 3B

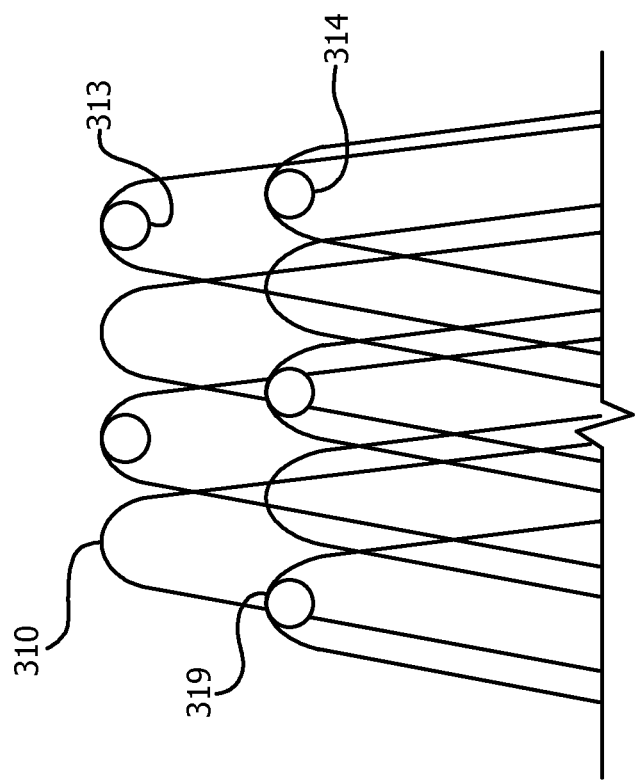

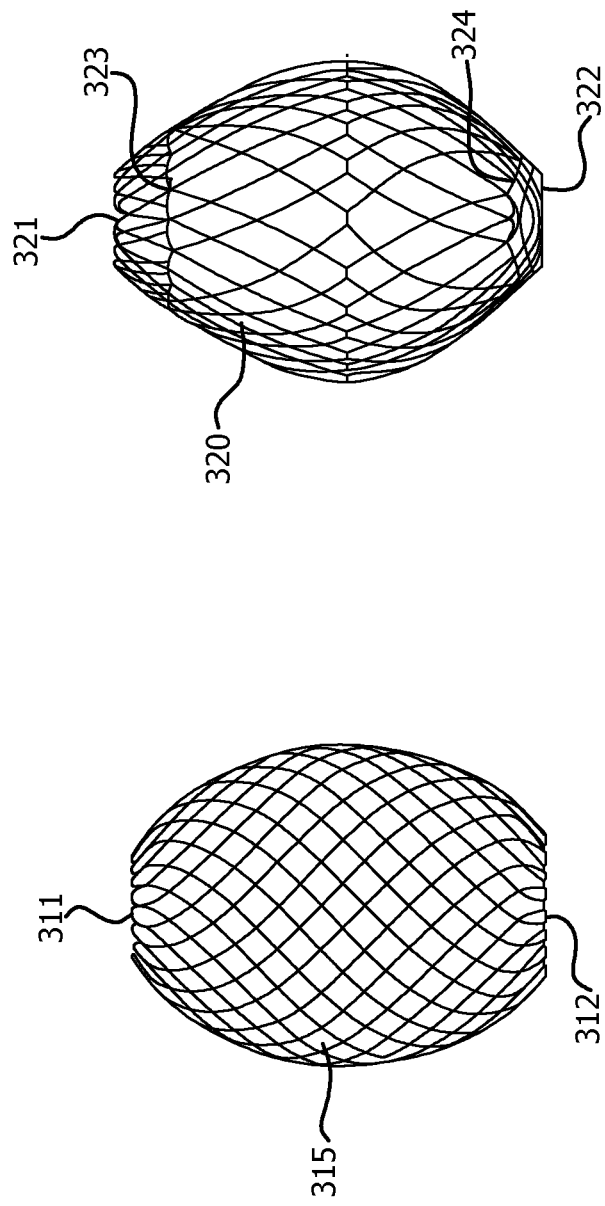
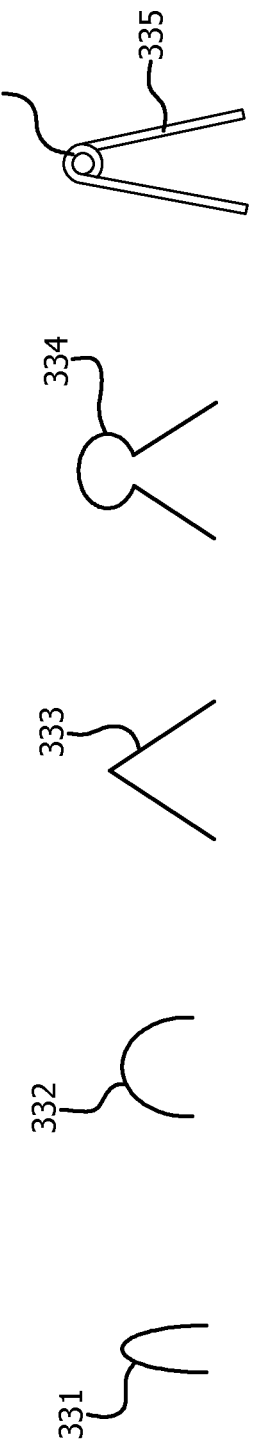

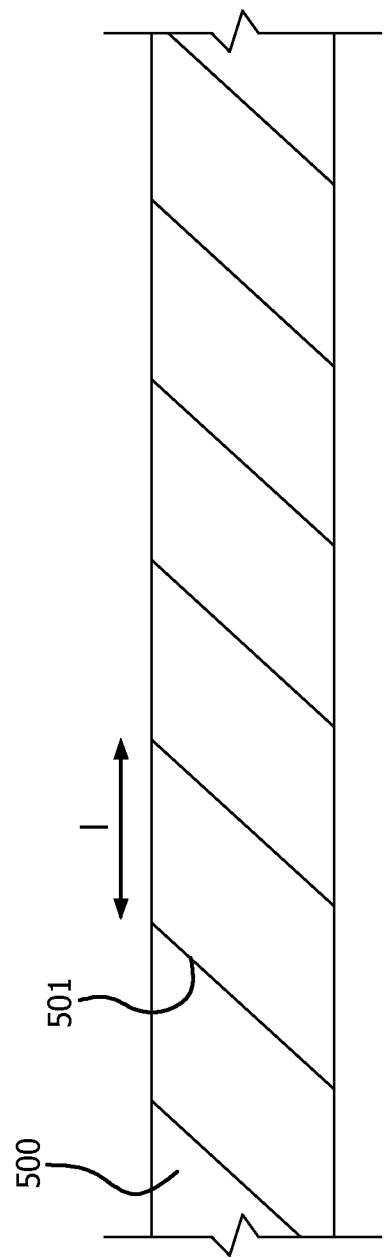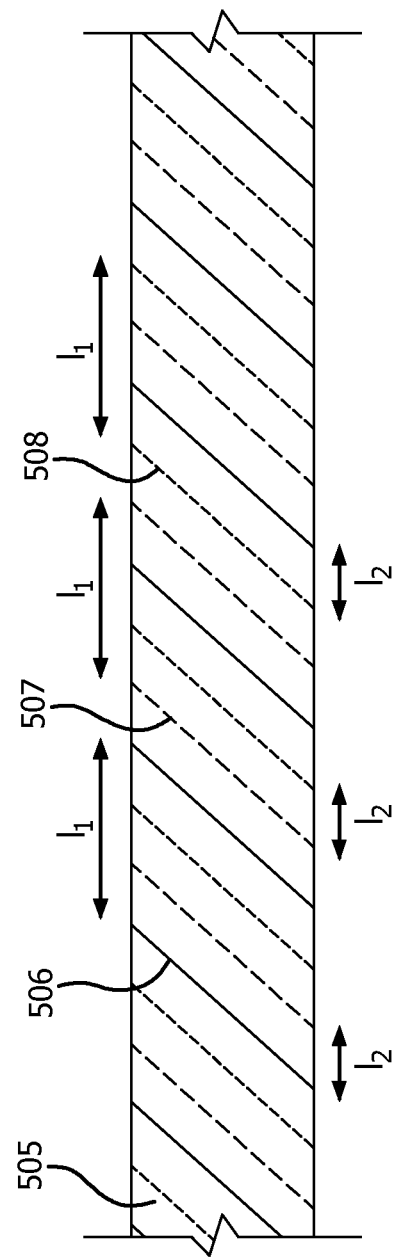

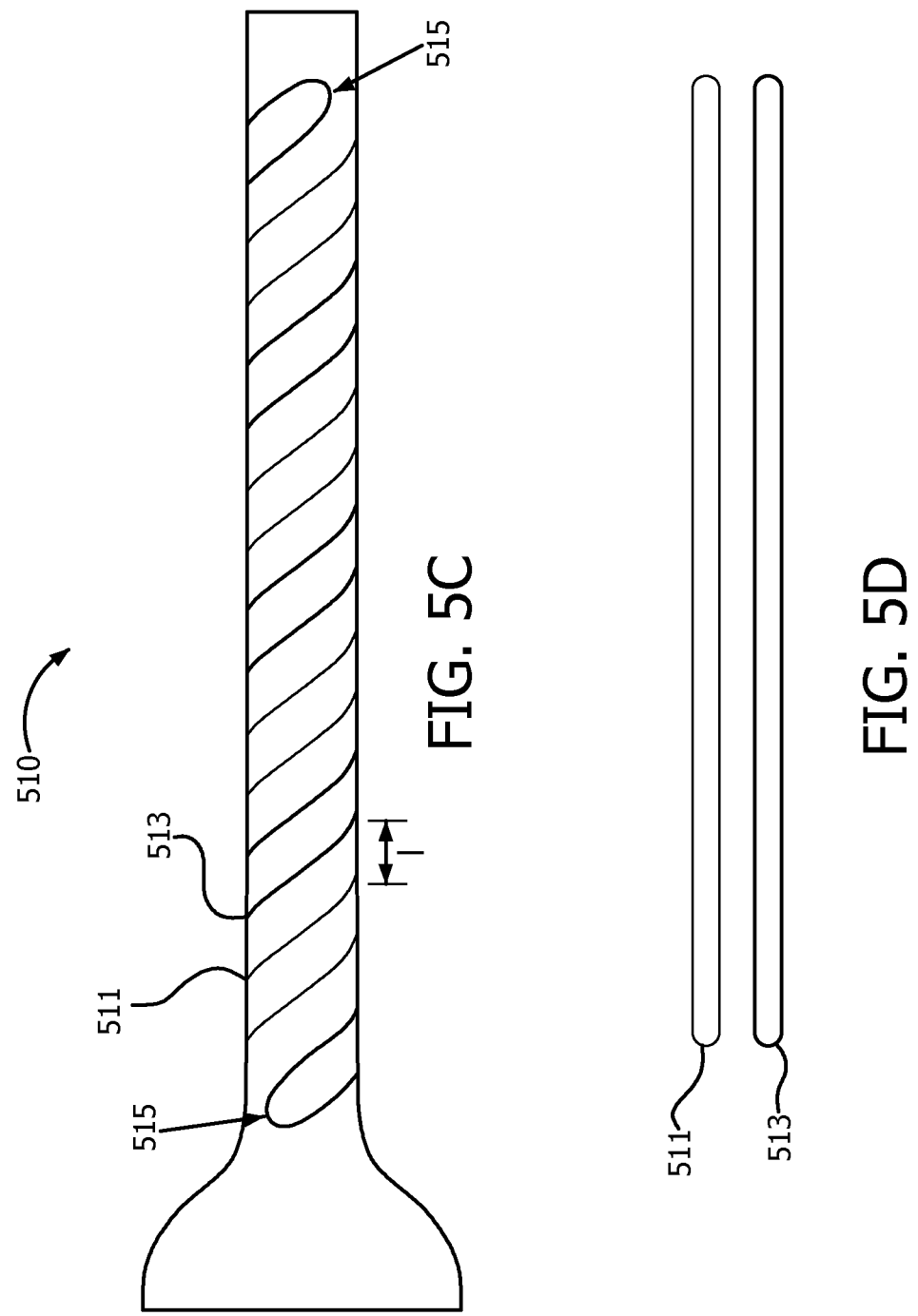

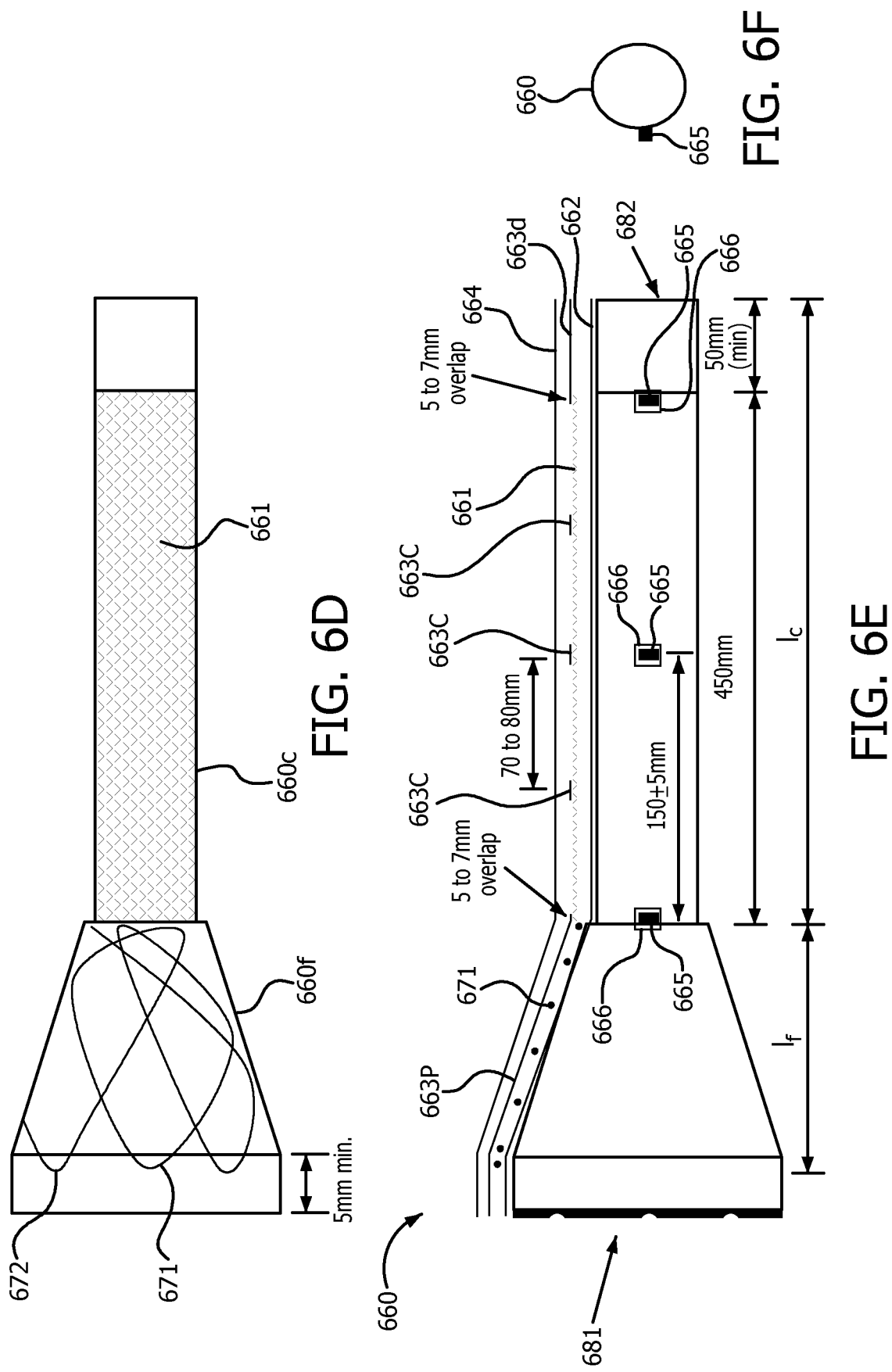

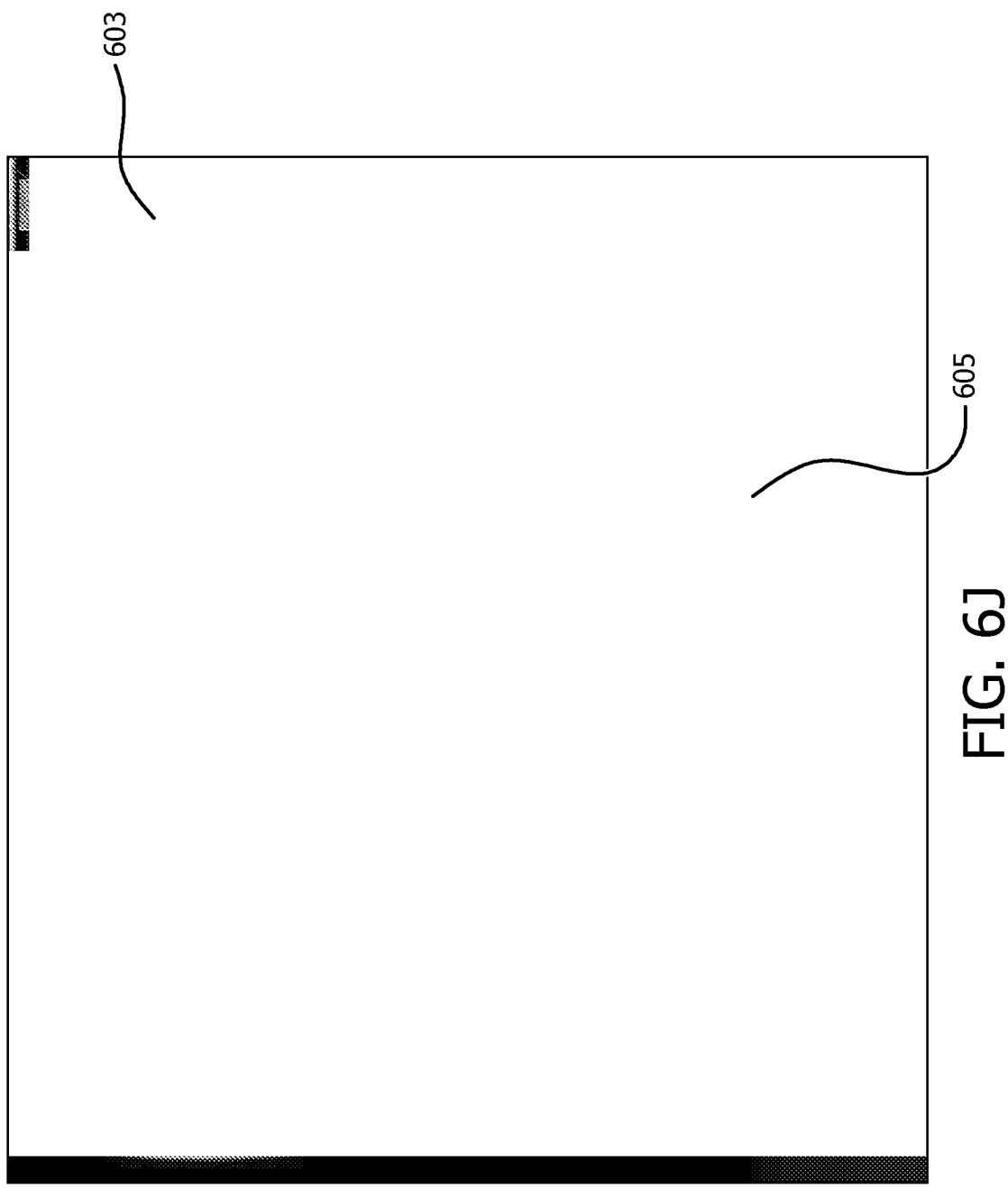

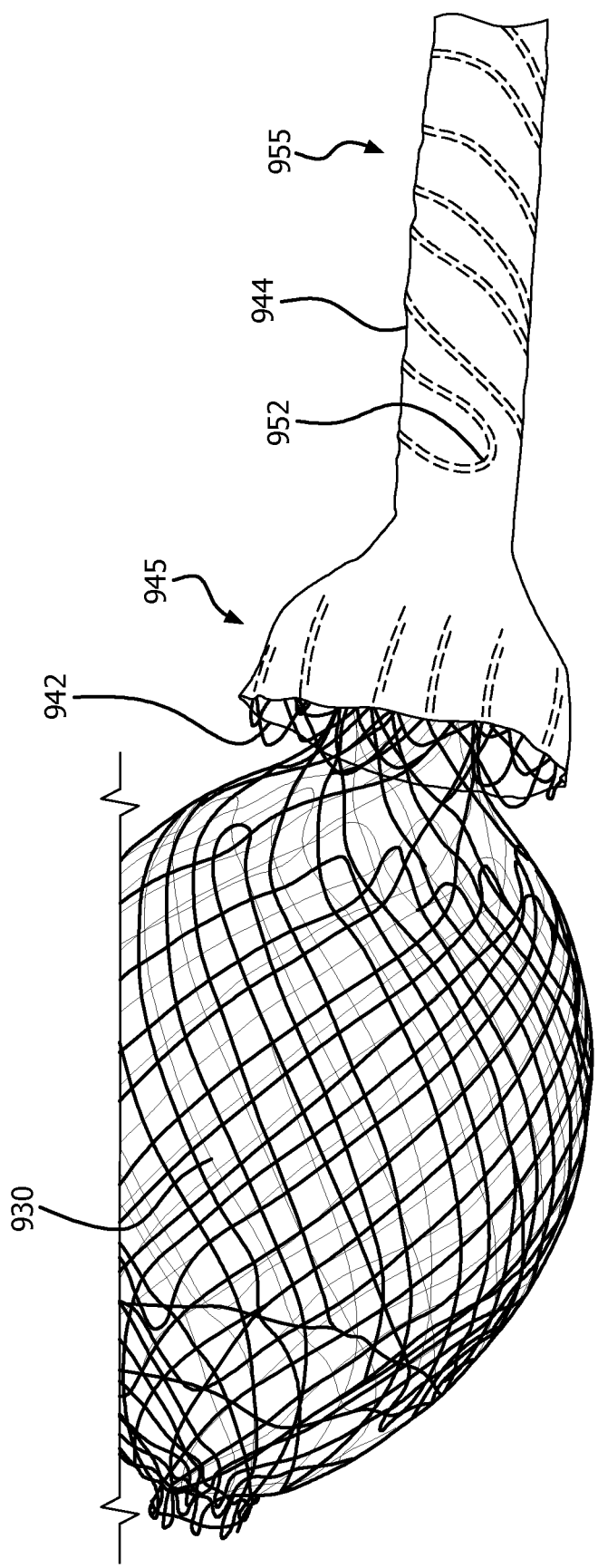

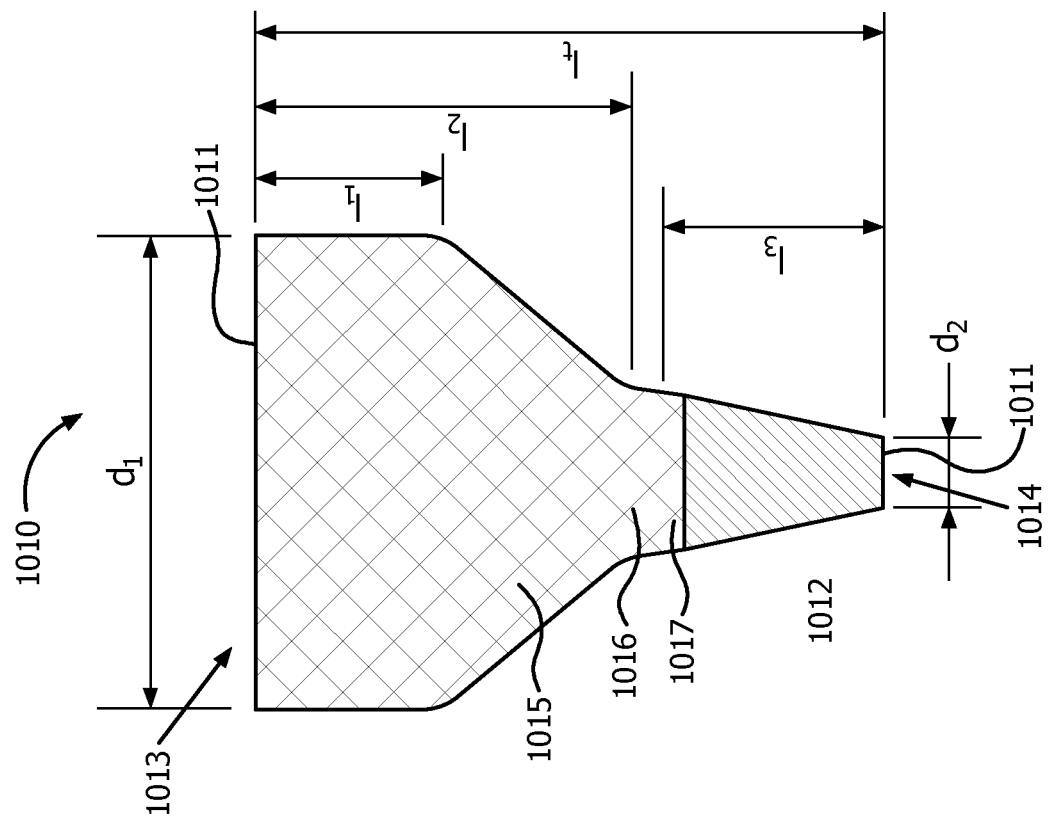
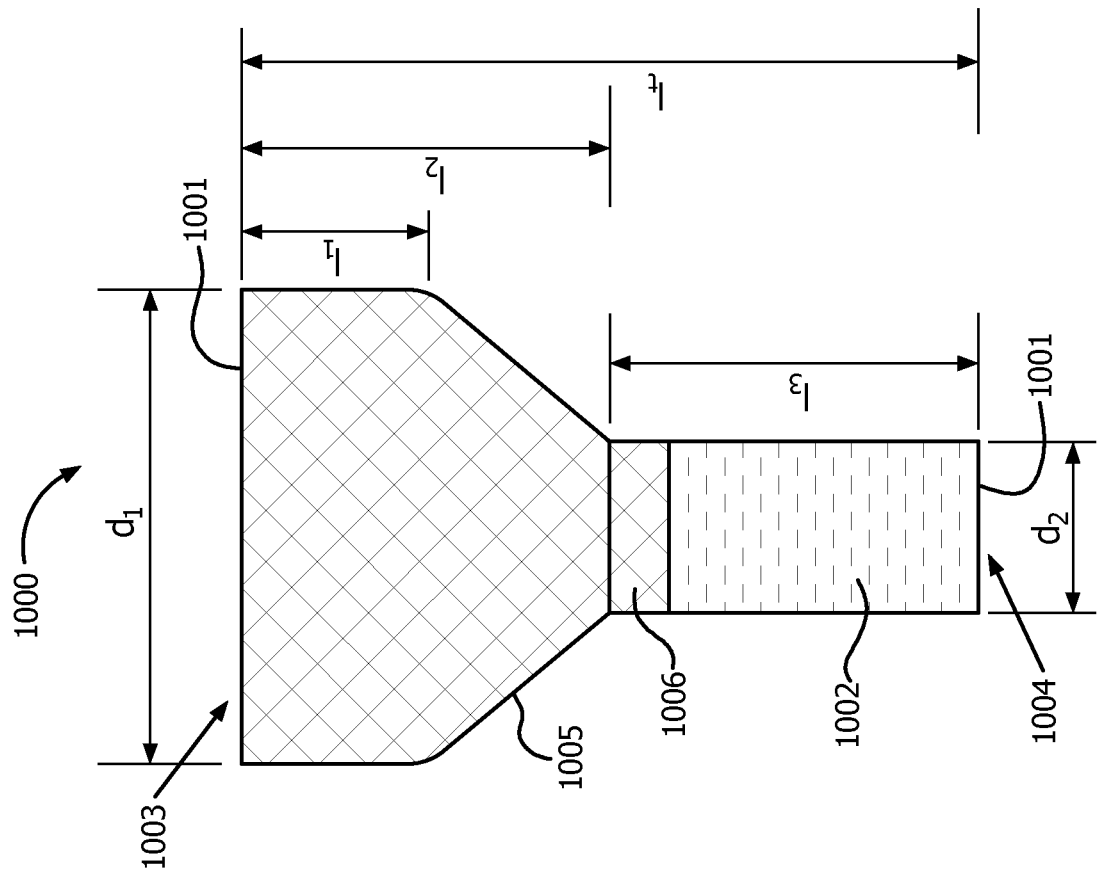
FIG. 10A
FIG. 10B

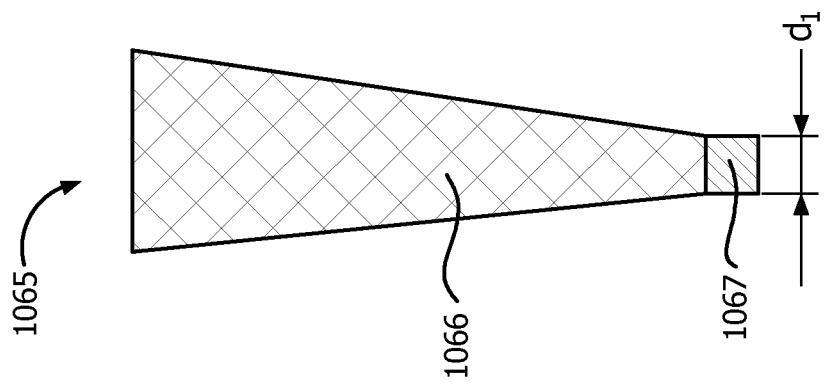
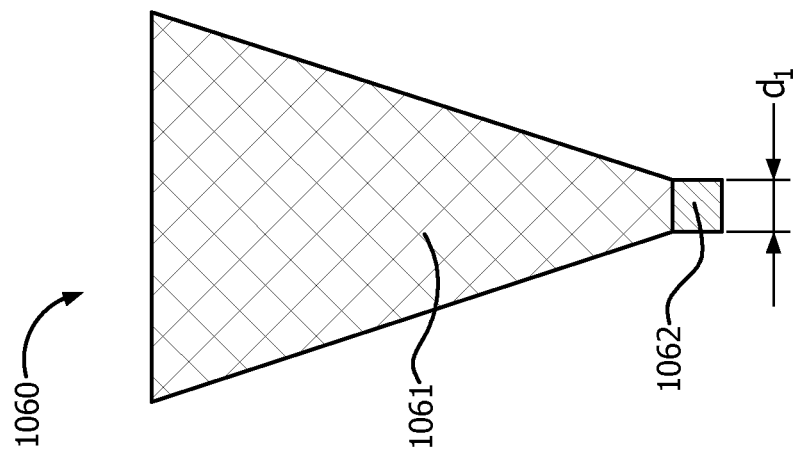

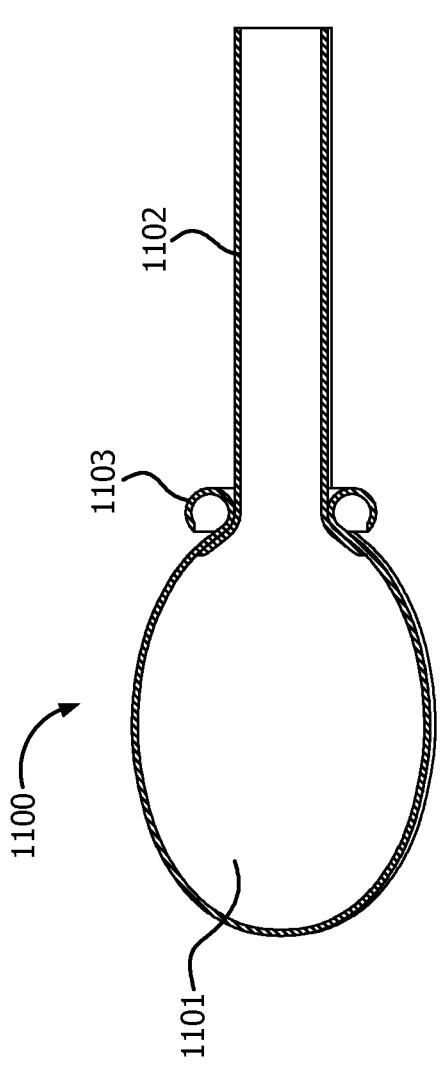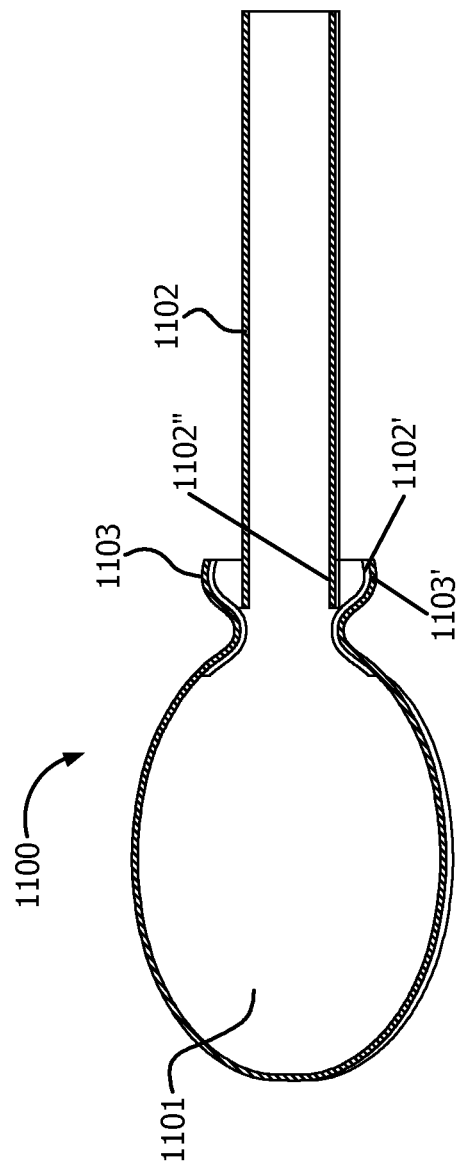
FIG. 11A
FIG. 11B

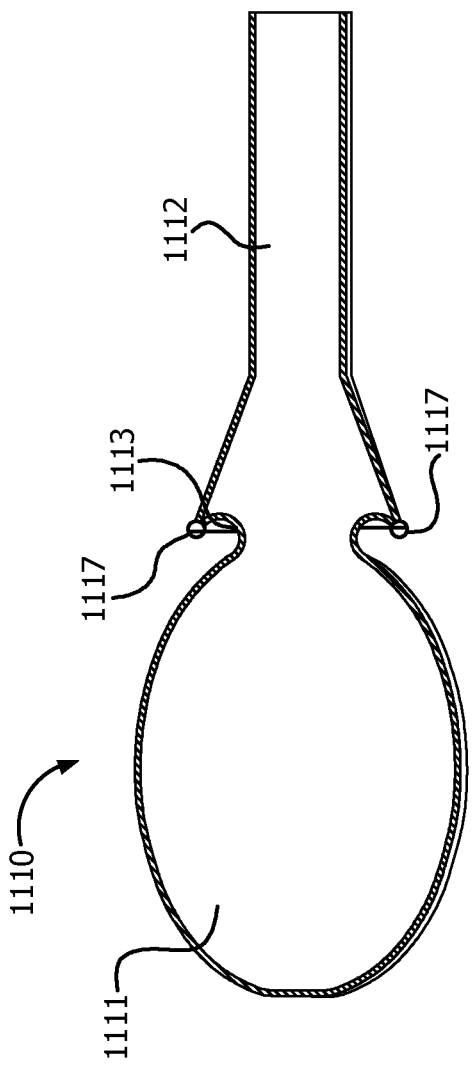
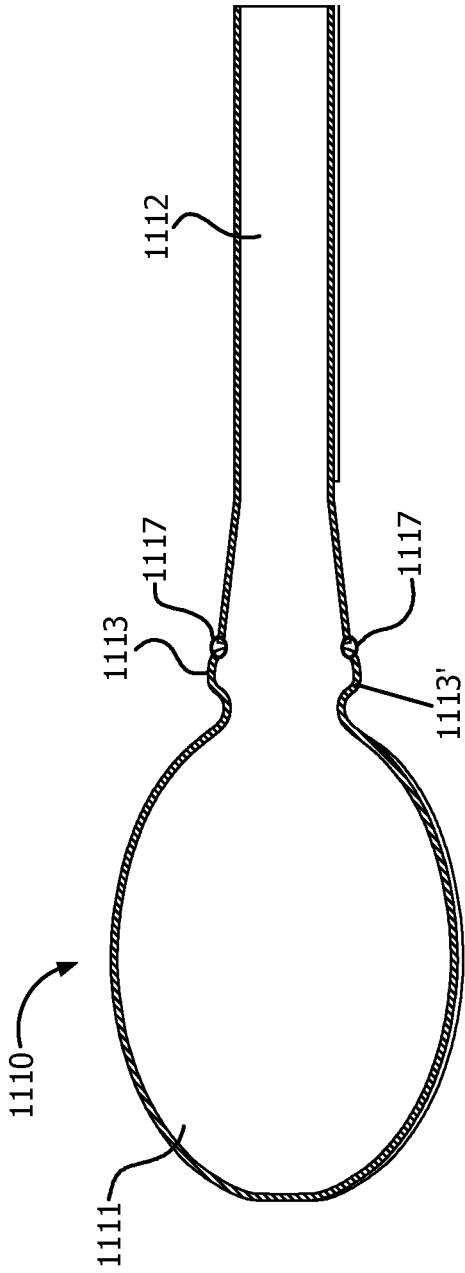

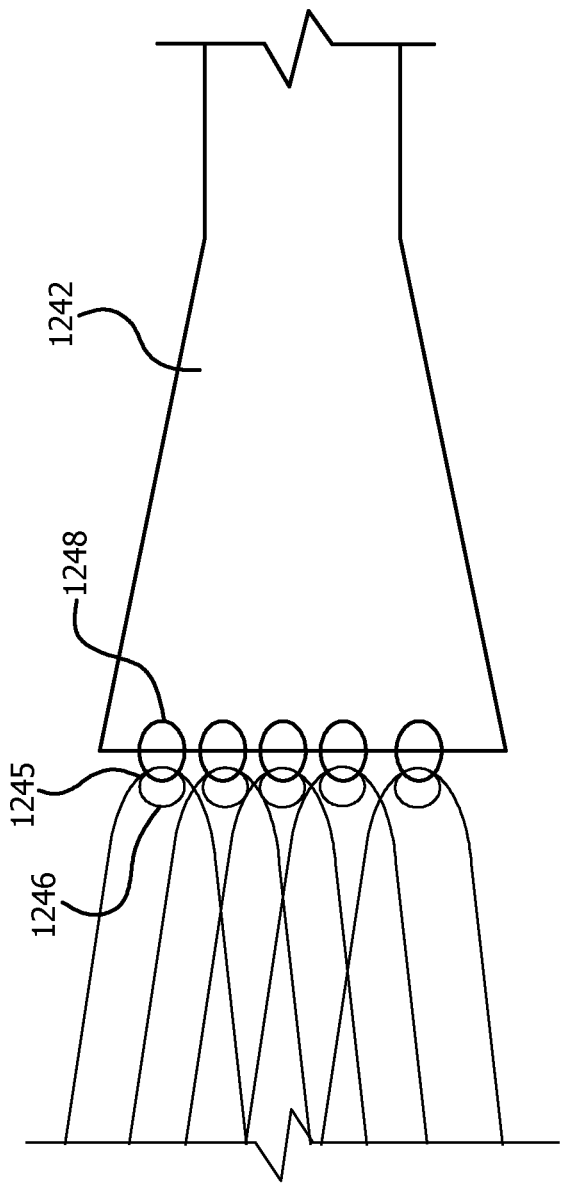
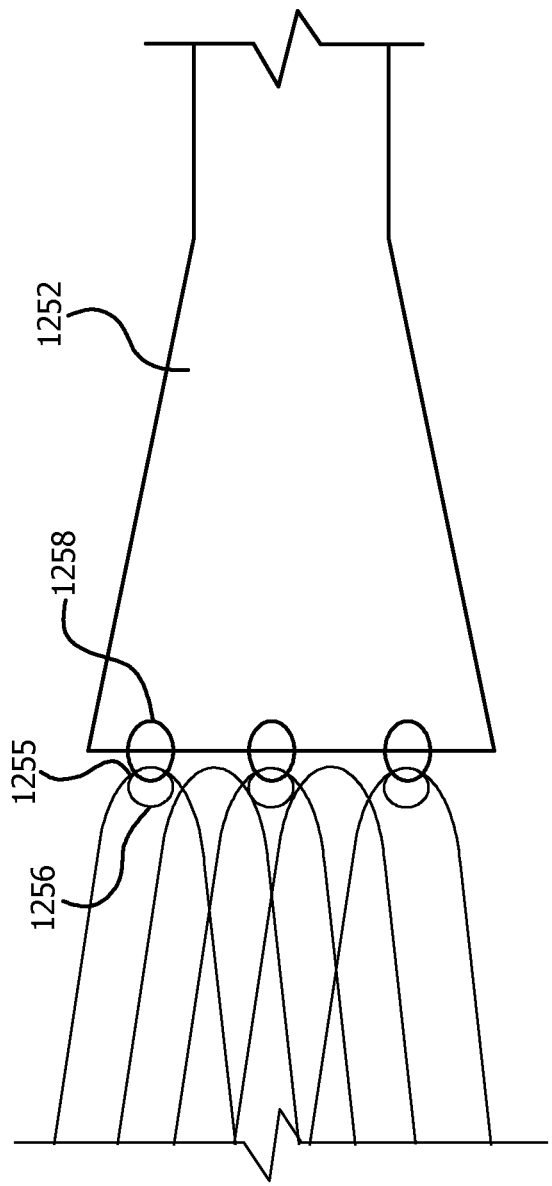
FIG. 12E
FIG. 12F

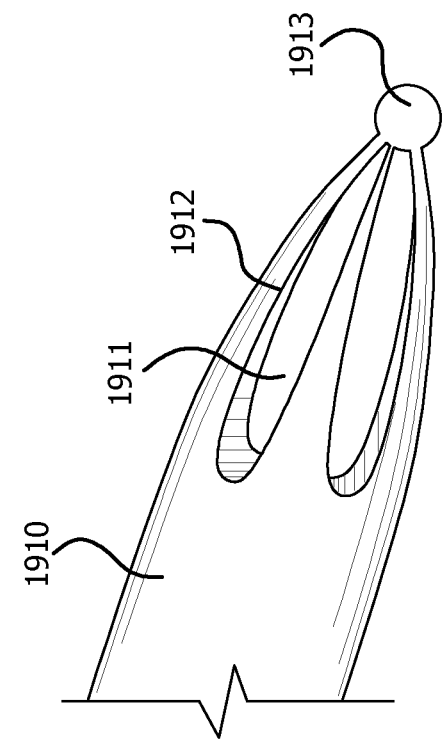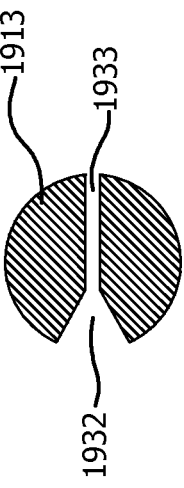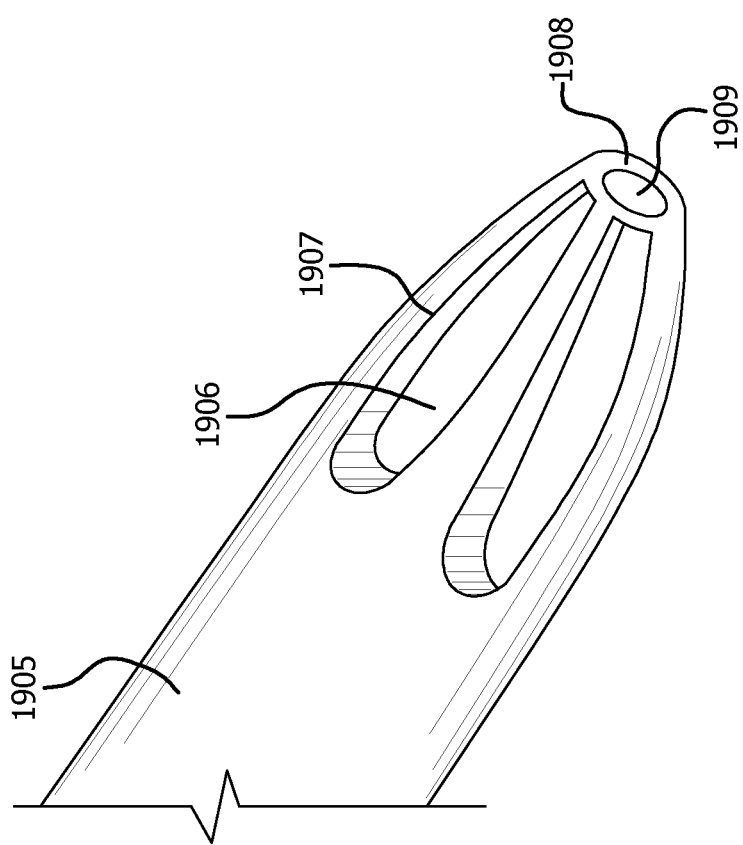
FIG. 19B
FIG. 19C
FIG. 19A

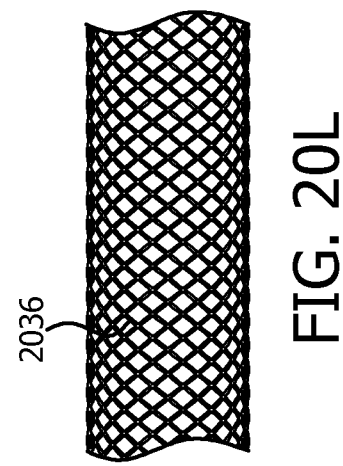
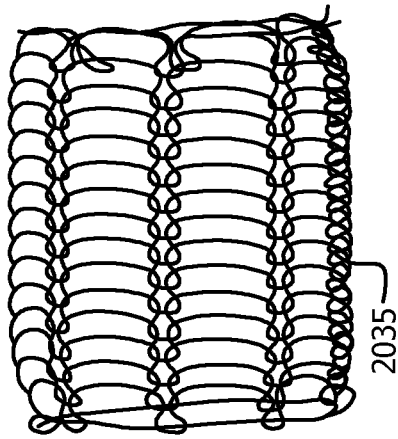
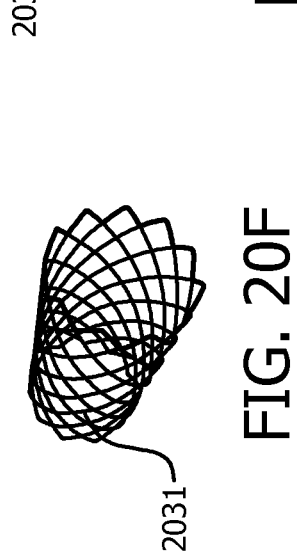
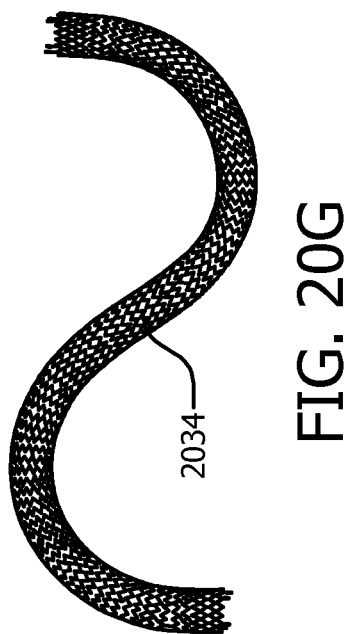
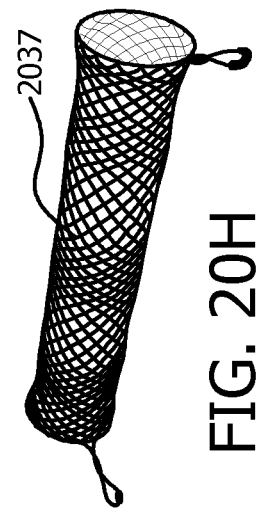

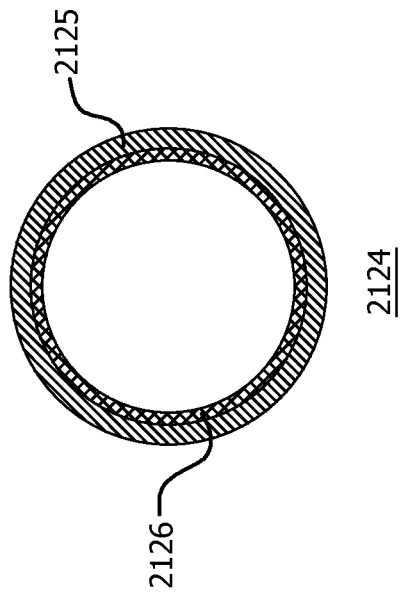
FIG. 21D
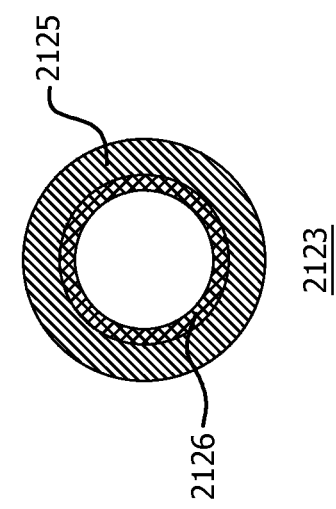
FIG. 21C

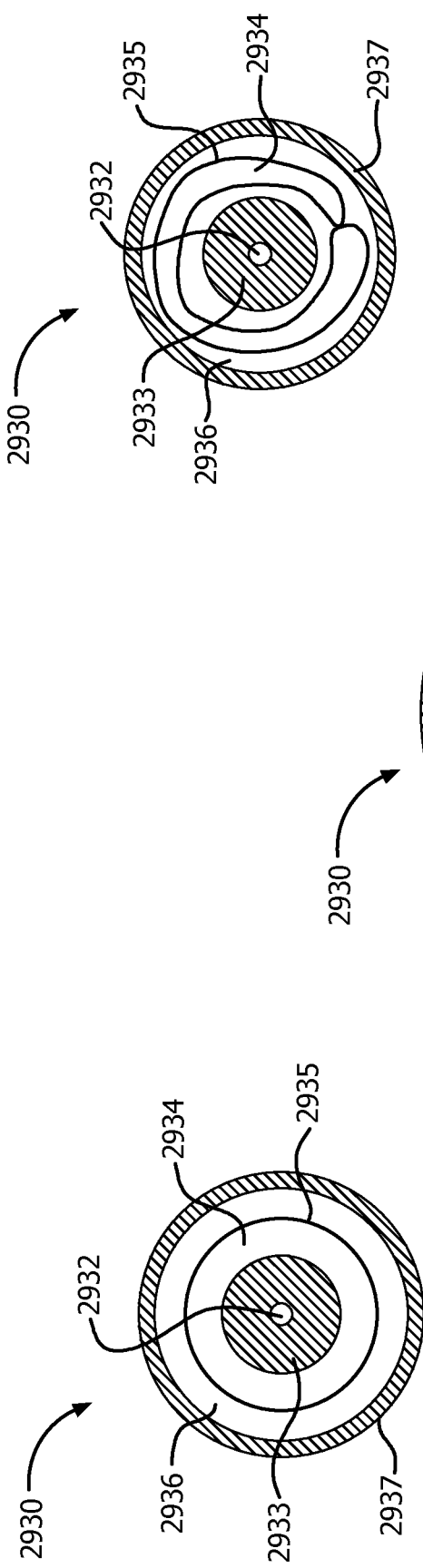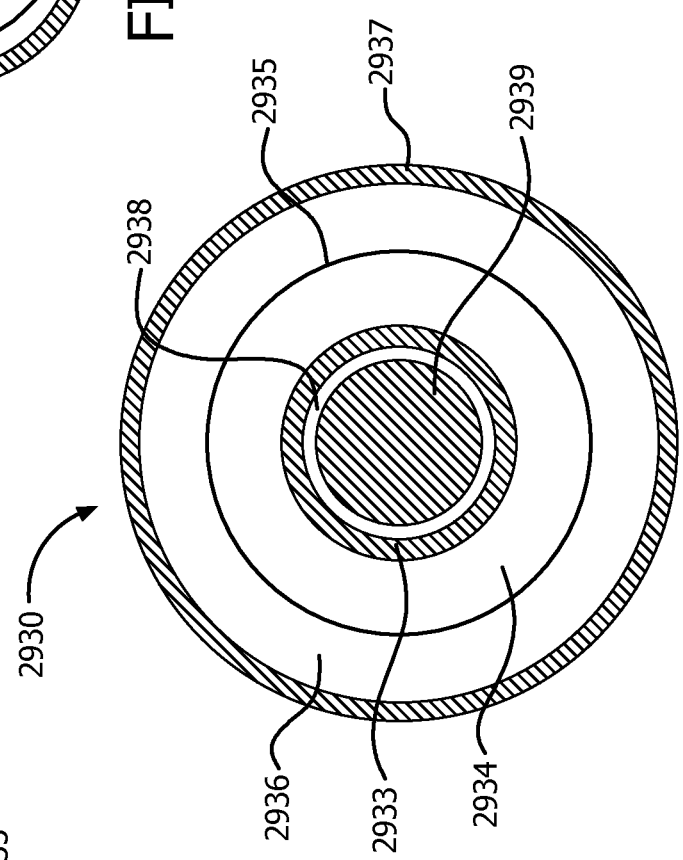
FIG. 29C
FIG. 29D
FIG. 29B

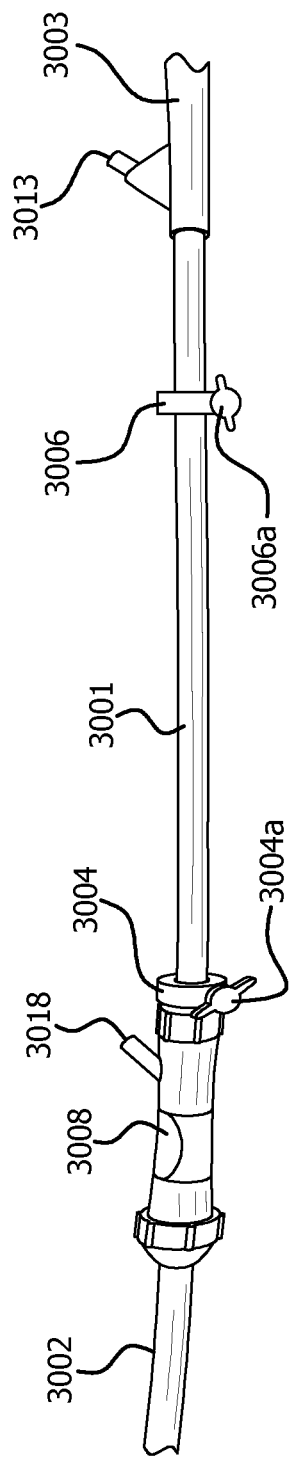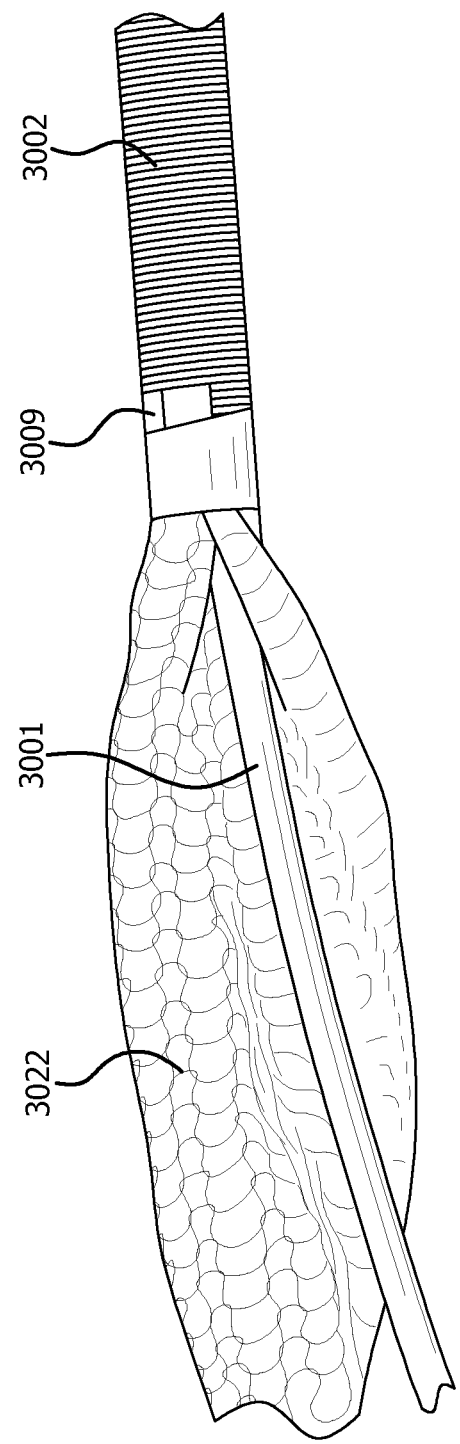
FIG. 30E
FIG. 30F

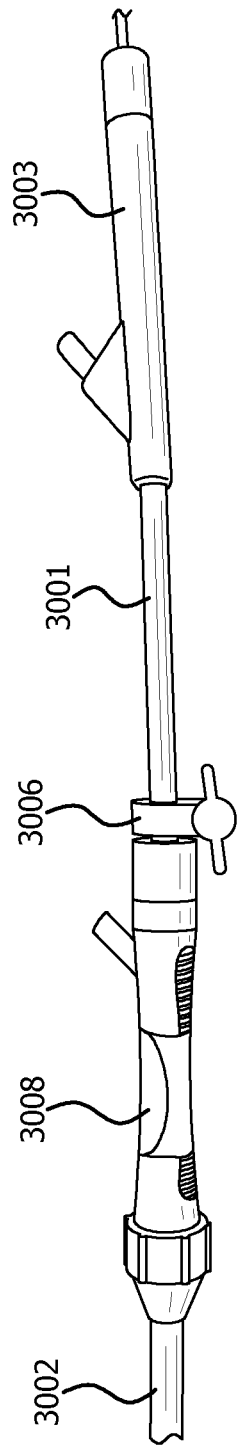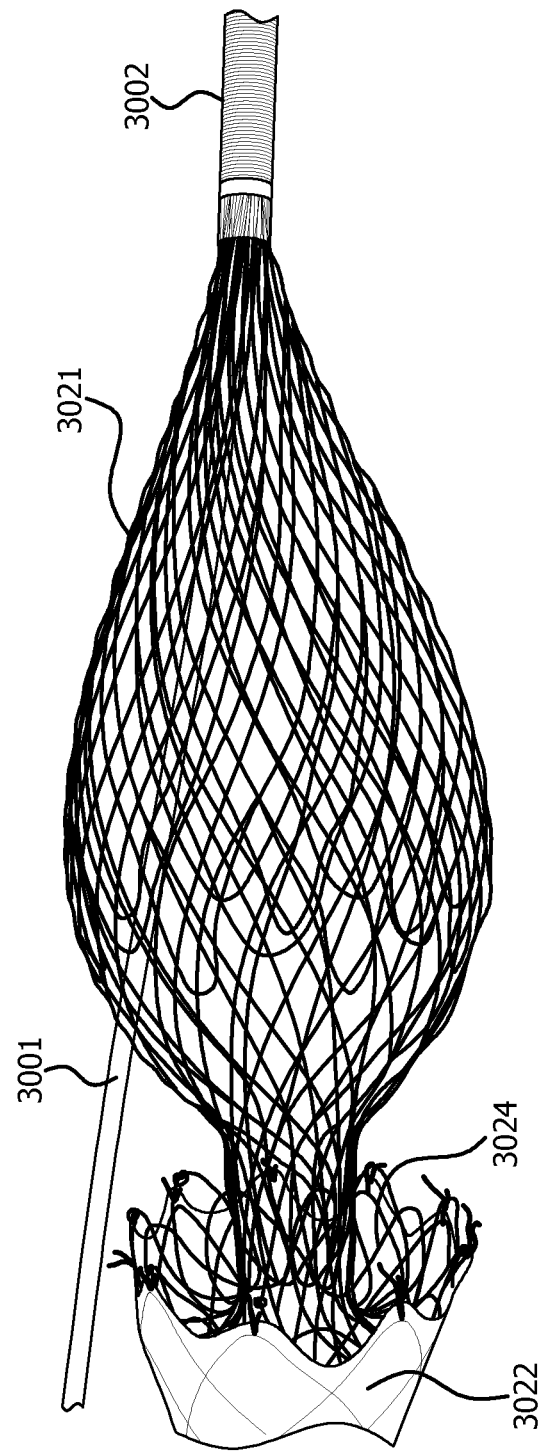
FIG. 30G
FIG. 30H

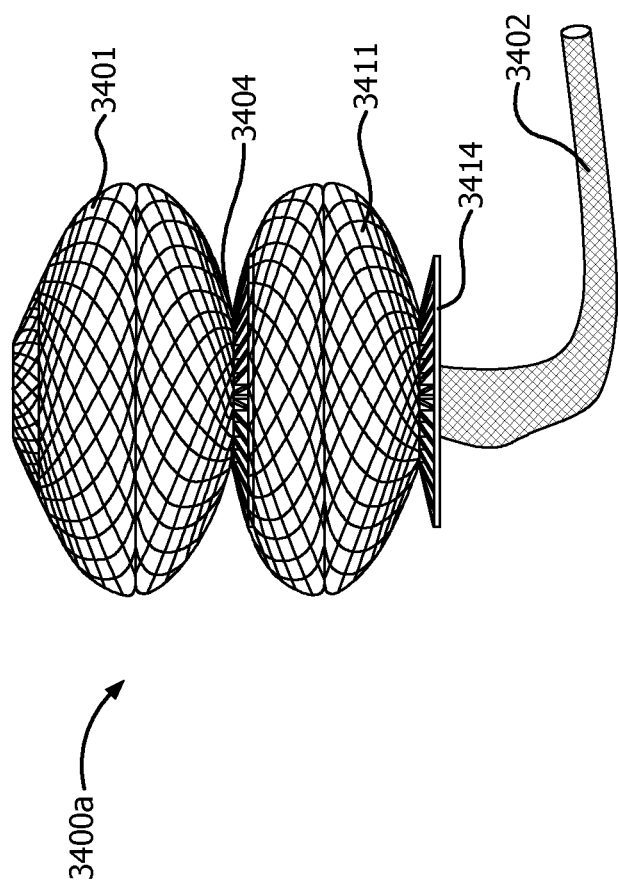

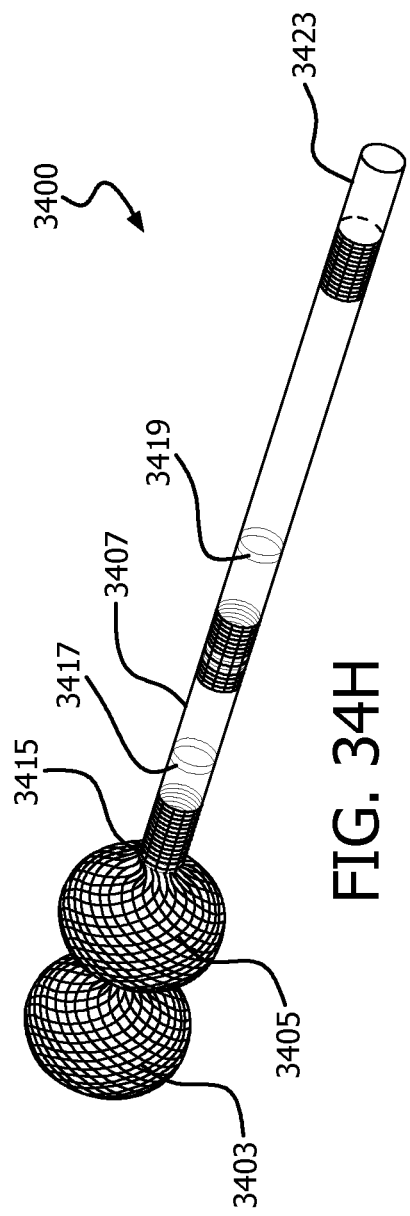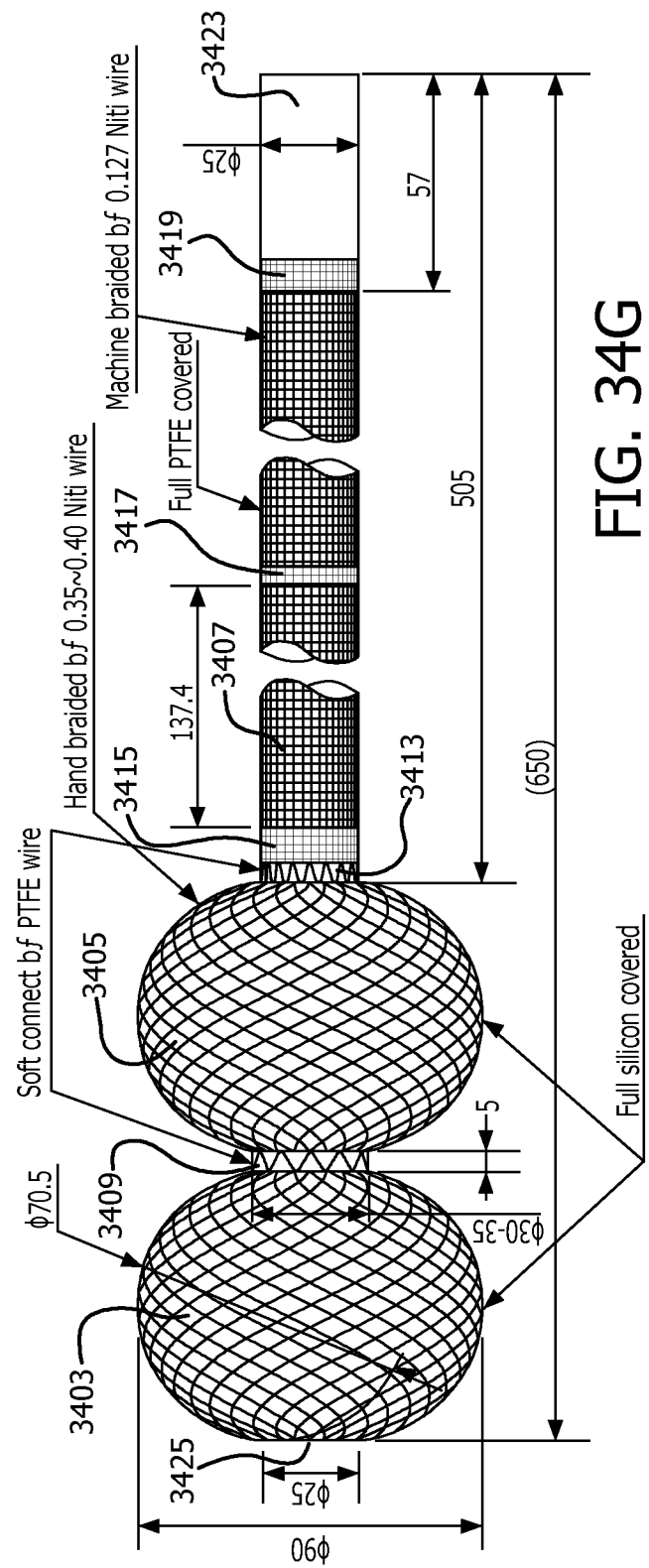

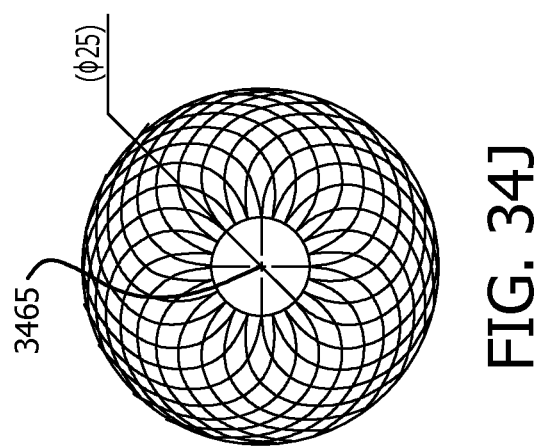
FIG. 34J
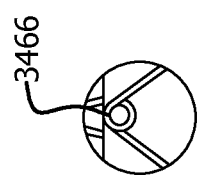
FIG. 34K
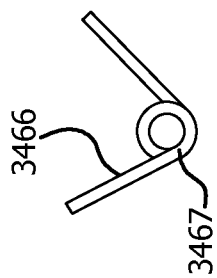
FIG. 34L
FIG. 34M
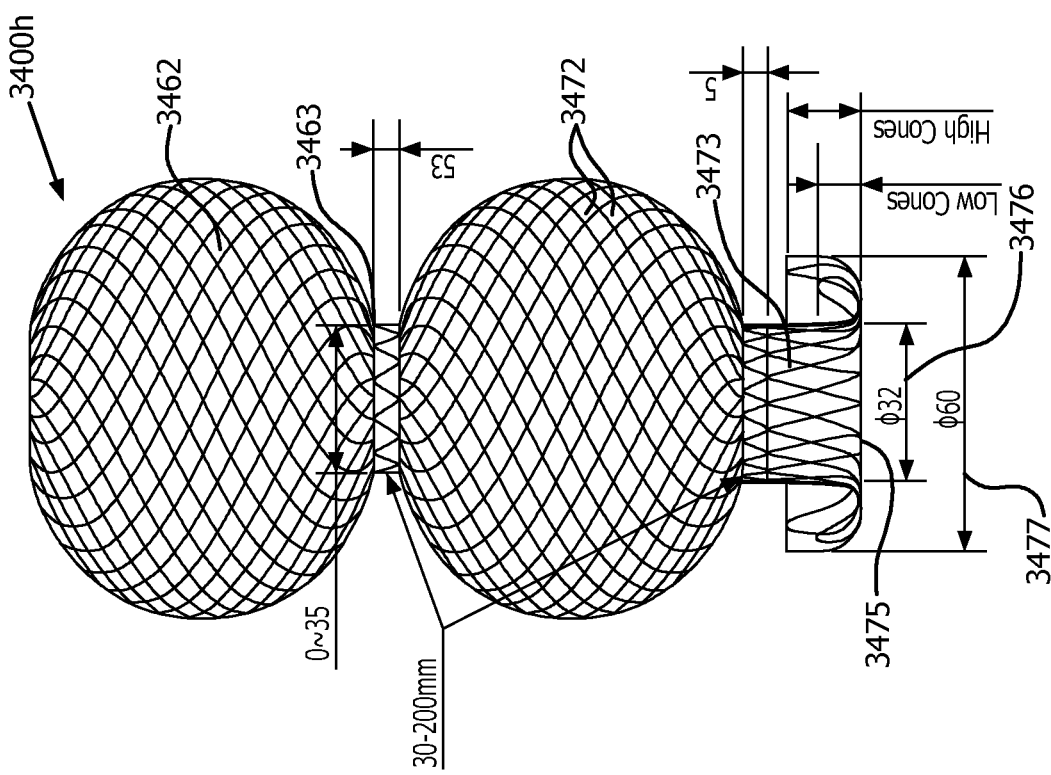
FIG. 34I

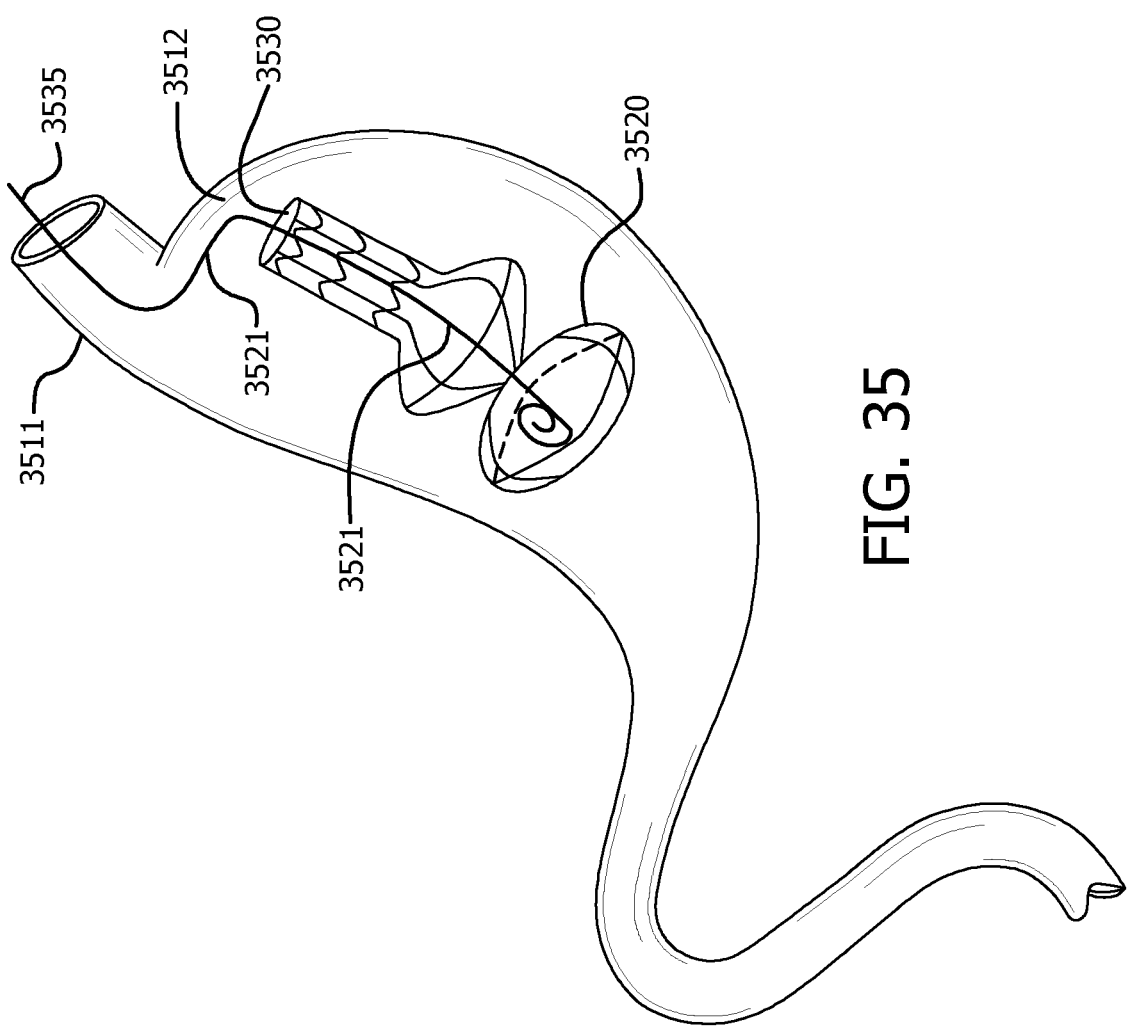

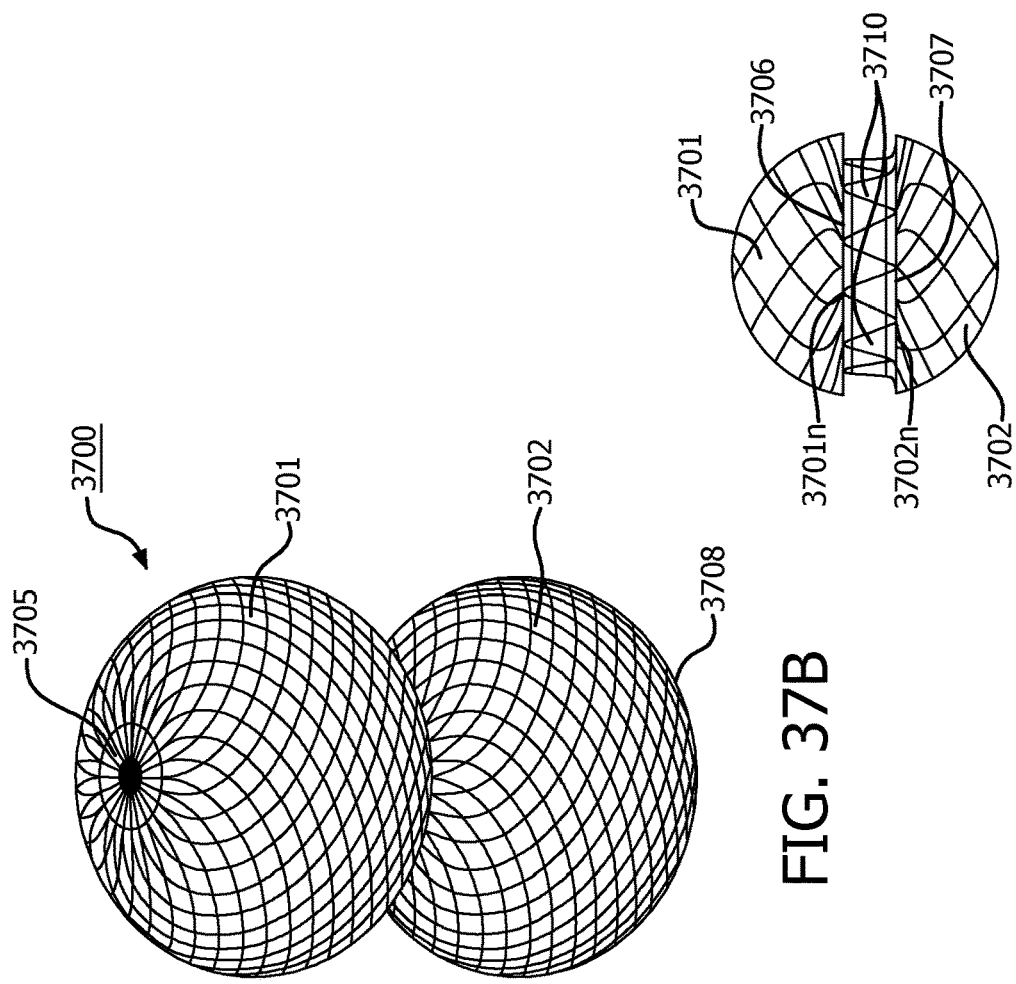
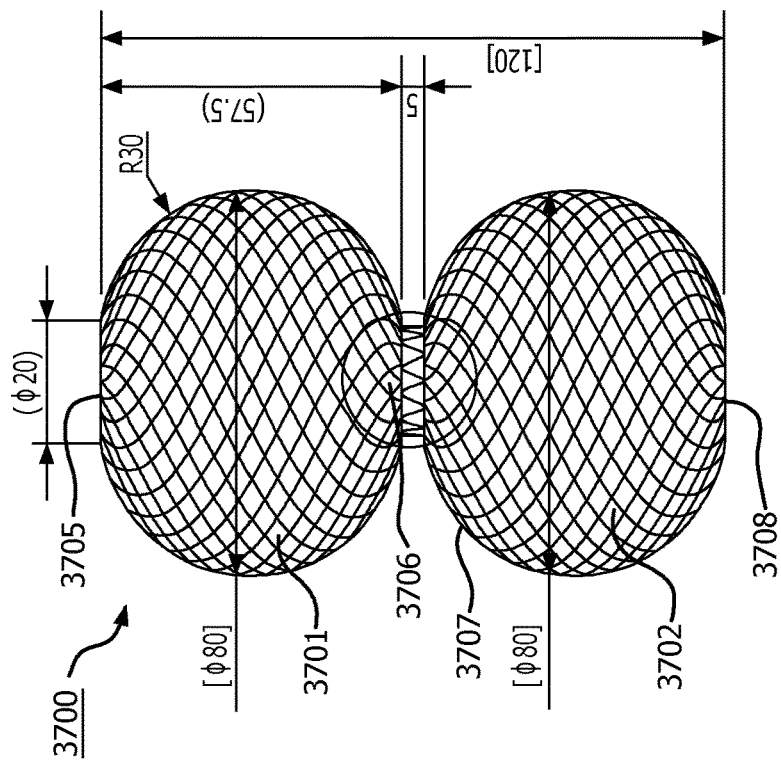
FIG. 37A
FIG. 37B
FIG. 37C

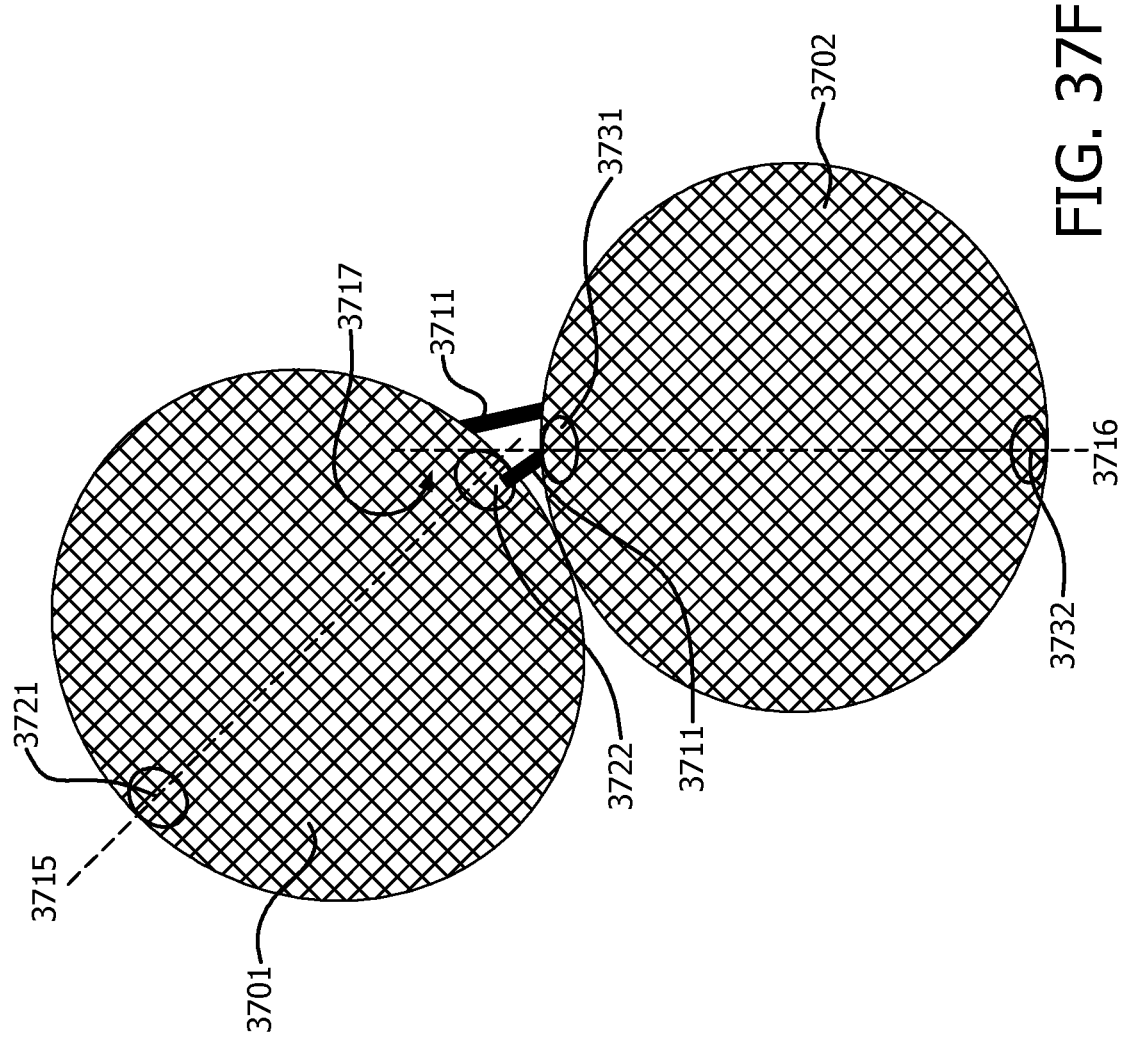

INTRAGASTRIC DEVICE FOR TREATING OBESITY

FIELD

The present specification relates generally to medical devices useful in the treatment of obesity. More particularly, the present specification relates to intragastric and gastrointestinal devices of dynamic weight that reduce gastric volume, slow gastric emptying, and/or bypass portions of the small intestine, thereby leading to patient weight loss.

BACKGROUND

Obesity is a common condition and growing public health problem in developed nations including the United States. As of 2009, more than two thirds of American adults, approximately 127 million people, were either overweight or obese. Over one third of American adults are obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States over $100 billion annually in direct and indirect health care expenses and in lost productivity. This trend is also apparent in many other developed nations.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m2 is associated with significant co-morbidities. Morbid obesity is defined as possessing either a body weight more than 100 pounds greater than ideal or a BMI greater than 40 kg/m2. Approximately 5% of the U.S. population meets at least one of the criteria for morbid obesity. Morbid obesity is associated with many diseases and disorders including, for example: diabetes; hypertension; heart attack; stroke; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are additionally associated with morbid obesity. Taken together, the diseases associated with morbid obesity markedly reduce the odds of attaining an average lifespan. The sequelae raise annual mortality rates in affected people by a factor of 10 or more.

Current treatments for obesity include diet, exercise, behavioral treatments, medications, surgery (open and laparoscopic), and endoscopic devices. New drug treatments for obesity are currently being evaluated in clinical trials. However, a high efficacy pharmaceutical treatment has not yet been developed. Further, short-term and long-term side effects of current pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive procedure with a malabsorptive procedure. Typical malabsorptive procedures divide small intestinal flow into a biliary-pancreatic conduit and a food conduit. Potential long-term side effects associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopic procedures and devices to produce gastric pouch and gastrojejunal anastomosis are used to replicate laparoscopic procedures. Endoscopically placed gastric balloons restrict gastric volume and result in satiety with smaller meals. For example, U.S. patent application Ser. No. 10/221,562, now issued as U.S. Pat. No. 7,172,613 and assigned to Districlass Medical SA, describes an "intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume."

The silicone intragastric balloon (IGB) has been developed as a temporary aid to achieve weight loss specifically for people who weigh 40% or more of their ideal weight and who have had unsatisfactory results in their treatment of obesity, despite being cared for by a multidisciplinary team. This treatment is also indicated for morbidly obese patients who have a high morbidity and mortality risk for surgery. The placement and removal of the IGB is an endoscopic procedure and the balloon is designed to float freely inside the stomach. The IGB technique reduces the volume of the stomach and leads to a premature feeling of satiety. However, use of IGBs did not show convincing evidence of a greater weight loss. The relative risks for minor complications, for example, gastric ulcers and erosions, were significantly raised. All inflatable IGB devices suffer from the problem of deterioration of the balloon over time. This deterioration can result in deflation with loss of efficacy and complications such as small bowel obstruction secondary to balloon migration. Due to loss of efficacy over time, IGB devices are recommended only for short (<6 month) durations. In addition, rapid inflation of the balloon poses the risk of esophageal or gastric perforations, both of which are surgical emergencies. Deaths have been reported in patients using IGB treatment.

Endoscopic procedures are also used to deploy mesh structures into the stomach in an effort to occupy stomach volume and create the artificial sensation of being full. For example, U.S. patent application Ser. No. 11/657,231, assigned to Wilson-Cook Medical, Inc., describes an "intragastric device generally compris[ing] a strip digestive-resistant mesh material that is operable between a first configuration and a second configuration. The first configuration is sufficiently small to permit introduction of the digestive-resistant mesh material into a gastric lumen of the mammal. The second configuration is sufficiently large to prevent the digestive-resistant mesh material from passing through the mammal's pylorus, thereby permitting the mesh member to act as an artificial bezoar."

Although endoscopically placed balloon structures can be effective, they are not without their associated risks and complications. Mesh structures are effective in occupying available gastric volume but they do not address gastric emptying. Migration and small bowel obstruction from such devices continue to remain a significant problem. Therefore, a need exists for an intragastric device to treat obesity that combines the benefits obtained through reducing stomach volume, slowing gastric emptying, and providing a bypass for food past the pylorus and a portion of the small intestine, while remaining relatively safe. The device should also include a component for preventing migration of the entire device out of the stomach. This device should limit side effects and be able to be deployed and removed in a non-invasive manner with relative ease. In addition, this device should have the option of further treating obesity by including the benefits obtained by malabsorptive diversion procedures. The addition of this optional benefit would make the device effective in treating not only obesity, but type II diabetes as well.

Typical metal structures cannot survive the hostile environment, particularly with respect to the high acidity, of the stomach. Intragastric devices comprising acid-sensitive components, such as metal wires, are typically covered or coated in an acid-resistant material (i.e. silicone) to prevent degradation of these components by acidic gastric contents. Conventional manufacturing processes for creating these coated intragastric devices first coat the metal wires of the device and then form the wires into the desired end shape of the device. As the shapes and structures of intragastric devices become more complicated, these conventional processes are unable to properly create the desired end product. A shape memory metal, such as Nitinol, is heat-set at temperatures in excess of 400° C. Coating the metal with an acid-resistant material and then heat-setting into the final shape would result in destruction of the coating during exposure to the high temperatures. Therefore, a method of manufacture is needed wherein the wires of the intragastric device are first formed into the desired end shape and are then coated with a corrosion-resistant material. Such a method will take care to prevent the coating and covering or clogging of the spaces or openings between the wires of the wire mesh. Such a method will also produce a finished device that is still flexible enough to be converted from a compressed, first pre-deployment shape to an expanded, post-deployment shape.

Specific surgical options for the treatment of obesity also include laparoscopic sleeve gastrectomy (LSG) and laparoscopic roux-en-y-gastric bypass (RGB) surgery. Gastrectomy refers to a partial or full surgical removal of the stomach. LSG is a restrictive treatment, surgical weight-loss procedure in which the stomach is reduced to approximately 25% of its original size by surgical removal of a large portion following the major curve. The open edges are then attached together (often with surgical staples) to form a sleeve or tube with a banana shape. The procedure permanently reduces the size of the stomach. The procedure is performed laparoscopically and is not reversible. Following the operation, the stomach empties its contents rapidly into the small intestine, but with little or no vomiting (characteristic of other restrictive procedures).

LSG involves a longitudinal resection of the stomach on the greater curvature from the antrum starting opposite the nerve of Latarjet up to the angle of His. The first step of the procedure is the division of the vascular supply of the greater curvature of the stomach which is achieved with the section of the gastro-colic and gastro-splenic ligaments close to the stomach. The greater curvature is completely freed up to the left crus of the diaphragm to resect the gastric fundus that harbors the ghrelin secreting cells of the stomach. The second step of the procedure is the longitudinal gastrectomy that "sleeves" the stomach to reduce its shape to a narrow tube. The pylorus and part of the antrum are preserved, resulting in a lesser curvature-based "restrictive" gastric sleeve.

Sleeve gastrectomy (also called gastric sleeve) is usually performed on extremely obese patients, with a body mass index of 40 or more, where the risk of performing a gastric bypass or duodenal switch procedure may be too large. A two-stage procedure is performed: the first is a sleeve gastrectomy; the second is a conversion into a gastric bypass or duodenal switch. Patients usually lose a large quantity of their excess weight after the first sleeve gastrectomy procedure but, if weight loss ceases, the second step is performed. For patients that are obese but not extremely obese, sleeve gastrectomy alone is a suitable operation with minimal risks. The sleeve gastrectomy is currently an acceptable weight loss surgery option for obese patients as a single procedure. Most surgeons prefer to use a bougie (tapering cylindrical instrument) having an outer diameter between 32-60 French (the optimal bougie size is 32 Fr-36 Fr) with the procedure. The ideal approximate remaining capacity of the stomach after the procedure is 15 ml.

One of the mechanisms involved in weight loss observed after the LSG is the dramatic reduction of the capacity of the stomach. The concept of restriction has been widely used in bariatric surgery in vertical banded gastroplasty (VBG) and laparoscopic adjustable gastric banding (LAGB). The distension of the small gastric pouch in the LAGB procedure or VBG is intended to account for the feeling of early fullness, enhanced satiety and decreased hunger experienced by a patient after the ingestion of small quantities of food.

The hormonal modifications induced by LSG differ from those found after a purely restrictive procedure such as LAGB. Ghrelin, a peptide hormone mainly produced in the fundus of the stomach, is believed to be involved in the mechanisms regulating hunger. There is a significant reduction in ghrelin associated with resection of the gastric fundus.

What makes LSG a preferable option lies in the fact that the operation is a straightforward procedure that can generally be completed laparoscopically, even in the case of an extremely obese patient. It does not involve any digestive anastomosis and no mesenteric defects are created, eliminating the risk of internal hernia. In addition, no foreign material is used as in the case of gastric banding, the whole digestive tract remains accessible to endoscopy, and it is not associated with Dumping syndrome. Also, the risk of peptic ulcer is low and the absorption of nutrients, vitamins, minerals and drugs is not altered.

Early reports of LSG have shown it to be safe and effective with marked weight loss and significant reduction of major obesity-related comorbidities. The question whether LSG may work as a sole bariatric procedure in the long term cannot yet be answered. For this reason, LSG is proposed as the first step of a staged approach in patients for whom a biliopancreatic diversion with duodenal switch (BPD-DS) or RGB seems too hazardous because of a very high BMI (super obesity=BMI>50 or super-super obesity=BMI>60) and/or associated diseases whether related or not to obesity.

Laparoscopic roux-en-y-gastric bypass (RGB) involves the creation of a small (20-30 ml) gastric pouch and a Roux limb (typically 75-105 cm) that reroutes a portion of the alimentary tract to bypass the distal stomach and proximal small bowel. Following RGB, a pleiotropic endocrine response may contribute to improved glycemic control, appetite reduction, and long-term changes in body weight. RGB also has a profoundly positive impact on obesity-related comorbidities and quality of life. Other advantages include established long-term effectiveness for sustained weight loss, reduction of comorbidities, minimal risk for long-term nutritional sequelae, and effective relief of gastroesophageal reflux disease (GERD). RGB is not without risks. Common causes of death include pulmonary embolism and anastomotic leaks. Nonfatal perioperative complications include anastomotic leaks, venous thromboembolism, wound infections, small bowel obstruction, and bleeding. Postoperative gastrointestinal complications include nausea and vomiting, micronutrient deficiencies, and possible weight regain.

Failures after these bariatric procedures are common and patients start regaining weight or the progressive weight loss stops at a sub-therapeutic level. Therefore, there is a need for salvage therapy after one or more failed bariatric procedures. What is needed is a device to be used following bariatric surgery that will combine the benefits of gastric volume reduction, bilio-pancreatic diversion and/or intestinal bypass to enhance the weight loss effects of the device. What is also needed is a device that will further reduce the volume of a surgically restricted stomach to reduce the amount of calories that can be consumed. The device will also bypass the proximal small intestine or the roux limb of the intestine in order to produce intestinal mal absorption, bilio-pancreatic diversion or both. The device can further act to delay gastric emptying, release the gastric hormones associated with satiety, and stimulate the gastric nerves associated with sensation of satiety. The device could be combined with other therapeutic agents such as electrical stimulation, magnetic stimulation, or pharmaceutical agents.

The device can be used as a primary therapeutic procedure for weight loss or as a bridge to surgery for a definitive weight loss procedure. The device may also be used in the treatment of other conditions including, but not limited to, metabolic syndrome, diabetes mellitus, dyslipidemias and cardiovascular disease.

SUMMARY

The present specification discloses an intragastric device configured for deployment in a stomach of a person, said device comprising: a catheter comprising a housing and a lumen extending through said housing, wherein the lumen has an internal diameter and wherein the internal diameter is equal to or less than 2 cm; a first wire mesh structure having a pre-deployment shape that is compressed within said lumen of the catheter and a post-deployment shape that is expanded within the stomach of the person, wherein said pre-deployment shape has a first volume that is equal or less than 110 ml and a first length that is equal to or less than 75 cm and wherein said post-deployment shape has a porous, enclosed second volume, defined by a first plurality of curved surfaces, that is equal to or greater than 125 ml, said first wire mesh structure further comprising an upper portion and a lower portion wherein the upper portion has a first surface area of openings configured to permit material to enter from outside the second volume to inside the second volume and wherein the lower portion has a second surface area of openings; a second wire mesh structure, separate from the first wire mesh structure, having a pre-deployment shape that is compressed within said lumen of the catheter and a post-deployment shape that is expanded within the stomach of the person, wherein said pre-deployment shape has a third volume that is equal or less than 100 ml and a second length that is equal to or less than 70 cm and wherein said post-deployment shape has a porous, enclosed fourth volume, defined by a second plurality of curved surfaces, that is equal to or greater than 110 ml, said second wire mesh structure further comprising an upper portion and a lower portion wherein the upper portion has a third surface area of openings configured to permit material to enter from outside the fourth volume to inside the fourth volume and wherein the lower portion has a fourth surface area of openings; a connection to flexibly couple said first and second wire mesh structures, wherein said connection is formed between a portion of the first wire mesh structure defining said second surface area of openings and a portion of the second wire mesh structure defining said third surface area of openings.

The first wire mesh structure and the second wire mesh structure may be positioned serially within the lumen of the catheter.

Optionally, at least one of the first plurality of curved surfaces is defined by an arc and wherein said arc is determined by a radius in a range of 0.2 cm to 20 cm and a central angle in a range of 5 to 175 degrees.

Optionally, at least one of the second plurality of curved surfaces is defined by an arc and wherein said arc is determined by a radius in a range of 0.1 cm to 15 cm and a central angle in a range of 1 to 179 degrees.

Optionally, said connection is formed between a portion of a plurality of free ends of the first wire mesh structure defining said second surface area of openings and a portion of a plurality of free ends of the second wire mesh structure defining said third surface area of openings.

The first wire mesh structure and second wire mesh structure may have at least one of a spherical and elliptical shape.

Optionally, said connection comprises a plurality of sutures. Optionally, the plurality of sutures include a first flexible suture attached, at one end, to a first point on said second surface area of openings and, at a second end, to a second point on said third surface area of openings. A length of a connection, from the first point on the second surface area of openings to the second point on said third surface area of openings, may be in a range of 0.01 mm to 200 mm.

Optionally, said plurality of sutures include a second flexible suture attached, at one end, to a third point on said second surface area of openings and, at a second end, to a fourth point on said third surface area of openings, wherein said first point is different from the third point and wherein said second point is different from the fourth point. A length of a connection, from the third point on the second surface area of openings to the fourth point on said third surface area of openings, may be in a range of 0.01 mm and 300 mm. The first flexible suture and the second flexible suture may be separated by 180 degrees. Optionally, the plurality of sutures include a third flexible suture attached, at one end, to a fifth point on said second surface area of openings and, at a second end, to a sixth point on said third surface area of openings, wherein said fifth point is different from the first point and the third point and wherein said sixth point is different from the second point and the fourth point. A length of a connection, from the fifth point on the second surface area of openings to the sixth point on said third surface area of openings, may be in a range of 0.01 mm and 300 mm. Optionally, the plurality of sutures include a fourth flexible suture attached, at one end, to a seventh point on said second surface area of openings and, at a second end, to a eighth point on said third surface area of openings, wherein said seventh point is different from the first point, the third point, and the fifth point and wherein said eighth point is different from the second point, the fourth point and the sixth point. A length of a connection, from the seventh point on the second surface area of openings to the eighth point on said third surface area of openings, is in a range of 0.01 mm and 300 mm.

Optionally, the first and second wire mesh structures have a degree of movement in all directions relative to each other, said degree of movement being defined by an angular displacement between a first longitudinal axis passing through a center of said first wire mesh structure, a center of the first surface area of openings, and a center of the second surface area of openings and a second longitudinal axis passing through a center of said second wire mesh structure, a center of the third surface area of openings, and a center of the fourth surface area of openings. The angular displacement may be equal to, or less than, 90 degrees.

Optionally, the connection of said first wire mesh structure to the second wire mesh structure has a length such that the first wire mesh structure can be compressed up to 99% of its equatorial diameter without leading to a compression of said second wire mesh structure.

Optionally, the connection of said first wire mesh structure to the second wire mesh structure has a length such that, upon more than 90% compression of the first wire mesh structure, the second wire mesh structure has an angular displacement relative to the first wire mesh structure of 10% or less, wherein said angular displacement is defined by a relative angle between a first longitudinal axis passing through a center of said first wire mesh structure, a center of the first surface area of openings, and a center of the second surface area of openings and a second longitudinal axis passing through a center of said second wire mesh structure, a center of the third surface area of openings, and a center of the fourth surface area of openings.

Optionally, the first wire mesh structure and the second wire mesh structure are connected by said connection within the lumen of the catheter.

Optionally, the first wire mesh structure and the second wire mesh structure are not connected by said connection within the lumen of the catheter.

Optionally, the connection is formed by interweaving a portion of a plurality of free ends of said second surface area of openings and a portion of a plurality of free ends of said third surface area of openings.

The second and fourth volumes together may occupy 25% to 95% of the stomach.

Optionally, the intragastric device further comprises a sleeve having a proximal end, a distal end, and a lumen, wherein said proximal end is coupled to said lower portion of said second wire mesh structure and said distal end is positioned in a duodenum of a patient, said sleeve further comprising a first opening in fluid communication with said fourth surface area of openings and a second opening at said distal end, wherein said sleeve is configured to transmit food from said intragastric device to said duodenum.

Optionally, the first wire mesh structure has at least one of a spherical shape and an elliptical shape and the first wire mesh structure has a volume that is greater than 5 ml and less than 5000 ml.

Optionally, the second wire mesh structure has at least one of a spherical shape and an elliptical shape and the second wire mesh structure has a volume that is greater than 20 ml and less than 4000 ml.

The present specification also discloses an intragastric device configured for deployment in a stomach of a person, said device comprising: a first wire mesh structure having a pre-deployment shape that is compressed within a lumen of a catheter and a post-deployment shape that is expanded within the stomach of the person, wherein said pre-deployment shape has a first volume that is equal or less than 110 ml and a first length that is equal to or less than 75 cm and wherein said post-deployment shape has a porous, enclosed second volume, defined by a first plurality of curved surfaces, that is equal to or greater than 125 ml, said first wire mesh structure further comprising an upper portion and a lower portion wherein the upper portion has a first surface area of openings configured to permit material to enter from outside the second volume to inside the second volume and wherein the lower portion has a second surface area of openings; a second wire mesh structure having a pre-deployment shape that is compressed within said lumen of the catheter and a post-deployment shape that is expanded within the stomach of the person, wherein said pre-deployment shape has a third volume that is equal or less than 100 ml and a second length that is equal to or less than 70 cm and wherein said post-deployment shape has a porous, enclosed fourth volume, defined by a second plurality of curved surfaces, that is equal to or greater than 110 ml, said first wire mesh structure further comprising an upper portion and a lower portion wherein the upper portion has a third surface area of openings configured to permit material to enter from outside the fourth volume to inside the fourth volume and wherein the lower portion has a fourth surface area of openings; a plurality of flexible members to flexibly couple said first and second wire mesh structures, wherein said plurality of flexible members include a first flexible member attached, at one end, to a first point on said second surface area of openings and, at a second end, to a second point on said third surface area of openings and wherein said plurality of flexible members include a second flexible member attached, at one end, to a third point on said second surface area of openings and, at a second end, to a fourth point on said third surface area of openings, wherein said first point is different from the third point and wherein said second point is different from the fourth point.

Optionally, a length of said first flexible member, from the first point on the second surface area of openings to the second point on said third surface area of openings, is in a range of 0.01 mm and 300 mm.

Optionally, a length of said second flexible member, from the third point on the second surface area of openings to the fourth point on said third surface area of openings, is in a range of 0.01 mm and 100 mm.

The first flexible member and the second flexible member may be separated by 180 degrees.

Optionally, the plurality of flexible members include a third flexible member attached, at one end, to a fifth point on said second surface area of openings and, at a second end, to a sixth point on said third surface area of openings, wherein said fifth point is different from the first point and the third point and wherein said sixth point is different from the second point and the fourth point. A length of said third flexible member, from the fifth point on the second surface area of openings to the sixth point on said third surface area of openings, may be in a range of 0.01 mm and 300 mm. Optionally, the plurality of flexible members include a fourth flexible member attached, at one end, to a seventh point on said second surface area of openings and, at a second end, to a eighth point on said third surface area of openings, wherein said seventh point is different from the first point, the third point, and the fifth point and wherein said eighth point is different from the second point, the fourth point and the sixth point. A length of said fourth flexible member, from seventh point on the second surface area of openings to the eighth point on said third surface area of openings, may be in a range of 0.01 mm and 100 mm.

Optionally, the first and second wire mesh structures have a degree of movement in all directions relative to each other, said degree of movement being defined by an angular displacement between a first longitudinal axis passing through a center of said first wire mesh structure, a center of the first surface area of openings, and a center of the second surface area of openings and a second longitudinal axis passing through a center of said second wire mesh structure, a center of the third surface area of openings, and a center of the fourth surface area of openings. The angular displacement may be equal to, or less than, 90 degrees.

Optionally, each of the plurality of flexible members has a length such that the first wire mesh structure can be compressed up to 95% of its equatorial diameter without leading to a compression of said second wire mesh structure.

Optionally, each of the plurality of flexible members has a length such that, upon more than 90% compression of the first wire mesh structure, the second wire mesh structure has an angular displacement relative to the first wire mesh structure of 10% or less, wherein said angular displacement is defined by a relative angle between a first longitudinal axis passing through a center of said first wire mesh structure, a center of the first surface area of openings, and a center of the second surface area of openings and a second longitudinal axis passing through a center of said second wire mesh structure, a center of the third surface area of openings, and a center of the fourth surface area of openings.

The present specification also discloses an intragastric device configured for deployment in a stomach of a person, said device comprising: a catheter comprising a housing and a lumen extending through said housing, wherein the lumen has an internal diameter and wherein the internal diameter is equal to or less than 2 cm; a first wire mesh structure having a pre-deployment shape that is compressed within said lumen of the catheter and a post-deployment shape that is expanded within the stomach of the person, wherein said pre-deployment shape has a first volume that is equal or less than 110 ml and a first length that is equal to or less than 75 cm and wherein said post-deployment shape has a porous, enclosed second volume, defined by a first plurality of curved surfaces, that is equal to or greater than 125 ml, said first wire mesh structure further comprising a first upper portion and a first lower portion wherein the first upper portion has a first opening configured to permit material to enter from outside the second volume to inside the second volume, and wherein the lower portion has a portion of said first plurality of curved surfaces that taper and converge into a second opening defined by a diameter; and a collar attached to the lower portion, wherein said collar is defined by a surface of revolution generated by revolving a semicircle in three-dimensional space about an axis extending through a center of the second opening and wherein said collar is defined by a diameter that is equal to or greater than 25 mm.

The present specification also discloses a delivery device for delivering a gastrointestinal device into a gastrointestinal tract of a patient, said gastrointestinal device comprising a porous structure configurable between a compressed pre-deployment configuration and an expanded post-deployment configuration, an anti-migration collar proximate a distal end of said porous structure, and an elongate sleeve coupled to the distal end of said porous structure, said delivery device comprising: a flexible outer catheter having a proximal end, a distal end, and a lumen; a flexible inner catheter having a proximal end, a distal end, and a lumen configured to slidably receive a guide wire, wherein said inner catheter is positioned coaxially and is configured to be slidably movable within the lumen of said outer catheter; wherein said outer catheter is configured to be retracted in a proximal direction over said inner catheter while maintaining said inner catheter in place to expose said gastrointestinal device from said distal end of said delivery device.

Optionally, said sleeve has length such that, once said gastrointestinal device is delivered, a proximal end of said sleeve is positioned proximal to a patient's pylorus and a distal end of said sleeve is positioned in a portion of a patient's duodenum.

Optionally, said outer catheter has a length of approximately 1.5 meters and said delivery device has an overall length of approximately 3 meters.

Optionally, the anti-migration collar of the gastrointestinal device is proximally sloping wherein a distal portion of the porous structure is folded such that the distally directed end of the porous structure is made to point toward the proximal end of the porous structure. Optionally, the anti-migration collar is any curved/atraumatic structure positioned circumferentially around the distal end of the porous structure.

Optionally, the outer catheter includes a radiopaque marker at its distal end for radiographic visualization during delivery.

Optionally, the delivery device further comprises: a first handle attached to the proximal end of said inner catheter and having a proximal end, a distal end, and a lumen configured to slidably receive said guide wire; a second handle attached to the proximal end of said outer catheter and having a proximal end, a distal end, and a lumen configured to slidably receive said inner catheter, wherein, prior to delivery of said intragastric device, a proximal portion of said inner catheter positioned between said first and second handles is exposed and not covered by said outer catheter; an elongate flexible pilot component having a proximal end, a distal end and a length having a variable stiffness, said pilot component comprising a distal spherical component and a proximal spherical component and extending from said distal end of said inner catheter; a first stopping mechanism removably attached to said exposed portion of said inner catheter; and a second stopping mechanism removably attached to said exposed portion of said inner catheter and positioned proximal to said first stopping mechanism; wherein said first and second stopping mechanisms are configured to be sequentially removed from said inner catheter as said outer catheter is retracted.

The delivery device may further comprise a hydrophilic coating over at least one of said pilot component and said distal end of said outer catheter, wherein, when activated, said hydrophilic coating is adapted to ease insertion and navigation of said delivery device.

The delivery device may further comprise a port on at least one of said first handle for injecting a fluid into said lumen of said inner catheter and said second handle for injecting a fluid into said lumen of said outer catheter.

Optionally, said proximal spherical component is configured to be atraumatic and includes a radiopaque marker for radiographic visualization during delivery and said distal spherical component is configured in an atraumatic ball-tip shape.

Optionally, said variable stiffness of said pilot component is less than a stiffness of said distal end of said outer catheter at its proximal end and similar to a stiffness of a 0.035 inch guide wire at its distal end.

Optionally, said first and second stopping mechanisms comprise plastic rings secured to said inner catheter using wing nuts.

The present specification also discloses a method of delivering a gastrointestinal device, using a delivery device, into a gastrointestinal tract of a patient, said gastrointestinal device comprising a porous structure configurable between a compressed pre-deployment configuration and an expanded post-deployment configuration, an anti-migration collar proximate a distal end of said porous structure, and an elongate sleeve coupled to a distal end of said porous structure, said delivery device comprising a flexible outer catheter having a proximal end, a distal end, and a lumen; a flexible inner catheter having a proximal end, a distal end, and a lumen configured to slidably receive a guide wire, wherein said flexible inner catheter is positioned coaxially, and is adapted to be slidably movable, within the lumen of said outer catheter; a first handle attached to the proximal end of said inner catheter and having a proximal end, a distal end, and a lumen configured to slidably receive said guide wire; a second handle attached to the proximal end of said outer catheter and having a proximal end, a distal end, and a lumen configured to slidably receive said inner catheter, a first stopping mechanism removably attached to an exposed portion of said inner catheter; and a second stopping mechanism removably attached to said exposed portion of said inner catheter and positioned proximal to said first stopping mechanism, said method comprising the steps of: sliding said delivery device over a guide wire and into said gastrointestinal tract of said patient; using fluoroscopy to determine a location of said distal end of said flexible outer catheter to ensure a correct positioning of said delivery device; holding said first handle to keep said inner catheter in place and retracting said outer catheter to said first stopping mechanism; retracting the entire delivery device until said distal end of said outer catheter is positioned just proximal to a pylorus of the patient; removing said first stopping mechanism from said inner catheter; holding said first handle to keep said inner catheter in place and retracting said outer catheter to said second stopping mechanism; removing said second stopping mechanism; holding said first handle to keep said inner catheter in place and retracting said outer catheter to said first handle; and removing said delivery device from said patient.

Optionally, when said outer catheter is retracted to said first stopping mechanism, a portion of said sleeve is delivered to, and positioned within, an intestinal portion of said patient's gastrointestinal tract.

Optionally, when said outer catheter is retracted to said second stopping mechanism, a portion of said sleeve and a portion of said porous structure are delivered to, and positioned within, a stomach portion of said patient's gastrointestinal tract.

Optionally, when said outer catheter is retracted to said first handle, all of said porous structure is delivered to, and positioned within, a stomach portion of said patient's gastrointestinal tract.

Optionally, the anti-migration collar of the gastrointestinal device is proximally sloping wherein a distal portion of the porous structure is folded such that the distally directed end of the porous structure is made to point toward the proximal end of the porous structure. Optionally, the anti-migration collar is any curved/atraumatic structure positioned circumferentially around the distal end of the porous structure.

Prior to delivery of said gastrointestinal device, a proximal portion of said inner catheter positioned between said first and second handles may be exposed and not covered by said outer catheter.

Optionally, said delivery device further comprises an elongate flexible pilot component having a distal spherical component and a proximal spherical component and extending from said distal end of said inner catheter.

At least one of said pilot component and said distal end of said outer catheter may include a hydrophilic coating and said method may further comprise activating said hydrophilic coating before sliding said delivery device over said guide wire.

The present specification also discloses a delivery system for delivering a gastrointestinal device into a gastrointestinal tract of a patient, said system comprising: a gastrointestinal device comprising: a porous structure configurable between a compressed pre-deployment configuration and an expanded post-deployment configuration; an anti-migration collar proximate a distal end of said porous structure; and an elongate sleeve coupled to a distal end of said porous structure; a delivery device comprising: a flexible outer catheter having a proximal end, a distal end, and a lumen; a flexible inner catheter having a proximal end, a distal end, and a lumen configured to slidably receive a guide wire, wherein said inner catheter is positioned coaxially and is adapted to be slidably movable within the lumen of said outer catheter; a first handle attached to the proximal end of said inner catheter and having a proximal end, a distal end, and a lumen configured to slidably receive said guide wire; a second handle attached to the proximal end of said outer catheter and having a proximal end, a distal end, and a lumen configured to slidably receive said inner catheter, wherein a proximal portion of said inner catheter positioned between said first and second handles is not covered in its entirety by said outer catheter; an elongate flexible component comprising a distal spherical component and a proximal spherical component and extending from said distal end of said inner catheter; a first stopping mechanism removably attached to said exposed portion of said inner catheter; a second stopping mechanism removably attached to said exposed portion of said inner catheter and positioned proximal to said first stopping mechanism; wherein said distal end of said inner catheter is adapted to be passed through openings of said porous structure, wherein said sleeve is wrapped coaxially about said inner catheter, wherein said outer catheter may be retracted in a proximal direction over said inner catheter while maintaining said inner catheter in place, and wherein said first and second stopping mechanisms are adapted to be sequentially removed from said inner catheter as said outer catheter is retracted to expose and deliver the gastrointestinal device from said distal end of said delivery device.

The delivery system may further comprise a hydrophilic coating over at least one of said elongate flexible component and said distal end of said outer catheter, wherein, when said hydrophilic coating is activated, the hydrophilic coating eases insertion and navigation of said delivery device.

The delivery system of claim may further comprise a port on at least one of said first handle for injecting a fluid into said lumen of said inner catheter and said second handle for injecting a fluid into said lumen of said outer catheter.

Optionally, said delivery devise has a variable stiffness along its length.

Optionally, the anti-migration collar of the gastrointestinal device is proximally sloping wherein a distal portion of the porous structure is folded such that the distally directed end of the porous structure is made to point toward the proximal end of the porous structure. Optionally, the anti-migration collar is any curved/atraumatic structure positioned circumferentially around the distal end of the porous structure.

The present specification also discloses a delivery device for endoscopically delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising: an elongate body having a proximal end and a distal end; and, a restraining mechanism for constricting said device in said pre-deployment configuration coaxially over said distal end of said elongate body.

In one embodiment, the delivery device further comprises a locking mechanism for locking said delivery device in a specific position.

In one embodiment, said distal end comprises a most distal portion and a proximal distal portion, wherein said most distal portion is more flexible than said proximal distal portion.

In one embodiment, the delivery device further comprises a thread pull port on said proximal end, wherein said restraining mechanism comprises a thread wrapped about said device in said pre-deployment configuration.

In one embodiment, said restraining mechanism comprises a zipped sheath coaxially covering said device in said pre-deployment configuration. In another embodiment, said restraining mechanism comprises a pull away sheath coaxially covering said device in said pre-deployment configuration. In another embodiment, said restraining mechanism comprises a tear away sheath coaxially covering said device in said pre-deployment configuration.

The delivery device may comprise an elongate body having a proximal end, a distal end, and a pull away sheath for coaxially sliding over said intragastric device for constricting said intragastric device in said pre-deployment configuration coaxially over said distal end of said body of said delivery device, and a method of delivering said intragastric device may comprise the steps of: coaxially placing said constricted intragastric device in said pre-deployment configuration over said distal end of said body of said delivery device; endoscopically inserting said delivery device into a patient and advancing said distal end of said body of said delivery device to a duodenum or jejunum of said patient; once intragastric device is positioned, using a working tool to pull said sheath coaxially away to remove said sheath from said constricted intragastric device, allowing said intragastric device to automatically expand into said post-deployment configuration; and, sliding said distal end of said body of said delivery device coaxially away from said expanded intragastric device and removing said delivery device from said patient.

Optionally, the method further comprises the step of applying a cooling element to said compressed intragastric device to slow the expansion of said porous structure during removal of said sheath, facilitating the removal of said delivery device.

The present specification also discloses a retrieval device for endoscopically removing an intragastric device from a gastrointestinal tract of a patient, said intragastric device comprising a porous structure configurable between a compressed pre-deployment configuration and an expanded post-deployment configuration and including at least one circumferential constricting mechanism positioned about said porous structure and a retrieval mechanism at its proximal end and, an elongate sleeve coupled to a distal end of said porous structure, said retrieval device comprising: an elongate body having a proximal end and a distal end and a lumen within; an elongate metal wire disposed within said lumen and having a proximal end and a distal end; a grasping mechanism formed from said distal end of said wire for grasping a free end of said at least one circumferential constricting mechanism and said retrieval mechanism of said porous structure; and, an actuator attached to said proximal end of said wire.

Optionally, the retrieval device further comprises a handle at said proximal end of said elongate body.

Optionally, said actuator rests in said handle.

In one embodiment, the retrieval device further comprises a grasper having two opposing jaws attached to said distal end of said elongate body and operatively connected to said actuator at said proximal end of said wire and at least one clamp positioned between said jaws of said grasper wherein said jaws are configured to compress said clamp about said free end of said at least one circumferential constricting mechanism.

The present specification also discloses a method of delivering an intragastric device into the gastrointestinal tract of a patient using a delivery device, wherein said intragastric device comprises a porous structure configurable between a compressed pre-deployment configuration and an expanded post-deployment configuration and an elongate sleeve coupled to a distal end of said porous structure, said method comprising the steps of: deploying said porous structure without said sleeve and allowing said porous structure to expand into said post-deployment configuration in a first procedure; deploying said sleeve within said expanded porous structure in a second procedure; and coupling a proximal end of said sleeve to a distal end of said porous structure during said second procedure.

Optionally, the method further comprises the step of applying a cooling element to said compressed intragastric device during said first procedure to slow the expansion of said porous structure during deployment.

Optionally, said first procedure is performed using a first catheter.

Optionally, said second procedure is performed using a second catheter.

The present specification also discloses a method of retrieving a device from a gastrointestinal tract of a patient using a retrieval device, wherein said device comprises a porous structure configurable between a compressed pre-deployment configuration and an expanded post-deployment configuration and includes at least one circumferential constricting mechanism positioned about said porous structure and a retrieval mechanism at its proximal end and, an elongate sleeve coupled to a distal end of said porous structure, and said retrieval device comprises an elongate body having a proximal end and a distal end and a lumen within, an elongate metal wire disposed within said lumen and having a proximal end and a distal end, a grasping mechanism formed from said distal end of said wire for grasping a free end of said at least one circumferential constricting mechanism and said retrieval mechanism of said porous structure, and an actuator attached to said proximal end of said wire, said method comprising the steps of: endoscopically inserting said retrieval device into said patient and advancing said distal end of said body of said retrieval device to a proximal end of said device; manipulating said grasping mechanism of said retrieval device to engage a free end of said at least one circumferential constricting mechanism positioned about said porous structure; pulling on said actuator of said retrieval device to constrict and automatically lock said at least one circumferential constricting mechanism, thereby compressing said porous structure into said pre-deployment shape; manipulating said grasping mechanism of said retrieval device to disengage said free end of said at least one circumferential constricting mechanism; manipulating said grasping mechanism to engage said retrieval mechanism at said proximal end of said porous structure; pulling said actuator to withdraw a proximal portion of said device into said lumen of said retrieval device; and, removing said retrieval device and said device from said patient.

The intragastric device may include three circumferential constricting mechanisms positioned about said porous structure and said method may further comprise the steps of: sequentially manipulating said grasping mechanism of said retrieval device to engage a free end of each of said three circumferential constricting mechanisms; and pulling on said actuator of said retrieval device to constrict and automatically lock each of said three circumferential constricting mechanisms, thereby fully compressing said porous structure into said pre-deployment shape.

In one embodiment, the method further comprises the step of applying a cooling element to said compressed device to prevent the re-expansion of said porous structure during removal of said retrieval device and said device.

The retrieval device may further comprise a grasper having two opposing jaws attached to said distal end of said elongate body and operatively connected to said actuator at said proximal end of said wire, and at least one clamp positioned between said jaws of said grasper, and said method may further comprise the step of manipulating said grasper of said retrieval device to apply said at least one clamp to said free end of said at least one circumferential constricting mechanism proximate said compressed porous structure.

The present specification also discloses a retrieval device for endoscopically removing an intragastric device from a gastrointestinal tract of a patient, said intragastric device comprising a porous structure configurable between a compressed pre-deployment configuration and an expanded post-deployment configuration and including an elongate sleeve coupled to a distal end of said porous structure, said retrieval device comprising: a flexible catheter having a proximal end, a distal end, and a lumen within; an elongate wire positioned within said lumen of said catheter and having a proximal end and a distal end wherein a portion of said distal end of said wire is formed into a grasping mechanism; a handle positioned at said proximal end of said catheter; and an elongate tube having a proximal end, a distal end, and a first lumen within wherein said tube is positioned coaxially over said catheter, wherein said grasping mechanism is configured to grasp said porous structure and said elongate tube is configured to receive said porous structure at its distal end.

The handle may comprise first and second handle components wherein said first and second handle components are disassembled to allow for sliding of said elongate tube onto or off of said catheter. Optionally, said first and second handle components are assembled and held together using a screw.

The elongate tube may further comprise an adapter at its proximal end wherein said adapter is configured to attach to said second handle component.

Optionally, the elongate tube further comprises: an inflatable balloon positioned at said distal end of said elongate tube; an insufflation port positioned at said proximal end of said elongate tube; a separate, second lumen in fluid communication with said inflatable balloon and said insufflation port; and a compartment positioned at said distal end of said elongate tube configured to contain said balloon when said balloon is deflated, wherein said balloon is inflatable via said insufflation port and said second lumen and said balloon, when inflated, is used to assist in compression of said porous structure into its pre-deployment configuration.

Optionally, the elongate tube further comprises an instillation port at its proximal end for instillation of a cold fluid into said first lumen of said elongate tube wherein said porous structure is comprised of a temperature sensitive material and said cold fluid is used to assist in compression of said porous structure into its pre-deployment configuration.

The catheter further may comprise a sheath for restraining said grasping mechanism. Optionally, the grasping mechanism comprises a hook.

The present specification also discloses a method of retrieving an intragastric device from a gastrointestinal tract of a patient using a retrieval device, wherein said intragastric device comprises a porous structure configurable between a compressed pre-deployment configuration and an expanded post-deployment configuration and includes an elongate sleeve coupled to a distal end of said porous structure and said retrieval device comprises a flexible catheter having a proximal end, a distal end, and a lumen within, an elongate wire positioned within said lumen of said catheter and having a proximal end and a distal end wherein a portion of said distal end of said wire is formed into a grasping mechanism, a handle positioned at said proximal end of said catheter, and an elongate tube having a proximal end, a distal end, and a first lumen within wherein said tube is positioned coaxially over said catheter, said method comprising the steps of: inserting said catheter into a working channel of an endoscope that has been inserted into said patient; positioning a distal end of said endoscope proximate in a stomach of said patient, proximate said intragastric device; manipulating said elongate wire to extend said grasping mechanism beyond said distal end of said catheter and grasping said porous structure with said grasping mechanism; removing said handle from said catheter; sliding said elongate tube over said catheter; replacing said handle; pulling on said elongate wire to pull said porous structure into said elongate tube; and removing said retrieval device, with said intragastric device therein, from said patient.

The elongate tube may further comprise an inflatable balloon positioned at said distal end of said elongate tube, an insufflation port positioned at said proximal end of said elongate tube, a separate, second lumen in fluid communication with said inflatable balloon and said insufflation port, and a compartment positioned at said distal end of said elongate tube configured to contain said balloon when said balloon is deflated, and said method may further comprises the step of inflating said balloon via said insufflation port and said second lumen, wherein said inflated balloon extends from said compartment and is used to assist in compression of said porous structure into its pre-deployment configuration.

Optionally, the elongate tube further comprises an instillation port at its proximal end for instillation of a cold fluid into said first lumen of said elongate tube wherein said porous structure is comprised of a temperature sensitive material, said method further comprising the step of instilling a cold fluid into said first lumen to assist in compression of said porous structure into its pre-deployment configuration.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh; and a collar positioned at said bottom of said porous structure, said collar having a bend wherein said bend comprises an extension of said wire curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening.

Optionally, said proximal end of said sleeve is coupled to said collar.

Each of said plurality of nodes may comprise 10 to 100 individual nodes. Optionally, each of said plurality of nodes comprises 44 nodes. Optionally, each of said plurality of nodes comprises 36 nodes.

The porous structure has a length and said porous structure may include 2 to 60 pluralities of nodes distributed latitudinally at different locations along said length. At least 10% of the total number of nodes in said porous structure may be positioned at said top and said bottom. Optionally, no more than 75% of a total number of nodes are positioned in any one of said plurality of nodes.

The wire mesh may be composed of a shape memory metal.

The wire has a wire thickness and said bend of said collar has a bend radius wherein said bend, when said collar is folded in a distal direction as said porous structure is compressed to said pre-deployment shape, may be defined by a bending strain percentage equal to two times said thickness divided by said radius multiplied by 100. Optionally, the bending strain percentage is in a range of 0.1 to 20%. Optionally, the bending strain percentage is no more than 8%.

Optionally, said thickness is in a range of 0.1 to 1 mm. Optionally, said bend radius is in a range of 0.013 to 20 cm.

The thickness and bend radius may be configured such that two times said thickness is less than said radius which is less than 2000 times said thickness.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh; and a collar positioned at said bottom of said porous structure, said collar having a bend wherein said bend comprises an extension of said wire curving in a direction away from a longitudinal center axis of said porous structure and then in a direction upward toward said top of said porous structure and wherein said wire has a wire thickness and said bend of said collar has a bend radius and wherein said bend, when said collar is folded in a distal direction as said porous structure is compressed to said pre-deployment shape, is defined by a bending strain percentage equal to two times said thickness divided by said radius multiplied by 100, further wherein said bending strain percentage is in a range of 0.1 to 20%; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening.

Optionally, said bending strain percentage is no more than 8%. Optionally, said thickness is in a range of 0.1 to 1 mm. Optionally, said bend radius is in a range of 0.013 to 20 cm.

The thickness and bend radius may be configured such that two times said thickness is less than said radius which is less than 2000 times said thickness.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh and wherein each plurality of nodes includes no more than 44 individual nodes; and a collar positioned at said bottom of said porous structure, said collar having a bend wherein said bend comprises an extension of said wire curving in a direction away from a longitudinal center axis of said porous structure and then in a direction upward toward said top of said porous structure and wherein said wire has a wire thickness and said bend of said collar has a bend radius and wherein said bend, when said collar is folded in a distal direction as said porous structure is compressed to said pre-deployment shape, is defined by a bending strain percentage equal to two times said thickness divided by said radius multiplied by 100, further wherein said bending strain percentage is in a range of 0.1 to 20%; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve further comprises at least one helical wire extending along said elongate body configured to provide support to said sleeve when in said post-deployment shape and wherein said helical wire has a strain percentage defined by a thickness of said wire and a pitch of said wire, further wherein said pitch is defined by the distance between any two points along said wire lying within the same plane along a longitudinal axis of said sleeve.

The helical wire may be composed of a shape memory metal. Optionally, the shape memory metal is Nitinol.

The helical wire, when compressed as the sleeve is compressed and folded to its pre-deployment shape, may have a strain percentage in a range of 0.1 to 20%. Optionally, the helical wire, when compressed as the sleeve is compressed and folded to its pre-deployment shape, has a strain percentage of no more than 8%. The pitch may have a range of 5 to 150 mm. Optionally, the pitch is equal to 60 mm.

The sleeve may have a length in a range of 1 cm-120 cm and may be configured to pass atraumatically into and out of a pylorus of a patient.

The sleeve may be substantially funnel shaped and have a diameter which decreases as said sleeve extends from said proximal end to said distal end.

Optionally, a proximal portion of said sleeve is funnel shaped wherein said proximal end of said sleeve has a diameter greater than a diameter along any other portion of said sleeve body and said proximal end diameter decreases gradually as said sleeve body extends distally.

Optionally, a distal portion of said sleeve body includes two or more layers configured to reinforce said distal portion and maintain said sleeve body in an elongate shape when in said post-deployment shape.

Optionally, the sleeve comprises a proximal portion and a distal portion wherein said proximal portion extends from said proximal end of said sleeve to a transition point on said sleeve body and said distal portion extends from said transition point to said distal end of said sleeve, further wherein said proximal portion is funnel shaped and has a diameter that decreases as said proximal portion extends from said proximal end of said sleeve to said transition point. Still optionally, said distal portion is funnel shaped and has a diameter that decreases as said distal portion extends from said transition point to said distal end of said sleeve. Alternatively, said distal portion is cylinder shaped and has a diameter that remains constant as said distal portion extends from said transition point to said distal end of said sleeve. Optionally, the diameter of said distal portion increases as said distal portion extends from said transition point to said distal end of said sleeve.

The sleeve may be comprised of at least one layer of any one or combination of polytetrafluoroethylene (PTFE), polyethylene (PE), low-density polyethylene (LDPE), high-density polyethylene (HDPE), and ultra-high-molecular-weight polyethylene (UHMWPE). Optionally, the sleeve comprises at least two layers of any one or combination of polytetrafluoroethylene (PTFE), polyethylene (PE), low-density polyethylene (LDPE), high-density polyethylene (HDPE), and ultra-high-molecular-weight polyethylene (UHMWPE) and further comprising at least one metal wire support positioned between said layers.

Optionally, the intragastric device further comprises a component attached to said distal end of said sleeve and configured to make said distal end atraumatic to body tissues, wherein said component comprises a cylindrical body, a proximal end, a distal end, and a lumen within and wherein said component is open at both ends and said lumen of said component is in fluid communication with said sleeve interior, further wherein an outer surface of said component includes a groove and a circular member positioned within said groove and said component is attached to said sleeve by positioning a portion of said sleeve within said groove and beneath said circular member.

Optionally, said component further includes a flange extending from said outer surface wherein said flange covers a free end of said distal end of said sleeve.

Alternatively, said component further includes a heat shrink tube positioned over said circular member and groove. Still optionally, distal end of said sleeve is folded beneath said circular member such that a free end of said distal end of said sleeve becomes positioned within said sleeve interior.

Optionally, the intragastric device further comprises at least one tail extending from said distal end of said sleeve wherein said tail is configured to pull on said sleeve in a distal direction to assist in proper orientation of said sleeve within a patient's gastrointestinal tract.

The distal portion of said sleeve may comprise a plurality of sleeve fringes wherein said fringes are attached to a member at said distal end of said sleeve, further wherein said member is configured to pull on said sleeve in a distal direction to assist in proper orientation of said sleeve within a patient's gastrointestinal tract. Optionally, the fringes and distal member are parachute shaped.

The distal end of said sleeve may include a plurality of sutures each having a proximal end and a distal end wherein said proximal ends of said sutures are attached to said distal end of said sleeve and said distal end of said sutures are attached to a member configured to pull on said sleeve in a distal direction to assist in proper orientation of said sleeve within a patient's gastrointestinal tract. Optionally, the fringes and distal member are parachute shaped.

The distal end of said sleeve may include a plurality of sutures each having a proximal end and a distal end and wherein said proximal ends of said sutures are attached to said distal end of said sleeve and said distal end of said sutures are each attached to an individual member wherein each individual member is configured to pull on said sleeve in a distal direction to assist in proper orientation of said sleeve within a patient's gastrointestinal tract.

Optionally, said sleeve is folded about itself at least once along a longitudinal axis of said sleeve to provide said sleeve with added structure.

The sleeve may include at least one channel extending along a longitudinal axis of said sleeve wherein said at least one channel receives a support member to provide said sleeve with added structure.

At least a portion of said sleeve may have a corrugated structure comprised of alternating grooves and ridges to provide said sleeve with added structure.

At least a portion of said sleeve may comprise a flexible wire configured into a knitted structure to provide said sleeve with added structure.

The sleeve may include at least one channel extending along a longitudinal axis of said sleeve wherein said at least one channel in configured to receive a fluid to provide said sleeve with added structure.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve further comprises three helical wires extending along said elongate body configured to provide support to said sleeve when in said post-deployment shape and wherein each of said helical wires has an individual strain percentage defined by a thickness of said individual wire and an individual pitch of said individual wire, further wherein said individual pitch is defined by the distance between any two points along said individual wire lying within the same plane along a longitudinal axis of said sleeve.

Each of said helical wires may be composed of a shape memory metal. Optionally, the shape memory metal is Nitinol.

Each of said helical wires, when compressed as the sleeve is compressed and folded to its pre-deployment shape, may have an individual strain percentage in a range of 0.1 to 20%. Optionally, each of said helical wires, when compressed as sleeve is compressed and folded to its pre-deployment shape, has an individual strain percentage of no more than 8%.

The individual pitch of each of said helical wires may have a range of 5 to 150 mm. Optionally, the individual pitch of each of said helical wires is equal to 60 mm.

Optionally, each of said wires includes an adjacent wire pitch defined as the distance between any two points along two adjacent wires lying within the same plane along a longitudinal axis of said sleeve wherein said adjacent wire pitch is equal to 20 mm.

Optionally, a proximal portion of said sleeve is funnel shaped wherein said proximal end of said sleeve has a diameter greater than a diameter along any other portion of said sleeve body and said proximal end diameter decreases gradually as said sleeve body extends distally.

Optionally, a distal portion of said sleeve body includes two or more layers configured to reinforce said distal portion and maintain said sleeve body in an elongate shape when in said post-deployment shape.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve further comprises at least one helical wire extending along said elongate body configured to provide support to said sleeve when in said post-deployment shape and wherein said helical wire has a strain percentage defined by a thickness of said wire and a pitch of said wire wherein said sleeve is foldable upon itself at least five times such that said strain percentage will not exceed 20%, further wherein said pitch is defined by the distance between any two points along said wire lying within the same plane along a longitudinal axis of said sleeve.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh; and a collar positioned at said bottom of said porous structure, said collar having a bend wherein said bend comprises an extension of said wire curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening, wherein at least a portion of a total number of nodes in said second plurality of nodes is coupled to said proximal end of said sleeve by sutures.

Each node of said portion of said total number of nodes in said second plurality of nodes may be sutured to said proximal end of said sleeve at a most distal position on each node. Optionally, the portion of said total number of nodes in said second plurality of nodes comprises all of said nodes within said second plurality of nodes. Optionally, the portion of said total number of nodes in said second plurality of nodes comprises every other node within said second plurality of nodes.

The sutures may be applied loosely to allow for some relative movement between said wire mesh and said sleeve.

Each suture coupling said sleeve to each of said nodes of said portion of said total number of nodes in said second plurality of nodes may comprise only one knot.

The wire of said wire mesh may include at least two ends wherein said ends are joined and crimped together using a metal tube.

The wire of said wire mesh may include at least two ends wherein said ends are looped back onto said wire to create atraumatic wire ends or looped outward to create attachment points to said sleeve.

The sleeve may include a wire for support and said wire may include at least two ends wherein said ends are looped back onto said wire to create atraumatic wire ends, looped outward to create attachment points for coupling to said wire mesh or are used to pull on said sleeve during compression of said device.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh; and a collar positioned at said bottom of said porous structure, said collar having a bend wherein said bend comprises an extension of said wire curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening, wherein a portion of said wire proximal to each node crosses with another portion of wire proximal an adjacent node to create an intersection and wherein at least a portion of a total number of said intersections at said bottom of said porous structure is coupled to said proximal end of said sleeve by sutures.

Optionally, the portion of said total number of said intersections at said bottom of said porous structure comprises all of said intersections proximate said bottom of said porous structure. Optionally, the portion of said total number of said intersections at said bottom of said porous structure comprises every other intersection proximate said bottom of said porous structure.

The sutures may be applied loosely to allow for some relative movement between said wire mesh and said sleeve.

Each suture coupling said sleeve to each of said intersections of said portion of said total number of intersections proximate said bottom of said porous structure may comprise only one knot.

The wire of said wire mesh may include at least two ends wherein said ends are joined and crimped together using a metal tube.

The wire of said wire mesh may include at least two ends wherein said ends are looped back onto said wire to create atraumatic wire ends or looped outward to create attachment points to said sleeve.

The sleeve may include a wire for support and said wire may include at least two ends wherein said ends are looped back onto said wire to create atraumatic wire ends, looped outward to create attachment points for coupling to said wire mesh or are used to pull on said sleeve during compression of said device.

The present specification also discloses a method for compressing an intragastric device for loading onto a delivery device prior to deployment, said intragastric device comprising a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises a wire mesh having a substantially spherical post-deployment shape and including at least a first plurality of nodes at said top, a second plurality of nodes at said bottom, and a third plurality of nodes positioned at a lateral location between said top and said bottom, wherein each node comprises a single unsupported free end or bend in a wire of said wire mesh; and a collar positioned at said bottom of said porous structure, said collar having a bend wherein said bend comprises an extension of said wire curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said second plurality of nodes of said porous structure such that food exiting said at least one second opening enters said sleeve through said third opening, passes through said sleeve interior, and exits said sleeve through said fourth opening, wherein at least a portion of a total number of nodes in said second plurality of nodes is coupled to said proximal end of said sleeve by sutures, said method comprising the steps of: compressing said wire mesh about a longitudinal center axis of said porous structure; and pulling on said distal end of said sleeve, causing said bend of said collar to curve in a downward direction such that said collar becomes substantially straightened.

The sutures may be applied loosely to allow for some relative movement between said wire mesh and said sleeve.

The sleeve may include a wire for support and said wire may include at least two ends wherein said ends are looped back onto said wire to create atraumatic wire ends, looped outward to create attachment points for coupling to said wire mesh or are used to pull on said sleeve during compression of said device.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening; and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve has a coefficient of friction which allows said sleeve to at least be folded upon itself, wrapped about a portion of a deployment device, pulled back and forth during deployment, and deployed fully without any structural damage to said sleeve.

The coefficient of friction may be in a range of 0.01-0.45. Optionally, the coefficient of friction is equal to or less than 0.10.

The sleeve has an outer surface and wherein said outer surface may be a matte surface. A particulate matter may be applied to an outer surface of said sleeve. Optionally, the particulate matter is corn starch. Optionally, the particulate matter is a biocompatible powder.

The sleeve may be folded upon itself at least 2 times.

The present specification also discloses a method of delivering an intragastric device in a gastrointestinal tract of a patient, said intragastric device comprising a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve has a coefficient of friction which allows said sleeve to at least be folded upon itself, wrapped about a portion of a deployment device, pulled back and forth during deployment, and deployed fully without any structural damage to said sleeve, said method comprising the steps of: loading said porous structure onto a delivery device; folding said sleeve upon itself; wrapping said folded sleeve about a portion of said delivery device; inserting said delivery device, including said porous structure and said sleeve, into said gastrointestinal tract of said patient; manipulating said delivery device to fully deploy said sleeve; further manipulating said delivery device to fully deploy said porous structure; and removing said delivery device from said patient.

The coefficient of friction may be in a range of 0.01-0.45.

The method may further comprise the step of applying a particulate matter to an outer surface of said sleeve prior to folding said sleeve upon itself. Optionally, the particulate matter is corn starch. Optionally, the particulate matter is a biocompatible powder.

The sleeve may be folded upon itself at least 2 times.

The present specification also discloses a method of delivering an intragastric device in a gastrointestinal tract of a patient, said intragastric device comprising a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening and a sleeve having a flexible elongate body, a proximal end with a third opening, a distal end with a fourth opening, and a sleeve interior, and having a pre-deployment shape with a first length and a post-deployment shape with a second length greater than said first length, wherein said proximal end of said sleeve is coupled to said bottom of said porous structure such that, when sleeve is in said post-deployment shape, food exiting said at least one second opening enters said sleeve through said third opening, passes through said sleeve interior, and exits said sleeve through said fourth opening, wherein said sleeve has a coefficient of friction which allows said sleeve to at least be folded upon itself, wrapped about a portion of a deployment device, pulled back and forth during deployment, and deployed fully without any structural damage to said sleeve, said method comprising the steps of: loading said porous structure onto a delivery device; folding said sleeve upon itself; wrapping said folded sleeve about a portion of said delivery device; inserting said delivery device, including said porous structure and said sleeve, into said gastrointestinal tract of said patient; manipulating said delivery device to partially deploy said sleeve, wherein said sleeve is released fully from said delivery device but only partially unfurls from said folding; further manipulating said delivery device to fully deploy said porous structure; removing said delivery device from said patient; and allowing said sleeve to fully unfurl through the actions of peristaltic intestinal contractions upon said sleeve.

The coefficient of friction may be in a range of 0.01-0.45.

The method may further comprise the step of applying a particulate matter to an outer surface of said sleeve prior to folding said sleeve upon itself. Optionally, the particulate matter is corn starch. Optionally, the particulate matter is a biocompatible powder.

The sleeve may be folded upon itself at least 2 times.

The present specification also discloses a delivery device for delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising: a flexible elongate body with a proximal end, a distal end, and a body lumen within, said body comprising an opening at said distal end and a first handle attached to said proximal end; a flexible plunger component positioned coaxially, and movable longitudinally, within the lumen of said body, said plunger including a proximal end, a distal end, and a plunger lumen within and comprising a tip at said distal end and a second handle attached to said proximal end; a flexible elongate rod positioned coaxially, and movable longitudinally, within said plunger lumen, said rod including a proximal end and a distal end and comprising a first spherical component positioned proximal to said distal end and a second spherical component positioned at said distal end wherein said first spherical component has a diameter greater than a diameter of said second spherical component, said rod further comprising a third handle attached to said proximal end; and a pulling mechanism comprising a first end and a second end wherein said first end is attached to said sleeve of said intragastric device and said second end is removably coupled to said rod at a position between said first spherical component and said second spherical component, wherein said intragastric device is loaded for delivery within said delivery device such that: said porous structure is positioned within said body lumen distal to said plunger tip and proximal to said sleeve and wherein said rod passes through at least two openings in said porous structure and wherein said at least two openings do not lie along a center longitudinal axis of said porous structure; said sleeve is positioned within said body lumen distal to said porous structure and proximal to said first spherical component and wherein said sleeve is folded upon itself and then wrapped about a portion of said rod, further wherein said sleeve is attached to said first end of said pulling mechanism.

The delivery device may further comprise a stopper positioned on said plunger between said tip and said second handle.

Optionally, the said pulling mechanism is biodegradable and comprises a suture or a hook. Alternatively, said pulling mechanism is non-biodegradable and comprises a suture with a loop end.

Optionally, the said sleeve is constrained by a ring, cone, or umbrella shaped constraining device.

Optionally, said tip of said plunger includes a mesh retention component comprising a plurality of fins wherein a proximal portion of said porous structure is positioned over said fins such that said fins cause said porous structure to move in a proximal direction when said plunger is moved in a proximal direction.

The sleeve may be folded upon itself two to ten times before being wrapped about said rod.

The delivery device may further comprise an inflatable balloon at said distal end of said body, an input port at said proximal end of said body, and a channel extending along said elongate body and in fluid communication with said balloon and said port, wherein said balloon is inflated using said port and said channel and said inflated balloon is used to anchor said delivery device within said gastrointestinal tract of said patient.

Optionally, the delivery device further comprises a flushing or irrigation mechanism to reduce deployment forces during delivery.

The elongate body includes a length and said length may include a variable stiffness. Optionally, the length includes at least three zones and a most distal zone is more flexible than a center distal zone, which is more flexible than a least distal zone.

The elongate body may comprise a braided catheter.

The distal ends of the elongate body, plunger, and rod may be configured to be atraumatic.

The present specification also discloses a delivery device for delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising: a flexible elongate body with a proximal end, a distal end, and a body lumen within, said body comprising an opening at said distal end and an actuating mechanism attached to said proximal end; a flexible plunger component positioned coaxially, and movable longitudinally, within the lumen of said body, said plunger including a proximal end, a distal end, and a plunger lumen within and comprising a tip at said distal end and wherein said proximal end is operatively attached to said actuating mechanism; an actuator handle and an actuator trigger attached to said actuating mechanism and configured, when operated, to cause said actuating mechanism to move said plunger back and forth in a longitudinal direction relative to said elongate body; a flexible elongate rod positioned coaxially, and movable longitudinally, within said plunger lumen, said rod including a proximal end and a distal end and comprising a first spherical component positioned proximal to said distal end and a second spherical component positioned at said distal end wherein said first spherical component has a diameter greater than a diameter of said second spherical component, said rod further comprising a rod handle attached to said proximal end; and a pulling mechanism comprising a first end and a second end wherein said first end is attached to said sleeve of said intragastric device and said second end is removably coupled to said rod at a position between said first spherical component and said second spherical component, wherein said intragastric device is loaded for delivery within said delivery device such that: said porous structure is positioned within said body lumen distal to said plunger tip and proximal to said sleeve and wherein said rod passes through at least two openings in said porous structure and wherein said at least two openings do not lie along a center longitudinal axis of said porous structure; said sleeve is positioned within said body lumen distal to said porous structure and proximal to said first spherical component and wherein said sleeve is folded upon itself and then wrapped about a portion of said rod, further wherein said sleeve is attached to said first end of said pulling mechanism.

The delivery device may further comprise a stopper positioned on said plunger between said tip and said actuating mechanism.

Optionally, the pulling mechanism is biodegradable and comprises a suture or a hook. Alternatively, said pulling mechanism is non-biodegradable and comprises a suture with a loop end.

Optionally, the sleeve is constrained by a ring, cone, or umbrella shaped constraining device.

Optionally, said tip of said plunger includes a mesh retention component comprising a plurality of fins wherein a proximal portion of said porous structure is positioned over said fins such that said fins cause said porous structure to move in a proximal direction when said plunger is moved in a proximal direction.

The sleeve may be folded upon itself two to ten times before being wrapped about said rod.

The delivery device may further comprise an inflatable balloon at said distal end of said body, an input port at said proximal end of said body, and a channel extending along said elongate body and in fluid communication with said balloon and said port, wherein said balloon is inflated using said port and said channel and said inflated balloon is used to anchor said delivery device within said gastrointestinal tract of said patient.

Optionally, the delivery device further comprises a flushing or irrigation mechanism to reduce deployment forces during delivery.

The elongate body may comprise a braided catheter.

The present specification also discloses a method of delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising a flexible elongate body with a proximal end, a distal end, and a body lumen within, said body comprising an opening at said distal end and a first handle attached to said proximal end, a flexible plunger component positioned coaxially, and movable longitudinally, within the lumen of said body, said plunger including a proximal end, a distal end, and a plunger lumen within and comprising a tip at said distal end and a second handle attached to said proximal end, a flexible elongate rod positioned coaxially, and movable longitudinally, within said plunger lumen, said rod including a proximal end and a distal end and comprising a first spherical component positioned proximal to said distal end and a second spherical component positioned at said distal end wherein said first spherical component has a diameter greater than a diameter of said second spherical component, said rod further comprising a third handle attached to said proximal end, and a pulling mechanism comprising a first end and a second end wherein said first end is attached to said sleeve of said intragastric device and said second end is removably coupled to said rod at a position between said first spherical component and said second spherical component, wherein said intragastric device is loaded for delivery within said delivery device such that said porous structure is positioned within said body lumen distal to said plunger tip and proximal to said sleeve and wherein said rod passes through at least two openings in said porous structure and wherein said at least two openings do not lie along a center longitudinal axis of said porous structure said sleeve is positioned within said body lumen distal to said porous structure and proximal to said first spherical component and wherein said sleeve is folded upon itself and then wrapped about a portion of said rod, further wherein said sleeve is attached to said first end of said pulling mechanism, said method comprising the steps of: sliding said delivery device over a guidewire into said gastrointestinal tract of said patient; using the first handle, positioning the distal end of said elongate body in a duodenum of the patient; pushing the second handle to push in the plunger component until the sleeve is pushed out of said elongate body; pushing the third handle to advance the rod within the plunger lumen until the sleeve is fully deployed; pulling said delivery device back to reposition the distal end of the elongate body within a stomach of the patient; pulling back on the first handle while holding the second handle steady, keeping the plunger in place and releasing the wire mesh structure; and removing the delivery device from the patient.

The delivery device may further comprise a stopper positioned on said plunger between said tip and said second handle wherein said stopper is configured to stop further distal movement of said plunger once said sleeve has been pushed out of said elongate body.

The delivery device may further comprise an inflatable balloon at said distal end of said body, an input port at said proximal end of said body, and a channel extending along said elongate body and in fluid communication with said balloon and said port, and said method may further comprise the step of using said port and said channel to inflate said balloon to anchor the delivery device in the gastrointestinal tract of said patient.

The present specification also discloses a delivery device for delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising: a flexible elongate body with a proximal end, a distal end, and a body lumen within, said body comprising an opening at said distal end and a first handle attached to said proximal end; a flexible elongate rod positioned coaxially, and movable longitudinally, within said body lumen, said rod including a proximal end and a distal end and comprising a first spherical component positioned proximal to said distal end and a second spherical component positioned at said distal end wherein said first spherical component has a diameter greater than a diameter of said second spherical component, said rod further comprising a second handle attached to said proximal end; a flexible plunger component positioned coaxially over a proximal portion of, and movable longitudinally with, said flexible elongate rod, said plunger including a proximal end and a distal end and comprising a tip at said distal end and attached to said second handle at said proximal end; a pulling mechanism comprising a first end and a second end wherein said first end is attached to said sleeve of said intragastric device and said second end is removably coupled to said rod at a position between said first spherical component and said second spherical component, wherein said intragastric device is loaded for delivery within said delivery device such that: said porous structure is positioned within said body lumen distal to said plunger tip and proximal to said sleeve and wherein said rod passes through at least two openings in said porous structure and wherein said at least two openings do not lie along a center longitudinal axis of said porous structure; said sleeve is positioned within said body lumen distal to said porous structure and proximal to said first spherical component and wherein said sleeve is folded upon itself and then wrapped about a portion of said rod, further wherein said sleeve is attached to said first end of said pulling mechanism.

The pulling mechanism may be biodegradable and comprise a suture or a hook. Alternatively, said pulling mechanism is non-biodegradable and comprises a suture with a loop end.

The sleeve may be constrained by a ring, cone, or umbrella shaped constraining device.

Optionally, said tip of said plunger includes a mesh retention component comprising a plurality of fins wherein a proximal portion of said porous structure is positioned over said fins such that said fins cause said porous structure to move in a proximal direction when said plunger is moved in a proximal direction.

Optionally, said sleeve is folded upon itself two to ten times before being wrapped about said rod.

Optionally, the delivery device further comprises an inflatable balloon at said distal end of said body, an input port at said proximal end of said body, and a channel extending along said elongate body and in fluid communication with said balloon and said port, wherein said balloon is inflated using said port and said channel and said inflated balloon is used to anchor said delivery device within said gastrointestinal tract of said patient.

Optionally, the delivery device further comprises a flushing or irrigation mechanism to reduce deployment forces during delivery.

The elongate body may include a length wherein said length includes a variable stiffness.

The elongate body may include at least three zones wherein a most distal zone is more flexible than a center distal zone, which is more flexible than a least distal zone.

The elongate body may comprise a braided catheter.

The distal ends of the elongate body, plunger, and rod may be configured to be atraumatic.

The present specification also discloses a method of delivering an intragastric device into a gastrointestinal tract of a patient, said intragastric device comprising a porous structure configurable between a compressed pre-deployment configuration and an expanded post-deployment configuration and an elongate sleeve coupled to a distal end of said porous structure, said delivery device comprising a flexible elongate body with a proximal end, a distal end, and a body lumen within, said body comprising an opening at said distal end and a first handle attached to said proximal end, a flexible elongate rod positioned coaxially, and movable longitudinally, within said body lumen, said rod including a proximal end and a distal end and comprising a first spherical component positioned proximal to said distal end and a second spherical component positioned at said distal end wherein said first spherical component has a diameter greater than a diameter of said second spherical component, said rod further comprising a second handle attached to said proximal end, a flexible plunger component positioned coaxially over a proximal portion of, and movable longitudinally with, said flexible elongate rod, said plunger including a proximal end and a distal end and comprising a tip at said distal end and attached to said second handle at said proximal end, a pulling mechanism comprising a first end and a second end wherein said first end is attached to said sleeve of said intragastric device and said second end is removably coupled to said rod at a position between said first spherical component and said second spherical component, wherein said intragastric device is loaded for delivery within said delivery device such that said porous structure is positioned within said body lumen distal to said plunger tip and proximal to said sleeve and wherein said rod passes through at least two openings in said porous structure and wherein said at least two openings do not lie along a center longitudinal axis of said porous structure, wherein said sleeve is positioned within said body lumen distal to said porous structure and proximal to said first spherical component and wherein said sleeve is folded upon itself and then wrapped about a portion of said rod, further wherein said sleeve is attached to said first end of said pulling mechanism, said method comprising the steps of: sliding said delivery device over a guidewire into said gastrointestinal tract of said patient; using the first handle, positioning the distal end of said elongate body in a duodenum of the patient; pushing the second handle to push in the plunger component and rod until the sleeve is fully deployed; pulling said delivery device back to reposition the distal end of the elongate body within a stomach of the patient; pulling back on the first handle while holding the second handle steady, keeping the plunger and rod in place and releasing the wire mesh structure; and removing the delivery device from the patient.

Optionally, said delivery device further comprises a stopper positioned on said plunger between said tip and said second handle wherein said stopper is configured to stop further distal movement of said plunger and rod once said sleeve has been pushed out of said elongate body.

Optionally, said delivery device further comprises an inflatable balloon at said distal end of said body, an input port at said proximal end of said body, and a channel extending along said elongate body and in fluid communication with said balloon and said port, and said method further comprises the step of using said port and said channel to inflate said balloon to anchor the delivery device in the gastrointestinal tract of said patient.

The present specification also discloses a delivery system for delivering an intragastric device, said delivery system comprising: an outer catheter having a proximal end and a distal end and variable stiffness along its length; and a flexible inner catheter coaxially positioned inside the outer catheter and having a proximal end, an atraumatic distal end, and a lumen for receiving a guiding device; wherein said intragastric device is positioned in a space between the inner catheter and the outer catheter and said inner catheter includes a flexible extension having a length of at least 5 cm at its distal end which extends beyond said distal end of said outer catheter.

Optionally, the guiding device is a guidewire. Alternatively, the guiding device is an endoscope for over the scope delivery.

The atraumatic distal end may be a ball-tip.

The said inner catheter may have a variable stiffness along its length.

Optionally, said flexible extension includes a proximal end and a distal end and has a variable stiffness along its length wherein the stiffness varies between a stiffness of a guidewire at said distal end to a stiffness of said inner catheter at said proximal end.

The present specification also discloses an intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, wherein said porous structure further comprises: a wire mesh having a substantially spherical post-deployment shape; and a collar positioned at said bottom of said porous structure, said collar having a bend wherein said bend comprises an extension of said wire curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said collar such that food exiting said at least one second opening enters said sleeve through said third opening, passes through said sleeve interior, and exits said sleeve through said fourth opening wherein the sleeve is designed to intermittently engage a patients pylorus without blocking said pylorus and allows for passage of the food through the said lumen of the sleeve from the stomach into the small intestine.

The present specification also discloses a system for delivering an intragastric device to a gastrointestinal tract of a patient, comprising: a porous mesh structure having a first lumen; a sleeve both attached to said porous mesh structure and having a second lumen; a coaxial catheter system comprising an outer catheter and an inner catheter wherein, prior to delivery, said porous mesh structure and said sleeve are constrained into a space between said outer and inner catheters and wherein the outer catheter covers a substantial portion of the intragastric device and the inner catheter passes within a majority of the first lumen of the mesh but outside of a majority of the second lumen of the sleeve.

Optionally, said inner catheter is operationally attached to the sleeve at a distal end of said inner catheter such that, when actuated, the inner catheter pushes the sleeve out of the coaxial catheter system and is then detached from the sleeve to deliver the intragastric device in the gastrointestinal tract.

The present specification also discloses a system for promoting weight loss in a patient, said system comprising an intragastric device, a delivery device, and a retrieval device, wherein said intragastric device is configured to be temporarily deployed within a gastrointestinal tract of a patient, said intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, said porous structure further comprising a collar positioned at said bottom of said porous structure, said collar having a bend wherein said bend comprises an extension of said porous structure curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said bottom of said porous structure such that food exiting said at least one second opening enters said sleeve through said third opening, passes through said sleeve interior, and exits said sleeve through said fourth opening; wherein, once said intragastric device has been deployed in a gastrointestinal tract of said patient, at least a portion of said intragastric device is in constant physical contact with a portion of said gastrointestinal tract of said patient without being physically attached to any portion of the anatomy of said patient.

The physical contact may be caused by peristaltic actions of a small intestine pulling on said sleeve of said intragastric device in said small intestine.

The portion of said intragastric device may comprise a portion of said porous structure and said portion of said gastrointestinal tract of said patient may comprise a portion of a stomach proximate a pylorus. Optionally, the portion of said stomach comprises said gastric emptying region of said stomach and said intragastric device does not occlude said region.

The portion of said intragastric device may comprise a portion of said sleeve and said portion of said gastrointestinal tract of said patient may comprise a portion of a pylorus.

The portion of said intragastric device may comprise a portion of said sleeve and said portion of said gastrointestinal tract of said patient may comprise a portion of a duodenum.

The intragastric device may direct food through itself, allowing food to pass from a stomach of said patient into a small intestine of said patient without blocking the passage of said food. Optionally, at least 10%, and preferably 50%, of the food passing from a stomach of said patient into a small intestine of said patient passes through said intragastric device.

The intragastric device may provide a constant and substantially complete bypass of a pylorus of said patient. Optionally, the intragastric device provides a constant and substantially complete bypass of a pylorus and a duodenum of said patient.

The present specification also discloses a system for promoting weight loss in a patient, said system comprising an intragastric device, a delivery device, and a retrieval device, wherein said intragastric device is configured to be temporarily deployed within a gastrointestinal tract of a patient, said intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, said porous structure further comprising a collar positioned at said bottom of said porous structure, said collar having a bend wherein said bend comprises an extension of said porous structure curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said bottom of said porous structure such that food exiting said at least one second opening enters said sleeve through said third opening, passes through said sleeve interior, and exits said sleeve through said fourth opening; wherein, once said intragastric device has been deployed in a gastrointestinal tract of said patient, said porous structure is positioned within, and physically contacts a portion of, a stomach of said patient and said sleeve is positioned within a pylorus and a duodenum of said patient such that said intragastric device provides a constant and substantially complete bypass of a pylorus of said patient wherein food ingested by said patient is unable to physically contact any portion of said pylorus.

The physical contact with said portion of said stomach may be caused by peristaltic actions of a small intestine pulling on said sleeve of said intragastric device in said small intestine.

The intragastric device may direct food through itself, allowing food to pass from a stomach of said patient into a small intestine of said patient without blocking the passage of said food. Optionally, at least 10%, and preferably 50%, of the food passing from a stomach of said patient into a small intestine of said patient passes through said intragastric device.

Optionally, the intragastric device is not physically attached to any portion of the anatomy of said patient.

The present specification also discloses a system for promoting weight loss in a patient, said system comprising an intragastric device, a delivery device, and a retrieval device, wherein said intragastric device is configured to be temporarily deployed within a gastrointestinal tract of a patient, said intragastric device comprising: a porous structure comprising a top, a bottom, and an interior and having a pre-deployment shape with a first volume and a post-deployment shape with a second volume greater than said first volume, wherein, in said post-deployment shape, said porous structure includes at least one first opening proximate said top and at least one second opening proximate said bottom such that food enters said porous structure through said at least one first opening, passes through said interior, and exits said porous structure through said at least one second opening, said porous structure further comprising a collar positioned at said bottom of said porous structure, said collar having a bend wherein said bend comprises an extension of said porous structure curving in a direction away from a longitudinal center axis of said porous structure and then in a direction upward toward said top of said porous structure; and a sleeve having a flexible elongate body, a proximal end with a third opening, a distal end with a fourth opening, and a sleeve interior, wherein said proximal end of said sleeve is coupled to said bottom of said porous structure such that food exiting said at least one second opening enters said sleeve through said third opening, passes through said sleeve interior, and exits said sleeve through said fourth opening; wherein, once said intragastric device has been deployed in a gastrointestinal tract of said patient, said porous structure is positioned within, and physically contacts a portion of, a stomach of said patient and said sleeve is positioned within a pylorus and a duodenum of said patient such that said intragastric device provides a constant and substantially complete bypass of a duodenum of said patient wherein food ingested by said patient is unable to physically contact any portion of said duodenum.

The system physical contact with said portion of said stomach may be caused by peristaltic actions of a small intestine pulling on said sleeve of said intragastric device in said small intestine.

The intragastric device may direct food through itself, allowing food to pass from a stomach of said patient into a small intestine of said patient without blocking the passage of said food. Optionally, at least 10%, and preferably 50%, of the food passing from a stomach of said patient into a small intestine of said patient passes through said intragastric device.

Optionally, the intragastric device is not physically attached to any portion of the anatomy of said patient.

The aforementioned and other embodiments of the present invention shall be described in greater depth in the drawings and detailed description provided below.

BRIEF DESCRIPTION OF THE DRAWINGS

These and other features and advantages of the present invention will be appreciated as they become better understood by reference to the following detailed description when considered in connection with the accompanying drawings, wherein:

FIGS. 2C and 2D are another illustrations of wire mesh structures, in accordance with other embodiments of the present specification;

FIG. 2E is an illustration of a wire loop in accordance with at least one embodiment;

FIG. 2F is a side view of the wire loop of FIG. 2E depicting a thickness of the loop in accordance with at least one embodiment;

FIG. 2G is an illustration of a wire piece in accordance with at least one embodiment;

FIG. 2H is an illustration of a width of a gap in the wire mesh structure in accordance with at least one embodiment;

FIG. 3A is an illustration depicting a plurality of free ends or nodes positioned at a proximal end of a wire mesh structure, in accordance with one embodiment of the present specification;

FIG. 3B is an illustration depicting a plurality of free ends or nodes positioned at a distal end of a wire mesh structure in accordance with at least one embodiment;

FIG. 3G is an illustration of first and second pluralities of nodes at an end of a wire mesh structure, depicting loops formed in alternating wires of both the first and second pluralities, in accordance with one embodiment of the present specification;

FIG. 3H is an illustration depicting a wire mesh structure having a first plurality of nodes at its proximal end and a second plurality of nodes at its distal end, in accordance with one embodiment of the present specification;

FIG. 3I is an illustration depicting a wire mesh structure having first and second pluralities of nodes at its proximal and distal ends respectively, and third and fourth pluralities of nodes distributed along its surface, in accordance with one embodiment of the present specification;

FIG. 3J to FIG. 3N are illustrations depicting various possible node shapes in accordance with multiple embodiments of the present specification;

FIG. 5A is an illustration of a portion of a sleeve component of an intragastric device in a post-deployment configuration depicting a single wire support spiraling along the body of the sleeve in accordance with at least one embodiment;

FIG. 5B is an illustration of a portion of a sleeve component of an intragastric device in a post-deployment configuration depicting multiple wire supports spiraling along the body of the sleeve in accordance with at least one embodiment;

FIG. 5C is an illustration of a funnel shaped sleeve component of an intragastric device in a post-deployment configuration depicting spiral wire loop supports on the sleeve in accordance with at least one embodiment;

FIG. 5D is an illustration of a set of wire loop supports for the funnel shaped sleeve of FIG. 5C in accordance with at least one embodiment;

FIGS. 6D and 6E are cross-sectional illustration of funnel shaped sleeve components of an intragastric device in a post-deployment configuration depicting a plurality of sleeve layers in accordance with at least one embodiment;

FIG. 6F is a cross-sectional illustration of a sleeve component of FIG. 6E in accordance with at least one embodiment;

FIG. 6J illustrates a portion of a sleeve of a wire mesh device covered with a nano-fiber membrane, in accordance with an embodiment of the present specification;

FIG. 9A is an illustration of a wire mesh structure with attached sleeve component in a post-deployment configuration depicting a blunt end of a wire mesh support toward the proximal end of the sleeve in accordance with at least one embodiment;

FIG. 10A is an illustration of a funnel shaped braided short sleeve component in a post-deployment configuration, in accordance with one embodiment of the present specification;

FIG. 10B is an illustration of a funnel shaped braided short sleeve component having a cone shaped distal end in a post-deployment configuration, in accordance with one embodiment of the present specification;

FIG. 10G is an illustration of a cone shape braided short sleeve component having an atraumatic distal tip and in a post-deployment configuration, in accordance with one embodiment of the present specification;

FIG. 10H is an illustration of a cone shape braided short sleeve component having an atraumatic distal tip and in a post-deployment configuration, in accordance with another embodiment of the present specification;

FIG. 11A is a cross-sectional illustration depicting one embodiment of an intragastric device with an attached sleeve in a post-deployment configuration in accordance with at least one embodiment;

FIG. 11B is a cross-sectional illustration depicting the intragastric device of FIG. 11A in a pre-deployment configuration in accordance with at least one embodiment;

FIG. 11C is a cross-sectional illustration depicting an intragastric device with an attached sleeve in a post-deployment configuration in accordance with at least one embodiment;

FIG. 11D is a cross-sectional illustration depicting the intragastric device of FIG. 11C in a pre-deployment configuration in accordance with at least one embodiment;

FIG. 12E is an illustration of a plurality of nodes positioned at the distal end of a wire mesh structure connected to the proximal end of a funnel shaped sleeve, in accordance with another embodiment of the present specification;

FIG. 12F is an illustration of a plurality of nodes positioned at the distal end of a wire mesh structure connected to the proximal end of a funnel shaped sleeve, in accordance with yet another embodiment of the present specification;

FIG. 19A is an illustration of a distal end of a sleeve comprising a plurality of fringes joined to a ring, in accordance with one embodiment of the present specification;

FIG. 19B is an illustration of a distal end of a sleeve comprising a plurality of fringes joined to a ball, in accordance with one embodiment of the present specification;

FIG. 19C is a cross sectional illustration of a ball attached to a distal end of a sleeve, in accordance with one embodiment of the present specification;

FIGS. 20F to 20L are illustrations of exemplary sleeve knit patterns in accordance with various embodiments of the present specification;

FIG. 21C is an illustration of several views of a pylorus of a patient in an open state and a closed state with and without a sleeve of an intragastric device passing therethrough, in accordance with some embodiments of the present specification;

FIG. 21D is an illustration of a pylorus of a patient in an open and closed state with a sleeve of an intragastric device passing therethrough in accordance with at least one embodiment;

FIG. 29B is a cross sectional illustration of a pre-deployment coaxial arrangement of a sleeve of an intragastric device within a delivery device, in accordance with one embodiment of the present specification;

FIG. 29C is a cross sectional illustration of a pre-deployment coaxial arrangement of a sleeve of an intragastric device within a delivery device, in accordance with another embodiment of the present specification;

FIG. 29D is a cross sectional illustration of a pre-deployment coaxial arrangement of a sleeve of an intragastric device within a delivery device depicted over an endoscope, in accordance with one embodiment of the present specification;

FIG. 30B is an illustration of one exemplary embodiment of an outer catheter for use in the delivery device of FIG. 30A in accordance with at least one embodiment;

FIG. 30C is an illustration of another embodiment of an outer catheter depicting the dimensions a compressed sleeve and compressed wire mesh structure of an intragastric device relative to the dimensions of the outer catheter in accordance with at least one embodiment;

FIG. 30D is a close up illustration of the distal end of the delivery device of FIG. 30A, depicting the pilot component and proximal and distal spherical components in accordance with at least one embodiment;

FIG. 30E is an illustration of the proximal end of the delivery device of FIG. 30A, depicting the outer catheter retracted to a first stopping mechanism in accordance with at least one embodiment;

FIG. 30F is an illustration of one embodiment of a sleeve of an intragastric device partially deployed corresponding to the outer catheter position depicted in FIG. 30E in accordance with at least one embodiment;

FIG. 30G is an illustration of the proximal end of the delivery device of FIG. 30A, depicting the outer catheter retracted to a second stopping mechanism in accordance with at least one embodiment;

FIG. 30H is an illustration of one embodiment of a wire mesh structure of an intragastric device partially deployed corresponding to the outer catheter position depicted in FIG. 30I in accordance with at least one embodiment;

FIG. 30I is a flow chart illustrating the steps involved in delivering an intragastric device using the delivery device of FIG. 30A, in accordance with one embodiment of the present specification;

FIG. 31A is an illustration of a wire mesh structure of an intragastric device being loaded onto a delivery device, in accordance with one embodiment of the present specification;

FIG. 31B is an illustration of the wire mesh structure of FIG. 31A further loaded onto the delivery device in accordance with at least one embodiment;

FIG. 31C is an illustration of the wire mesh structure of FIG. 31A loaded onto the delivery device such that only the anti-migration collar remains to be loaded in accordance with at least one embodiment;

FIG. 31D is an illustration of the wire mesh structure of FIG. 31A fully loaded onto the delivery device in accordance with at least one embodiment;

Figure 31A:
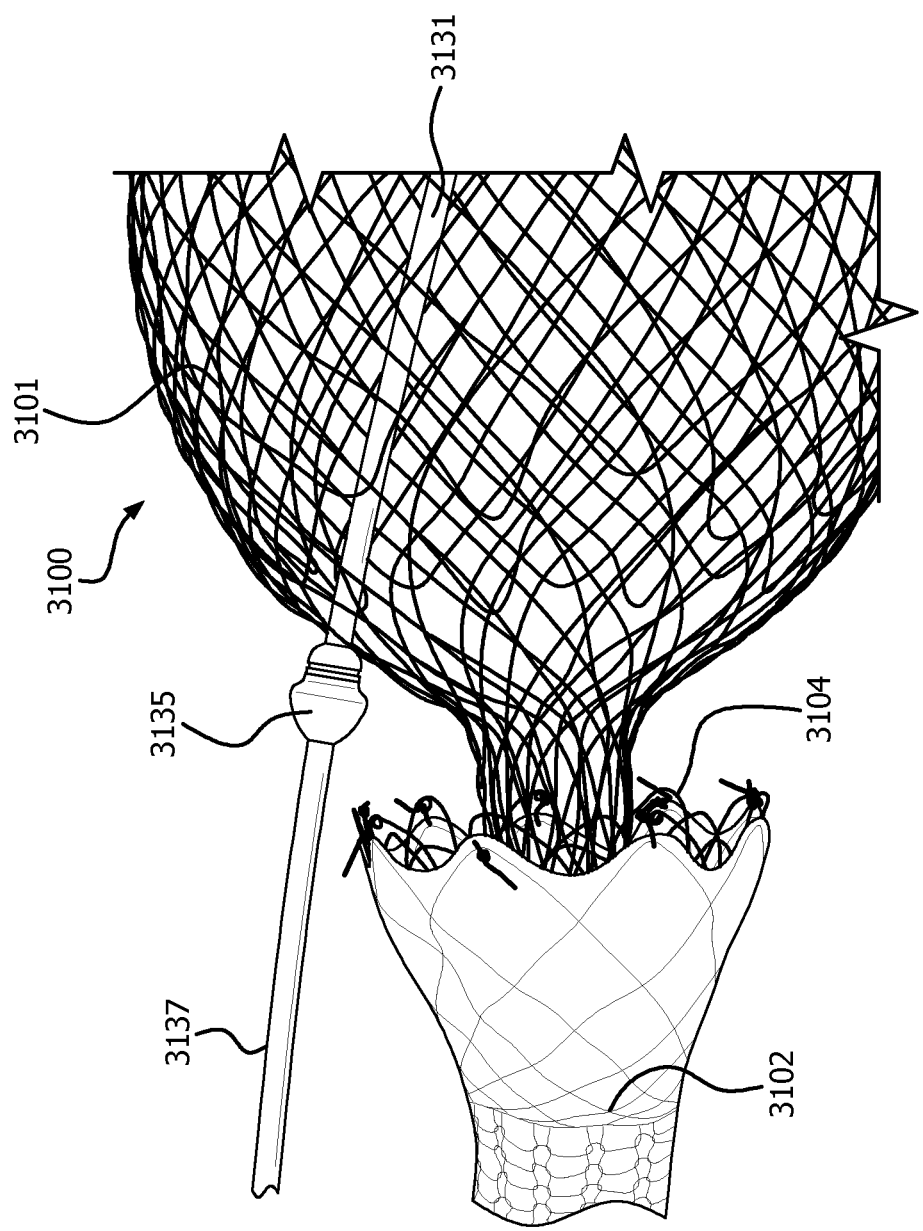
Figure 31B:
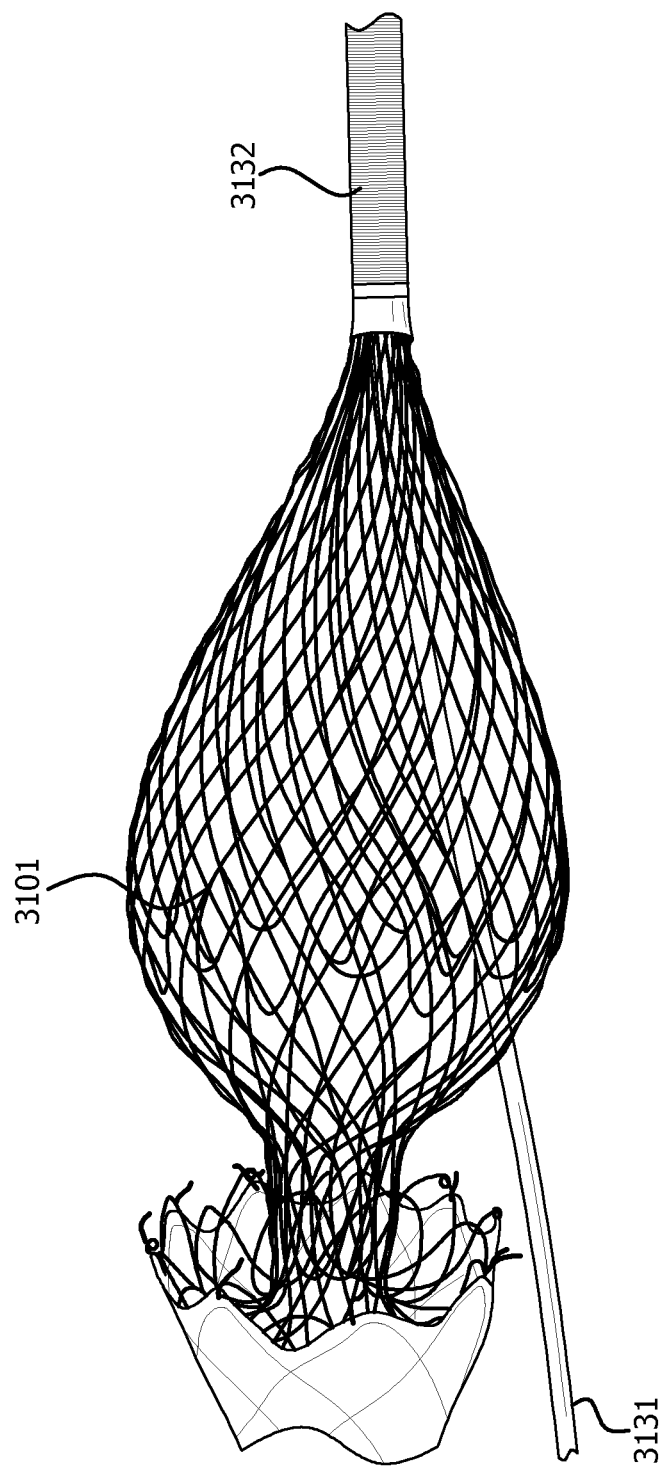
Figure 31C:
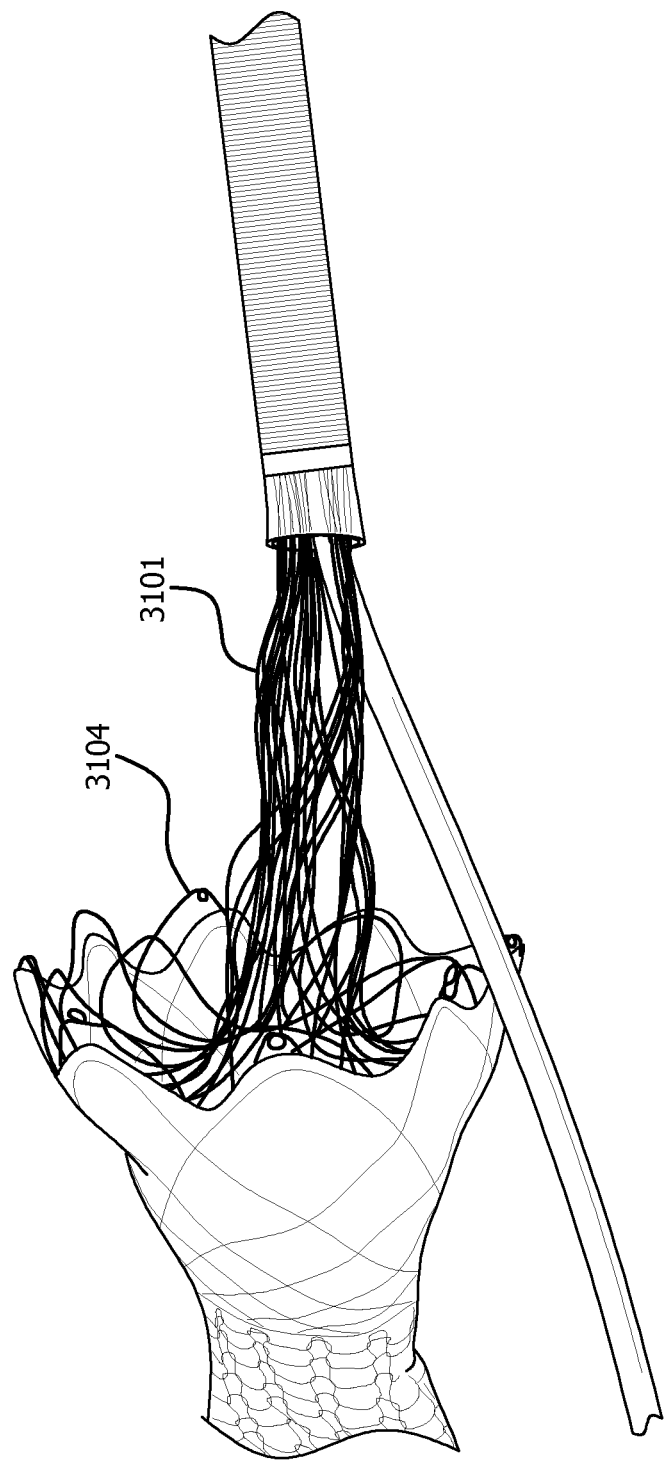
Figure 31D:
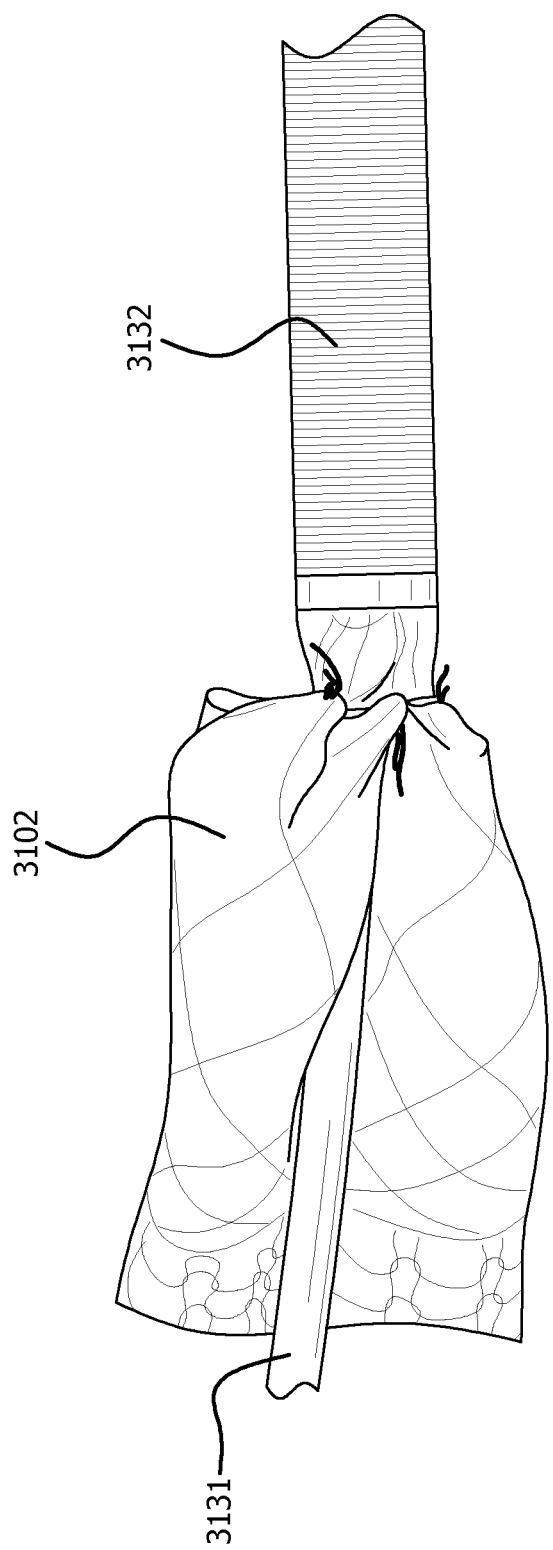
Figure 31E:
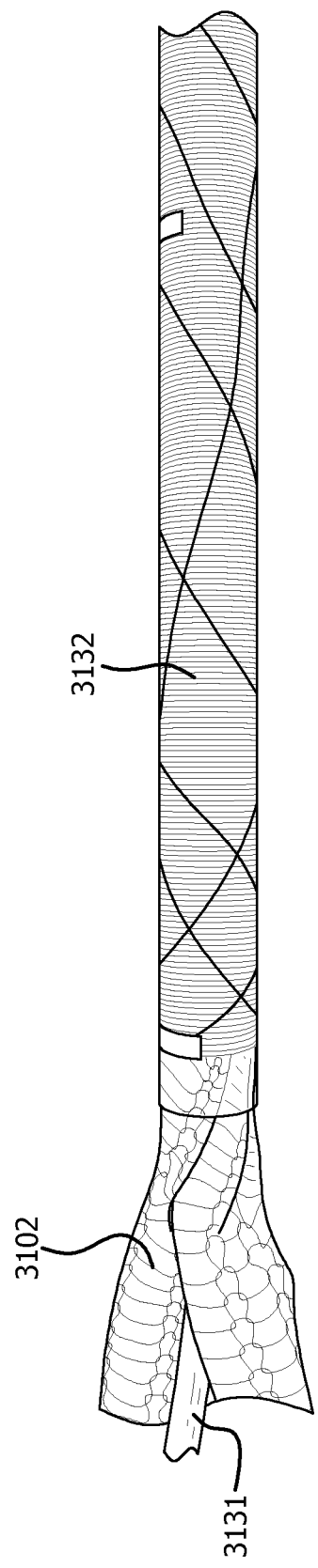
Figure 31F:
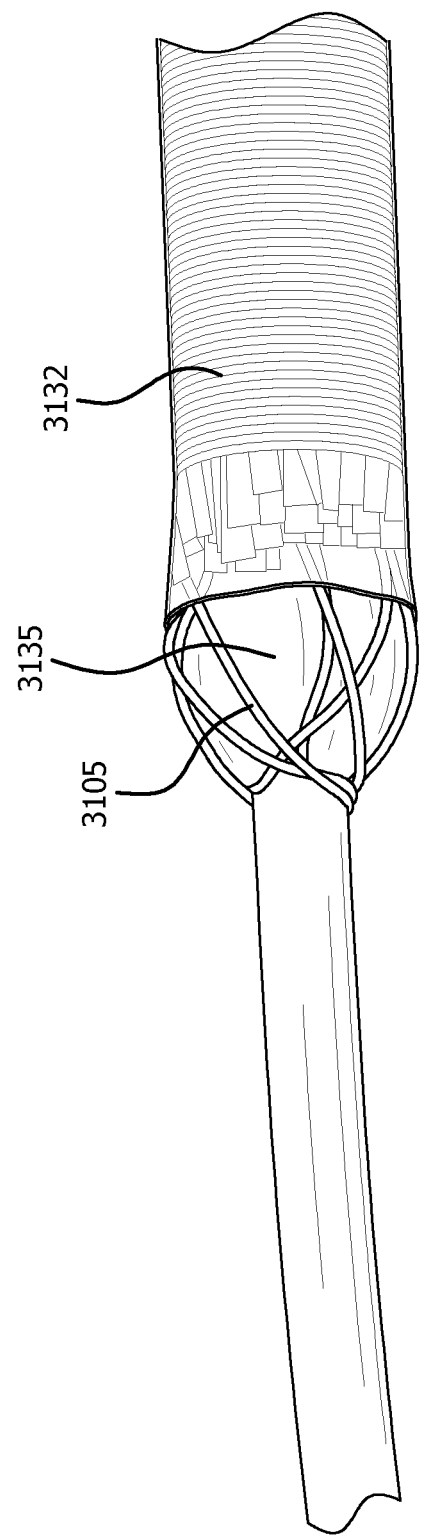
Figure 32A:
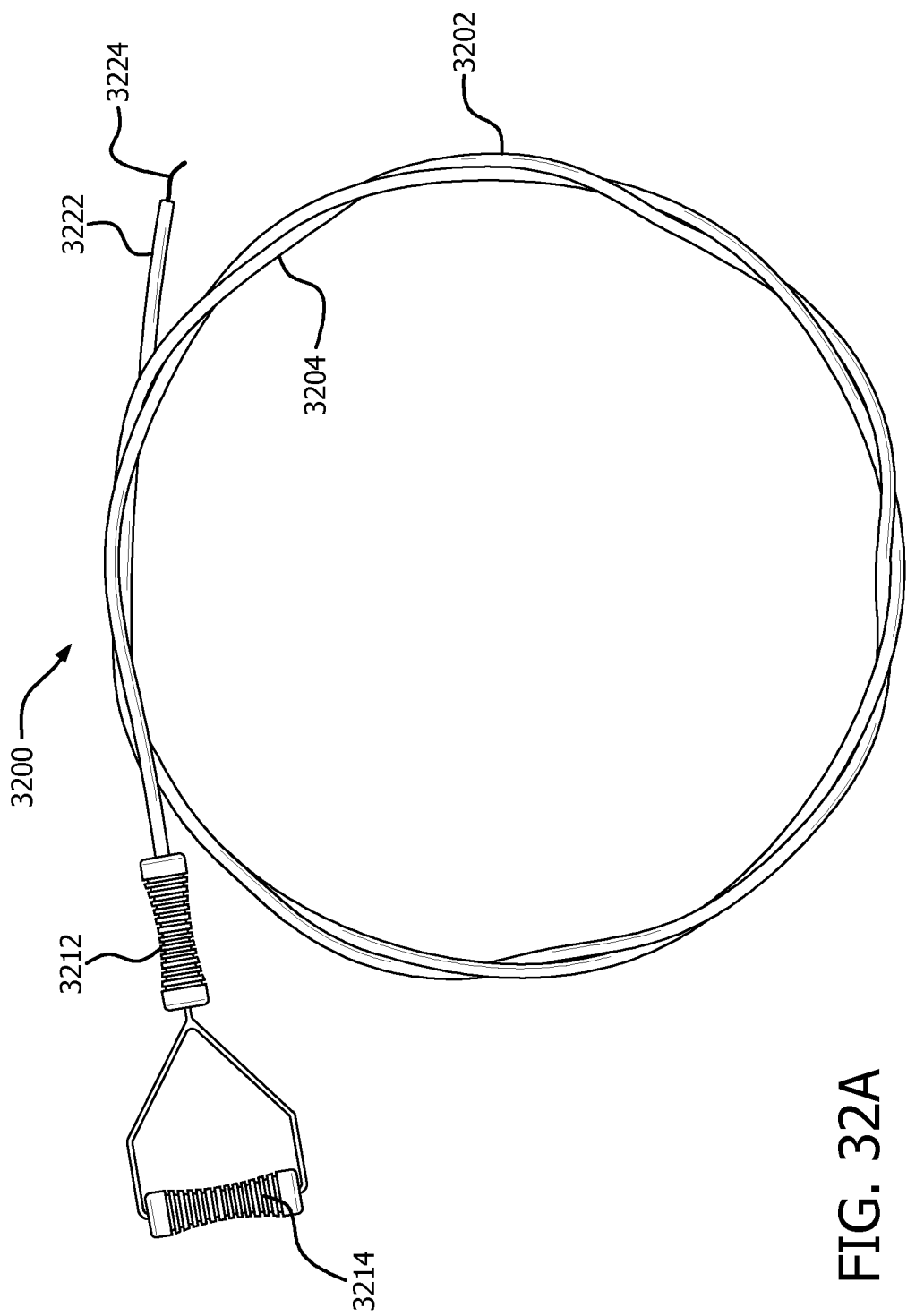
Figure 32B:
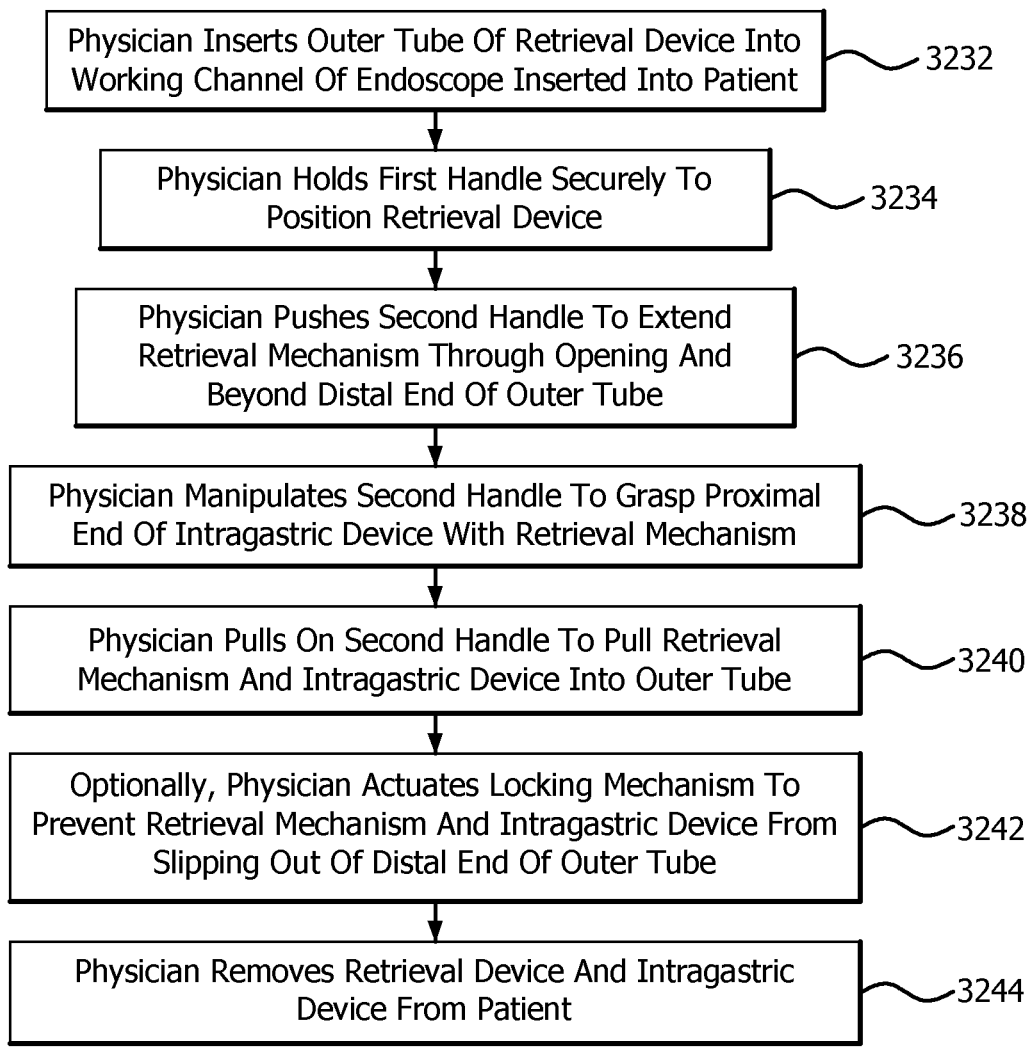
Figure 33A:
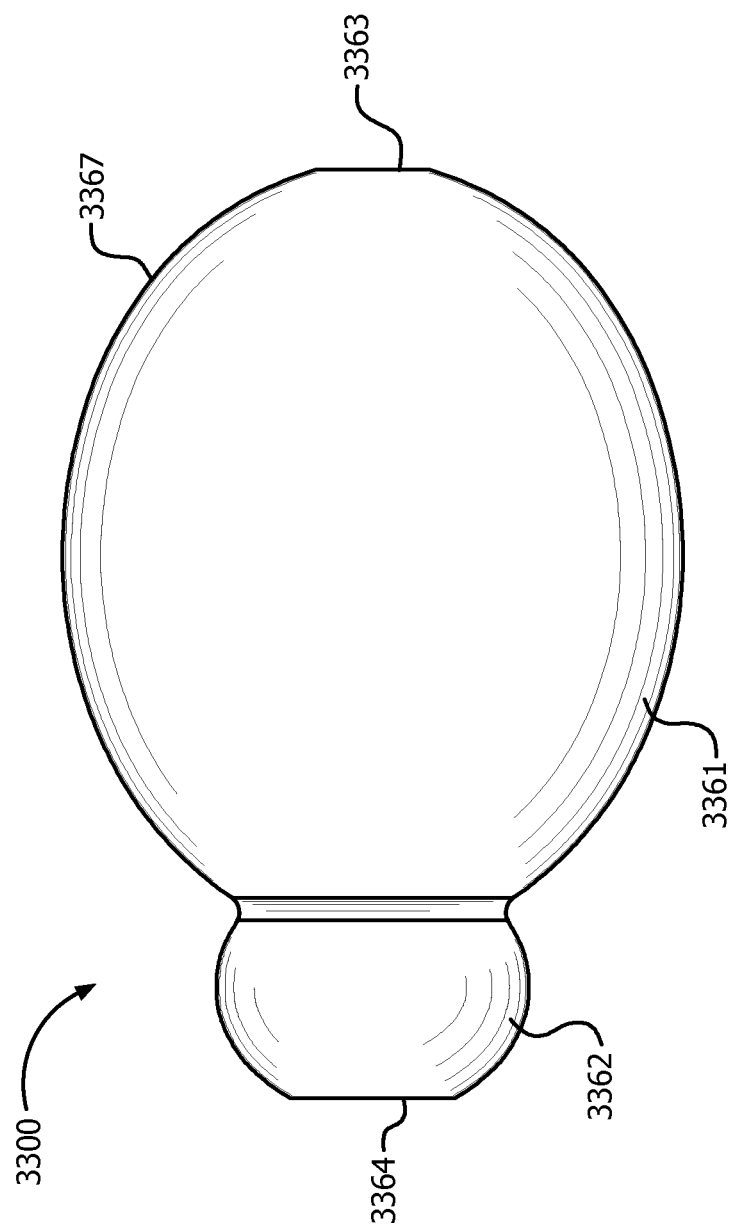
Figure 33B:
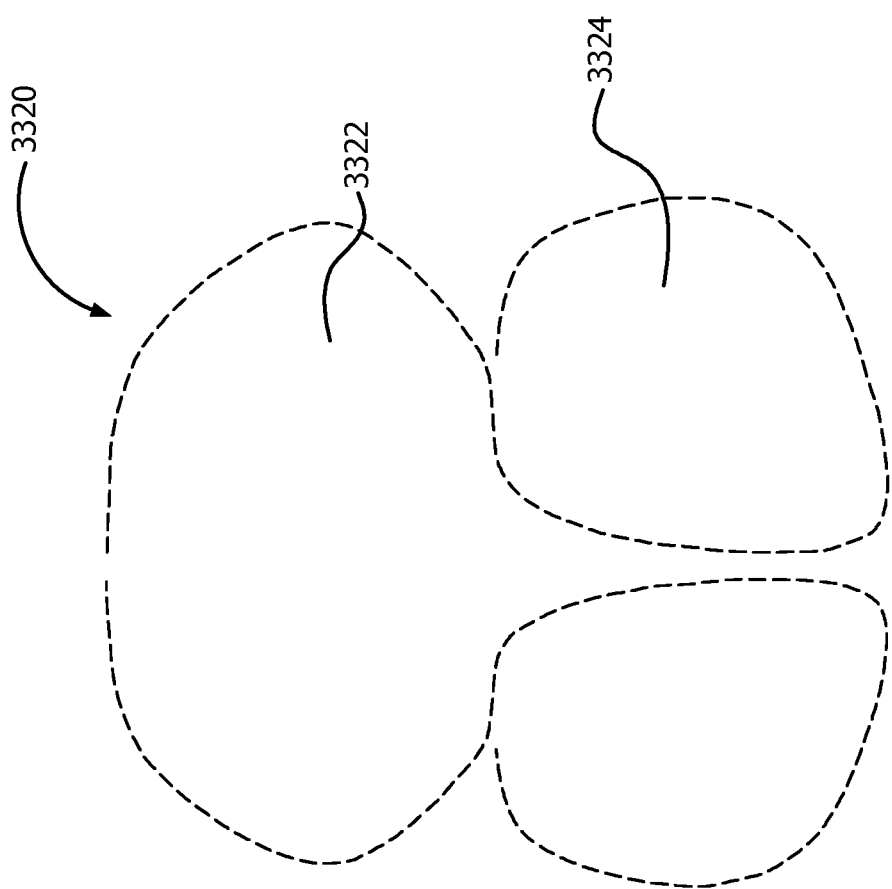
Figure 34B:
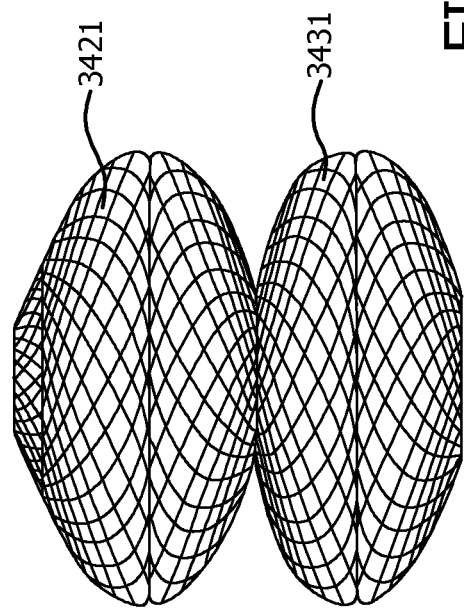
Figure 34C:
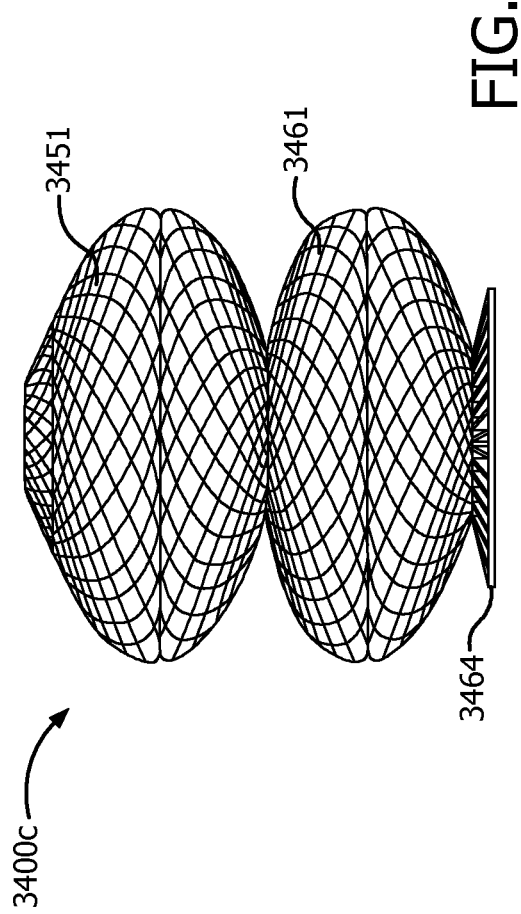
Figure 34F:
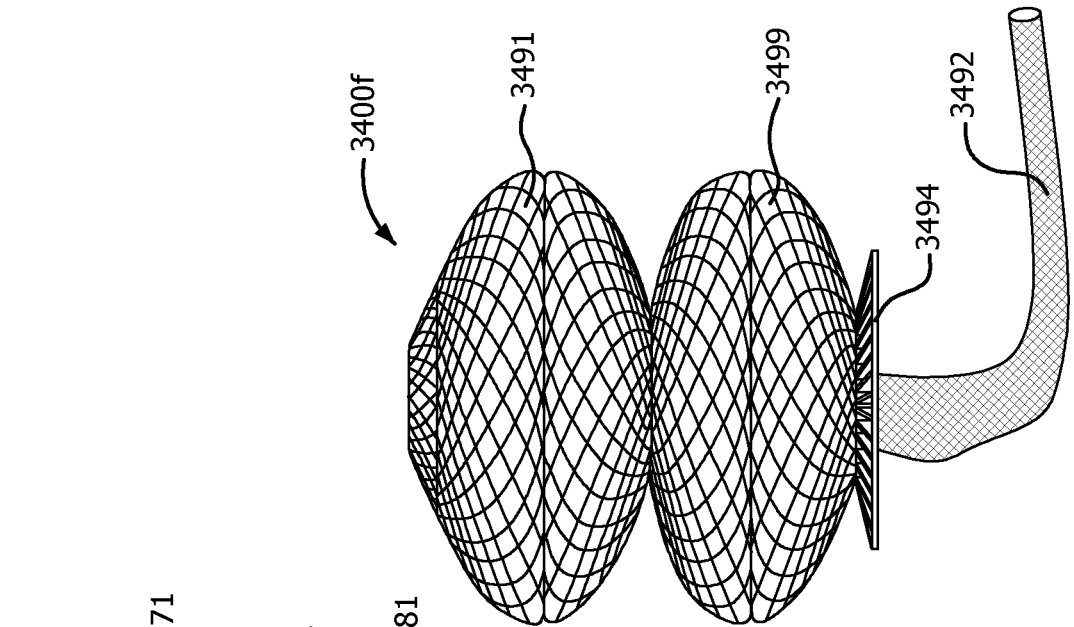
Figure 34D:
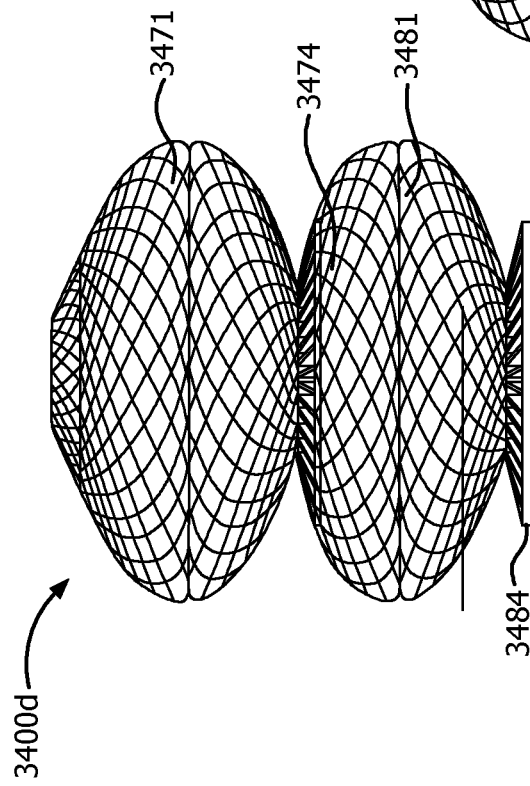
Figure 34E:
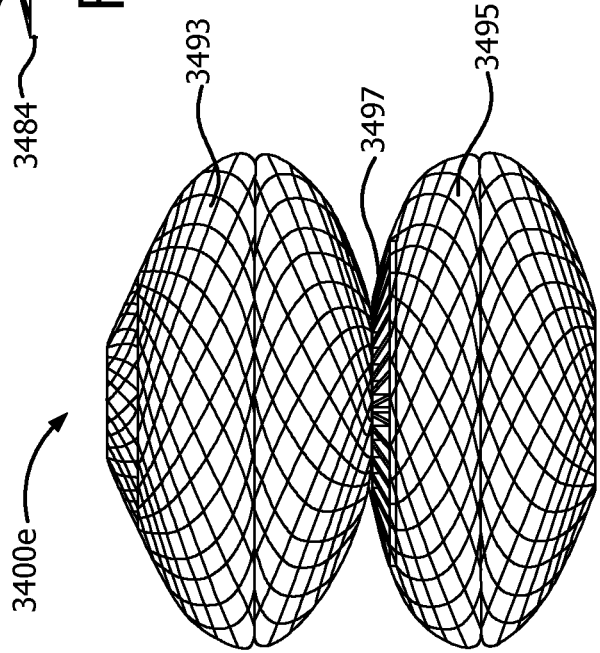
Figure 36:
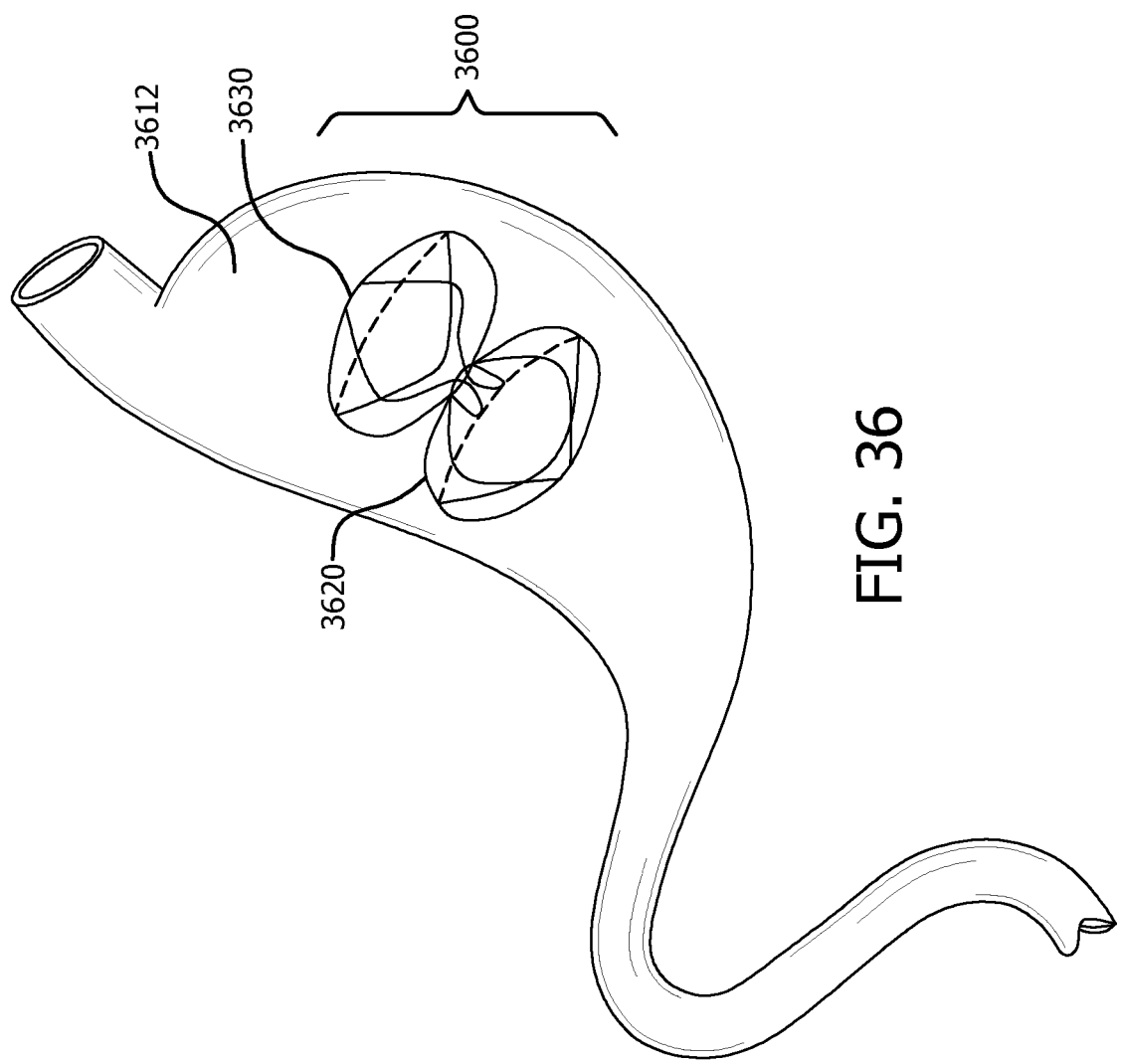
Figure 37D:
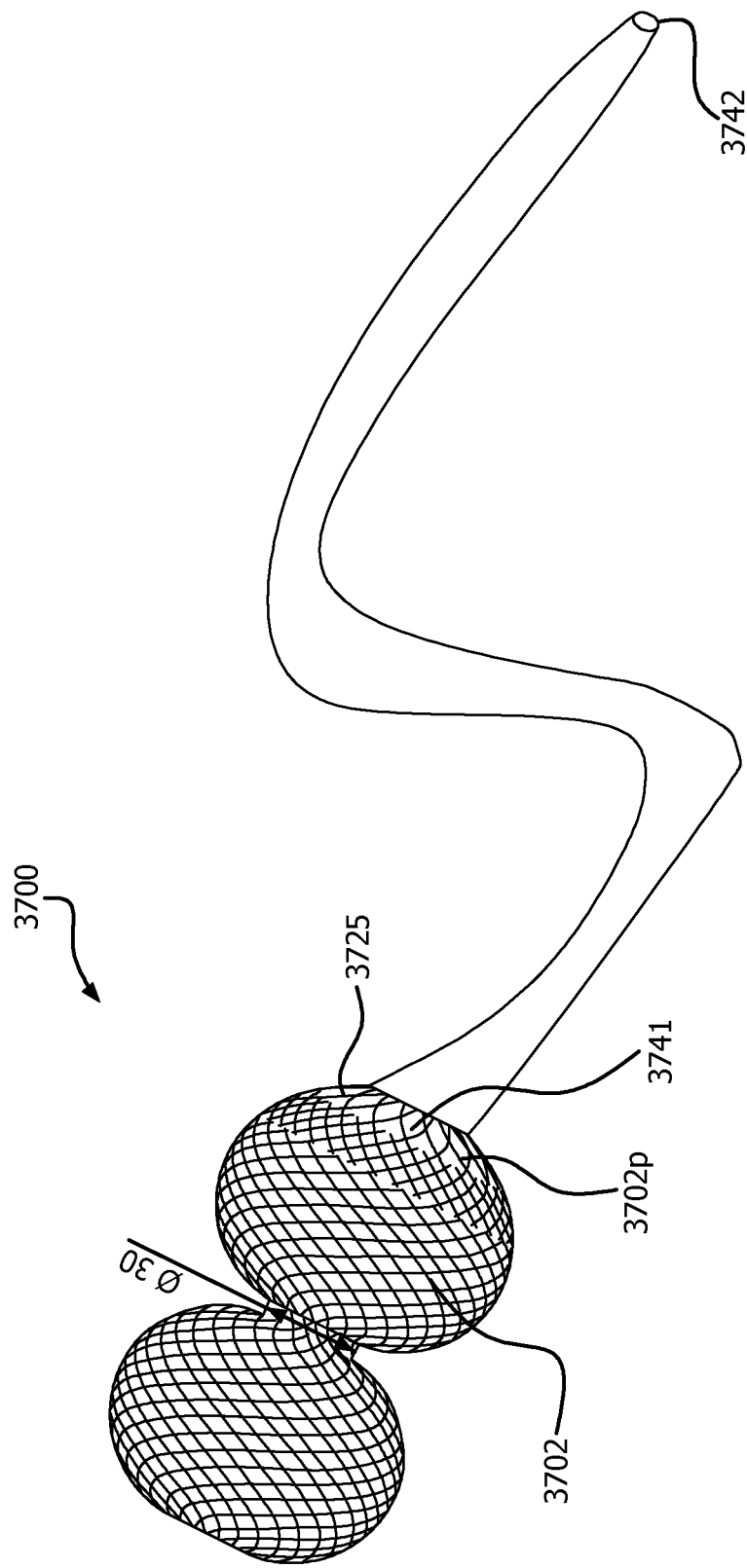
Figure 37E:
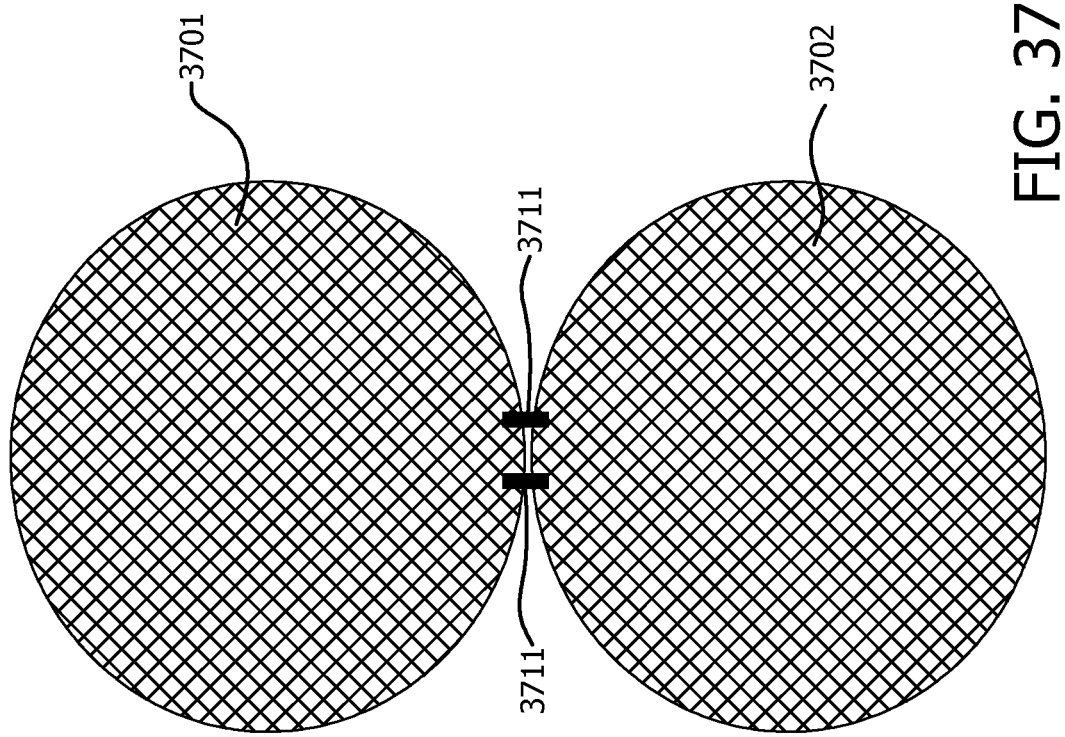
Figure 38A:
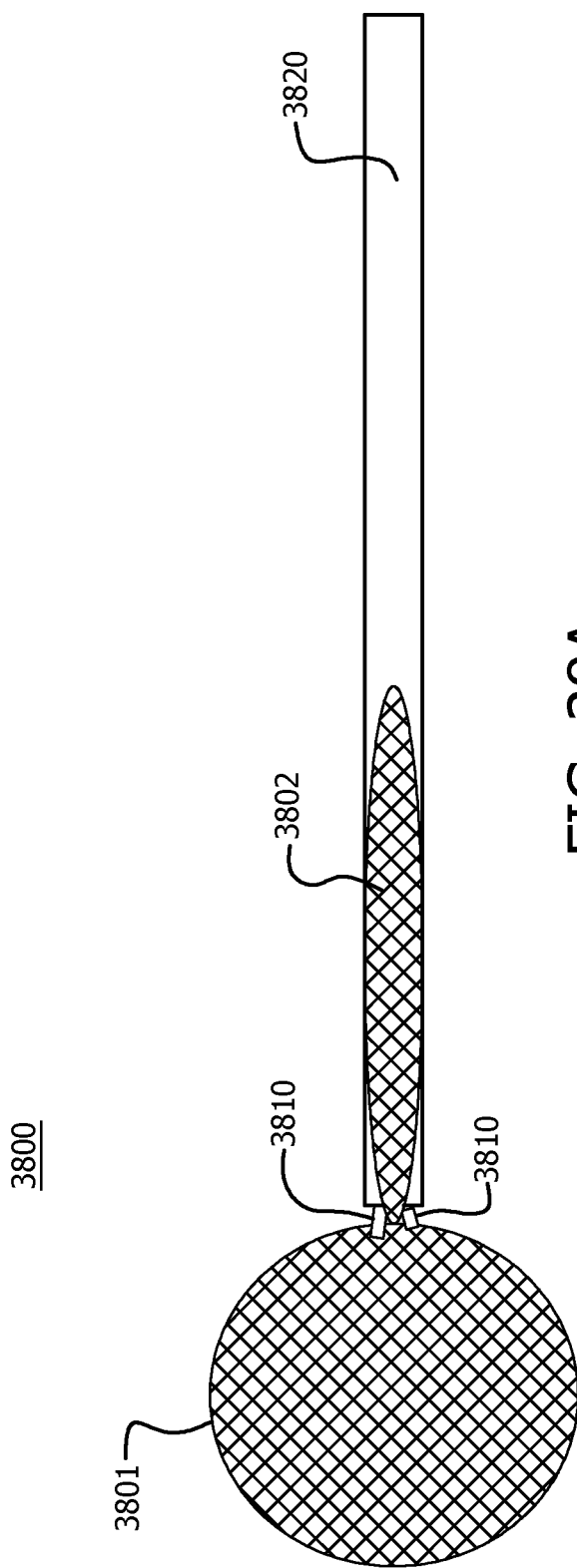
Figure 38B:
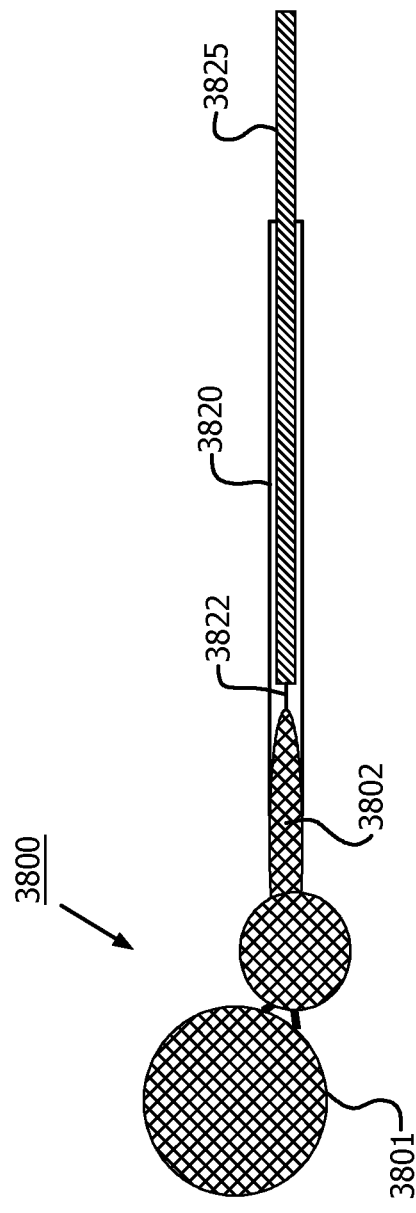
Figure 38C:
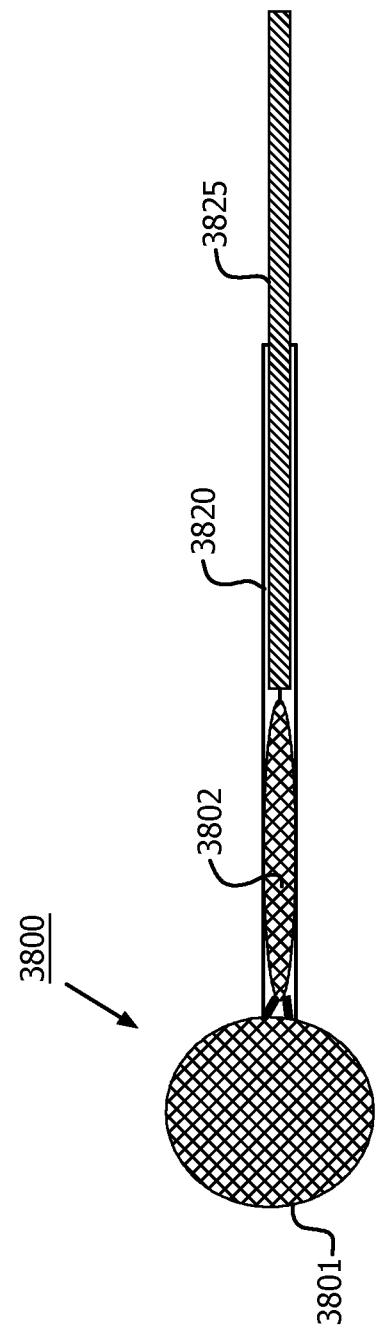
Figure 38D:
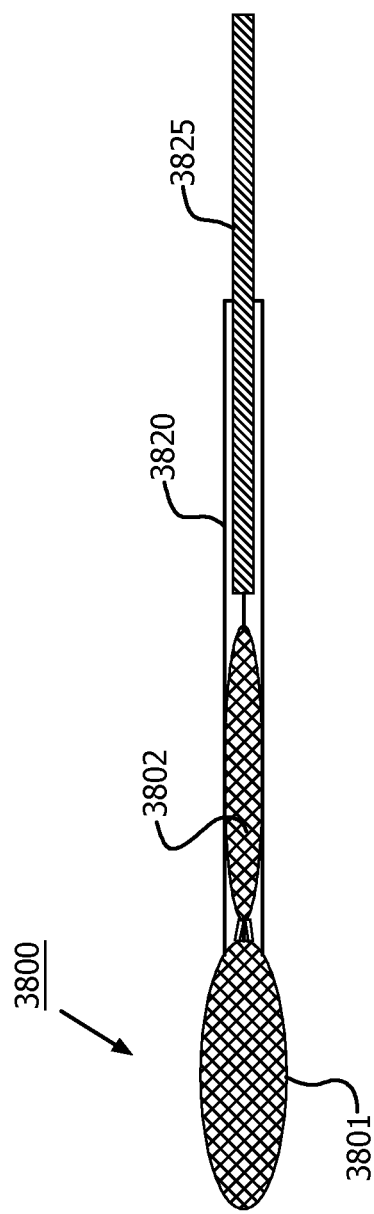

FIG. 31E is an illustration of a sleeve of the intragastric device of FIG. 31A partially loaded onto the delivery device in accordance with at least one embodiment;

FIG. 31F is an illustration of the intragastric device of FIG. 31A fully loaded onto the delivery device in accordance with at least one embodiment;

FIG. 32A is an illustration of a retrieval device for removing an intragastric device, in accordance with one embodiment of the present specification;

FIG. 32B is a flow chart illustrating the steps involved in removing an intragastric device from a patient using the retrieval device of FIG. 31A, in accordance with one embodiment of the present specification;

FIG. 33A is an illustration of an embodiment of an intragastric device in an exemplary post-deployment configuration having a dumbbell shape in accordance with at least one embodiment;

FIG. 33B is an illustration of an embodiment of an intragastric device having a double-wire mesh structure wherein the lower wire mesh is formed from an everted anti-migration component in accordance with at least one embodiment;

FIG. 34A is an illustration of an exemplary intragastric device having a double-wire mesh structure in a post-deployment configuration in accordance with one embodiment of the present specification;

FIG. 34B is an illustration of another exemplary intragastric device having a double-wire mesh structure in a post-deployment configuration in accordance with one embodiment of the present specification;

FIG. 34C is an illustration of another exemplary intragastric device having a double-wire mesh structure in a post-deployment configuration in accordance with one embodiment of the present specification;

FIG. 34D is an illustration of another exemplary intragastric device having a double-wire mesh structure in a post-deployment configuration in accordance with one embodiment of the present specification;

FIG. 34E is an illustration of another exemplary intragastric device having a double-wire mesh structure in a post-deployment configuration in accordance with one embodiment of the present specification;

FIG. 34F is an illustration of another exemplary intragastric device having a double-wire mesh structure in a post-deployment configuration in accordance with one embodiment of the present specification;

FIGS. 34G and 34H are illustrations of another exemplary double-wire mesh intragastric device in a post-deployment configuration in accordance with one embodiment of the present specification;

FIG. 34I is an illustration of an intragastric device having two wire meshes coupled with an anti-migration feature, in accordance with an embodiment of the present specification;

FIG. 34J is an illustration of a top view of the intragastric device of FIG. 34I showing the diameter of the opening in accordance with at least one embodiment;

FIG. 34K is an illustration of a portion of an anti-migration component attached to a portion of the first and second wire mesh structure by wires in accordance with at least one embodiment;

FIGS. 34L and 34M are illustrations of loops formed in the wire mesh structures in accordance with at least one embodiment;

FIG. 35 is an illustration of one single exemplary intragastric device being attached to a previously deployed single intragastric device in a stomach in accordance with at least one embodiment;

FIG. 36 is an illustration of an exemplary fully deployed combined intragastric device in a stomach in accordance with at least one embodiment;

FIG. 37A is a side perspective view of an exemplary intragastric device having a combined dual-wire mesh structure in a post-deployment configuration in accordance with one embodiment of the present specification;

FIG. 37B is an oblique perspective view of the intragastric device of FIG. 37A in accordance with at least one embodiment;

FIG. 37C is an illustration of a plurality of sutures to flexibly connect first and second wire mesh structures of the intragastric device of FIG. 37A in accordance with at least one embodiment;

FIG. 37D is an illustration of a sleeve coupled to the intragastric device of FIG. 37A, in accordance with an embodiment of the present specification;

FIG. 37E is an illustration of two exemplary suture points that flexibly connect first and second wire mesh structures of the intragastric device of FIG. 37A in accordance with at least one embodiment;

FIG. 37F is an illustration of a relative degree of movement of first and second wire mesh structures of the intragastric device of FIG. 37A in accordance with at least one embodiment;

FIG. 38A is an illustration of a process of deploying a combined intragastric device wherein one wire mesh structure is nearly completely deployed while the other wire mesh structure is still constrained in a catheter in accordance with at least one embodiment;

FIG. 38B is an illustration of a process of withdrawing or removing the combined intragastric device wherein one wire mesh structure is partially constrained within the catheter while the other wire mesh structure is still in unconstrained or deployed state in accordance with at least one embodiment;

FIG. 38C is an illustration of the process of withdrawing or removing the combined intragastric device wherein one wire mesh structure when fully constrained within the catheter causes the other wire mesh structure to be aligned or oriented for compression within the catheter in accordance with at least one embodiment; and FIG. 38D illustrates that the aligned or oriented wire mesh structure begins to get constrained or compressed into the catheter for removal, as the fully compressed wire mesh structure is further withdrawn into the catheter in accordance with at least one embodiment.

DETAILED DESCRIPTION

In one embodiment, the present specification is directed toward an intragastric device of dynamic weight used in obese patients to induce weight loss. In various embodiments, the intragastric device comprises a porous three dimensional structure having a pre-deployment shape and a post-deployment shape. In one embodiment, the porous three dimensional structure is a non-inflatable wire mesh structure, or a spiral structure made of shape memory metal or shape memory polymer that changes from a pre-deployment compressed cylindrical shape to a post-deployment sphere, oval, kidney bean or any predefined shape of significant volume. In another embodiment, the intragastric device is made of a plastic material or a polymer such as polyether ether ketone (PEEK) or polyester or a bioresorbable material. The device changes back and forth from the pre-deployment to post-deployment shape by minimal mechanical force and/or temperature changes arising from the room temperature pre-deployment shape to the body temperature post-deployment shape. The device is delivered endoscopically to the stomach via a catheter. The device can be placed through the endoscope, over an endoscope or over a guidewire with endoscopic or fluoroscopic guidance/assistance.

The device has a pre-deployment compressed shape to facilitate insertion and a post-deployment expanded shape that resides in the gastric lumen. Post-deployment volume of the device is significantly larger than pre-deployment volume. In one embodiment, the post-deployment device has a volume of at least 100 ml. The post-deployment device occupies a significant volume in the stomach, thereby reducing available gastric volume available for storage of ingested food. This restricts the amount of food intake, inducing satiety and curbing one's appetite. In one embodiment, the device is also designed to intermittently, with gastric peristalsis, slow or block the passage of the food from the stomach into the small intestine, thereby slowing gastric emptying. In various embodiments, the device also functions to create a biliopancreatic diversion, either by bypassing ingested food past pancreatic secretions or by bypassing pancreatic secretions past ingested food.

In one embodiment, the device comprises a shape memory metal and self-expands once deployed to change from the pre-deployment shape to the post-deployment shape. In another embodiment, the device comprises a temperature sensitive metal that is cooled in its pre-deployment shape and then self-expands when exposed to human body temperature to achieve its post-deployment shape. In another embodiment, an expansion tool is used to apply minimal mechanical force to change the device shape from its pre-deployment shape to its post-deployment shape. In another embodiment, a plastic, polymer, carbon fiber or a bioresorbable material is used to construct the intragastric device.

In one embodiment, the wire structure contains differently weighted material to assist in proper positioning within the stomach. In one embodiment, lighter weighted material is positioned at the top of the wire structure proximate to the top openings and heavier weighted material is positioned at the bottom of the structure, proximate to the bottom openings. This differential weighting insures that the device will be properly situated within the stomach to effectuate the intended effect of slower gastric emptying. In addition, the differential weighting provides for proper gastric positioning without the need of physically anchoring the wire mesh structure to the stomach wall. The differential weight property can also be provided by the ingested food material that enters the device and is selectively accumulated toward the bottom of the device facilitated by the gravitational pull. The differential weight can also be provided by using different amounts of material in the top and bottom halves. The wire mesh structure is free to move about within the stomach while still maintaining its correct top to bottom alignment facilitated by the gravitational pull.

In one embodiment, the device comprises a wire mesh structure which, when in the post-deployment shape, includes mesh openings between the wires of the mesh structure. In one embodiment, the mesh openings are greater than 1 mm in diameter. In one embodiment, the wires of the wire mesh structure are coated with a corrosion-resistant material. The corrosion resistant material prevents exposure and subsequent degradation of the wires of the wire mesh structure from acidic gastric contents once deployed. The corrosion-resistant material completely covers the wires of the wire mesh but does not cover the mesh openings. In one embodiment, the corrosion-resistant material comprises parylene. Parylene is beneficial as a coating in that it is durable, may mitigate nickel ion leaching, and has a lower profile (is thinner once applied). In various embodiments, the corrosion-resistant material comprises silicone, polyester, polyether ether ketone (PEEK), a medical grade epoxy, ceramic, an additional metal, or any other suitable, flexible corrosive resistant material. In one embodiment, the coating metal is tantalum. Tantalum provides corrosive resistance and radio-opacity. In one embodiment, wherein the coating is ceramic, the ceramic coating has a thickness of several angstroms. In various embodiments, any one or combination of the above corrosive resistant materials is used to coat the metal of the wire mesh structure.

In one embodiment, the mesh openings are differentially structured to regulate the flow of food in and out of the mesh. In one embodiment, at least one opening on the bottom half of the device is larger than any of the openings on the upper half of the device, allowing food entering the mesh to exit without the need for further reduction in size of food material.

In another embodiment, the intragastric device further includes an anti-migration component, or collar, coupled to a portion of its distal end. The anti-migration component, similar to the wire mesh of the intragastric device, is configurable between a first, compressed configuration for delivery, and a second, expanded configuration once deployed. The anti-migration component functions as a physical stopper preventing passage of the intragastric device through the pylorus. In various embodiments, the anti-migration component has a diameter that is greater than the diameter of a relaxed pylorus. In one embodiment, the anti-migration component comprises an extension of the wire mesh structure of the intragastric device. In another embodiment, the anti-migration component is a separate piece of wire mesh which is attached to a portion of the distal end of the intragastric device. In various embodiments, the anti-migration component has a shape approximating a bumper, half-bumper, disc, saucer, or any other shape which will prevent migration of the device past the pylorus. In general, the anti-migration collar has a dimension, such as a diameter or length, which 1) is greater than a diameter of the distal opening of the wire mesh structure and 2) is attached to, or integrally formed with, the wire mesh structure distal to the distal opening. In one embodiment, such a diameter or length is in a range of 10 mm to 300 mm.

In other embodiments, a sleeve can be attached to the intragastric device, where the sleeve extends from the stomach into the duodenum where it empties, or through the duodenum and into the jejunum. In one embodiment, the sleeve functions to transit the sequestered chyme from the wire mesh structure directly to the mid duodenum or mid-jejunum. In another embodiment, the sleeve is coupled to the intragastric device but does not directly receive food from the device. In this embodiment, the proximal end of the sleeve is distal to the device and receives food directly from either the stomach or the duodenum. The food entering the sleeve exits at the distal end, into the duodenum or jejunum, bypassing a portion of the small intestine.

The sleeve therefore acts to bypass portions of the gastrointestinal (GI) tract in order to limit the absorption of specific materials in the intestine. The benefits provided by a sleeve are similar to those provided by Roux-en-Y gastric bypass surgery, namely, weight loss and improvement of type II diabetes.

After implantation, the gastrointestinal device of the present specification, particularly the collar, is in constant physical contact with the patient's anatomy without being actually physically attached to the patient's anatomy. This is accomplished by the sleeve being pulled down by the peristaltic actions of the small intestine. As the sleeve is pulled down, the collar of the wire mesh structure contacts the stomach proximal to the pylorus. The sleeve is constantly in physical contact with the pylorus. However, this constant contact with the pylorus does not block food passage. The openings of the wire mesh structure and the lumen of the sleeve pass food through pylorus without occluding it at any point, allowing the food to pass into the intestines. The intragastric device of the present specification physically engages the gastric emptying region of stomach without fully occluding it any point. The intragastric device of the present specification functions as a variable outlet drain and does not act as a stopper to the passage of food.

The gastrointestinal device of the present specification is designed to maximize the amount of food captured and passed through the sleeve and into the intestines rather than minimizing the amount of food passing into intestines. By being in constant contact with the pylorus and stomach, the device is designed to prevent food from passing around and outside of it. In various embodiments, at least 10% of the food exiting a patient's stomach passes through the device and not around the device. In one embodiment, at least 50% of the food exiting a patient's stomach passes through the device and not around the device. In various embodiments, this food that passes into the device and through the sleeve never comes into contact with the patient's duodenum, thereby allowing the device to function as a true pyloric bypass.

In one embodiment, the device is an inflatable balloon with an attached sleeve, wherein the balloon is not in fluid communication with a lumen of the sleeve and the balloon merely acts to hold the sleeve in position without the need to anchor or fix the sleeve to the gastrointestinal wall. The balloon can be inflated or deflated with fluid and is designed to reside in a person's stomach. The sleeve is flexibly attached to the balloon and has a proximal opening and a distal opening wherein the proximal opening is designed to reside proximal to a patient's ampulla and the distal opening is designed to reside distal to a patient's ampulla. Partially digested food enters the proximal opening and exits the distal opening, bypassing the ampullary region. The sleeve is not anchored or fixed to any portion of the gastrointestinal wall.

Wire Mesh Structure

In various embodiments, the intragastric device comprises a porous three dimensional structure having a pre-deployment shape and a post-deployment shape. In one embodiment, the device, in the post-deployment configuration, comprises a three dimensional wire mesh structure defining an internal volume and having a proximal end and a distal end.

In various embodiments, the wire mesh structure includes free ends or 'nodes' comprising bends or curves in the wire of the wire mesh structure wherein these bends or curves are unsupported and not connected to any other portion of the wire mesh. In some embodiments, the wire mesh structure includes two pluralities of nodes. A first plurality is positioned at the proximal end of the structure and a second plurality is positioned at the distal end of the structure. When the wire mesh structure is compressed to its pre-deployment configuration, the first and second plurality of nodes at the proximal and distal ends of the structure respectively, become gathered together or 'bunched up'. This creates a larger cross-sectional area (or diameter) at the proximal and distal ends of the structure when compared to the cross-sectional area of the compressed structure between said ends. As its cross-sectional area becomes larger, the compressed wire mesh structure becomes increasingly difficult to deploy through a narrow delivery device or catheter. This delivery problem can be addressed in at least two different ways. In various embodiments, the number of nodes in each plurality of nodes is reduced. Reducing the number of nodes in each plurality makes the structure easier to compress and creates a smaller cross-sectional area at the ends of the structure. This reduces the force applied by the compressed structure to the delivery catheter, thereby making it easier to pass the compressed structure through the catheter. In various embodiments, a portion of the nodes from one or both of the first and second plurality of nodes is moved from said ends of the structure and positioned along the body of the structure, creating additional pluralities of nodes. This 'staggering' of the nodes reduces the cross-sectional area of the compressed structure at any given point and distributes the force applied by the compressed structure to the delivery catheter, again easing the passage of the delivery structure through the catheter. In various embodiments, the number of nodes in each plurality is reduced and the nodes are staggered in multiple pluralities throughout the structure to reduce and distribute the force applied by the compressed structure to the delivery catheter. Reducing and distributing said force allows for easier delivery and for the use of a delivery catheter having a smaller diameter. Reduced and distributed forces also allow for the creation of larger mesh structures that can be compressed to smaller sizes.

In various embodiments, each plurality of nodes comprises 10 to 100 individual nodes. In one embodiment, each plurality of nodes comprises 44 nodes. In another embodiment, each plurality of nodes comprises 36 nodes. In various embodiments, a wire mesh structure includes 2 to 60 pluralities of nodes distributed latitudinally at different locations along its length. In one embodiment, the nodes are staggered such that at least 10% of the total number of nodes in the structure are positioned at the proximal and distal ends. In various embodiments, no more than 75% of the total number of nodes are positioned in any one plurality of nodes. In various embodiments, the nodes are distributed within at least three different lateral pluralities along the length of the structure.

The compressibility of the wire mesh structure also depends on the flexibility of the mesh. The flexibility, in turn, depends upon, among other variables, the thickness of the wire, the angle of wire intersections, and the number of wires. Regarding the angle of wire intersections, as the wires of the structure are arranged more parallel to one another, the structure becomes more flexible. In various embodiments, the wire mesh structure, in a pre-deployment configuration, has an overall length of 5 to 50 cm and each wire has a thickness in a range of 0.1 to 1 mm. In one embodiment, each wire has a thickness of 0.44 mm. The wires of the wire mesh structure have a bending strain which determines how they behave as the structure is compressed. In various embodiments, the wires are comprised of a shape memory metal, such as, in one embodiment, Nitinol. The shape memory metal has a certain bending strain percentage beyond which the metal loses its ability to exactly regain its previous shape. The strain percentage (%) can be defined by the following formula:

$$\text{strain \%} = 2t/R \times 100$$

wherein t=thickness of the wire and R=radius of the bend. In one embodiment, once the strain percentage reaches 8%, a permanent change is introduced to the shape memory metal such that it will no longer return fully to its original shape. This factor becomes important as the wire mesh structure is compressed to its pre-deployment shape for delivery. In various embodiments, the wire mesh structure includes a collar or circular extension of the wire mesh at its distal end which functions as an anti-migration component. This collar must me folded out distally during compression such that the compressed structure will fit into the delivery device or catheter. A 'bump' in the wire mesh structure is introduced as the collar is folded out during compression. A strain percentage of less than 8% creates a smaller bump in the compressed wire mesh structure, allowing for easier passage of the compressed structure through a delivery catheter. Therefore, in various embodiments, the wire mesh structure is configured having a wire thickness and a bend radius at the collar such that the strain percentage at the collar will be no more than 20%, and preferably less than 8%. In various embodiments, the radius of the collar is less than 10 times the wire thickness. In various embodiments, the strain percentage is in a range of 0.1 to 20%. In various embodiments, the wire of the wire mesh has a thickness of 0.1 to 1.0 mm and the collar has a bend radius of 0.013 to 20 cm. In one embodiment, the wire of the wire mesh has a thickness of 0.4 mm. In various embodiments, the wire thickness and bend radius are configured to satisfy the following statement:

$$2t < R < 2000t$$

wherein t=thickness of the wire and R=radius of the bend.

In various embodiments, the ends of the wire(s) of the wire mesh structure are terminated in such a way to minimize the possibility of traumatic injury to body tissues during delivery and retrieval and while deployed. In some embodiments, the wire mesh structure comprises a single wire folded into a three dimensional structure. In other embodiments, the wire mesh structure comprises more than one wire joined and folded into a three dimensional structure. In various embodiments, the free ends of the wire or wires are joined by crimping a titanium tube or Nitinol (or other shape memory metal) tube over said free ends. In other embodiments, the free ends of the wire or wires are joined by spot welding said free ends together. In one embodiment, the intersections of the wires are not welded. In another embodiment, the intersections of the wires are welded.

Sleeve

In various embodiments, the intragastric device of the present specification further comprises a flexible sleeve component coupled to the wire mesh structure. In multiple embodiments, any of the wire mesh structures discussed above is coupled with any of the sleeve components discussed below. The sleeve component comprises an elongate tubular body having a proximal end and a distal end a lumen within.

In one embodiment, the sleeve has a consistent diameter along its entire length. In other embodiments, the sleeve comprises a funnel shape proximate its proximal end wherein the diameter of the sleeve is greatest at the first opening at the proximal end of the sleeve body and then decreases gradually as it extends distally until it reaches a minimum diameter at a position proximal to the midpoint of its length. The diameter then remains constant distally along the remainder of its length.

In various embodiments, wherein the wire mesh structure includes a collar at its distal end, the proximal end of the sleeve is attached to the bottom surface of said collar by one of the means listed above. In various embodiments, when the device is compressed into its pre-deployment configuration, the sleeve body is pulled upon to assist in folding out the collar. If the proximal end of the sleeve is attached to the bottom surface of the collar as described above, the collar is not fully straightened when folded out, resulting in the creation of a large bulge at the collar when the device is in the pre-deployment configuration. The bulge has a large diameter comprising the thickness of the wire mesh structure and double the thickness of the sleeve. Therefore, in preferred embodiments, the proximal end of the sleeve is attached to the free ends, or nodes, of the collar by a plurality of loose sutures. The sleeve is sutured to each node much similar to the way in which the fabric of an umbrella is attached to the end of each spine of the umbrella. When an umbrella is closed, the fabric collapses down to allow for compression. The intragastric device of the present specification functions in a similar manner. In various embodiments, as the wire mesh structure is compressed for loading onto a delivery device, the distal end of the sleeve is pulled upon. The loose sutures attaching the sleeve to the nodes of the wire mesh allow the sleeve to move relative to the wire mesh such that the collar is pulled distally and extended into a more linear shape. Such an attachment avoids the creation of a large bulge at the collar of the pre-deployment configuration. When the sleeve body is pulled upon during compression, the collar is folded out more completely and the resultant bulge has a smaller diameter, comprising only the thickness of the wire mesh structure. In various embodiments, when the intragastric device is in the pre-deployment configuration, there is minimum to zero overlap between the collar and the sleeve. Upon deployment, the shape memory properties of the wire mesh structure cause the collar to pull the sleeve onto itself as it expands, much like an umbrella expanding its fabric as it opens.

In various embodiments, each node at the distal end of the wire mesh structure (or collar) is attached to the proximal end of the sleeve via a suture. This can lead to bulking at the attachment of the wire mesh structure to the sleeve. Therefore, in other embodiments, fewer nodes are sutured to the sleeve. For example, in one embodiment, every other node is sutured to the sleeve to reduce the number of suture knots and decrease bulking. The inclusion of glue and multiple loops in each suture knot can also lead to bulking at the attachment point of the wire mesh structure to the sleeve. As such, in various embodiments, glue is not used and each suture knot is limited to one loop. Suturing of the sleeve to the nodes can lead to sliding of the suture knots along the length of wire comprising the nodes, resulting in unintended movement of the sleeve relative to the wire mesh structure. To prevent sliding, in various embodiments, each suture knot is placed at the first junctions of the wires proximal to each node. In effect, each suture is then placed over two wires and cannot slide along one or the other. To eliminate excessive bulking, in various embodiments, fewer than every first wire junction is sutured to the sleeve. For example, in one embodiment, every other first wire junction is sutured to the sleeve.

In various embodiments, any sharp ends of wires in the wire mesh and/or sleeve are crimped and looped onto themselves or looped outward to act as pulling points for moving the sleeve into the intestines or for connecting the sleeve to the wire mesh structure.

The distal end of the sleeve can be designed to be weighted so that the sleeve remains in an elongated shape extending through a portion of the duodenum. In one embodiment, the sleeve includes a small weight attached to its distal end. In another embodiment, wherein the second opening at the distal end of the sleeve body is positioned along the sleeve body at its distal end, the distal end of the sleeve body further includes a blind pouch. The blind pouch functions to intermittently trap a small portion of food or fluid there within. The trapped food or fluid acts to weigh down the distal end of the sleeve body, thereby keeping the sleeve component elongated. In one embodiment, the distal end of the sleeve is reinforced with at least a second layer to assist in keeping the distal end positioned downward and prevent it from folding up.

In one embodiment, the sleeve comprises a wire mesh configuration having a plurality of nodes, similar to the configuration described above for the wire mesh structure.

In another embodiment, the sleeve component comprises a membrane that is flexible and compressible by the contractions of the small intestine. In one embodiment, the sleeve includes a minimum level of structure which imparts upon the sleeve a minimum amount of structural strength to resist buckling from gastrointestinal forces and remain functional. In one embodiment, the minimum level of structure comprises a single structure extending along at least 10% of a length of the sleeve to provide the sleeve with linear strength. In various embodiments, the single structure is a straight wire, a wire helix, or a wire mesh. In one embodiment, the membranous sleeve component comprises a plurality of horizontal and/or vertical support elements along the length of the sleeve body. In one embodiment, the horizontal elements include wire rings spaced apart along the length of the sleeve body. In various embodiments, the rings are spaced between 2 and 24 inches apart. In one embodiment, the rings are spaced 6 inches apart. In one embodiment, the vertical support elements include elongate metal wires. In various embodiments, the wires are between 2 and 60 inches in length. In one embodiment, the metal wires are 6 inches in length. In another embodiment, the membranous sleeve component comprises a spiral metal wire extending along its length. The spiral metal wire provides support to the sleeve component and maintains its elongated shape. In various embodiments, the spiral metal wire is comprised of a shape memory metal, such as Nitinol. The spiral metal wire must not be too tight such that, once the sleeve in compressed for delivery, it becomes kinked and cannot regain its full shape. In various embodiments, the spiral metal wire of the sleeve has a thickness of 0.1 to 1.0 mm. In one embodiment, the spiral metal wire of the sleeve has a thickness of 0.2 mm. As similarly discussed above with reference to the collar bend radius, the bend radius of the spiral metal wire of the sleeve should be such to create a strain percentage that will be in a range of 0.1 to 20%, and preferably less than 8%. In various embodiments, the strain percentage (%) of the spiral metal wire can be defined by the following formula:

$$\text{Strain\%} = \frac{d}{2} \times \left[ \frac{1}{Rf} - \frac{1}{Ri} \right] \times 100$$

wherein d is the diameter of the wire, Rf is the final bend radius, and Ri is the initial bend radius. Therefore, in various embodiments, the spiral metal wire has a pitch in a range of 5 to 150 mm. In one embodiment, the spiral metal wire has a pitch of 60 mm. In various embodiments, the sleeve includes more than one spiral metal wire to provide greater support while still preventing permanent kinking. In one embodiment, the sleeve includes three spiral metal wires wherein each individual wire has a pitch of 60 mm and the wires are spaced such that the pitch between two separate wires is 20 mm. In another embodiment, the sleeve includes six spiral or helical wires to provide structural support to the sleeve. In various embodiments, the membrane of the sleeve component extends proximally onto the lower portion of the wire mesh structure and covers all or a portion of said lower portion.

The sleeve is flexible and compressible such that during delivery it is restrained in a compressed configuration on the distal end of a delivery device. In one embodiment, the sleeve telescopes into itself to shorten its length and facilitate delivery. In addition, when the device is in the pre-deployment configuration, the sleeve can be folded onto itself to shorten its length and assist with placement in a delivery device or catheter. In various embodiments, the sleeve is folded 2 to 10 times upon itself and then folded or wrapped along a delivery device or catheter for delivery. In one embodiment, the sleeve is fed coaxially over a guidewire, a delivery device or catheter. In another embodiment, the sleeve is folded along the side or around a delivery device or catheter. This helps prevent the sleeve from sticking to the guidewire and/or delivery device/catheter as the guidewire and delivery device/catheter are retracted, which is sometimes encountered when the sleeve has been fed coaxially over the guidewire or delivery device/catheter.

In other embodiments, some intragastric devices of the present embodiment include a sleeve having a shorter length than the lengths described above. In various embodiments, the short sleeve has an overall length of 100-120 mm. In various embodiments, the short sleeve has a funnel shape or cone shape. In some embodiments, the short sleeve comprises a wire formed into a wire mesh structure or braid having a plurality of nodes, similar to the configuration described above for the wire mesh structure. In one embodiment, the braid is created using a single wire. In one embodiment, the wire is composed of a shape memory metal. In one embodiment, the shape memory metal is Nitinol. In other embodiments, the braid is created by machine braiding multiple wires. In some embodiments, the pitch, or distance between nodes, is uniform. In other embodiments, the pitch is variable. The ends of the braid are designed to be atraumatic. In one embodiment, the ends are blunted. In another embodiment, the ends are capped with a soft polymeric tip. In some embodiments, a portion of the short sleeve is coated with a covering. In some embodiments, the covered portion comprises the floating nodes. In one embodiment, the covering is silicone. In various embodiments, the diameter of the proximal end of the sleeve is approximately equal to the outer diameter of an anti-migration collar at the distal end of a wire mesh structure. In such embodiments, the proximal end of the sleeve is fitted over and attaches to the anti-migration collar. In other embodiments, the diameter of the proximal end of the sleeve is smaller than the outer diameter of an anti-migration collar and approximately equal to the diameter of a neck of the collar connecting said collar to said wire mesh structure. In these embodiments, the proximal end of the sleeve is attached to said neck of said collar.

In one embodiment, the number of nodes is uniform across the braid. In one embodiment, the number of nodes is 24. In other embodiments, the number of nodes is variable across the braid. For example, in various embodiments, the short sleeve braid includes 24 nodes at the proximal end and 18 or 12 nodes at the distal end. In these embodiments, the nodes comprising the difference in number of nodes between the two ends (for example, 6 or 12 nodes) are floating nodes and are positioned along the body of the short sleeve.

Once an intragastric device having a short sleeve is deployed, the short sleeve intermittently engages and blocks a patient's pylorus without being anchored to the pylorus. This prevents food from passing through the pylorus and forces the food to pass through the short sleeve from the stomach and into the duodenum, thus regulating gastric outflow. In various embodiments, an opening at the distal end of the short sleeve is 1-30 mm in diameter wherein the size of the diameter determines the rate of gastric outflow. In one embodiment, the opening can be 0 mm when the pylorus is engaged, thereby completely blocking outflow. Therefore, food is allowed to enter the duodenum from the stomach only when the pylorus is not engaged or only partially engaged.

In various embodiments, the sleeve has a high coefficient of friction compared to sleeves of the prior art. In various embodiments, the sleeve has a coefficient of friction ranging from 0.01-0.45. In one embodiment, the sleeve has a coefficient of friction equal to or less than 0.10. It has been encountered with relatively smooth sleeves that, during deployment, the smooth sleeve can become stuck to the inside of a delivery catheter or stuck to itself, resulting in destruction of the sleeve as force is applied to free the sleeve. Therefore, a sleeve with a rougher outer surface can be easier to feed into a delivery device or catheter and then deploy. In various embodiments, the sleeve includes a matte outer surface. In other embodiments, a particulate matter or relatively rough substance, such as corn starch or biocompatible powder, is applied to the outer surface of the sleeve prior to loading the sleeve into a delivery device and deployment.

In various embodiments, the sleeve includes one or more radiopaque markers to ensure proper positioning of the sleeve using radiographic imaging. In various embodiments, the radiopaque markers include a plurality of individual markings along an outer surface of the sleeve body. In other embodiments, the radiopaque marker includes a single line extending along an outer surface of the sleeve body. A spiraled single line can indicate twisting of the sleeve. In still other embodiments, the radiopaque markers include a plurality of individual markings and a single line extending along an outer surface of the sleeve body. In other embodiments, no radiopaque markings are necessary as the wire thickness of the support elements of the sleeve is great enough to allow for radiographic visualization.

Retrieval Mechanism

In various embodiments, the wire mesh structure or wire mesh structure with coupled sleeve component includes one or more retrieval mechanisms with at least one retrieval mechanism positioned proximate the at least one opening at the proximal end of the wire mesh structure. In one embodiment, the retrieval mechanism comprises an 80 lb. break strength rated retrieval suture.

Anti-Migration Component

In various embodiments, the wire mesh structure or wire mesh structure with coupled sleeve component includes one or more anti-migration components or collars. In one embodiment, the anti-migration component is comprised of a metal. In one embodiment, the metal is a shape memory metal, such as Nitinol. The anti-migration component is preferably positioned at the distal end of the wire mesh structure (at the junction of the wire mesh structure with the sleeve component in the embodiment of the device including a sleeve) and, once the device is deployed, comes to rest proximal to the pylorus. The anti-migration component functions to prevent passage of the wire mesh structure or entire device through the pylorus. The anti-migration component is in the form of a collar, an open torus, or a surface of revolution generated by revolving a semi-circle in three-dimensional space about an axis extending through the center of the wire mesh (spherical or elliptical) device or the center of the opening of the lower portion of the wire mesh device.

In various embodiments, various components of the device, including the wire mesh structure, retrieval mechanism, and/or anti-migration component are coated with a therapeutic drug to enhance functionality of the device.

In various embodiments, the wire mesh structure, hook, and/or anti-migration component include a radiopaque marker for radiographic visualization to facilitate delivery and retrieval. In various embodiments, the wire mesh structure, hook, and/or anti-migration component include an ultrasound marker for ultrasound visualization to facilitate delivery and retrieval.

Delivery Device

The present specification also discloses various embodiments of a delivery device used to deploy an intragastric device in the gastrointestinal tract of a patient. An intragastric device is preloaded onto a delivery device which is then used to deliver the wire mesh of the intragastric device into the stomach and the sleeve of the intragastric device into the proximal small intestine.

In one embodiment, a delivery device comprises an elongate tubular body having a coaxial plunger and catheter and a plurality of handles. The handles are manipulated to deploy the sleeve and wire mesh structure of the intragastric device in multiple stages. In one embodiment, the tubular body includes a trigger which controls movement of the various components of the delivery device to effectuate intragastric device deployment.

In various embodiments, the intragastric device can be retrieved using a standard overtube, endoscope, and grasper.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
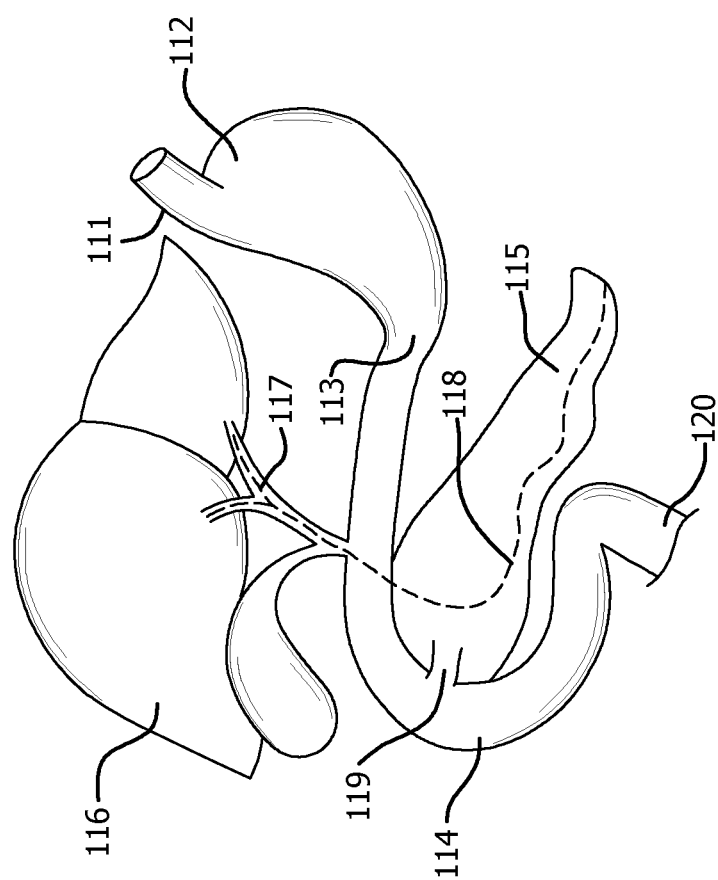
FIG. 1 is an illustration of an upper gastrointestinal system.

FIG. 1 is an illustration of an upper gastrointestinal system. After swallowing, food passes rapidly through the esophagus 111 into the stomach 112. There, it is digested for a period of time and undergoes the process of dilution to an iso-osmotic concentration by grinding and mixing with gastric juices. The stomach 112 relaxes to accommodate the volume of ingested food. As the stomach 112 gets filled with food the sensation of fullness or satiety is generated by stretch receptors in the gastric wall and the person stops eating. The iso-osmotic food, known as chyme, then passes through the pylorus 113 into the duodenum 114. Passage of chyme into the duodenum 114 results in the release of enzyme rich pancreatic secretions from the pancreas 115 and bile salt rich biliary secretions from the liver 116. The biliary secretions travel through the common bile duct 117 where they combine with the pancreatic secretions arriving through the pancreatic duct 118 and the two ducts combine to form the ampulla of vater 119. The ampulla of vater 119 serves as the entry point for the secretions to be deposited into the duodenum 114. In the jejunum 120, the mixing of pancreatic and biliary secretions with the chyme results in the digestion of proteins, fats, and carbohydrates, which are then absorbed into the blood stream.

Figure 2A:
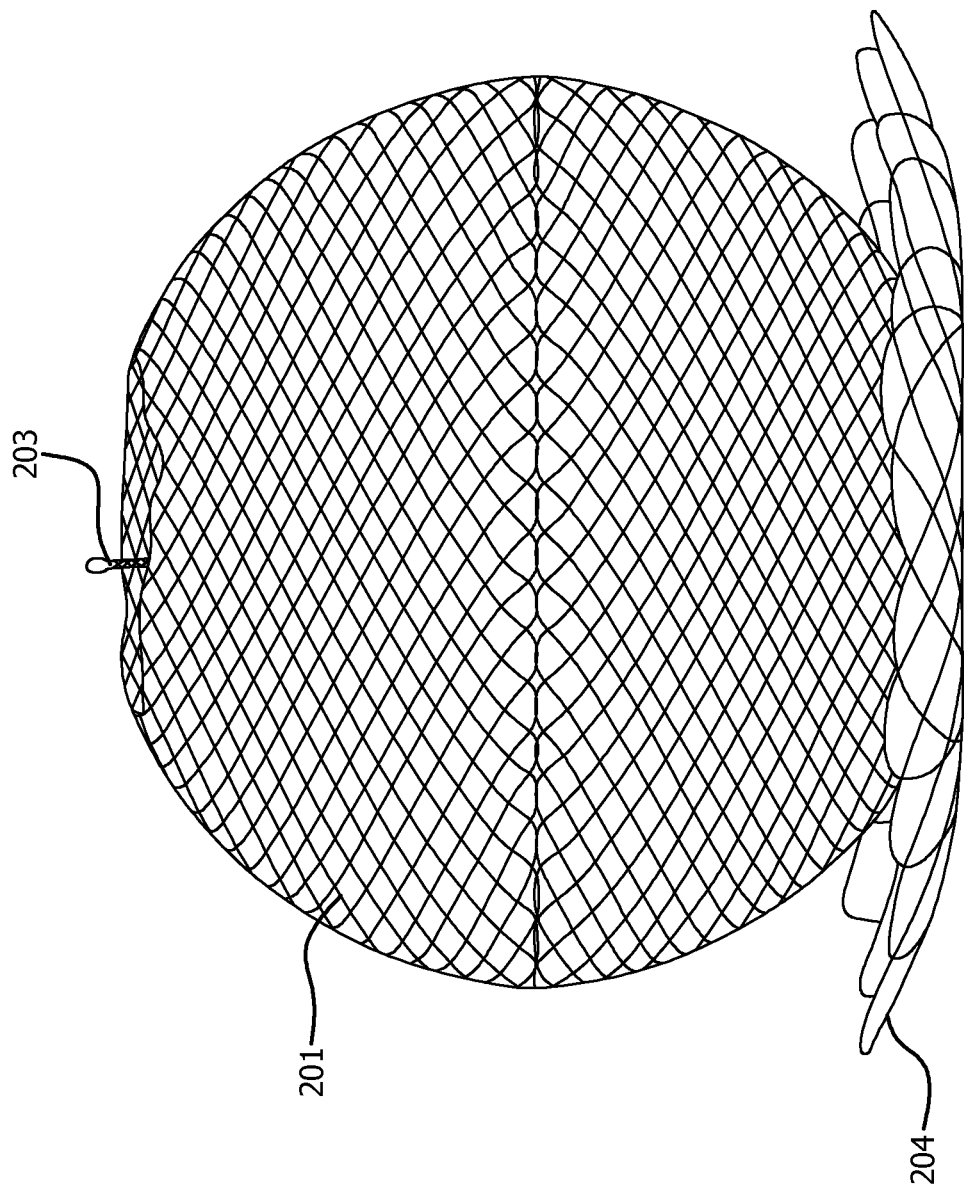
FIG. 2A is an illustration of a wire mesh structure in a post-deployment configuration with a proximally sloping anti-migration disc or collar attached to its distal end, in accordance with one embodiment of the present specification.

FIG. 2A is an illustration of a wire mesh structure 201 of an intragastric device in a post-deployment configuration with a proximally sloping anti-migration disc or collar 204 extending from or attached to its distal end, in accordance with one embodiment of the present specification. The wire mesh structure 201 comprises a three dimensional porous structure having an internal volume. The wire mesh structure 201 has an oval shape and includes a retrieval mechanism 203. In one embodiment, the retrieval mechanism is a silk suture loop. In one embodiment, the retrieval mechanism is an 80 lb. retrieval suture. The anti-migration collar 204 is proximally sloping in that it comprises a distal portion of the wire mesh structure 201 that is folded such that the distally directed end of the wire mesh structure 201 is made to point toward the proximal end of the wire mesh structure 201. In other embodiments, the collar 204 comprises any curved/atraumatic structure positioned circumferentially around the distal end of the wire mesh structure 201. The collar 204 helps prevent the wire mesh structure 201 from entering and passing through the pylorus. In one embodiment, the wire mesh structure 201 includes a bulbous, predominantly spherical or ovoid proximal end and an expanded distal end. In one embodiment, the distal half of the structure is covered with a membrane to impede the passage of food out of the structure 201, directing the food through a distal opening. In one embodiment, the structure 201 has an optional anti-reflux valve at the proximal end and another optional valve at the distal end. The valve at the distal end acts to control the flow of chyme or partially digested food from the inside of the structure 201 to the outside of the structure 201.

Figure 2B:
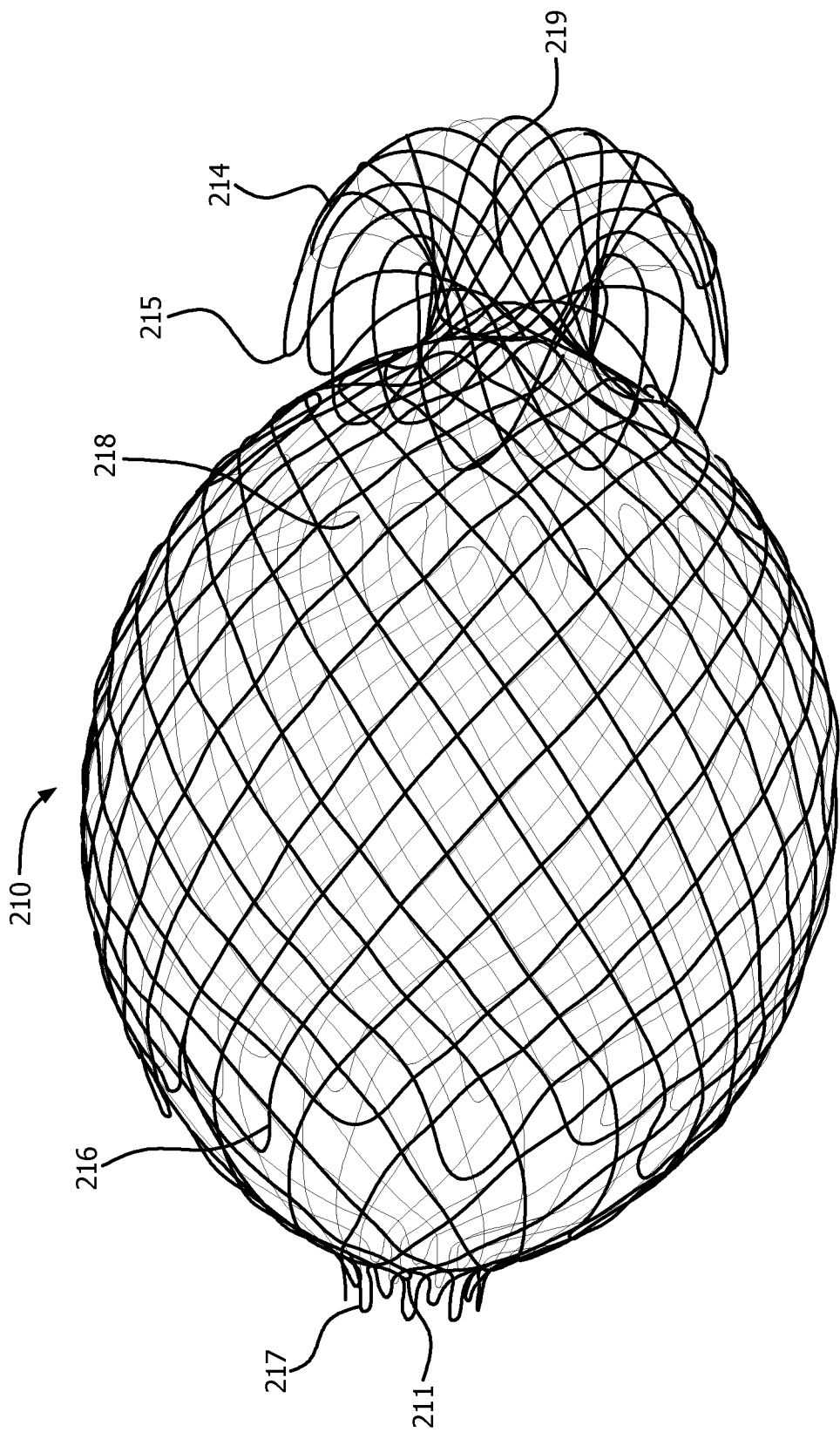
FIG. 2B is an illustration of a wire mesh structure in a post-deployment configuration with a proximally curving anti-migration collar formed at its distal end, in accordance with one embodiment of the present specification.

FIG. 2B is an illustration of a wire mesh structure 210 in a post-deployment configuration with a proximally curving anti-migration collar 214 formed at its distal end, in accordance with one embodiment of the present specification. The wire mesh structure 210 has an oval shape with a proximal end and a distal end. The wire mesh structure 210 includes a first opening 211 at its proximal end and a second opening 219 at its distal end. The wire mesh structure 210 includes staggered nodes 216, 218 within its body to facilitate compression for delivery and removal. The wire mesh structure 210 also includes a set of staggered nodes 217 at its proximal end. The staggered nodes 217 at the proximal end provide a location for grasping, thereby enhancing ease of retrieval. The anti-migration collar 214 is formed from a continuation of the wire of the wire mesh structure 210 at its distal end. The anti-migration collar 214 bends proximally, toward the body of the wire mesh structure 210, and its ends 215 are formed in a rounded fashion to be atraumatic to body tissues. In various embodiments, the wire mesh structure 210 has no sharp edges, preventing the occurrence of abrasions, and a radial force high enough to prevent any significant or permanent deformation by gastric contractions and passage through the pylorus, but low enough such that the wire mesh structure 210 is not too rigid, allowing it to be affected by gastric contractions enough to facilitate movement of food through the wire mesh structure 210. In some embodiments, the wire mesh structure can withstand a contractile force up to 200 mm Hg without being completely compressed. The anti-migration collar 214 is defined by a surface of revolution generated by revolving a semi-circle in three-dimensional space about an axis extending through a center of the second opening 219 of the lower portion of the wire mesh device. The collar 214 is also defined by a diameter equal to or greater than 25 mm.

FIG. 2C is another illustration of a wire mesh structure, in accordance with one embodiment of the present specification. In various embodiments, the length of the wire mesh structure measured from a proximal end 222 to a distal end 224 of anti-migration collar 214 ranges from 169 mm to 180 mm. In some embodiments, the length measured from the proximal end 222 to a distal end 226 of the oval structure is approximately 141 mm and the length of the anti-migration collar 214 measured from a proximal end 228 to a distal end 224 of the anti-migration collar 214 ranges from 31 mm to 36 mm. In an embodiment, a length of a middle portion 230 of the oval structure is approximately 109 mm measured from a distal end of a proximal set of nodes 233 to a proximal end of a distal set of nodes 239, while that of portion 232 is 117 mm measured from a proximal end of the proximal set of nodes 233 to a distal end of a distal set of nodes 239. Also, in an embodiment, lengths of a proximal portion 234 extending from said proximal end 222 to said proximal end of said proximal set of nodes and a distal portion 236 extending from said distal end of said distal set of nodes 239 to said distal end 226 of the oval structure are 12 mm. In other embodiments, length of portion 232 ranges between 114 mm and 129 mm, while the lengths of proximal and distal portions 234, 236 of the oval structure ranges from 8 mm to 12 mm and 7 mm to 14 mm respectively. In embodiments, an inner diameter 238 of anti-migration collar 214, defining an opening at the distal end 224 of the device, ranges from 27 mm to 35 mm while an outer diameter 240, defining the outer limit of the anti-migration collar 214, ranges from 58 mm to 77 mm. Further, in some embodiments, the diameter of the wire mesh structure at a center widest part of the oval structure ranges from 116 mm to 123 mm. In embodiments, a diameter of a circular opening 250 at the proximal end 222 ranges from 17 mm to 20 mm.

As explained with reference to FIGS. 2A and 2B, the wire mesh structure comprises a plurality of openings or gaps 242 forming the mesh. In some embodiments, the gaps 242 are diamond shaped as a result of the crisscrossing pattern of the wire of the wire mesh structure. In an embodiment, a width 244 of the gaps 242 in the middle portion 230 of the mesh ranges from 9.6 mm to 9.7 mm while a length 246 is 16 mm. In various embodiments, individual pieces of wire, such as wire piece 248, are joined together using processes such as riveting or crimping to form the wire mesh structure. In some embodiments, the length of wire piece 248 ranges from 5 mm to 5.5 mm and its diameter is approximately 1 mm.

In embodiments, as explained with reference to FIGS. 2C and 2H, the wire mesh structure comprises a plurality of loops formed in the wires of the mesh proximal end 222, distal end 224 of anti-migration collar 214, and distal end 236 of the oval structure. In some embodiments, a thickness of the wire forming the loops, such as wire loop 252 shown in FIGS. 2E and 2F, is approximately 0.4 mm, the diameter of the circular portion 254 of wire loop 252 is approximately 2 mm, and a thickness 256 of the loop 252 is approximately 1 mm. In an embodiment, the distal end 224 of anti-migration collar 214 comprises 9 loops such as the wire loop 252 shown in FIGS. 2E and 2F.

Figure 3C:
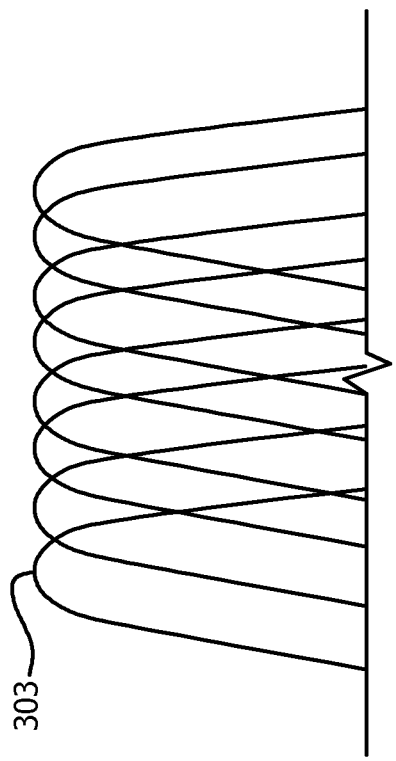
FIG. 3C is an illustration depicting a plurality of overlapping nodes positioned at one end of a wire mesh structure, in accordance with one embodiment of the present specification.

FIGS. 3A and 3B are illustrations depicting a plurality of free ends or nodes 301, 302 positioned at a proximal end and a distal end of a wire mesh structure, in accordance with one embodiment of the present specification. Nodes 301 are positioned at the proximal end of a wire mesh structure and nodes 302 are positioned at a distal end of a wire mesh structure. The nodes comprise bends or curves in the wires of the wire mesh structure which are unsupported or not connected to other portions of the wire mesh. In other words, the nodes are the loops or bends comprising the free ends at each end of the wire mesh structure. Each wire mesh structure comprises at least two pluralities of nodes, one plurality of nodes 301 at its proximal end and at least one plurality of nodes 302 at its distal end. Other wire mesh structure embodiments, for example, those discussed with reference to FIGS. 3C and 3D below, comprise more than two pluralities of nodes which imparts greater compressibility to the wire mesh structures. Such wire mesh structures include free ends or nodes at each end of the structure plus free ends or nodes positioned at lateral locations along the body length of the structure.

Figure 3D:
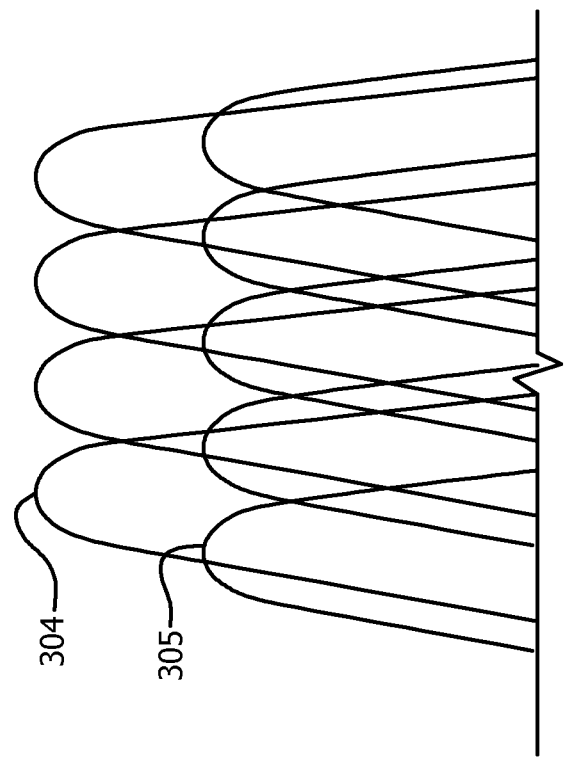
FIG. 3D is an illustration depicting a first plurality of nodes positioned at one end of a wire mesh structure and a second plurality of nodes positioned proximal to the first plurality of nodes, in accordance with one embodiment of the present specification.

FIG. 3C is an illustration depicting a plurality of overlapping nodes 303 positioned at one end of a wire mesh structure, in accordance with one embodiment of the present specification. As depicted in FIG. 3C, the nodes 303 are all positioned at the same lateral location. This creates a bulge in said lateral location when the wire mesh structure is compressed into its pre-deployment configuration. The bulge creates drag force on a delivery device or catheter during delivery of the wire mesh structure. FIG. 3D is an illustration depicting a first plurality of nodes 304 positioned at one end of a wire mesh structure and a second plurality of nodes 305 positioned proximal to the first plurality of nodes 304, in accordance with one embodiment of the present specification. The two pluralities of nodes 304, 305 are staggered across two different lateral locations in FIG. 3D. The staggering of nodes results in a smaller bulge when the wire mesh structure is compressed into its pre-deployment shape, resulting in less drag force applied to a delivery device or catheter and therefore easier delivery and retrieval of the wire mesh structure.

Figure 3E:
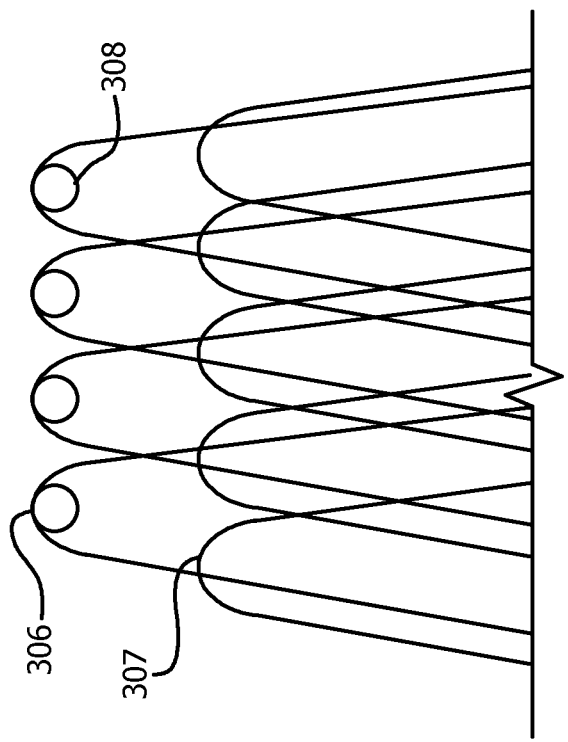
FIG. 3E is an illustration of first and second pluralities of nodes at an end of a wire mesh structure, depicting loops formed in the wires of the first plurality in accordance with one embodiment of the present specification.

FIG. 3E is an illustration of first and second pluralities of nodes 306, 307 at an end of a wire mesh structure, depicting loops 308 formed in the wires of the first plurality 306 in accordance with one embodiment of the present specification. Referring to FIG. 3E, the loops 308 extend in a direction toward the center of the wire mesh structure. In other embodiments, the loops extend outward in a direction away from the center of the wire mesh structure. In some embodiments, the loops 308 serve as attachment points for other device components, for example, a sleeve component, as further discussed with reference to FIGS. 4B and 4C.

Figure 3F:
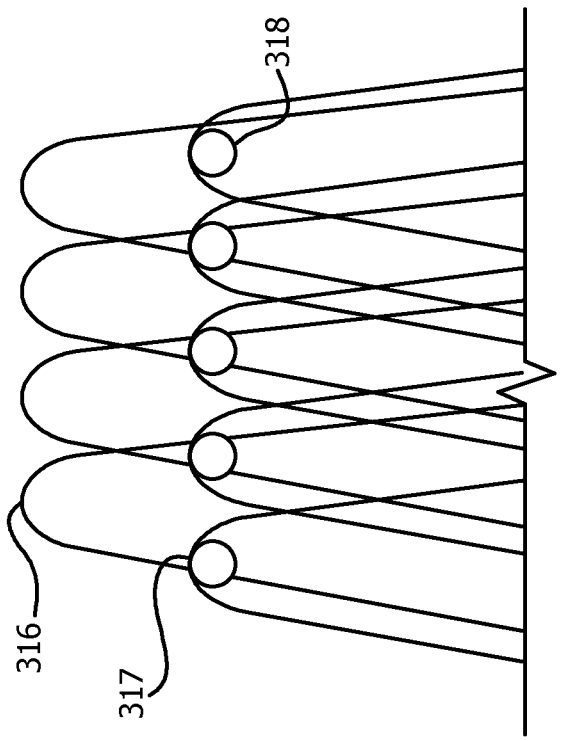
FIG. 3F is an illustration of first and second pluralities of nodes at an end of a wire mesh structure, depicting loops formed in the wires of the second plurality in accordance with one embodiment of the present specification.

FIG. 3F is an illustration of first and second pluralities of nodes 316, 317 at an end of a wire mesh structure, depicting loops 318 formed in the wires of the second plurality 317 in accordance with one embodiment of the present specification. FIG. 3G is an illustration of first and second pluralities of nodes 310, 319 at an end of a wire mesh structure, depicting loops 313, 314 formed in alternating wires of both the first 310 and second 319 pluralities, in accordance with one embodiment of the present specification. The wire loop embodiments depicted in FIGS. 3E through 3G disclose various options for node looping and are not intended to be limiting. In various embodiments, any number or percentage of the wires of a first plurality of nodes, a second plurality of nodes, or both a first and second plurality of nodes, may be looped. For example, in one embodiment, only the outermost nodes, with respect to a center of the wire mesh structure, are looped. In another embodiment, only the nodes just proximal to the outermost nodes are looped. In some embodiments, a percentage between 0 and 100% of the nodes are looped. In one embodiment, 50% of the nodes are looped. In another embodiment, 30% of the nodes are looped.

FIG. 3H is an illustration depicting a wire mesh structure 315 having a first plurality of nodes 311 at its proximal end and a second plurality of nodes 312 at its distal end, in accordance with one embodiment of the present specification. The wire mesh structure 315 of FIG. 3H includes the fewest plurality of nodes possible (two) and will have the largest bulges at its proximal and distal ends when compressed into its pre-deployment configuration. FIG. 3I is an illustration depicting a wire mesh structure 320 having first and second pluralities of nodes 321, 322 at its proximal and distal ends respectively, and third 323 and fourth 324 pluralities of nodes distributed along its surface, in accordance with one embodiment of the present specification. The increased number of pluralities of nodes allows for fewer individual nodes to be positioned at the lateral location of each plurality. As such, when compressed, the wire mesh structure will comprise a bulge at each lateral location of each plurality of nodes but each bulge will be smaller in diameter than the bulges at the proximal and distal ends created when the wire mesh structure seen in FIG. 3H is compressed. Therefore, the compressed pre-deployment configuration of the wire mesh structure of FIG. 3I will create less drag force on a delivery device or catheter and will be easier to deploy. Although four pluralities of nodes 321, 322, 323, 324 are depicted in the wire mesh structure 320 of FIG. 3I, a wire mesh structure can have three or more than four pluralities of nodes. In various embodiments, the wire mesh structure includes 2 to 60 pluralities of nodes positioned at different lateral locations.

FIGS. 3J to 3N are illustrations depicting various possible node shapes in accordance with multiple embodiments. Possible node shapes include, but are not limited to, a sharp bend 331, a shallow bend 332, a pointed bend 333, a circular bend 334, and a shape similar to an end of a safety pin 335, including a wire loop 345 at the end of the node.

Figure 4A:
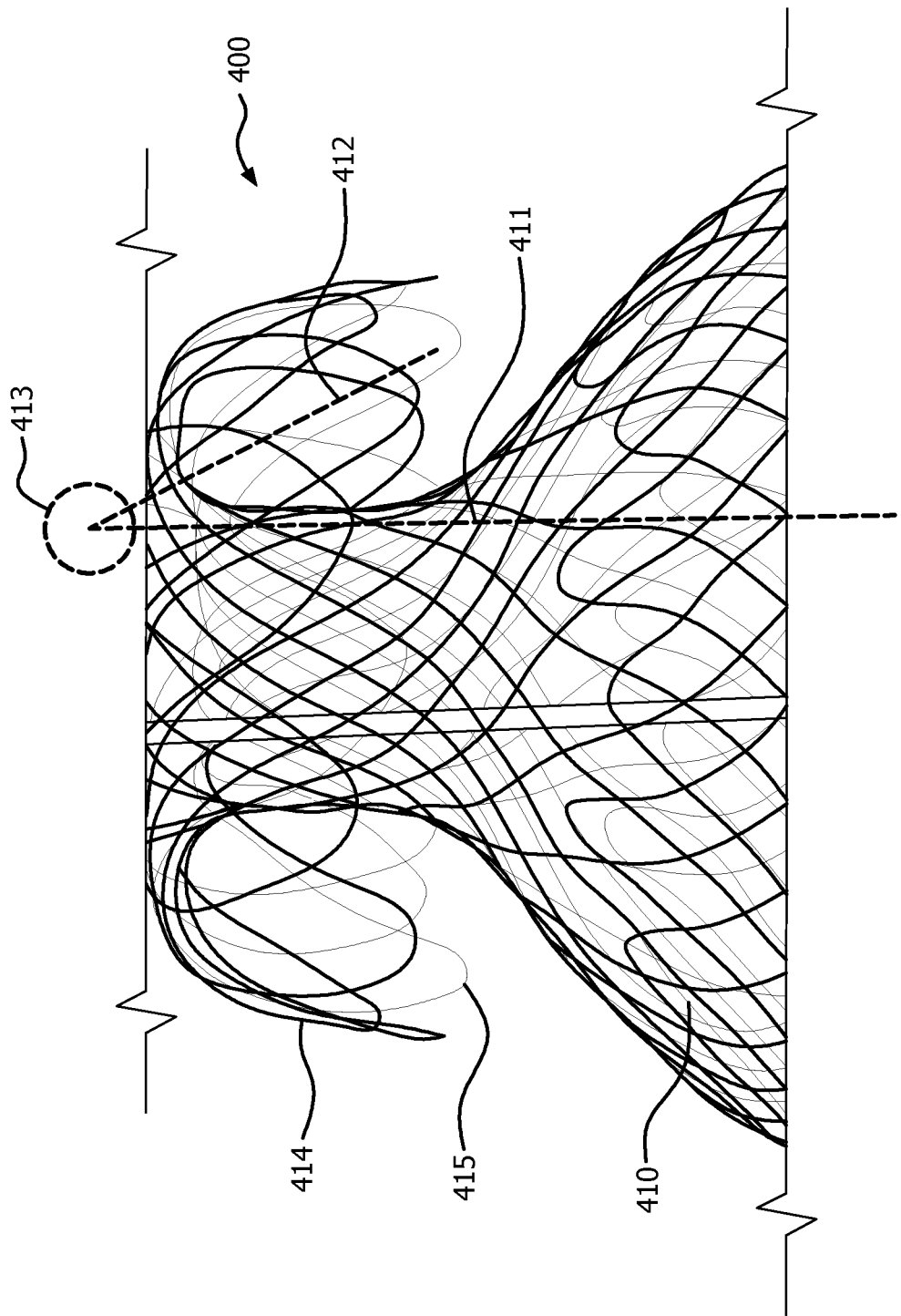
FIG. 4A is a close-up illustration of an atraumatic anti-migration collar of a wire mesh structure of an intragastric device, in accordance with one embodiment of the present specification.

FIG. 4A is a close-up illustration of an atraumatic anti-migration collar 414 of a wire mesh structure 410 of an intragastric device 400, in accordance with one embodiment of the present specification. The anti-migration collar 414 has a toroid bulb shape and comprises rounded ends 415 which extend proximally toward the wire mesh structure 410. The rounded ends 415 are designed to be atraumatic to body tissues. As discussed above, in some embodiments, the ends 415 are separated into various nodes to prevent bunching of the wires when compressed, which could lead to erosions. The long axis of the collar 412 is curved at an angle 413 greater than 90° compared to the long axis of the mesh 411 such that the rounded ends 415 are pointing in the direction toward the wire mesh structure 410.

Figure 4B:
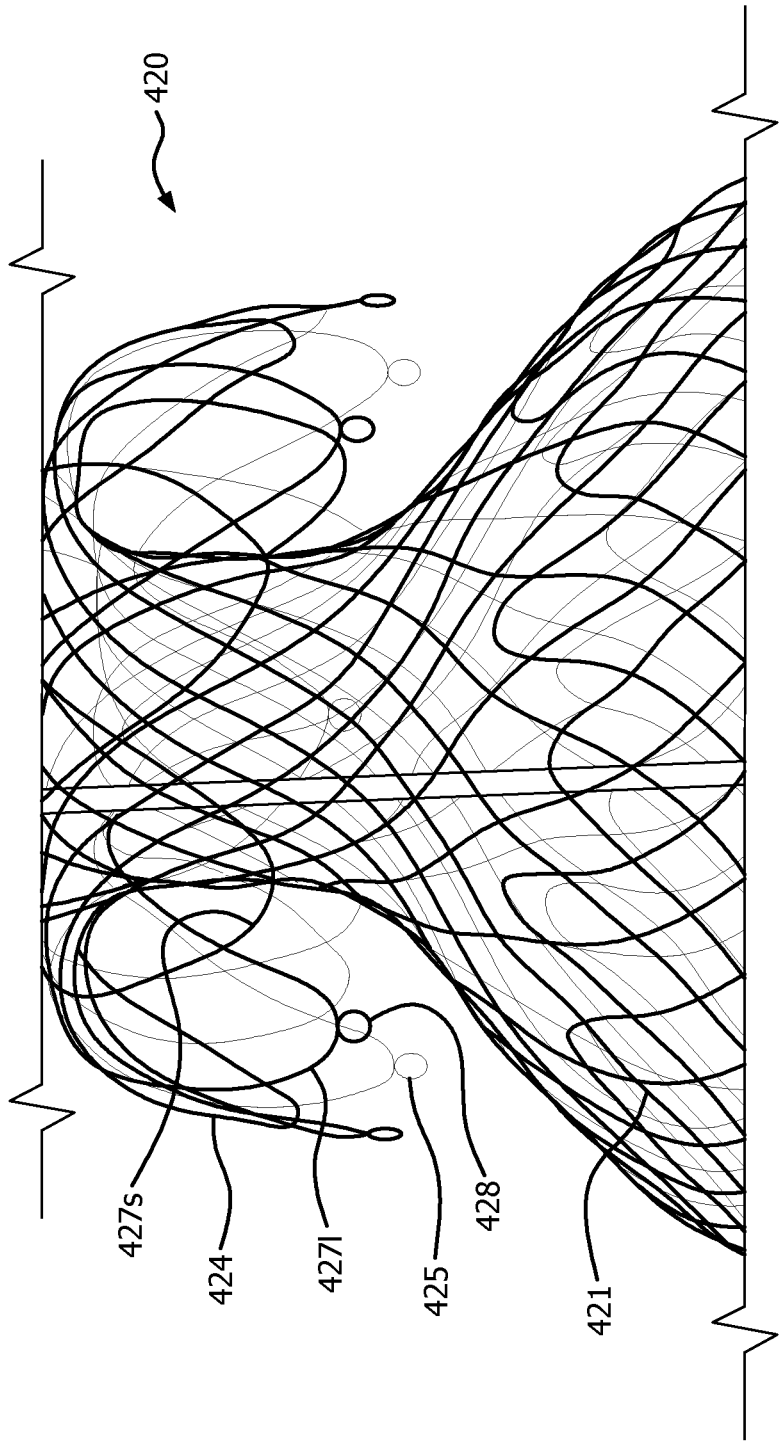
FIG. 4B is a close-up illustration of an atraumatic anti-migration collar of a wire mesh structure of an intragastric device, in accordance with another embodiment of the present specification.
Figure 4D:
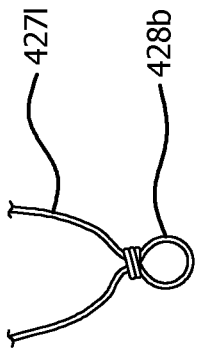
FIG. 4D is an illustration of hoops that are sutured to the free ends of long nodes in accordance with at least one embodiment.
Figure 4C:
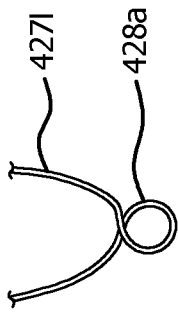
FIG. 4C is an illustration of hoops formed from twisting free ends of long nodes in accordance with at least one embodiment.

FIG. 4B is a close-up illustration of an atraumatic anti-migration collar 424 of a wire mesh structure 421 of an intragastric device 420, in accordance with another embodiment of the present specification. The anti-migration collar 424 has a toroid bulb shape and comprises rounded ends 425 which extend proximally toward the wire mesh structure 421. The rounded ends 425 are designed to be atraumatic to body tissues. In some embodiments, the ends 425 are separated into various nodes 4271, 427s to prevent bunching of the wires when compressed, which could lead to erosions. The nodes include long nodes 4271 and short nodes 427s, wherein the long nodes 4271 extend further in a proximal direction back toward the top of the wire mesh structure 421 than the short nodes 427s. In some embodiments, the collar 424 includes 9 long nodes 4271 and 9 short nodes 427s. The free ends of the long nodes 4271 include hoops 428 for suturing a proximal end of a sleeve component. The hoops 428 extend outward away from the free ends of the long nodes 4271. In one embodiment depicted in FIG. 4C, hoops 428a are formed from twisting the free ends of the long nodes 4271 into a hoop shape. In another embodiment depicted in FIG. 4D, hoops 428b comprise separate wire hoops that are sutured to the free ends of the long nodes 4271. In some embodiments, once the sleeve is attached, additional suture knots are placed at the junction of the twist or separate wire hoop to prevent sliding of the sleeve attachment.

Figure 4E:
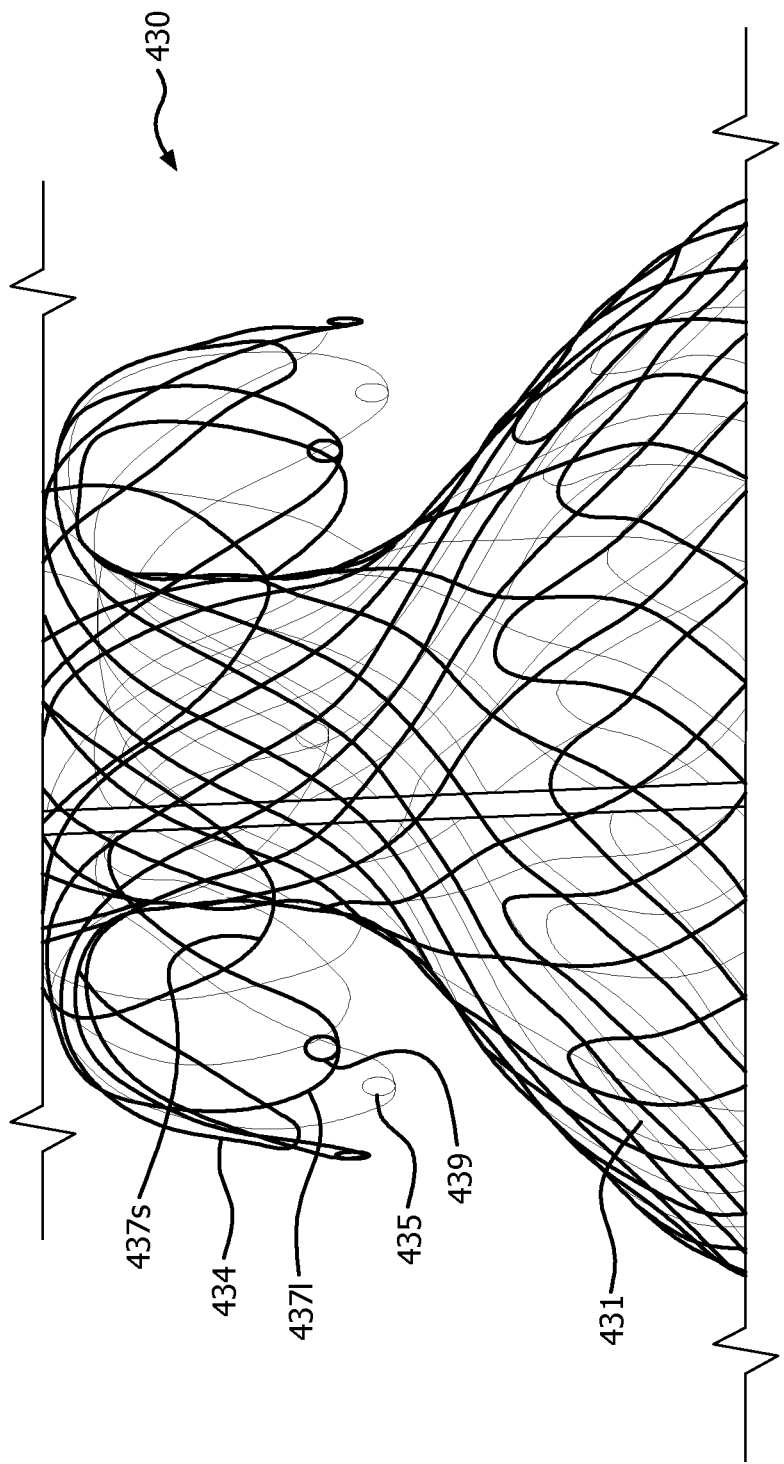
FIG. 4E is a close-up illustration of an atraumatic anti-migration collar of a wire mesh structure of an intragastric device, in accordance with yet another embodiment of the present specification.
Figure 4G:
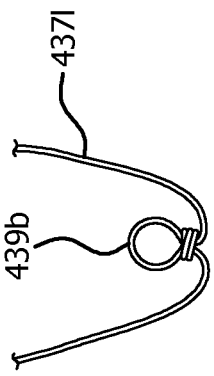
FIG. 4G is an illustration of hoops that are sutured to the free ends of long nodes in accordance with at least one embodiment.
Figure 4F:
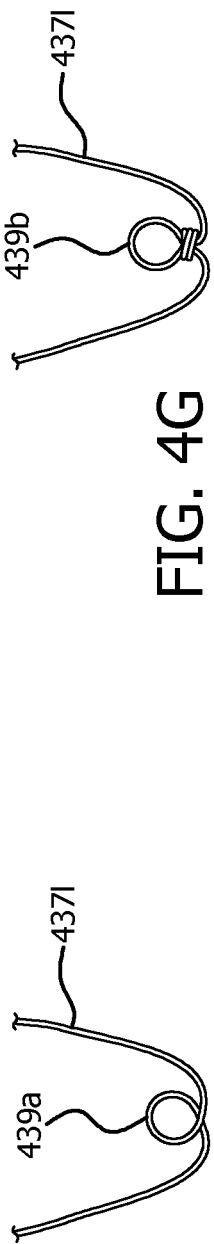
FIG. 4F is an illustration of hoops formed from twisting free ends of long nodes in accordance with at least one embodiment.

FIG. 4E is a close-up illustration of an atraumatic anti-migration collar 434 of a wire mesh structure 431 of an intragastric device 430, in accordance with yet another embodiment of the present specification. The anti-migration collar 434 has a toroid bulb shape and comprises rounded ends 435 which extend proximally toward the wire mesh structure 431. The rounded ends 435 are designed to be atraumatic to body tissues. In some embodiments, the ends 435 are separated into various nodes 4371, 437s to prevent bunching of the wires when compressed, which could lead to erosions. The nodes include long nodes 4371 and short nodes 437s, wherein the long nodes 4371 extend further in a proximal direction back toward the top of the wire mesh structure 431 than the short nodes 717s. In some embodiments, the collar 434 includes 9 long nodes 4371 and 9 short nodes 437s. The free ends of the long nodes 4371 include hoops 439 for suturing a proximal end of a sleeve component. The hoops 439 extend inward toward the curve at the distal end of the wire mesh structure 431. In one embodiment shown in FIG. 4F, hoops 439a are formed from looping the free ends of the long nodes 4371 into a hoop shape. In another embodiment depicted in FIG. 4G, hoops 439b comprise separate wire hoops that are sutured to the free ends of the long nodes 4371. In some embodiments, once the sleeve is attached, additional suture knots are placed at the junction of the loop or separate wire hoop to prevent sliding of the sleeve attachment.

In some embodiments, a sleeve component is attached to the distal end of the wire mesh structure or the collar of the intragastric device. In various embodiments, the sleeve component of the present specification is made of polytetrafluoroethylene (PTFE) or polyethylene or cast PTFE (e.g., Teflon), PTFE with fluorinated ethylene propylene (FEP) or perfluoroalkoxy (PFA) coating, PFA, extruded FEP and extruded PFA or extruded PTFE or a fluoropolymer or silicone. In one embodiment, a silicone sleeve is manufactured by hand pouring and braiding. In another embodiment, a silicone sleeve is manufactured by machine braiding. In various embodiments, the sleeve component has a length in a range of 6 inches to 6 feet or longer. In one embodiment, the sleeve component has a length of 24 inches. In another embodiment, the sleeve component has a length of 30 inches. In various embodiments, the sleeve component has a diameter in a range of 1 cm to 10 cm. In one embodiment, the sleeve component has a diameter of 3 cm.

FIG. 5A is an illustration of a portion of a sleeve component 500 of an intragastric device in a post-deployment configuration in accordance with one embodiment of the present specification, depicting a single wire support 501 spiraling along the body of the sleeve 500. The metal wire needs to have a tight enough spiral to provide support but must not be too tight such that, once the sleeve in compressed for delivery, it becomes kinked and cannot regain its full shape. Referring to FIG. 5A, the spiral metal wire 501 has a pitch depicted by length l which is equal to 60 mm. With a wire thickness of 0.1 to 1 mm, this pitch gives the spiral metal wire a strain percentage that will be no more than 20%, and preferably less than 8%.

FIG. 5B is an illustration of a portion of a sleeve component 505 of an intragastric device in a post-deployment configuration in accordance with one embodiment of the present specification, depicting multiple wire supports 506, 507, 508 spiraling along the body of the sleeve 505. The sleeve includes more than one spiral metal wire to provide greater support while still preventing permanent kinking. Referring to FIG. 5B, each individual wire 506, 507, 508 has a pitch depicted by length $l_1$ which is equal to 60 mm. The wires 506, 507, 508 are spaced such that the pitch between two separate wires, depicted by length $l_2$, is equal to 20 mm.

FIG. 5C is an illustration of a funnel shaped sleeve component 510 of an intragastric device in a post-deployment configuration in accordance with one embodiment of the present specification, depicting spiral wire loop supports 511, 513 on the sleeve 510. In the embodiment depicted in FIG. 5D, the sleeve 510 includes two sets of wire loop supports 511, 513. Each set of wire loop supports 511, 513 includes a loop comprising two individual wires, for a total of four wires on the sleeve 510. Each wire loop support 511, 513 is finished with blunted ends 515 to be atraumatic to body tissues. The wire loop supports 511, 513 are twisted into a spiral configuration and looped along the length of the sleeve 510. In one embodiment, the pitch, or distance between each loop 511, 513 (and between each wire of each loop 511, 513) is defined by length l and is approximately 15 mm.

Figure 5E:
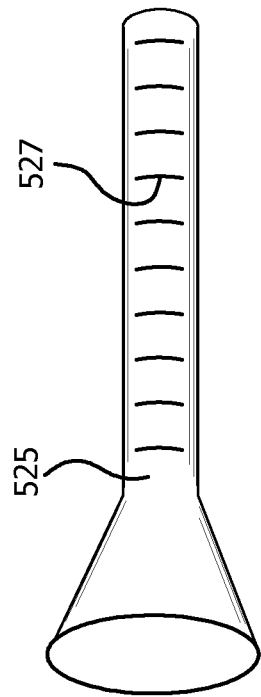
FIG. 5E is an illustration of a sleeve component of an intragastric device in a post-deployment configuration depicting a funnel shaped opening at the proximal end of the sleeve in accordance with at least one embodiment.

FIG. 5E is an illustration of a sleeve component 520 of an intragastric device in a post-deployment configuration in accordance with one embodiment of the present specification, depicting a funnel shaped opening 521 at the proximal end of the sleeve. The funnel shaped opening 521 is well suited for attachment to the nodes of the collar positioned at the distal end of the wire mesh structure of some embodiments of the intragastric device of the present specification, as discussed in detail with references to FIGS. 11C and 11D below.

Figure 5F:
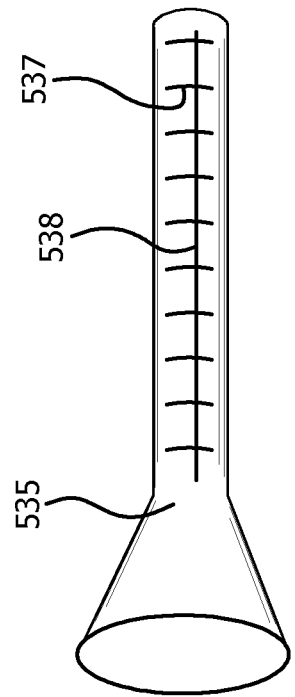
FIG. 5F is an illustration of a funnel shaped sleeve component of an intragastric device in a post-deployment configuration depicting a plurality of markings on an outer surface of the sleeve body in accordance with at least one embodiment.

FIG. 5F is an illustration of a funnel shaped sleeve component 525 of an intragastric device in a post-deployment configuration in accordance with one embodiment of the present specification, depicting a plurality of markings 527 on an outer surface of the sleeve body. The markings 527 are radiopaque and their radiographic visualization assists proper placement of the sleeve during device delivery.

Figure 5G:
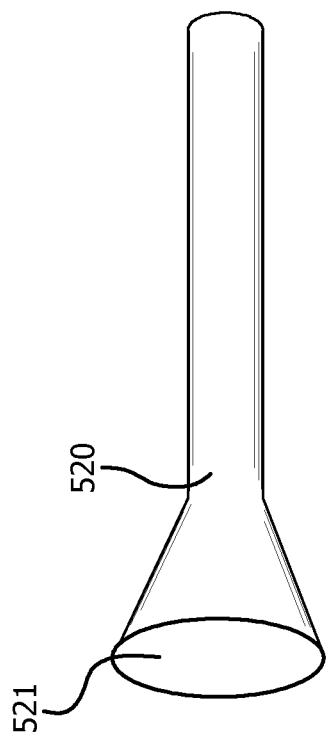
FIG. 5G is an illustration of a funnel shaped sleeve component of an intragastric device in a post-deployment configuration depicting a marking line extending along the length of the sleeve on an outer surface of the sleeve body in accordance with at least one embodiment.

FIG. 5G is an illustration of a funnel shaped sleeve component 530 of an intragastric device in a post-deployment configuration in accordance with one embodiment of the present specification, depicting a marking line 533 extending along the length of the sleeve 530 on an outer surface of the sleeve body. The line 533 is radiopaque and its radiographic visualization assists proper placement of the sleeve during device delivery. In addition, spiraling or rotation of the line about a center axis of the sleeve can indicate twisting of the sleeve.

Figure 5H:
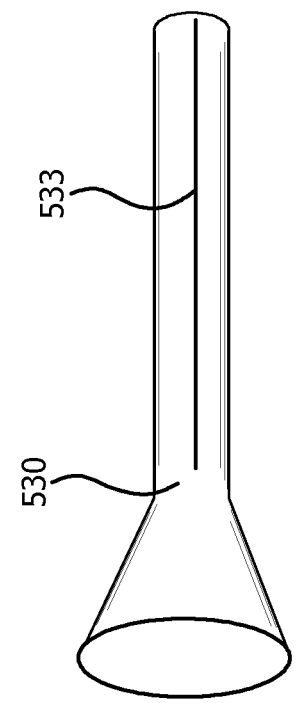
FIG. 5H is an illustration of a funnel shaped sleeve component of an intragastric device in a post-deployment configuration depicting a plurality of markings and a marking line extending along the length of the sleeve on an outer surface of the sleeve body in accordance with at least one embodiment.

FIG. 5H is an illustration of a funnel shaped sleeve component 535 of an intragastric device in a post-deployment configuration in accordance with one embodiment of the present specification, depicting a plurality of markings 537 and a marking line 538 extending along the length of the sleeve 535 on an outer surface of the sleeve body. The markings 537 and the line 538 are radiopaque and their radiographic visualization assists proper placement of the sleeve during device delivery and help to detect twisting of the sleeve 535.

Figure 6A:
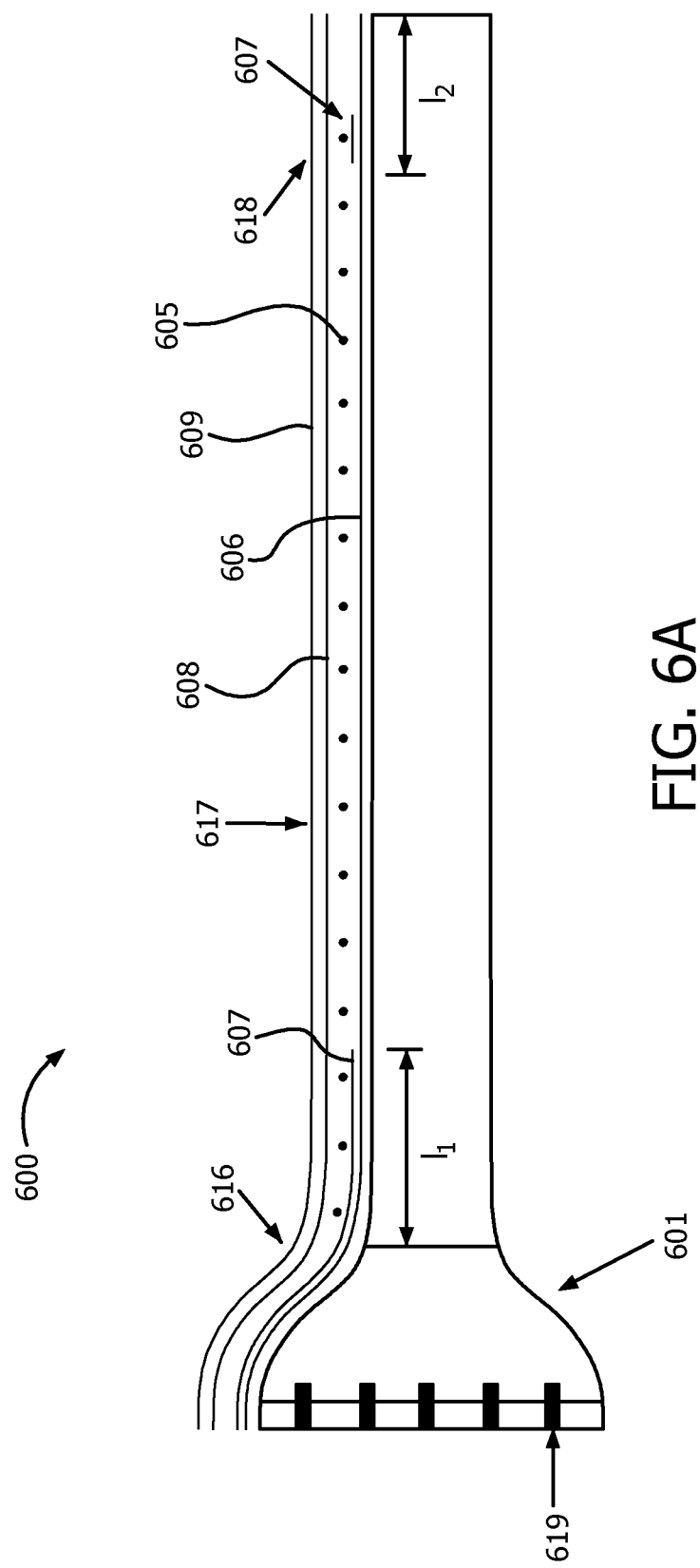
FIG. 6A is a cross-sectional illustration of a funnel shaped sleeve component of an intragastric device in a post-deployment configuration depicting a plurality of sleeve layers in accordance with at least one embodiment.

FIG. 6A is a cross-sectional illustration of a funnel shaped sleeve component 600 of an intragastric device in a post-deployment configuration in accordance with one embodiment of the present specification, depicting a plurality of sleeve layers 606, 607, 608, 609. In one embodiment, the sleeve layers 606, 607, 608, 609 are comprised of PTFE. The sleeve 600 includes an innermost first layer 606 which is approximately 0.06 mm thick and extends in a configuration along the length of the sleeve. The first layer 606 extends along the entire length of the sleeve 600. The sleeve 600 includes a second layer 607, overlaying said first layer 606, which is approximately 0.06 mm thick and extends only along a proximal portion 616 of the sleeve 600 and a distal portion 618 of the sleeve 600. In one embodiment, the proximal portion 616 includes a funnel portion 601 and an additional portion having a length $l_1$ which extends approximately 30-40 mm distally beyond said funnel portion 601. In one embodiment, the sleeve 600 includes a distal end having a length $l_2$ of approximately 20-30 mm. The distal portion 618 comprises approximately only the most proximal 10 mm of length $l_2$. In one embodiment, the second layer 607 extends in a configuration along the width of the sleeve 600. The sleeve 600 includes a third layer 608, overlaying said second layer 607 and a center portion 617 of said first layer 606. The third layer 608 is approximately 0.06 mm thick and extends in a configuration along the width of the sleeve 600. The sleeve 600 includes a fourth layer 609, overlaying said third layer 608, which is approximately 0.06 mm thick and extends in a configuration along the length of the sleeve 600. Therefore, in the embodiment depicted in FIG. 6A, the sleeve 600 comprises four layers at its proximal section 616, three layers at its center section 617, and four layers at its distal section 618. The layers 606, 607, 608, 609 are cross-layered bonded, or applied in different configurations (along the length versus along the width of the sleeve 600), to give the sleeve added durability. In one embodiment, the sleeve 600 further includes metal wire supports 605 between the second layer 607 and the third layer 608 (or between the first layer 606 and the third layer 608 in the center portion 617 of the sleeve 600) to provide structural support. In one embodiment, the sleeve includes suture points 619 for connection to a wire mesh structure.

Figure 6B:
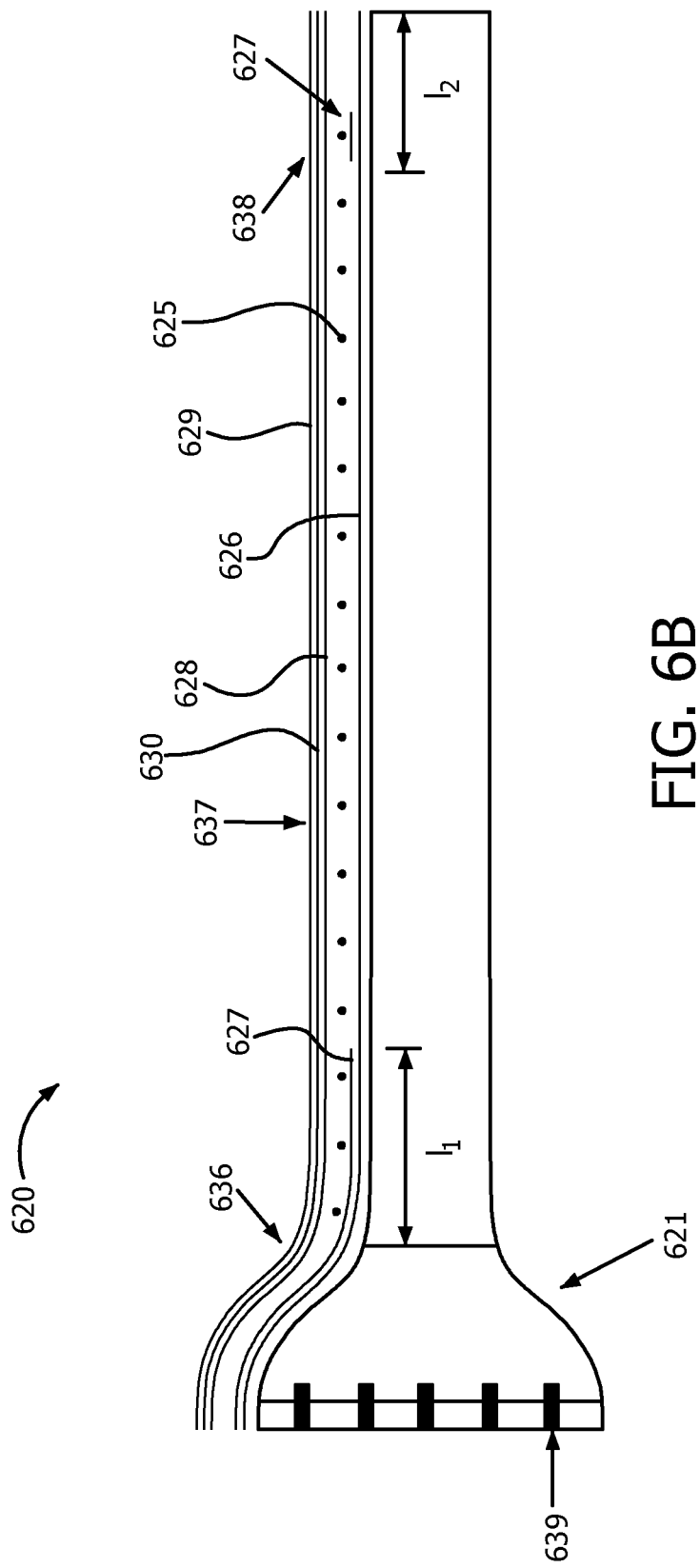
FIG. 6B is a cross-sectional illustration of a funnel shaped sleeve component of an intragastric device in a post-deployment configuration depicting a plurality of sleeve layers in accordance with at least one embodiment.

FIG. 6B is a cross-sectional illustration of a funnel shaped sleeve component 620 of an intragastric device in a post-deployment configuration in accordance with another embodiment of the present specification, depicting a plurality of sleeve layers 626, 627, 628, 629, 630. In various embodiments, the sleeve layers 626, 627, 628, 629, 630 are comprised of any one or combination of polytetrafluoroethylene (PTFE), low-density polyethylene (LDPE), high-density polyethylene (HDPE), and ultra-high-molecular-weight polyethylene (UHMWPE). In one embodiment, the sleeve 620 includes an innermost first PTFE layer 626 which is approximately 0.06 mm thick and extends in a configuration along the length of the sleeve. The first PTFE layer 626 extends along the entire length of the sleeve 620. The sleeve 620 includes a second PTFE layer 627, overlaying said first PTFE layer 626, which is approximately 0.06 mm thick and extends only along a proximal portion 636 of the sleeve 620 and a distal portion 638 of the sleeve 620. In one embodiment, the proximal portion 636 includes a funnel portion 621 and an additional portion having a length $l_1$ which extends approximately 30-40 mm distally beyond said funnel portion 621. In one embodiment, the sleeve 620 includes a distal end having a length $l_2$ of approximately 20-30 mm. The distal portion 638 comprises approximately only the most proximal 10 mm of length $l_2$. In one embodiment, the second PTFE layer 627 extends in a configuration along the width of the sleeve 620. The sleeve 620 includes a PTFE third layer 628, overlaying said second PTFE layer 627 and a center portion 637 of said first PTFE layer 626. The third PTFE layer 628 is approximately 0.06 mm thick and extends in a configuration along the width of the sleeve 620. The sleeve 620 includes a fourth PTFE layer 629, overlaying said third PTFE layer 628, which is approximately 0.06 mm thick and extends in a configuration along the length of the sleeve 620. In one embodiment, the sleeve further includes a fifth PFTE layer 630 sandwiched between the third PTFE layer 628 and the fourth PTFE layer 629. In one embodiment, the fifth PTFE layer 630 is approximately 0.06 mm thick and extends in a configuration along the length of the sleeve 620. Therefore, in the embodiment depicted in FIG. 6B, the sleeve 620 comprises five total layers at its proximal section 636, four total layers at its center section 637, and five total layers at its distal section 638. In various embodiments, the layers 626, 627, 628, 629, 630 are cross-layered bonded, or applied in different configurations (along the length versus along the width of the sleeve 620), to give the sleeve added durability. In one embodiment, the sleeve 620 further includes metal wire supports 625 between the second PTFE layer 627 and the third PTFE layer 628 (or between the first PTFE layer 626 and the third PTFE layer 628 in the center portion 637 of the sleeve 620) to provide structural support. In one embodiment, the sleeve includes suture points 639 for connection to a wire mesh structure.

Figure 6C:
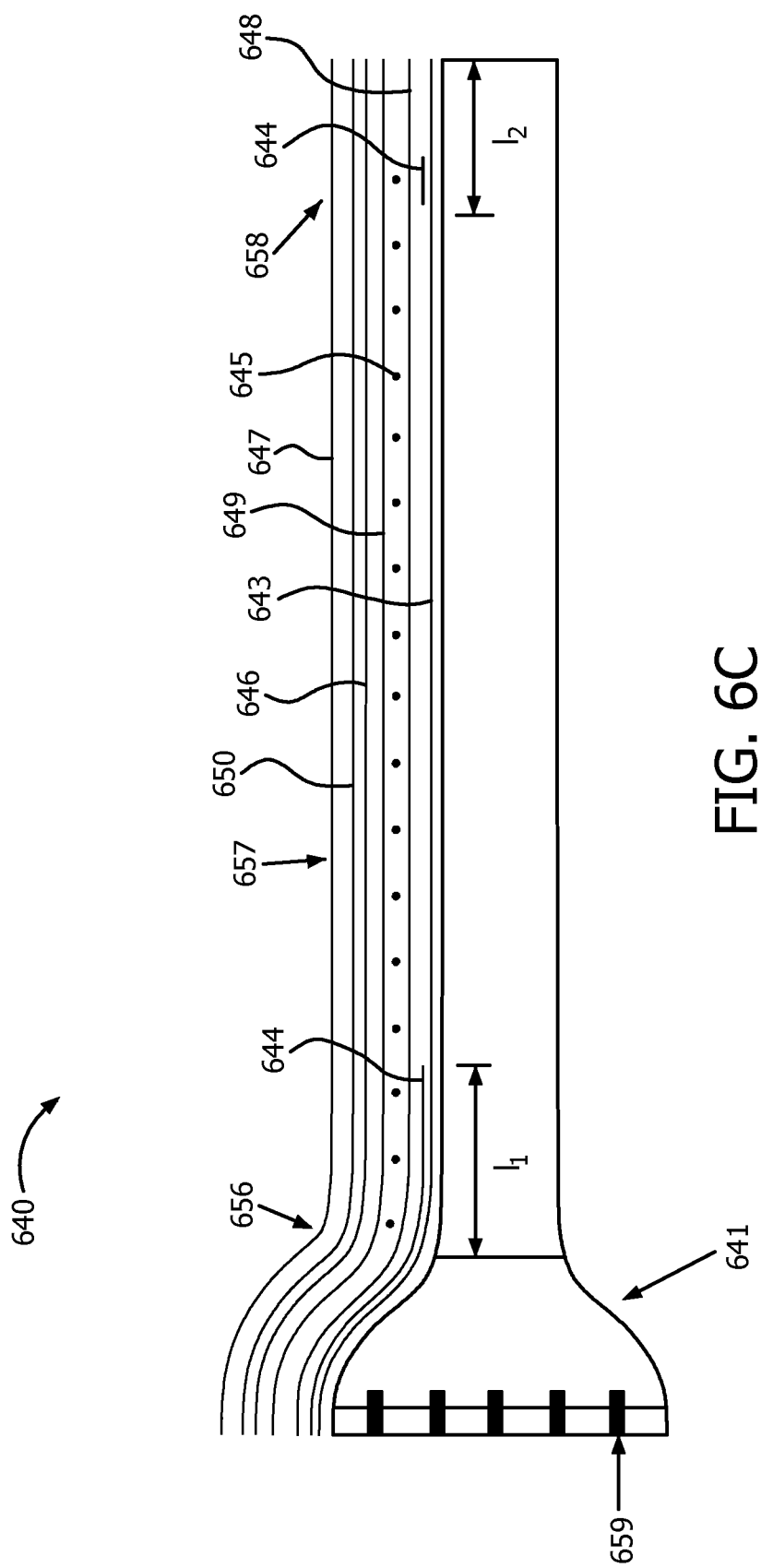
FIG. 6C is a cross-sectional illustration of a funnel shaped sleeve component of an intragastric device in a post-deployment configuration depicting a plurality of sleeve layers in accordance with at least one embodiment.

FIG. 6C is a cross-sectional illustration of a funnel shaped sleeve component 640 of an intragastric device in a post-deployment configuration in accordance with one embodiment of the present specification, depicting a plurality of sleeve layers 643, 644, 646, 647, 648, 649, 650. In various embodiments, the sleeve layers 643, 644, 646, 647, 648, 649, 650 are comprised of any one or combination of polytetrafluoroethylene (PTFE), low-density polyethylene (LDPE), high-density polyethylene (HDPE), and ultra-high-molecular-weight polyethylene (UHMWPE). In one embodiment, the sleeve 640 includes an innermost first PTFE layer 643 which is approximately 0.06 mm thick and extends in a configuration along the length of the sleeve. The first PTFE layer 643 extends along the entire length of the sleeve 640. The sleeve 640 includes a second PTFE layer 644, overlaying said first PTFE layer 643, which is approximately 0.06 mm thick and extends only along a proximal portion 656 of the sleeve 640 and a distal portion 658 of the sleeve 640. In one embodiment, the proximal portion 656 includes a funnel portion 641 and an additional portion having a length $l_1$ which extends approximately 30-40 mm distally beyond said funnel portion 641. In one embodiment, the sleeve 640 includes a distal end having a length $l_2$ of approximately 20-30 mm. The distal portion 658 comprises approximately only the most proximal 10 mm of length $l_2$. In one embodiment, the second PTFE layer 644 extends in a configuration along the width of the sleeve 640. The sleeve 640 includes a third PTFE layer 646, overlaying said second PTFE layer 644 and a center portion 657 of said first PTFE layer 643. The third PTFE layer 646 is approximately 0.06 mm thick and extends in a configuration along the width of the sleeve 640. The sleeve further includes a first intermediate PFTE layer 648 and a second intermediate PFTE layer 649 sandwiched between the second PTFE layer 644 and the third PTFE layer 646. In one embodiment, the first intermediate PFTE layer 648 and second intermediate PFTE layer 649 are both approximately 0.06 mm thick. In one embodiment, the first intermediate PFTE layer 648 and second intermediate PFTE layer 649 both extend in a configuration along the length of the sleeve 640. In another embodiment, the first intermediate PFTE layer 648 and second intermediate PFTE layer 649 both extend in a configuration along the width of the sleeve 640. In another embodiment, the first intermediate PFTE layer 648 extends in a configuration along the length of the sleeve 640 and the second intermediate PFTE layer 649 extends in a configuration along the width of the sleeve 640. In yet another embodiment, the first intermediate PFTE layer 648 extends in a configuration along the width of the sleeve 640 and the second intermediate PFTE layer 649 extends in a configuration along the length of the sleeve 640. The sleeve 640 includes a fourth PTFE layer 647, overlaying said third PTFE layer 646, which is approximately 0.06 mm thick and extends in a configuration along the length of the sleeve 640. The sleeve further includes a third intermediate PFTE layer 650 sandwiched between the third PTFE layer 646 and the fourth PTFE layer 647. In one embodiment, the third intermediate PFTE layer 650 is approximately 0.06 mm thick and extends in a configuration along the length of the sleeve 640. Therefore, in the embodiment depicted in FIG. 6C, the sleeve 640 comprises seven total layers at its proximal section 656, six total layers at its center section 657, and seven total layers at its distal section 658. In various embodiments, the layers 643, 644, 646, 647, 648, 649, 650 are cross-layered bonded, or applied in different configurations (along the length versus along the width of the sleeve 640), to give the sleeve added durability. In one embodiment, the sleeve 640 further includes metal wire supports 645 between the first intermediate PFTE layer 648 and the second intermediate PFTE layer 649 to provide structural support. In one embodiment, the sleeve includes suture points 659 for connection to a wire mesh structure.

While FIGS. 6A through 6C depict sleeves having multiple PTFE layers, these configurations are not intended to be limiting and other sleeve embodiments are envisioned having more or fewer PTFE layers or layers comprising other materials with varied stacking of the individual layers.

FIGS. 6D and 6E are cross-sectional illustrations of a funnel shaped sleeve component 660 of an intragastric device in a post-deployment configuration depicting a plurality of sleeve layers. The sleeve includes a cylindrical portion 660c and a funnel shaped portion 660f. In some embodiments, the cylindrical portion 660c has a length $l_c$ of approximately 500 mm and the funnel portion has a length $l_f$ of approximately 100 mm. The sleeve component 660 of FIG. 6F is comprised of a single machine braided wire 661 sandwiched between multiple sleeve layers. In one embodiment, the single machine braided wire 661 is in an axially stretched configuration. The single machine braided wire 661 extends along only a proximal portion of the cylindrical portion 660c of the sleeve 660. In one embodiment, approximately 450 mm of the proximal portion of the cylindrical portion 660c of the sleeve 660 includes the single machine braided wire 661 while at least 50 mm at the distal end of the sleeve 660 contains no wire. In one embodiment, the distal end of the sleeve 660 includes a distal opening 682 having a diameter of approximately 24.5 mm. The funnel portion 660f includes a wire support 671 ending proximally in a plurality of nodes 672. In one embodiment, the sleeve 660 includes a total of 18 nodes equidistant from one another and comprising alternating long and short nodes as described above. In some embodiments, the sleeve layers extend proximally beyond the long nodes a distance of at least 5 mm. In one embodiment, the proximal end of the sleeve 660 includes a proximal opening 681 having a diameter of approximately 63 mm. In various embodiments, the single machine braided wire 661 and wire support 671 each comprise a wire having a diameter in a range of 0.100 to 0.150 mm. In one embodiment, the single machine braided wire 661 and wire support 671 each comprise a wire having a diameter of 0.127 mm. In another embodiment, the single machine braided wire 661 and wire support 671 each comprise a wire having a diameter of 0.140 mm.

The sleeve 660 includes an innermost first PTFE layer 662 which extends in a configuration along the width of the sleeve 660. The first PTFE layer 662 extends along the entire length of the sleeve 660. In one embodiment, the first PTFE layer 662 has a thickness of approximately 0.06 mm. The single machine braided wire 661 overlays said first PTFE layer 662 along the proximal portion of said cylindrical portion 660c and the wire support 671 overlays the first PTFE layer 662 along the funnel portion 660f of the sleeve 660. A proximal intermediate PFTE layer 663p overlays the wire support 671 along the funnel portion 660f and extends distally approximately 5 to 7 mm over the single machine braided wire 661 of the cylindrical portion 660c of the sleeve 660. A distal intermediate PFTE layer 663d overlays the first PFTE layer 662 at the distal end of the sleeve and extends proximally approximately 5 to 7 mm over the single machine braided wire 1601 of the cylindrical portion 660c of the sleeve 660. A plurality of cylindrical intermediate PFTE layers 663c overlay the single machine braided wire 661 along sections of the cylindrical portion of the sleeve 660. In some embodiments, the sleeve 660 includes three cylindrical intermediate PFTE layers 663c, each having a length of approximately 3 to 5 mm and spaced 70 to 80 mm from one another and from the proximal intermediate PFTE layer 663p and distal intermediate PFTE layer 663d at the proximal and distal ends of the sleeve respectively. The sleeve 660 includes an outermost second PTFE layer 664 which is approximately 0.06 mm thick and extends in a configuration along the length of the sleeve 660.

In some embodiments, the sleeve 660 further includes at least one marker for visualization upon radiographic inspection to determine proper placement after delivery. Referring to FIG. 6E, the sleeve includes three markers 665 positioned proximate a proximal end of the single machine braided wire 661, proximate a center of the single machine braided wire 661, and proximate a distal end of the single machine braided wire. In one embodiment, each marker 665 is covered and held in place by a patch of PTFE 666 having a length of approximately 5 mm, a width of approximately 5 mm, and a thickness of approximately 0.06 mm. In one embodiment, the markers 665 are separated from one another by a distance of approximately 145 mm to 155 mm. In one embodiment, the markers 665 are positioned at every alternate cylindrical intermediate PFTE layer 663c. In one embodiment, the markers 665 are positioned on one side of the sleeve 660. In one embodiment, the markers 665 are tantalum markers.

Referring to FIGS. 6A through 6F, in various embodiments, the sleeve layers comprised of PTFE can also be comprised of polyethylene (PE), low-density polyethylene (LDPE), high-density polyethylene (HDPE), and ultra-high-molecular-weight polyethylene (UHMWPE). As an alternate to being bonded, the sleeve layers may be sutured.

Figure 6G:
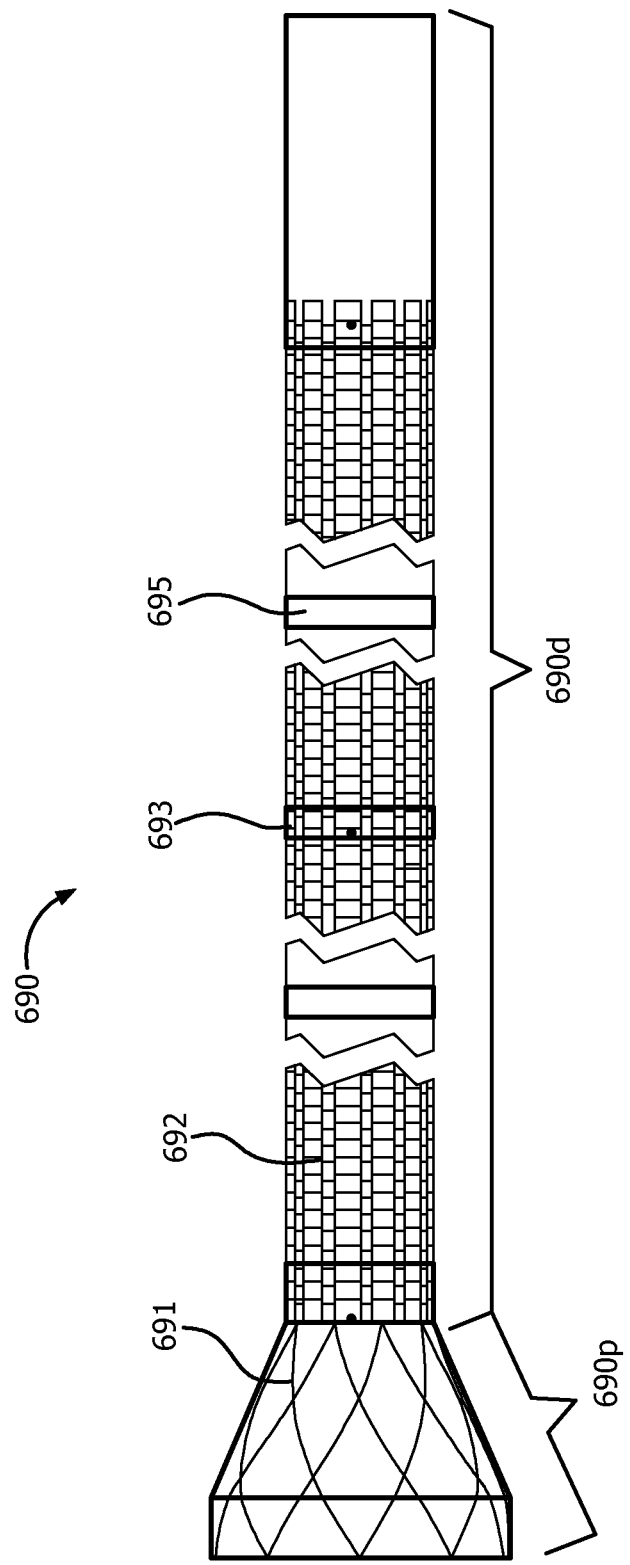
FIG. 6G is a cross-sectional illustration of a funnel shaped sleeve component of an intragastric device in a post-deployment configuration in accordance with yet another embodiment of the present specification.

FIG. 6G is a cross-sectional illustration of a funnel shaped sleeve component 690 of an intragastric device in a post-deployment configuration in accordance with yet another embodiment of the present specification. Referring to FIG. 6E, the sleeve 690 includes a proximal funnel shaped portion 690p and a distal cylindrically shaped portion 690d. The proximal portion 690p comprises a hand-braided Nitinol wire mesh 691 covered with PTFE. The distal portion 690d comprises a machine-braided Nitinol wire mesh 692 covered with PTFE. The distal portion 690d also includes at least one fluoropolymer band 695 overlaid for improved bonding of the Nitinol wire mesh with the PTFE. At least one radiopaque marker band 693 is also included in the distal portion 690d.

Figure 6I:
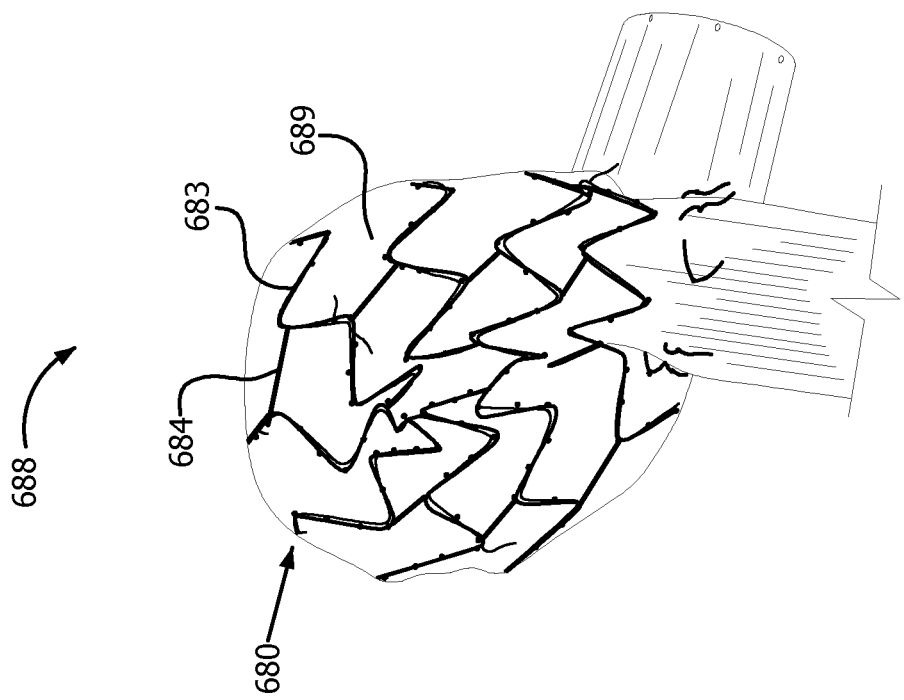
FIG. 6I is an illustration of a sleeve component of an intragastric device having the stent support of FIG. 6F in accordance with at least one embodiment.
Figure 6H:
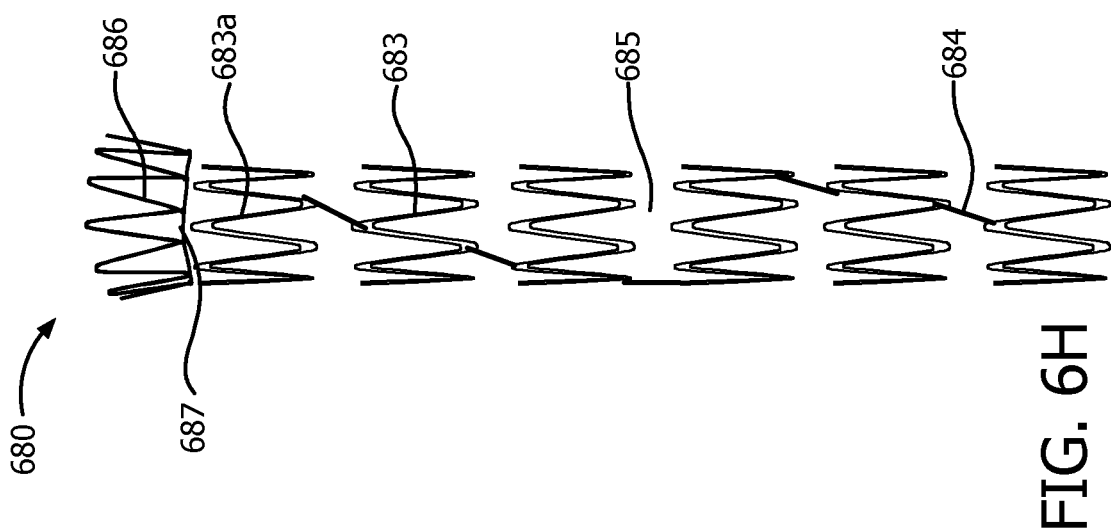
FIG. 6H is an illustration of a stent support for a sleeve component of an intragastric device, in accordance with one embodiment of the present specification.

FIG. 6H is an illustration of a stent support 680 for a sleeve component of an intragastric device, in accordance with one embodiment of the present specification. In the pictured embodiment, the stent support 680 includes a plurality of rings 683 formed from 'Z' shape segments of wire. In another embodiment, the stent support comprises a continuous spiral wire support wherein wires of the spiral are configured into 'Z' shapes. In one embodiment, the stent support 680 has a shape similar to the pattern 2033 depicted in FIG. 20F. Referring again to FIG. 6H, in one embodiment, each ring 683 is connected by a straight wire 684, such that a space 685 exists between each ring 683 which will comprise only the remaining layers of the sleeve component. In some embodiments, each ring 683 has length in a range of 1-2 cm. In some embodiments, each connecting straight wire 684 has a length in a range of 1-2 inches and each space 685 also has a length in a range of 1-2 inches. In one embodiment, the proximal end of the stent support 680 includes a funnel shaped ring segment 686. In one embodiment, the funnel shaped ring segment 686 includes a sutured connection 687 to the first distal ring 683a. In various embodiments, the funnel shaped ring segment 686 has a diameter sized to match the diameter of an anti-migration component at the distal end of a wire mesh structure to which it will be attached.

FIG. 6I is an illustration of a sleeve component 688 of an intragastric device having the stent support 680 of FIG. 6H. The stent support 680 includes rings 683 connected by straight wires 684. The other layers 689, such as PTFE, of the sleeve component 688 are depicted between each set of rings 683. The 'Z' shaped stent support 680 provides the sleeve component 688 with structural integrity such that it will not collapse as a result of intestinal contractions while still allowing the sleeve component 688 to be flexible enough to conform to the curves of the gastrointestinal tract.

In an embodiment, the sleeve and wire mesh of the present gastric wire mesh device may be covered with a web in order to make the sleeve portion flexible and kink resistant, while at the same time controlling the porosity of the device. In an embodiment, the web is produced through electrospinning PTFE into polymeric fibers with extremely small thickness ranging from 0.10 nanometers to 100 microns. Electrospinning allows materials to possess high surface-to-weight and volume ratios while still maintaining excellent mechanical properties. It is similar in nature to expanded PTFE, but with a lower basis weight and has comparable chemical and temperature resistance. If a strand of the web breaks, it can be easily repaired. In an embodiment, a first web layer is webbed over a sleeve of an intragastric device. Then, a scaffolding followed by a second web layer is placed over the first web layer to form an outer layer, thus encapsulating the nitinol or polymer scaffold.

In an embodiment, the mesh device of the present specification may comprise a braided sleeve or over-braid that is both expandable and flexible for aerospace, automotive and medical markets created by using drawn fibers. The woven braiding guards against chaffing and provides additional chemical wear resistance and flexibility to a sleeve of the present wire mesh device. In embodiments, the drawn fiber may be a perfluoroalkoxy (PFA) drawn fiber, fluorinated ethylene propylene (FEP) drawn fiber, ethylenetetrafluoroethylene (ETFE) drawn fiber, polyetheretherketone (PEEK) drawn fiber, polyvinylidene fluoride (PVDF) drawn fiber or ethylene chlorotrifluoroethylene (ECTFE) drawn fiber. In an embodiment, a high temperature resistant nano-fiber membrane, which has the ability to capture greater than 0.1 micron-sized particles, may be used to cover the wire mesh device of the present specification. FIG. 6H illustrates a portion 603 of a sleeve of a wire mesh device covered with a nano-fiber membrane 605, in accordance with an embodiment of the present specification.

Figure 7:
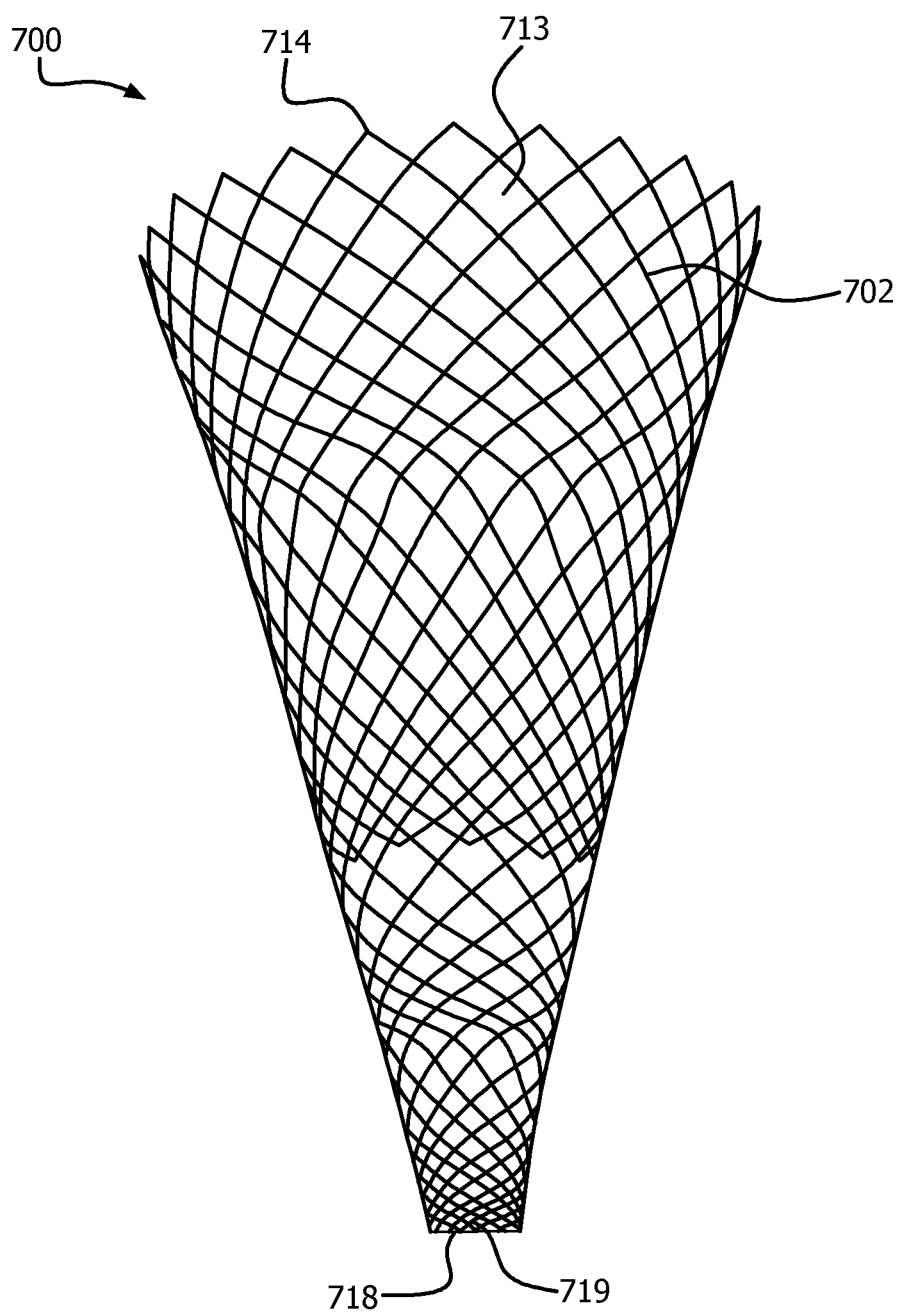
FIG. 7 is an illustration of a funnel shape sleeve for an intragastric device, in accordance with one embodiment of the present specification.

FIG. 7 is an illustration of a funnel shape sleeve 700 for an intragastric device, in accordance with one embodiment of the present specification. The sleeve 700 has a funnel shape with a diameter that decreases as the sleeve extends from a first opening 713 at its proximal end to a second opening 719 at its distal end. The sleeve 700 comprises at least one wire 702 folded about itself to create the funnel shape with a crisscross weave pattern. As the sleeve 700 extends distally, its diameter decreases and the intersections of the wire of the crisscross weave become positioned closer together. The sleeve 700 includes curves, or free ends, at its proximal end and distal end. The free ends are designed to be atraumatic to body tissues. In some embodiments, the first opening 713 has a diameter that is substantially equal to or slightly greater than a diameter of an anti-migration collar of a wire mesh structure. The sleeve 700 is slid over an anti-migration collar and then secured in place by suturing free ends 714 at the proximal end of the sleeve to nodes comprising the anti-migration collar. The free ends 718 at the distal end of the sleeve 700 circumscribe the second opening 719. In various embodiments, the sleeve 700 is a short sleeve having a total length in a range of 1 cm-120 cm. In one embodiment, the sleeve 700 is a short sleeve having a total length of 10 cm. In the pictured embodiment, the conical funnel section comprises 100% of the sleeve length.

Figure 8:
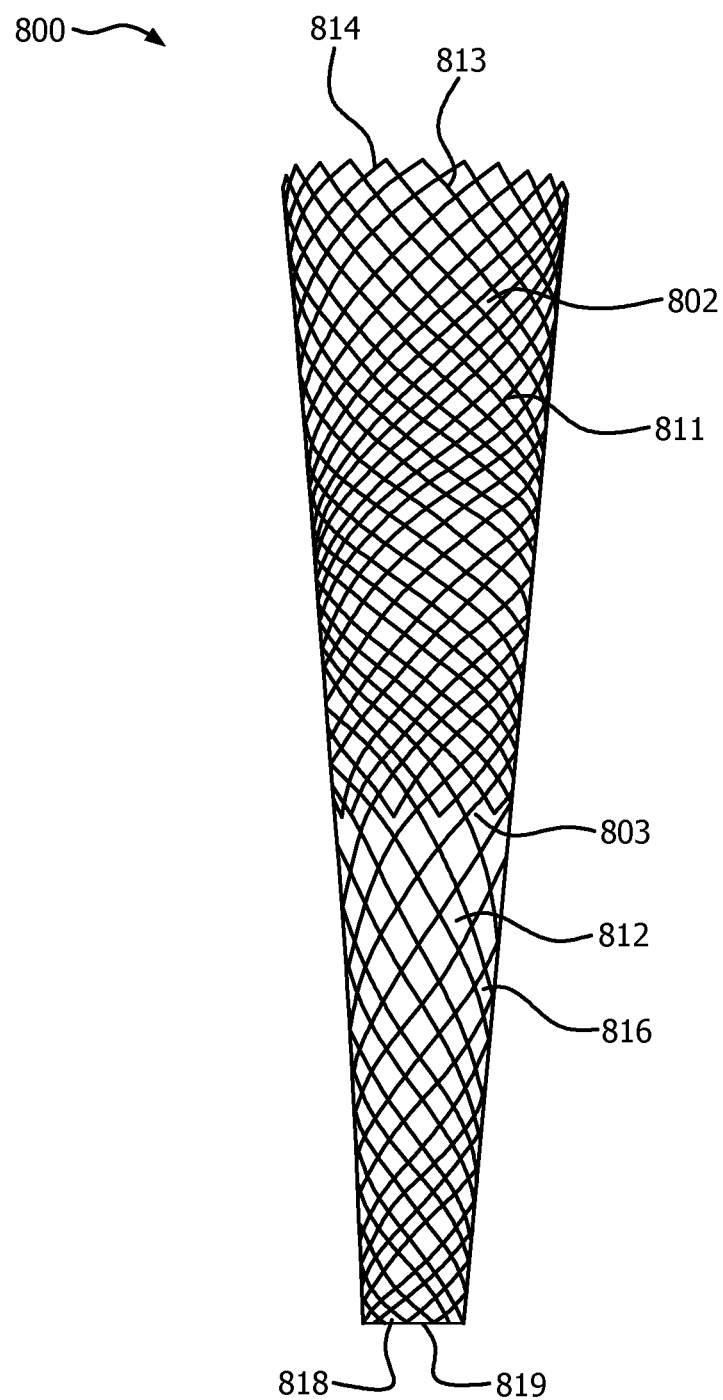
FIG. 8 is an illustration of a funnel shape sleeve for an intragastric device, in accordance with another embodiment of the present specification.

FIG. 8 is an illustration of a funnel shape sleeve 800 for an intragastric device, in accordance with another embodiment of the present specification. The sleeve includes a proximal end with a first opening 813 and a distal end with a second opening 819. The sleeve 800 further includes a proximal portion 811 and a distal portion 816. Both the proximal portion 811 and the distal portion 816 of the sleeve 800 are funnel shaped, each having a diameter that decreases as the portions 811, 816 extend distally. The diameter of the proximal portion 811 is greatest at the proximal end of the sleeve 800, at the position of the first opening 813, and decreases as the proximal portion 811 extends distally until the sleeve 800 transitions into its distal portion 816 at a transition point 803. At the transition point 803, the diameters of the proximal portion 811 and the distal portion 816 are equal. The diameter of the distal portion 816 then decreases as said distal portion 816 extends distally. In another embodiment, the diameter of the distal portion remains the same along its length. In yet another embodiment, the diameter of the distal portion increases as it extends distally. The distal portion 816 of the sleeve 800 ends in a second opening 819 at a distal end of the intragastric device 800. The proximal portion comprises a first wire 802 folded upon itself to create a funnel shape with a first crisscross weave pattern. The distal portion comprises a second wire 812 folded upon itself to create a funnel shape with a second crisscross weave pattern. In some embodiments, the second wire 812 is an extension of the first wire 802. In other embodiments, the first wire 802 and second wire 812 are separate wires which are joined together at the transition point 803. In one embodiment, the separate wires are spot welded together. In both the proximal 811 and distal portions 816, the intersecting sections of the wires come closer to one another as the portions 811, 816 extend distally and the funnel shape narrows, such that the weave pattern becomes tighter at the distal ends of each portion 811, 816. In one embodiment, the proximal portion 811 has the same weave pattern as the distal portion 816. In another embodiment, the weave pattern of the proximal portion 811 is tighter than the weave pattern of the distal portion 816. In another embodiment, the weave pattern of the distal portion 816 is tighter than the weave pattern of the proximal portion 811.

In one embodiment, the proximal portion 811 has a length equal to a length of the distal portion 816. In another embodiment, the proximal portion 811 has a length that is less than a length of the distal portion 816. In another embodiment, the proximal portion 811 has a length that is greater than the length of the distal portion 816. The sleeve 800 includes curves, or free ends, at its proximal end and distal end. The free ends are designed to be atraumatic to body tissues. In some embodiments, the first opening 813 has a diameter that is substantially equal to or slightly less than a diameter of a neck of an anti-migration collar of a wire mesh structure. The sleeve 800 is slid into the neck an anti-migration collar and then secured in place by suturing free ends 814 at the proximal end of the sleeve to wire intersections in the neck of the anti-migration collar. The free ends 818 at the distal end of the sleeve 800 circumscribe the second opening 819. In various embodiments, the sleeve 800 is a short sleeve having a total length in a range of 1 cm-120 cm. In one embodiment, the sleeve 800 is a short sleeve having a total length of 10 cm. In the pictured embodiment, the conical funnel section comprises 100% of the sleeve length.

FIG. 9A is an illustration of a wire mesh structure 930 with attached sleeve component 944 in a post-deployment configuration in accordance with one embodiment of the present specification, depicting a blunt end 952 of a wire mesh support toward the proximal end of the sleeve 944. The sleeve 944 is connected to a proximally curving, atraumatic anti-migration collar 942 at the distal end of the wire mesh structure 930 and includes a proximal section 945 having four layers and a center section 955 having three layers.

Figure 9B:
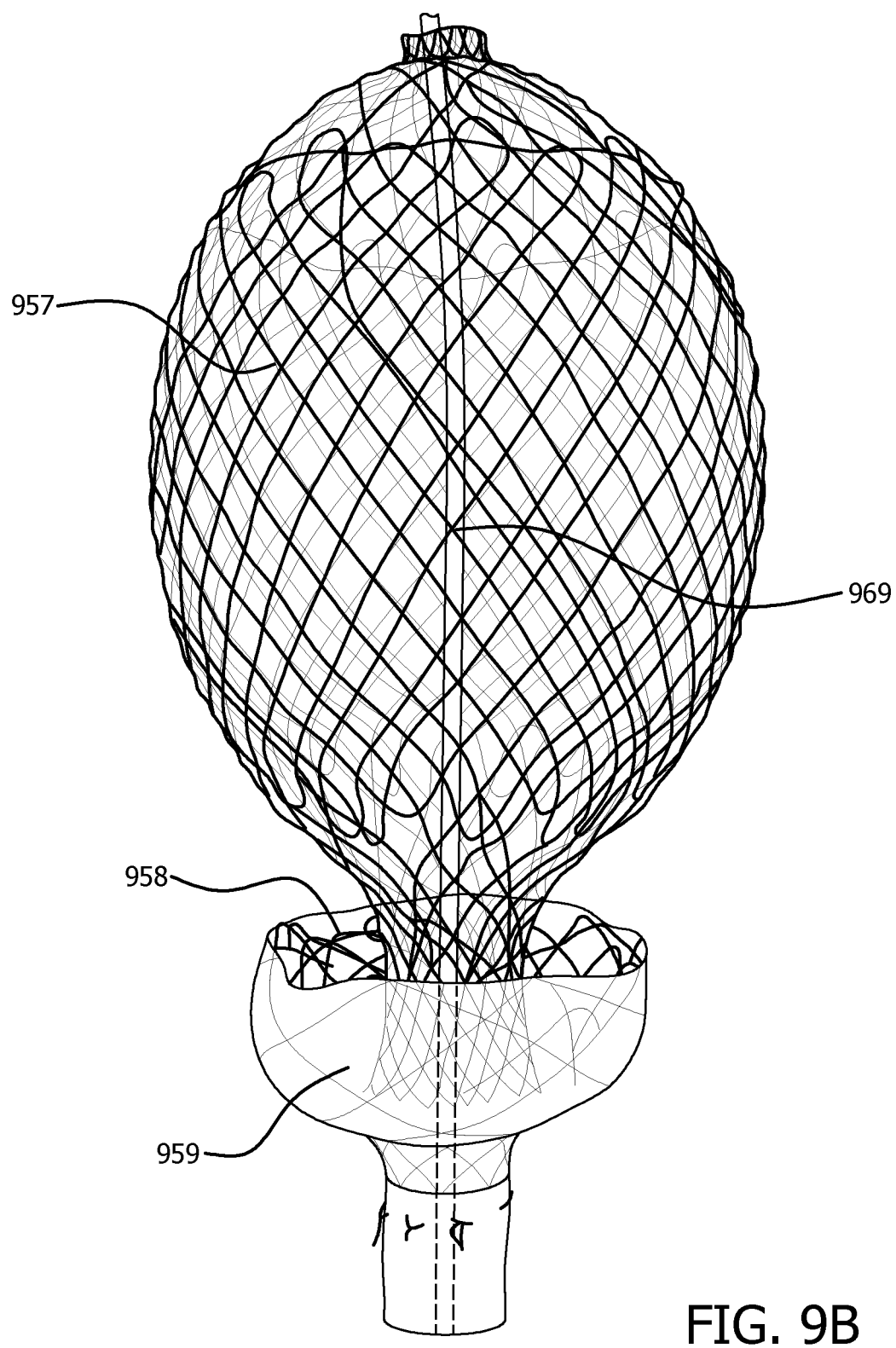
FIG. 9B is an illustration of a wire mesh structure with a proximal portion of an attached sleeve component in a post deployment configuration depicting a delivery catheter positioned within the wire mesh structure in accordance with at least one embodiment.

FIG. 9B is an illustration of a wire mesh structure 957 with a proximal portion of an attached sleeve component 959 in a post deployment configuration in accordance with one embodiment of the present specification, depicting a delivery catheter 969 positioned within the wire mesh structure 957. The sleeve 959 is attached to a proximally curving anti-migration component 958.

FIG. 10A is an illustration of a funnel shaped braided short sleeve component 1000 in a post-deployment configuration, in accordance with one embodiment of the present specification. The sleeve 1000 comprises a wire shape braided structure having a plurality of nodes 1001 at the proximal and distal ends of the sleeve 1000. The nodes 1001 are similar in structure to those described with reference to FIG. 3A above and comprise unsupported free bends in the wire of the braided structure. In one embodiment, the number of nodes is uniform such that the number of nodes at the proximal end of the sleeve 1000 equals the number of nodes at the distal end of the sleeve 1000. In one embodiment, the number of uniform nodes is 24 at both ends. In other embodiments, the number of nodes is variable such that the number of nodes at the proximal end of the sleeve 1000 is different than the number of nodes at the distal end of the sleeve 1000. Any nodes not present at the distal end of the sleeve are staggered within the body of the sleeve. For example, in one embodiment, the sleeve includes 24 nodes at its proximal end and 18 nodes at its distal end. The remaining 6 nodes are staggered in the body of the sleeve. In another embodiment, the sleeve includes 24 nodes at its proximal end and 12 nodes at its distal end. The remaining 12 nodes are staggered in the body of the sleeve. Different embodiments include different staggering of nodes. In one embodiment, a distal portion of the sleeve includes a coating 1002. In various embodiments, approximately 30-60 mm of the distal end is covered with the coating 1002. In one embodiment, the coating 1002 is silicone. In one embodiment, staggered nodes are positioned in the distal portion with the coating 1002 and are covered to eliminate traumatic surfaces.

The sleeve 1000 depicted in FIG. 10A includes a funnel shaped portion 1005 at its proximal end and a cylindrically shaped portion 1006 at its distal end. In one embodiment, the funnel portion 1005 includes a proximal section having a length $l_1$ and a distal section. In one embodiment, the length $l_1$ is approximately 30 mm. The entire funnel portion has a length $l_2$ which, in one embodiment, is approximately 60 mm. The cylindrical portion 1006 has a length $l_3$ which, in one embodiment, is approximately 60 mm. Therefore, in one embodiment, the sleeve 1000 has a total length $l_t$ of approximately 120 mm. The sleeve 1000 has a first opening 1003 at its proximal end with a diameter $d_1$. In one embodiment, the diameter $d_1$ is approximately 75 mm. The sleeve has a second opening 1004 at its distal end. In various embodiments, the diameter $d_2$ of the second opening 1004 is 1-30 mm.

FIG. 10B is an illustration of a funnel shaped braided short sleeve component 1010 having a cone shaped distal end 1017 in a post-deployment configuration, in accordance with one embodiment of the present specification. In various embodiments, the sleeve 1010 is comprised of a wire braid structure having a plurality of nodes 1011 wherein said plurality of nodes is uniform or variable as described with reference to FIG. 10A. In one embodiment, a distal portion of the sleeve includes a coating 1012. In various embodiments, approximately 30-60 mm of the distal end is covered with the coating 1012. In one embodiment, the coating 1012 is silicone. In one embodiment, staggered nodes are positioned in the distal portion with the coating 1012 and are covered to eliminate traumatic surfaces.

The sleeve 1010 depicted in FIG. 10B includes a funnel shaped portion 1015 at its proximal end and a cone shaped portion 1017 at its distal end. In one embodiment, the funnel portion 1015 includes a proximal section having a length $l_1$ and a distal section. In one embodiment, the length $l_1$ is approximately 30 mm. The entire funnel portion has a length $l_2$ which, in one embodiment, is approximately 60 mm. The cone portion 1787 has a length $l_3$ which, in one embodiment, is approximately 55 mm. In one embodiment, a short straight section 1016 of sleeve is positioned between the funnel portion 1015 and the cone portion 1017. In one embodiment, the short straight section 1016 has a length of 5 mm. Therefore, in one embodiment, the sleeve 1010 has a total length $l_t$ of approximately 120 mm. The sleeve 1010 has a first opening 1013 at its proximal end with a diameter $d_1$. In one embodiment, the diameter $d_1$ is approximately 75 mm. The sleeve has a second opening 1014 at its distal end with a diameter $d_2$. In one embodiment, the diameter $d_2$ is approximately 10 mm.

Figure 10D:
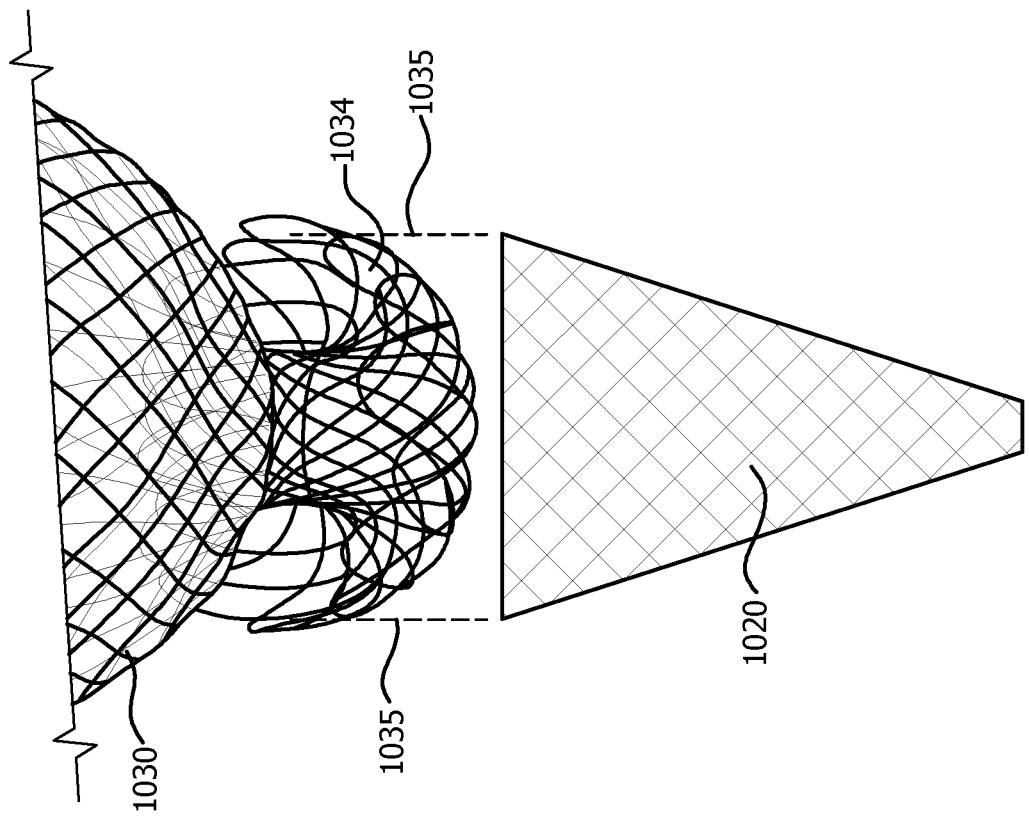
FIG. 10D is an illustration of the cone shape braided short sleeve component of FIG. 10C attached to a wire mesh structure in accordance with one embodiment of the present specification.
Figure 10C:
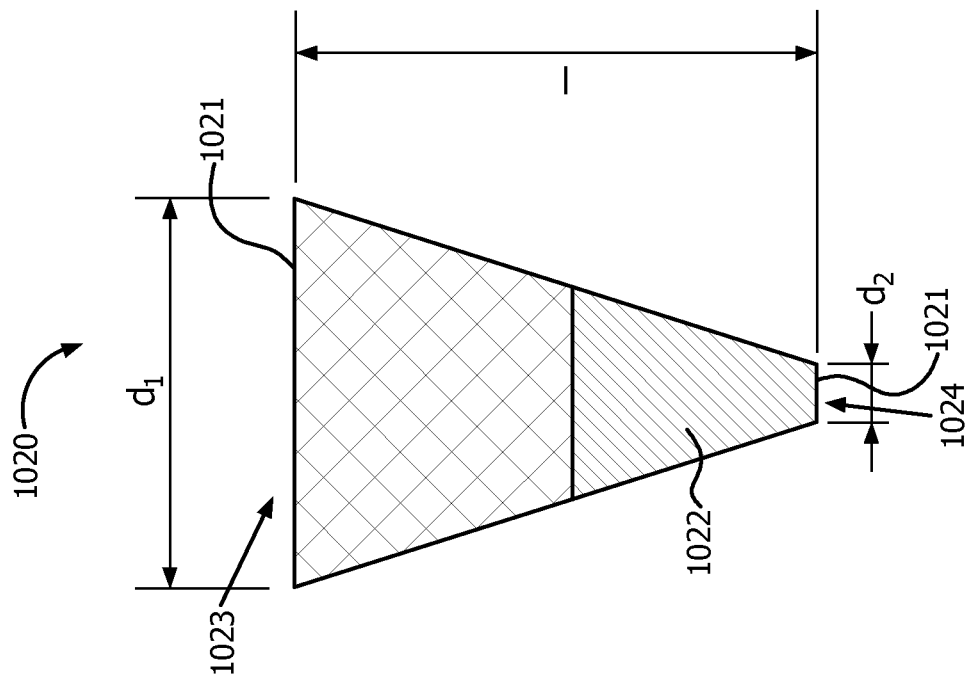
FIG. 10C is an illustration of a cone shape braided short sleeve component in a post-deployment configuration, in accordance with one embodiment of the present specification.

FIG. 10C is an illustration of a cone shape braided short sleeve component 1020 in a post-deployment configuration, in accordance with one embodiment of the present specification. In various embodiments, the sleeve 1020 is comprised of a wire braid structure having a plurality of nodes 1021 wherein said plurality of nodes is uniform or variable as described with reference to FIG. 10A. In one embodiment, a distal portion of the sleeve includes a coating 1022. In various embodiments, approximately 30-60 mm of the distal end is covered with the coating 1022. In one embodiment, the coating 1022 is silicone. In one embodiment, staggered nodes are positioned in the distal portion with the coating 1022 and are covered to eliminate traumatic surfaces. In one embodiment, the sleeve 1020 has a total length $l$ of approximately 120 mm. The sleeve 1020 has a first opening 1023 at its proximal end with a diameter $d_1$. In one embodiment, the diameter $d_1$ is approximately 75 mm. The sleeve has a second opening 1024 at its distal end with a diameter $d_2$. In one embodiment, the diameter $d_2$ is approximately 10 mm.

FIG. 10D is an illustration of the cone shape braided short sleeve component 1020 of FIG. 10C attached to a wire mesh structure 1030 in accordance with one embodiment of the present specification. Referring to FIGS. 10C and 10D simultaneously, the diameter $d_1$ of the first opening 1023 of the sleeve 1020 is sized similarly to the diameter of an anti-migration collar 1034 of the wire mesh structure 1030. To attach the wire mesh structure 1030 and sleeve 1020, the sleeve 1020 is slipped over the anti-migration collar 1034 and is attached thereto, as denoted by dashed lines 1035. Since they include first openings with similarly sized diameters, sleeve 1000 and sleeve 1010 of FIGS. 10A and 10B respectively, are attached to a wire mesh structure is the same manner as sleeve 1020 of FIG. 10C. In other words, the sleeves 1000, 1010 are slid over an anti-migration collar of a wire mesh structure.

Figure 10F:
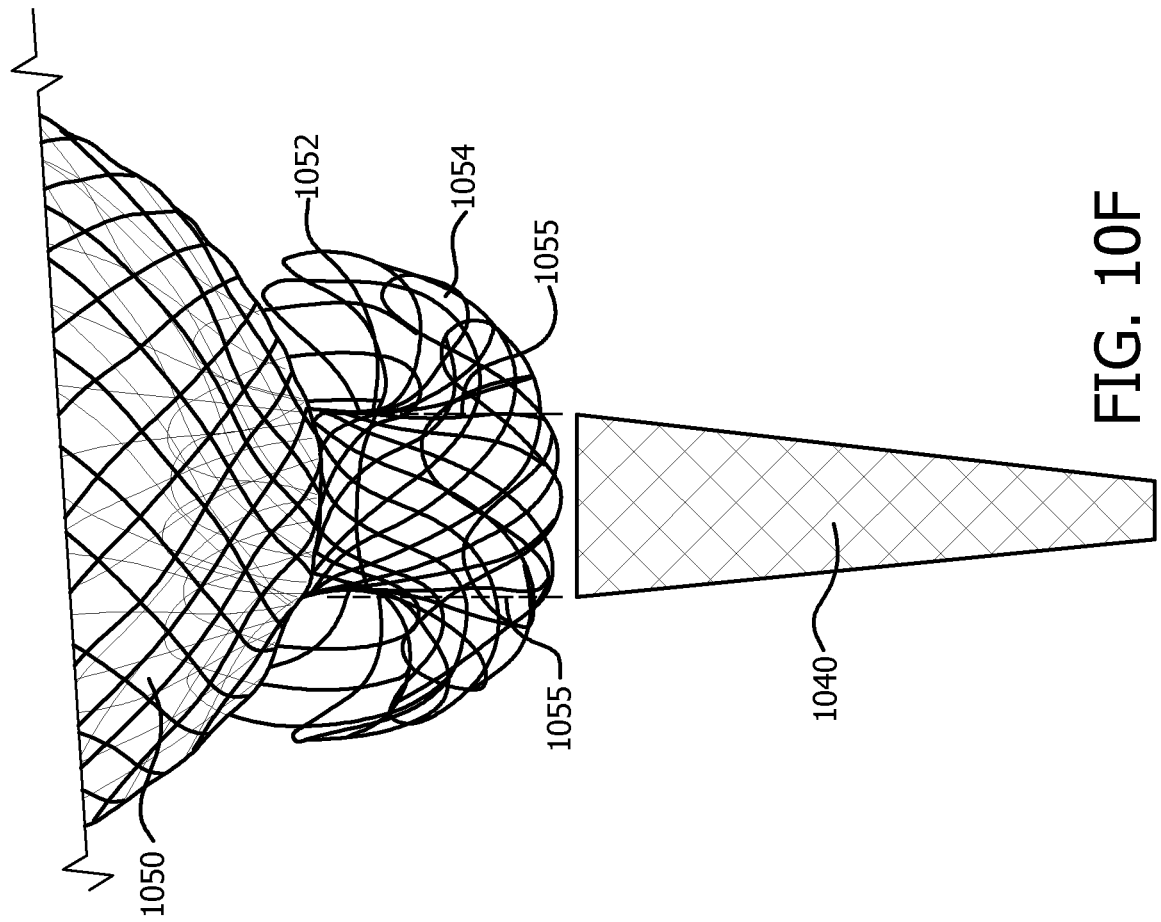
FIG. 10F is an illustration of the cone shape braided short sleeve component of FIG. 10E attached to a wire mesh structure in accordance with one embodiment of the present specification.
Figure 10E:
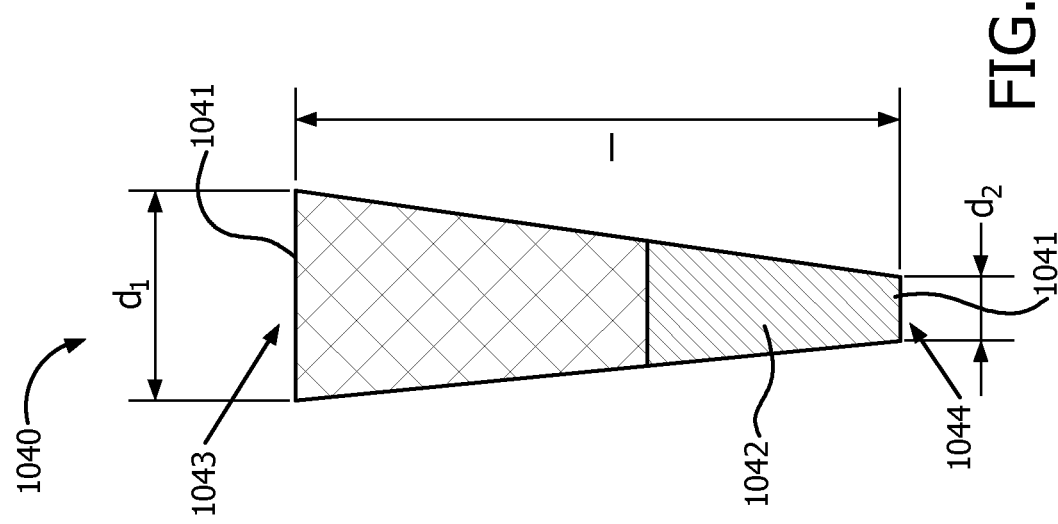
FIG. 10E is an illustration of a cone shape braided short sleeve component in a post-deployment configuration, in accordance with another embodiment of the present specification.

FIG. 10E is an illustration of a cone shape braided short sleeve component 1040 in a post-deployment configuration, in accordance with another embodiment of the present specification. The sleeve 1040 is similar to sleeve 1020 of FIG. 10C, with the exception that sleeve 1040 has a smaller first opening 1043. Referring to FIG. 10E, in various embodiments, the sleeve 1040 is comprised of a wire braid structure having a plurality of nodes 1041 wherein said plurality of nodes is uniform or variable as described with reference to FIG. 10A. In one embodiment, a distal portion of the sleeve includes a coating 1042. In various embodiments, approximately 30-60 mm of the distal end is covered with the coating 1042. In one embodiment, the coating 1042 is silicone. In one embodiment, staggered nodes are positioned in the distal portion with the coating 1042 and are covered to eliminate traumatic surfaces. In one embodiment, the sleeve 1040 has a total length $l$ of approximately 120 mm. The sleeve 1040 has a first opening 1043 at its proximal end with a diameter $d_1$. In one embodiment, the diameter $d_1$ is approximately 30 mm. The sleeve has a second opening 1044 at its distal end with a diameter $d_2$. In one embodiment, the diameter $d_2$ is approximately 10 mm.

FIG. 10F is an illustration of the cone shape braided short sleeve component 1040 of FIG. 10E attached to a wire mesh structure 1050 in accordance with one embodiment of the present specification. Referring to FIGS. 10E and 10F simultaneously, the diameter $d_1$ of the first opening 1043 of the sleeve 1040 is sized similarly to the diameter of the neck 1052 of an anti-migration collar 1054 of the wire mesh structure 1050. An outer diameter of the anti-migration collar 1054 itself is greater than diameter $d_1$. Therefore, to attach the wire mesh structure 1050 and sleeve 1040, the sleeve 1040 is slid into the anti-migration collar 1054 and is attached to the collar neck 1052, as denoted by dashed lines 1055.

FIGS. 10G and 10H are illustrations of cone shape braided short sleeve components 1060, 1065 having an atraumatic distal tip 1062, 1067 and in a post-deployment configuration, in accordance with embodiments of the present specification. Referring to FIGS. 10G and 10H simultaneously, the wires 1061, 1066 of the sleeve components

1060, 1065 do not extend into the distal tips 1062, 1067. The distal tips 1062, 1067 only include the more flexible sleeve layers, such as PTFE, and, as such, are atraumatic to the gastrointestinal mucosa. In some embodiments, the distal tips 1062, 1067 have a diameter $d_1$ of approximately 10 cm and a length in a range of 5-15 cm. In some embodiments, the sleeve components depicted in FIGS. 10A through 10F each include an atraumatic distal tip similar to those discussed with reference to FIGS. 10G and 10H.

FIG. 11A is a cross-sectional illustration depicting one embodiment of an intragastric device 1100 with an attached sleeve 1102 in a post-deployment configuration. The device 1100 includes a wire mesh structure 1101 having a collar 1103 positioned at its distal end. The sleeve 1102 has a cylindrically shaped body with a proximal end that is attached to the bottom surface of the collar 1103. FIG. 11B is a cross-sectional illustration depicting the intragastric device 1100 of FIG. 11A in a pre-deployment configuration. As the device 1100 is compressed into its pre-deployment configuration, the body of the sleeve 1102 is pulled upon to assist in folding out the collar 1103 of the wire mesh structure 1101. The collar 1103 must be folded out so that the device 1100 will have a small enough diameter to fit through a delivery device or catheter. Referring to FIG. 11B, because the proximal end of the sleeve 1102 is attached to the bottom surface of the collar 1103, when the collar 1103 is folded out it creates a bulge comprising the thickness 1103' of the collar and twice the thickness 1102', 1102" of the sleeve.

FIG. 11C is a cross-sectional illustration depicting another embodiment of an intragastric device 1110 with an attached sleeve 1112 in a post-deployment configuration. The device 1110 includes a wire mesh structure 1111 having a collar 1113 positioned at its distal end. The sleeve 1112 has a cylindrically shaped body with a funnel shaped proximal end that is attached to the nodes or free ends at the distal end of the collar 1113. The sleeve 1112 is attached to the collar 1113 via a plurality of sutures 1117. FIG. 11D is a cross-sectional illustration depicting the intragastric device of FIG. 11C in a pre-deployment configuration. As the device 1110 is compressed into its pre-deployment configuration, the body of the sleeve 1112 is pulled upon to assist in folding out the collar 1113 of the wire mesh structure 1111. The sutures 1117 joining the sleeve 1112 to the collar 1113 are secured loosely to allow for some minimal movement between the sleeve 1112 and the collar 1113. Therefore, as seen in FIG. 11D, when the collar 1113 is folded out, the funnel portion of the sleeve 1112 and the collar 1113 move relative to one another such that the resultant bulge in the compressed device comprises only the thickness 1113' of the collar. This creates a lower cross-sectional area or diameter in the compressed device and allows for easier deployment through a delivery device or catheter.

In addition, the collar 1113 depicted in FIG. 11C has less of a sharp bend (is more rounded) than the collar 1103 depicted in FIG. 11A. A less sharp bend in the collar will make the collar less traumatic to body tissues and will allow it to retain its shape since it will have a lower strain percentage.

Figure 12A:
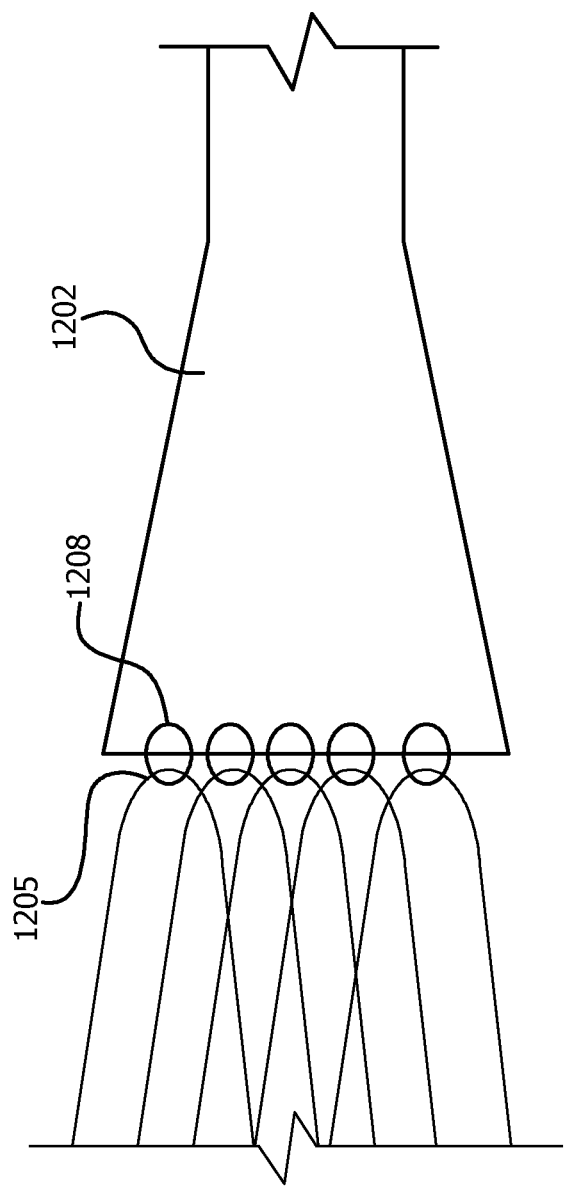
FIG. 12A is an illustration of a plurality of nodes positioned at the distal end of a wire mesh structure connected to the proximal end of a funnel shaped sleeve, in accordance with one embodiment of the present specification.

FIG. 12A is an illustration of a plurality of nodes 1205 positioned at the distal end of a wire mesh structure connected to the proximal end of a funnel shaped sleeve 1202, in accordance with one embodiment of the present specification. The nodes 1205 are positioned at the distal end of the wire mesh structure or at the distal end of a collar, as seen in FIGS. 11C and 11D. Referring to FIG. 12A, each node 1205 is attached to the sleeve 1202 by a suture 1208. As described with reference to FIGS. 11C and 11D, the sutures are secured loosely to allow some movement of the sleeve 1202 relative to the wire mesh structure.

Figure 12B:
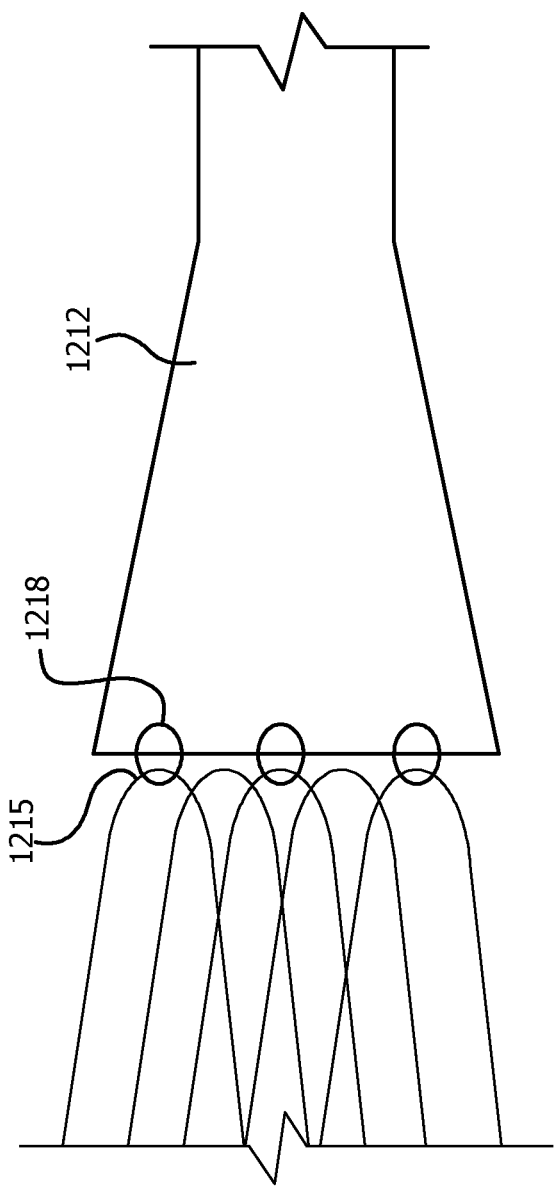
FIG. 12B is an illustration of a plurality of nodes positioned at the distal end of a wire mesh structure connected to the proximal end of a funnel shaped sleeve, in accordance with another embodiment of the present specification.

FIG. 12B is an illustration of a plurality of nodes 1215 positioned at the distal end of a wire mesh structure connected to the proximal end of a funnel shaped sleeve 1212, in accordance with another embodiment of the present specification. As depicted in FIG. 12B, only every other node 1215 is attached to the sleeve via a suture 1218. While still fixedly attaching the wire mesh structure to the sleeve 1212, the reduction in the number of sutures 1218, when compared with the embodiment shown in FIG. 12A, creates a device in the compressed pre-deployment configuration having a bulge with a smaller diameter. Such a compressed device will pass more easily through a delivery device or catheter.

Figure 12C:
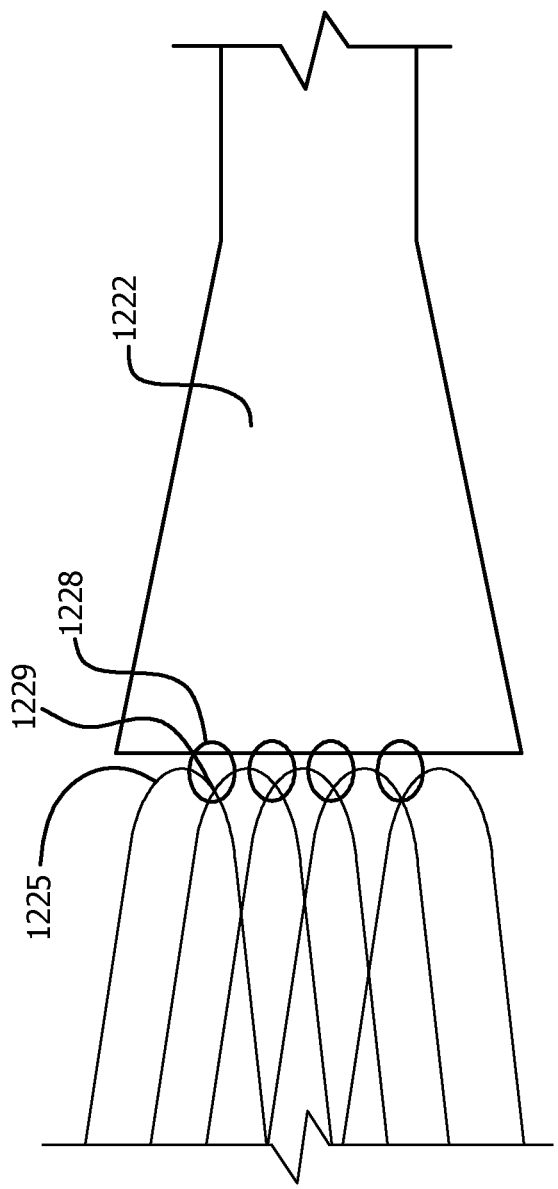
FIG. 12C is an illustration of a plurality of nodes positioned at the distal end of a wire mesh structure connected to the proximal end of a funnel shaped sleeve, in accordance with another embodiment of the present specification.

Securing the sutures directly to the most distal end of the nodes can result in too much movement of the sleeve relative to the wire mesh structure as the sutures slide along the wires of each node. FIG. 12C is an illustration of a plurality of nodes 1225 positioned at the distal end of a wire mesh structure connected to the proximal end of a funnel shaped sleeve 1222, in accordance with another embodiment of the present specification. Rather than placing the suture on the most distal end of each node 1225, the sutures 1228 are placed about the intersections 1229 of the wires of two adjacent nodes 1225. This prevents sliding of the sutures too far along any one wire while still allowing for the minimum movement of the sleeve 1222 relative to the wire mesh structure during compression.

Figure 12D:
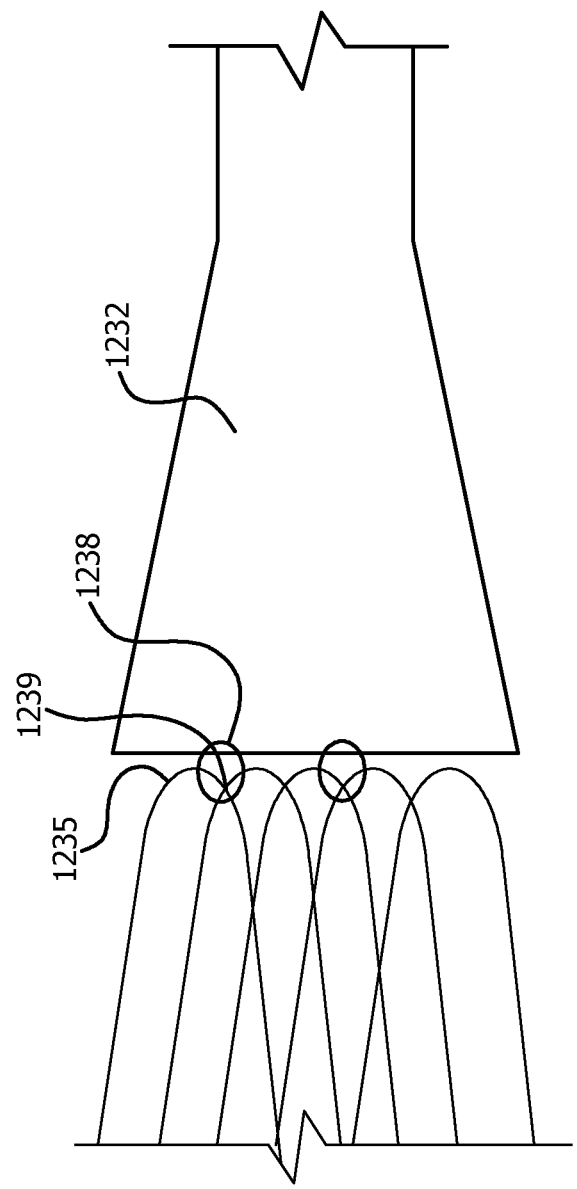
FIG. 12D is an illustration of a plurality of nodes positioned at the distal end of a wire mesh structure connected to the proximal end of a funnel shaped sleeve, in accordance with another embodiment of the present specification.

FIG. 12D is an illustration of a plurality of nodes 1235 positioned at the distal end of a wire mesh structure connected to the proximal end of a funnel shaped sleeve 1232, in accordance with another embodiment of the present specification. As depicted in FIG. 12D, only every other intersection 1239 of wires of adjacent nodes 1235 is attached to the sleeve via a suture 1238. While still fixedly attaching the wire mesh structure to the sleeve 1232, the reduction in the number of sutures 1238, when compared with the embodiment shown in FIG. 12C, creates a device in the compressed pre-deployment configuration having a bulge with a smaller diameter. Such a compressed device will pass more easily through a delivery device or catheter.

FIG. 12E is an illustration of a plurality of nodes 1245 positioned at the distal end of a wire mesh structure connected to the proximal end of a funnel shaped sleeve 1242, in accordance with another embodiment of the present specification. The nodes 1245 are positioned at the distal end of the wire mesh structure or at the distal end of an anti-migration collar and include loops 1246 formed from the wire of the nodes 1245 and extending in a direction toward the center of the wire mesh structure. Each loop 1246 of each node 1205 is attached to the sleeve 1242 by a suture 1248.

FIG. 12F is an illustration of a plurality of nodes 1255 positioned at the distal end of a wire mesh structure connected to the proximal end of a funnel shaped sleeve 1252, in accordance with yet another embodiment of the present specification. The nodes 1255 are positioned at the distal end of the wire mesh structure or at the distal end of an anti-migration collar and include loops 1256 formed from the wire of the nodes 1255 and extending in a direction toward the center of the wire mesh structure. Each loop 1256 of each node 1255 is attached to the sleeve 1252 by a suture 1258. As depicted in FIG. 12F, only every other node 1255 is attached to the sleeve via a suture 1258. While still fixedly attaching the wire mesh structure to the sleeve 1252, the reduction in the number of sutures 1258, when compared with the embodiment shown in FIG. 12E, creates a device in the compressed pre-deployment configuration having a bulge with a smaller diameter. Such a compressed device will pass more easily through a delivery device or catheter.

Figure 13B:
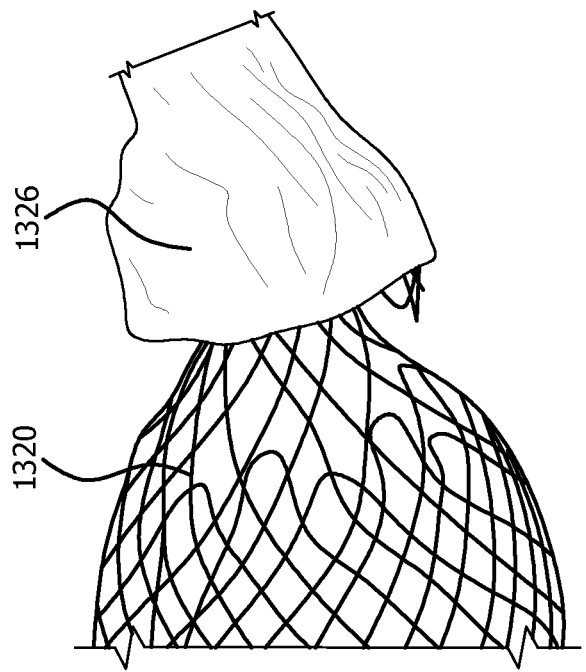
FIG. 13B is an illustration of a distal end of a wire structure and connected proximal end of a funnel shaped sleeve covered with a heat shrink tube, in accordance with one embodiment of the present specification.
Figure 13A:
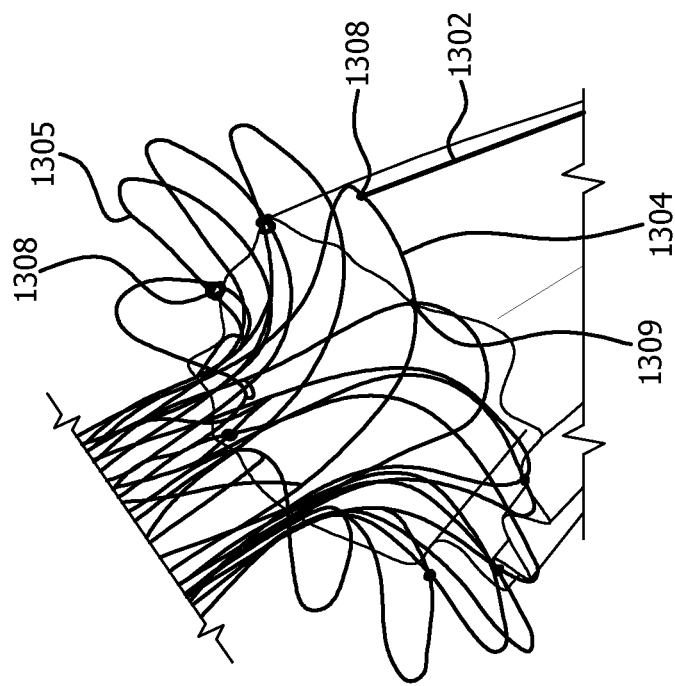
FIG. 13A is an illustration of a plurality of nodes positioned at the distal end of a wire mesh structure connected to the proximal end of a funnel shaped sleeve, in accordance with an embodiment of the present specification.

FIG. 13A is an illustration of a plurality of nodes 1305 positioned at the distal end of a wire mesh structure connected to the proximal end of a funnel shaped sleeve 1302, in accordance with an embodiment of the present specification. As depicted in FIG. 13A, both the intersections 1309 between some adjacent nodes 1305 and the ends 1304 of some nodes 1305 are sutured to the sleeve 1302 with knots 1308.

In one embodiment, the distal end of a wire mesh structure is connected to the proximal end of a sleeve at 9 standalone connection points. Each connection point comprises a FIG. eight knot additionally secured with glue and a heat shrink tube. In one embodiment, each knot comprises 30 lb. break-strength ultra-high-molecular-weight-polyethylene (UHMWPE) braided suture line to provide a reliable connection between wire mesh and sleeve. FIG. 13B is an illustration of a distal end of a wire mesh structure 1320 and connected proximal end of a funnel shaped sleeve covered with a heat shrink tube 1326, in accordance with one embodiment of the present specification.

Figure 14:
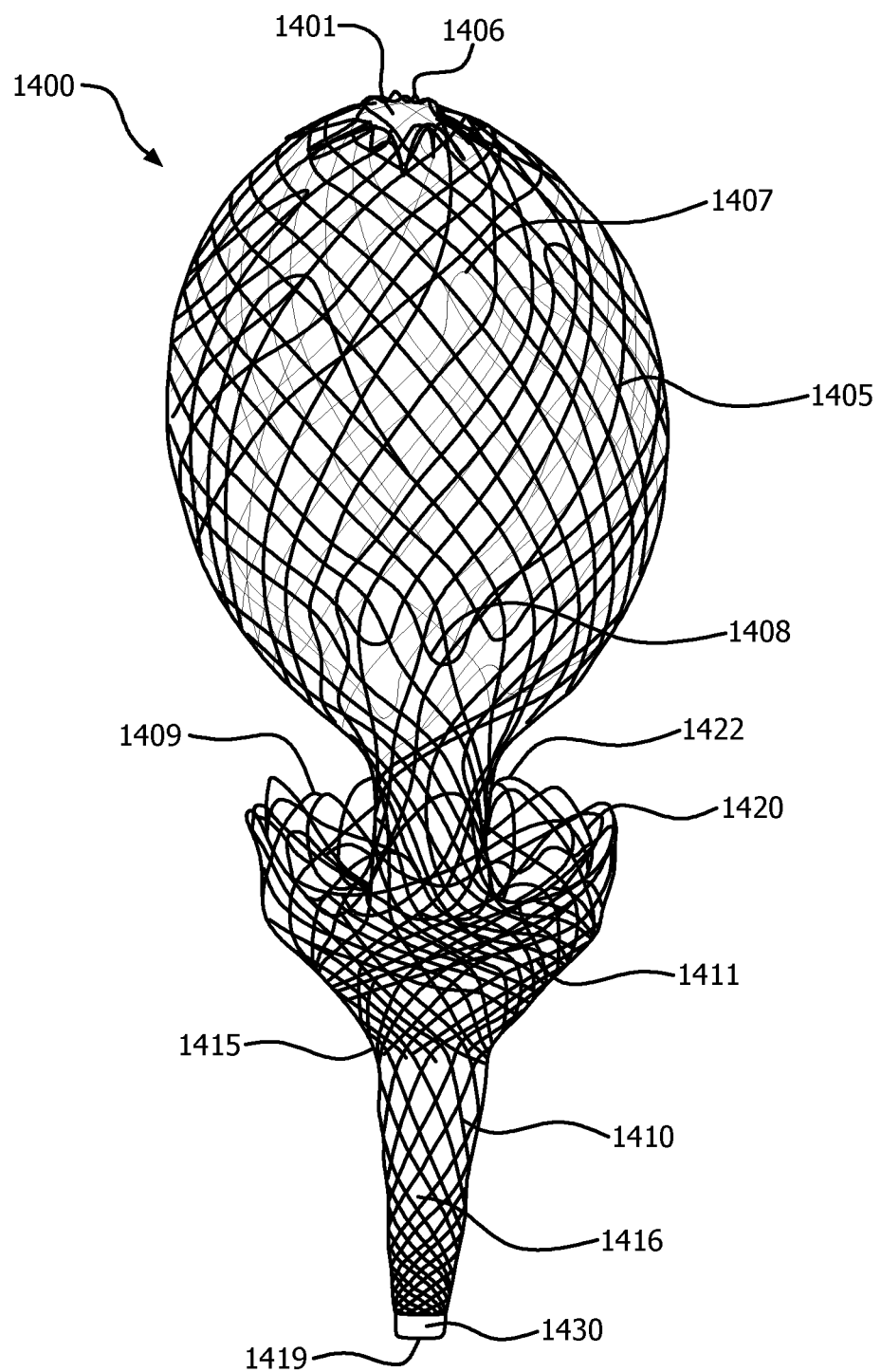
FIG. 14 is an illustration of an intragastric device with a funnel shaped sleeve in a post-deployment configuration, in accordance with one embodiment of the present specification.

FIG. 14 is an illustration of an intragastric device 1400 with a funnel shaped sleeve 1410 in a post-deployment configuration, in accordance with one embodiment of the present specification. The intragastric device 1400 includes a wire mesh structure 1405 having a proximal end and a distal end with an anti-migration collar 1420 formed at said distal end. The sleeve 1410 includes a proximal end and a distal end and is attached via its proximal end to the anti-migration collar 1420.

The wire mesh structure 1405 comprises at least one metal wire folded about itself to create a crisscross weave pattern with a plurality of free curved ends, or nodes, along the structure. In its expanded, post-deployment configuration, the wire mesh structure 1405 has an oval shape. To facilitate optimal expansion and compression for easier delivery and removal, the wire mesh structure 1405 includes a plurality of staggered nodes 1406, 1407, 1408, 1409 along its length. A first set of staggered nodes 1406 is positioned at the proximal end of the wire mesh structure 1405 and circumscribes a first opening 1401. In one embodiment, each node in said first set of staggered nodes 1406 is bent upwards to extend in a direction opposite from an interior of the wire mesh structure 1405. The nodes in said first set of staggered nodes 1406 are used as grasping points for a retrieval device during removal of the intragastric device 1400. The wire mesh structure 1405 includes a second set of staggered nodes 1407 distal to said first set 1406 and proximal to a midpoint of said wire mesh structure 1405. A third set of staggered nodes 1408 is positioned distal to said midpoint and proximal to the distal end of the wire mesh structure 1405. A fourth set of staggered nodes 1409 is positioned at the distal end of the wire mesh structure 1405 and comprises the free end of the anti-migration component 1420. All of the curves comprising the nodes in each set of staggered nodes 1406, 1407, 1408, 1409 are designed to have a bend that is atraumatic to body tissues. The nodes are staggered to prevent bunching of the bending points of the wire and bulking of the wire mesh structure as it is compressed to its pre-deployment configuration. Spreading the nodes along the length of the wire mesh structure allows for an overall smaller diameter of the device once it is compressed.

The sleeve 1410 includes a proximal portion 1411 and a distal portion 1416 which join at a transition point 1415 along the sleeve 1410 body. Both the proximal portion 1411 and the distal portion 1416 of the sleeve 1410 are funnel shaped, each having a diameter that decreases as the portions 1411, 1416 extend distally. In one embodiment, the diameter of the proximal portion 1411 is substantially the same as the diameter of the anti-migration collar 1420 at a proximal end of said proximal portion 1411. The diameter of the proximal portion 1411 decreases as the proximal portion 1411 extends distally until the sleeve 1410 transitions into its distal portion 1416, at which point the diameters of the proximal portion 1411 and the distal portion 1416 are equal. The diameter of the distal portion 1416 then decreases as said distal portion 1416 extends distally. The distal portion 1416 of the sleeve 1410 ends in a second opening 1419 at a distal end of the intragastric device 1400. In one embodiment, the proximal portion 1411 has a length that is less than a length of the distal portion 1416. In various embodiments, the funnel shaped sleeve 1410 comprises at least one wire support. In some embodiments, the at least one wire support comprises the same wire(s) in both the proximal portion 1411 and distal portion 1416. In other embodiments, the proximal portion 1411 and distal portion 1416 comprise separate wire supports and the wires are joined together at a distal end of the proximal portion 1411 and a proximal end of the distal portion 1416. In one embodiment, the separate wires are spot welded together. The wire is folded upon itself to create a crisscross weave pattern in the sleeve 1410. In both the proximal 1411 and distal portions 1416, the intersecting sections of the wire come closer to one another as the portions 1411, 1416 extend distally and the funnel shape narrows, such that the weave pattern becomes tighter at the distal ends of each portion 1411, 1416. The sleeve 1410 includes curves or free ends, similar to the nodes of the wire mesh structure 1405, at its proximal end and distal end. The free ends are designed to be atraumatic to body tissues. The free ends at the proximal end of the sleeve 1410 are attached to the nodes of the fourth set of staggered nodes 1409 of the wire mesh structure 1405 via one or more sutures 1422. The free ends at the distal end of the sleeve 1410 circumscribe the second opening 1419. In various embodiments, the sleeve 1410 is a short sleeve having a total length in a range of 5 cm-120 cm. In one embodiment, the sleeve 1410 is a short sleeve having a total length of 60 cm. In one embodiment, the sleeve 1410 includes a soft atraumatic tip 1430 at its distal end. The tip 1430 contains no wires and is included to prevent injury to the intestinal mucosa from the sleeve tip.

When the sleeve 1410 is attached to the wire mesh structure 1405, the proximal end of the proximal portion 1411 of the sleeve 1410 is slid over and covers at least a portion of the anti-migration component 1420 such that the proximal portion 1411 of the sleeve 1410 covers an opening at the distal end of the wire mesh structure. This positioning enables fluid communication between the interior of the wire mesh structure 1405 and an interior of the sleeve 1410 and establishes a pathway for food from said first opening 1401, into said interior of said wire mesh structure 1405, through said interior of said sleeve 1410, and out of said second opening 1419.

Figure 15:
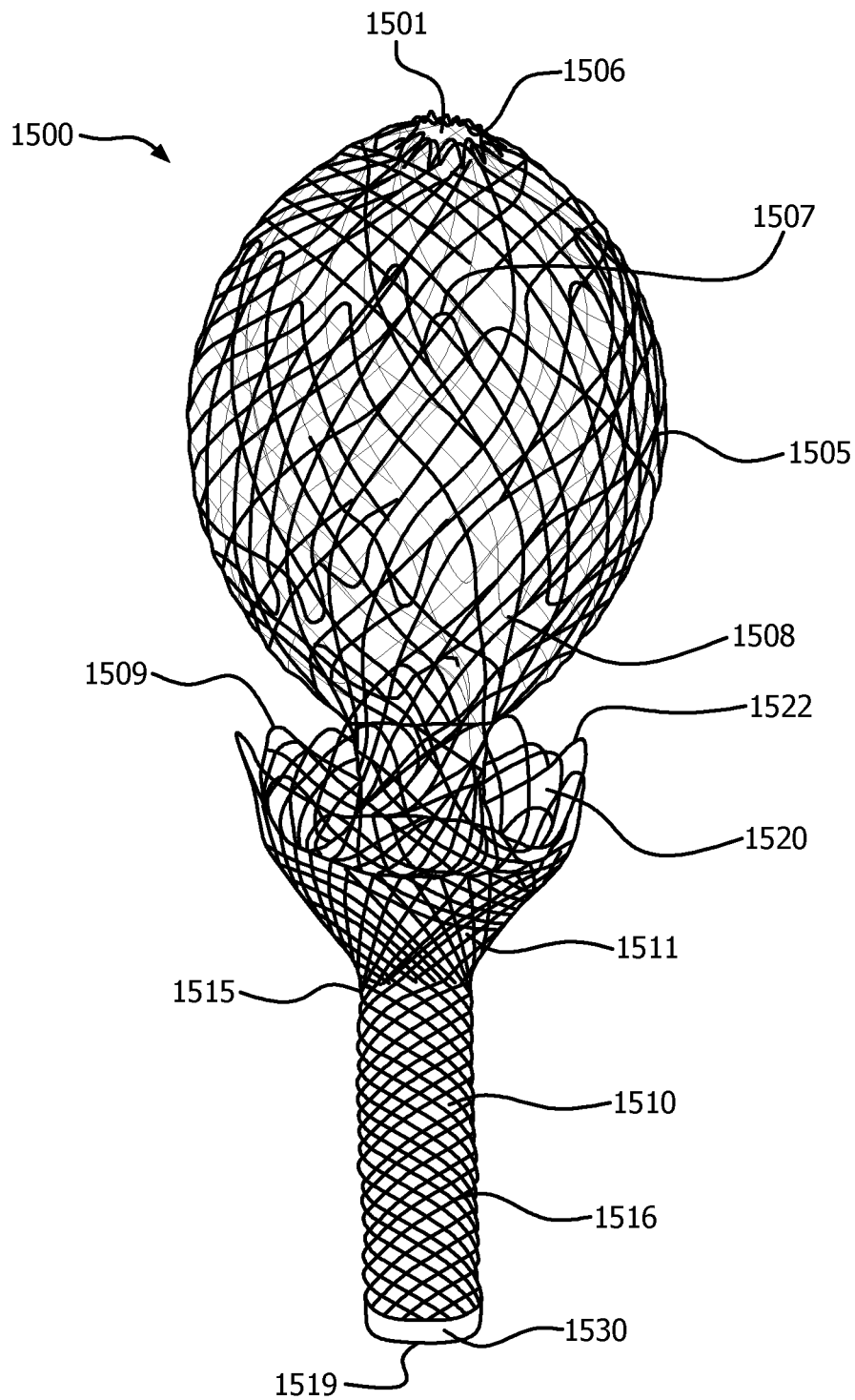
FIG. 15 is an illustration of an intragastric device with a cylindrically shaped sleeve in a post-deployment configuration, in accordance with one embodiment of the present specification.

FIG. 15 is an illustration of an intragastric device 1500 with a cylindrically shaped sleeve 1510 in a post-deployment configuration, in accordance with one embodiment of the present specification. The intragastric device 1500 includes a wire mesh structure 1505 having a proximal end and a distal end with an anti-migration collar 1520 formed at said distal end. The sleeve 1510 includes a proximal end and a distal end and is attached via its proximal end to the anti-migration collar 1520. In one embodiment, the sleeve 1510 includes a soft atraumatic tip 1530 at its distal end. The tip 1530 contains no wires and is included to prevent injury to the intestinal mucosa from the sleeve tip.

The wire mesh structure 1505 is similar to the structure 1405 discussed with reference to FIG. 14 and includes an oval shape with a crisscross weave pattern, a plurality of staggered nodes 1506, 1507, 1508, 1509, and a first opening 1501 at its proximal end. All of the curves comprising the nodes in each set of staggered nodes 1506, 1507, 1508, 1509 are designed to have a bend that is atraumatic to body tissues.

The sleeve 1510 includes a proximal portion 1511 and a distal portion 1516 which join at a transition point 1515 along the sleeve 1510 body. The proximal portion 1511 of the sleeve 1510 is funnel shaped and includes a diameter that decreases as the portion 1511 extends distally. In one embodiment, the diameter of the proximal portion 1511 is substantially the same as the diameter of the anti-migration collar 1520 at a proximal end of said proximal portion 1511. The diameter of the proximal portion 1511 decreases as the proximal portion 1511 extends distally until the sleeve 1510 transitions into its distal portion 1516, at which point the diameters of the proximal portion 1511 and the distal portion 1516 are equal. The diameter of the distal portion 1516 then continues at the same size as said distal portion 1516 extends distally, giving the distal portion 1516 a substantially cylindrical shape. The distal portion 1516 of the sleeve 1510 ends in a second opening 1519 at a distal end of the intragastric device 1500. In one embodiment, the proximal portion 1511 has a length that is less than a length of the distal portion 1516.

In various embodiments, the funnel shaped proximal portion 1511 of the sleeve 1510 comprises at least one wire support. The wire is folded upon itself to create a crisscross weave pattern in the sleeve 1510. The intersecting sections of the wire come closer to one another as the portion 1511 extends distally and the funnel shape narrows, such that the weave pattern becomes tighter at the distal end of the proximal portion 1511. In various embodiments, the distal portion 1516 includes at least one helical wire support extending along its cylindrical length. The helical wire support has a consistent pitch such that a resultant helical weave structure has the same pattern along the length of the distal portion 1516 of the sleeve 1510. In some embodiments, the helical wire support of the distal portion 1516 is an extension of the at least one wire support of the proximal portion 1511. In other embodiments, the proximal portion 1511 and distal portion 1516 comprise separate wire supports and the wires are joined together at a distal end of the proximal portion 1511 and a proximal end of the distal portion 1516. In one embodiment, the separate wires are spot welded together. The sleeve 1510 includes curves or free ends, similar to the nodes of the wire mesh structure 1505, at its proximal end and distal end. The free ends are designed to be atraumatic to body tissues. The free ends at the proximal end of the sleeve 1510 are attached to the nodes of the fourth set of staggered nodes 1509 of the wire mesh structure 1505 via one or more sutures 1522. The free ends at the distal end of the sleeve 1510 circumscribe the second opening 1519. In various embodiments, the sleeve 1510 is a short sleeve having a total length in a range of 5 cm-120 cm. In one embodiment, the sleeve 1510 is a short sleeve having a total length of 60 cm. The funnel shaped conical section can vary from being 1% of the total sleeve length to being 100% of the total sleeve length.

When the sleeve 1510 is attached to the wire mesh structure 1505, the proximal end of the proximal portion 1511 of the sleeve 1510 is slid over the anti-migration component 1520 such that the proximal portion 1511 of the sleeve 1510 covers an opening at the distal end of the wire mesh structure. This positioning enables fluid communication between the interior of the wire mesh structure 1505 and an interior of the sleeve 1510 and establishes a pathway for food from said first opening 1501, into said interior of said wire mesh structure 1505, through said interior of said sleeve 1510, and out of said second opening 1519.

Figure 16A:
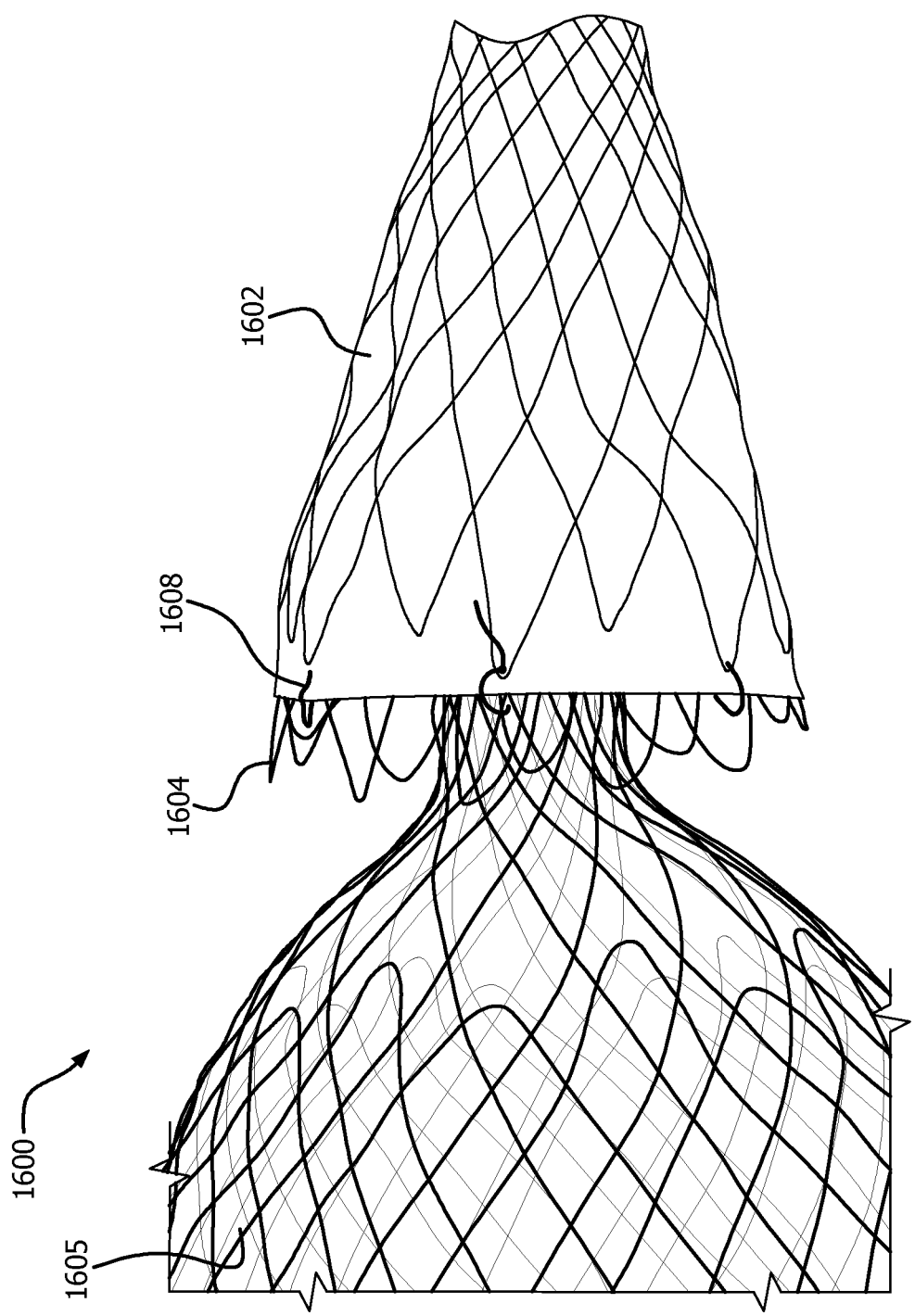
FIG. 16A is a close-up illustration of a funnel shaped sleeve attached to an anti-migration collar of a wire mesh structure of an intragastric device, in accordance with one embodiment of the present specification.

FIG. 16A is a close-up illustration of a funnel shaped sleeve 1602 attached to an anti-migration collar 1604 of a wire mesh structure 1605 of an intragastric device 1600, in accordance with one embodiment of the present specification. The sleeve 1602 is attached to the anti-migration collar 1604 via a plurality of sutures 1608.

Figure 16B:
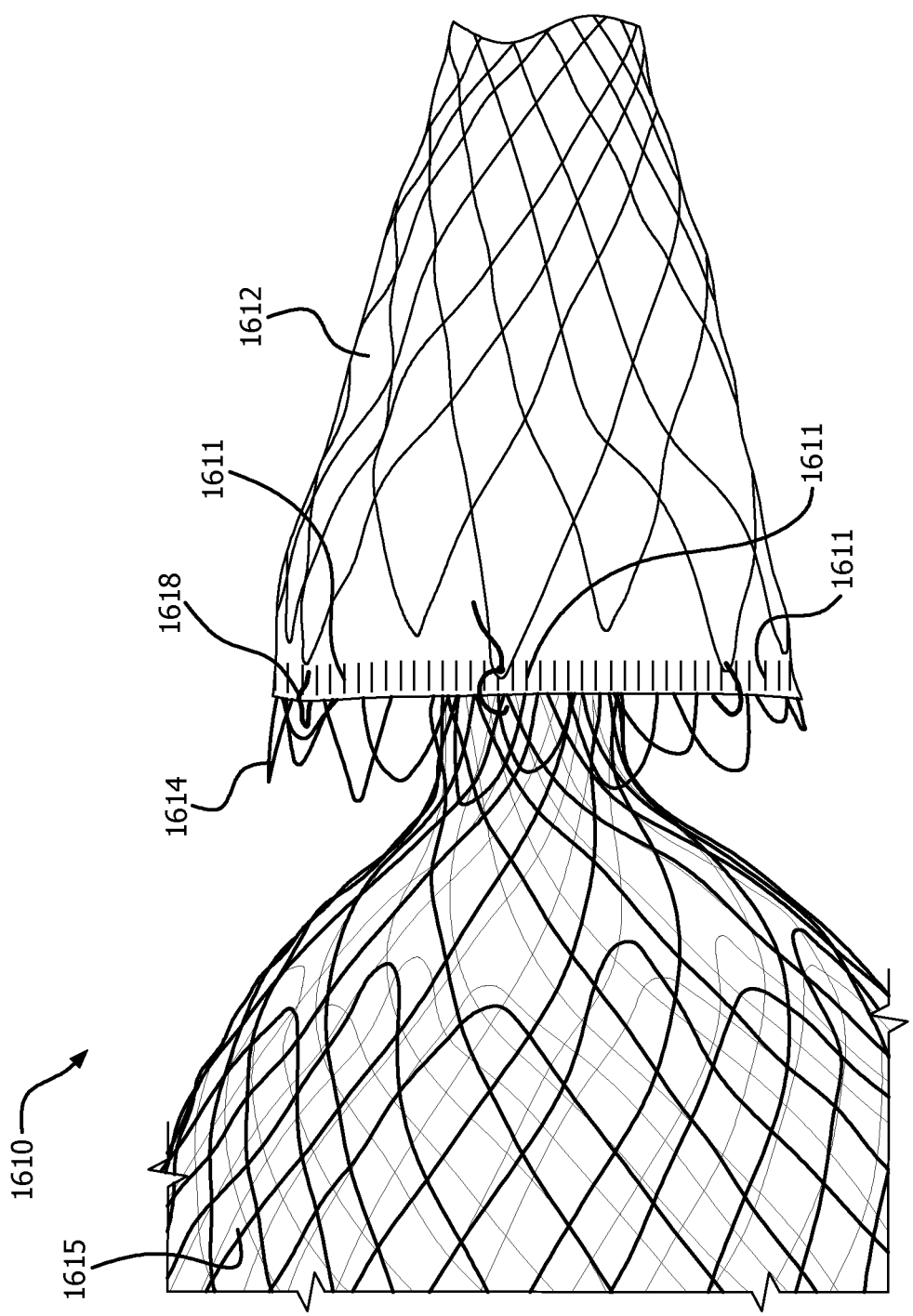
FIG. 16B is a close-up illustration of a funnel shaped sleeve attached to an anti-migration collar of a wire mesh structure of an intragastric device and having a proximal sleeve end having frayed edges, in accordance with another embodiment of the present specification.

FIG. 16B is a close-up illustration of a funnel shaped sleeve 1612 attached to an anti-migration collar 1614 of a wire mesh structure 1615 of an intragastric device 1610, in accordance with another embodiment of the present specification. The sleeve 1612, attached to the anti-migration collar 1614 via a plurality of sutures 1618, includes a plurality of frayed edges 1611 at its proximal end to make said edges less traumatic to body tissues.

Figure 16D:
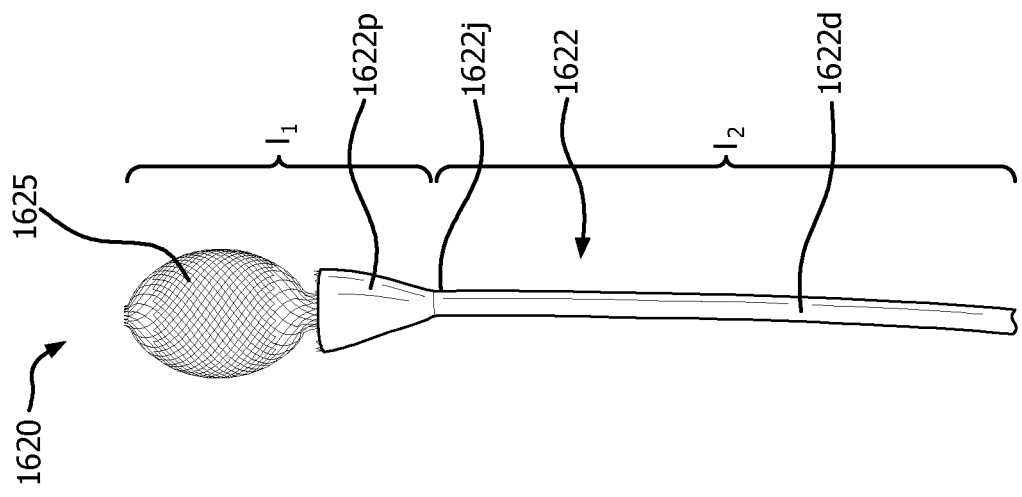
FIG. 16D is an illustration of the intragastric device of FIG. 16C with the sleeve straightened to depict the device dimensions relative to the surrounding anatomy.
Figure 16C:
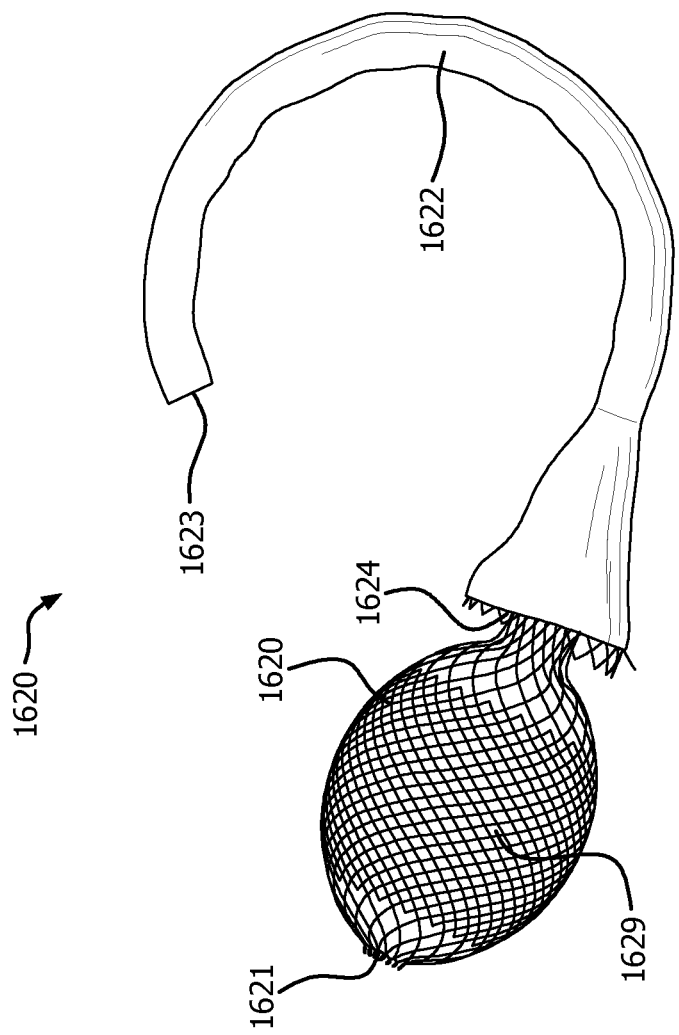
FIG. 16C is an illustration of an intragastric device comprising a wire mesh structure and attached sleeve, in accordance with one embodiment of the present specification.

FIG. 16C is an illustration of an intragastric device 1620 comprising a wire mesh structure 1625 and attached sleeve 1622, in accordance with one embodiment of the present specification. The wire mesh structure 1625 is anchorless and includes atraumatic wire ends. In one embodiment, the wire mesh structure 1625 is composed of Nitinol. The wire mesh structure 1625 includes an anti-migration collar 1624 to which the sleeve 1622 is attached. In some embodiments, the wire mesh structure 1625 includes retrieval drawstrings positioned proximate its proximal end, as depicted with reference to FIG. 16E. The sleeve 1622 comprises an anchorless, impermeable, fluoropolymer liner designed to extend into the proximal portion of the small bowel, particularly the mid-duodenum. In various embodiments, the sleeve 1622 includes an embedded Nitinol stent structure within polymer layers such that the sleeve 1622 is atraumatic and no portion of the Nitinol comes into contact with the small intestine. In one embodiment, the sleeve 1622 includes radiopaque markers for assistance with proper delivery and placement.

The wire mesh structure 1625 is anchorless and occupies a space within the stomach. The wire mesh structure 1625 is free to float within the stomach and intermittently exerts gentle, atraumatic stretching forces on a portion of the stomach as it comes into contact with the inner stomach wall. The stretching forces induce the sensation of satiety in the patient. The anti-migration collar 1624 is appropriately shaped to receive the attached sleeve 1622. Gastric contents enter the wire mesh structure 1625 through a first opening 1621 at the proximal end of the wire mesh structure 1625 or through openings 1629 between the wires of the wire mesh structure 1625 and are directed into the attached sleeve 1622. The gastric contents then pass through the sleeve 1622 and empty out a second opening 1623 at the distal end of the sleeve 1622, either into the duodenum or jejunum, depending on the length of the sleeve 1622. The sleeve 1622 is pre-attached to the anti-migration collar 1624 of the wire mesh structure 1625. The Nitinol stent structure embedded in the sleeve 1622 provides support to the sleeve 1622 and prevents it from torsion or being kinked by actions of the intestinal musculature. Additionally, the Nitinol stent structure provides a gentle, radial stretching force on the small intestinal wall, inducing a sensation of satiety in the patient and preventing the passage of chyme around the sleeve 1622.

FIG. 16D is an illustration of the intragastric device 1620 of FIG. 16C with the sleeve 1622 straightened to depict the device 1620 dimensions relative to the surrounding anatomy. The sleeve 1622 includes a proximal, funnel or cone shaped portion 1622p attached to the anti-migration collar of the wire mesh structure 1625 and a distal, cylindrically shaped portion 1622d extending distally from said proximal portion 1622p. The wire mesh structure 1625 and proximal portion 1622p of the sleeve 1622 are configured to reside in the stomach of the patient and together have a maximum outer diameter of approximately 8 inches and a length $l_1$. In some embodiments, length $l_1$ is approximately 10 inches. In some embodiments, the volume of a fully deployed wire mesh structure 1625 is approximately 1 liter. The proximal portion 1622p of the sleeve 1622 and the distal portion 1622d of the sleeve 1620 meet at a junction point 1622j which is configured to sit at the patient's pylorus. The distal portion 1622d of the sleeve 1620 is configured to reside in the small intestine of the patient, particularly the duodenum, and has a maximum outer diameter of approximately 1.0 inches and a length $l_2$. In some embodiments, length $l_2$ is approximately 10 to 25 inches. In some embodiments, the length $l_2$ of the distal portion 1622d is such that the distal end of the sleeve 1622 is positioned in the duodenum so gastric contents pass from the stomach, through the device 1620, and directly into the duodenum, bypassing the pylorus. In other embodiments, the length $l_2$ is such that the distal end of the sleeve 1622 is positioned in the jejunum so gastric contents pass from the stomach, through the device 1620, and directly into the jejunum, bypassing the pylorus and duodenum. In other embodiments, the wire mesh structure has a maximum diameter of 18 inches, a maximum length of 24 inches, and a maximum volume of 2.5 liters.

Figure 16E:
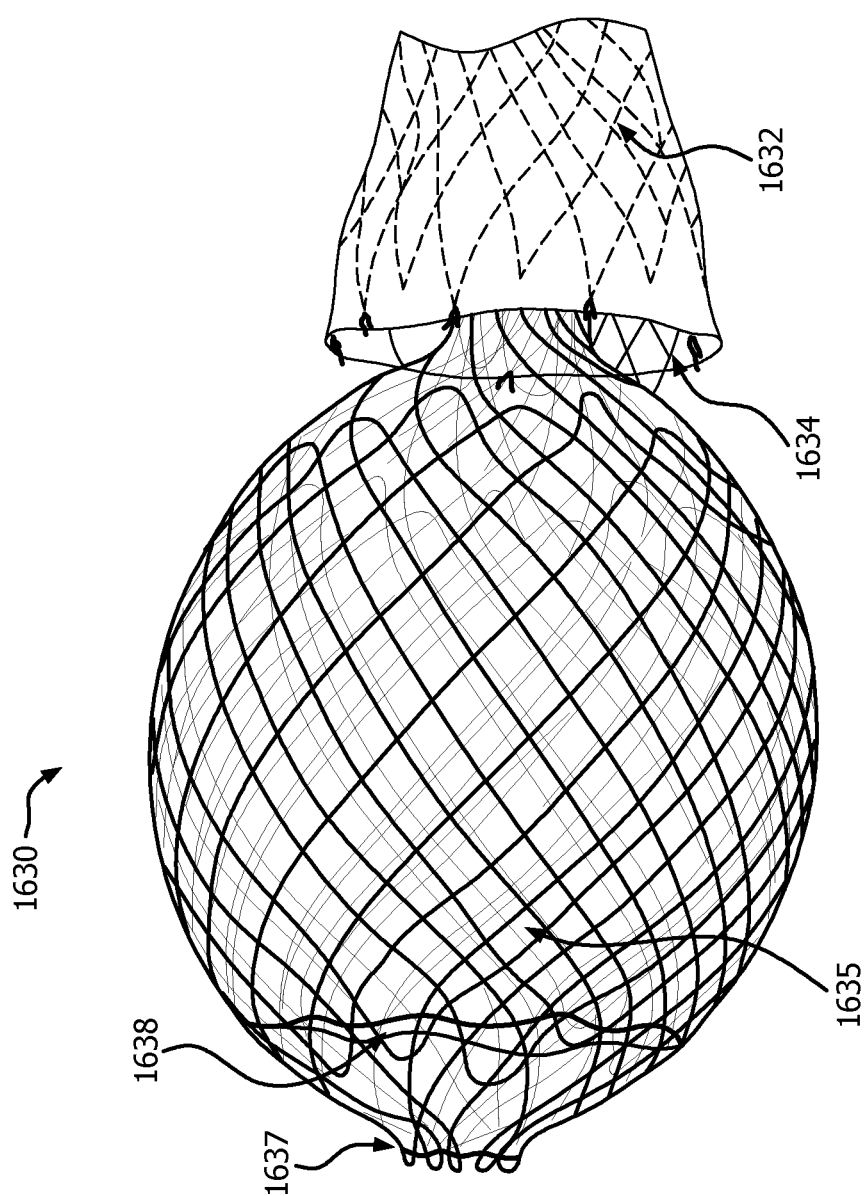
FIG. 16E is an illustration of a wire mesh structure and sleeve of an intragastric device, depicting retrieval drawstrings on said wire mesh structure, in accordance with one embodiment of the present specification.

FIG. 16E is an illustration of a wire mesh structure 1635 and sleeve 1632 of an intragastric device 1630, depicting retrieval drawstrings 1637, 1638 on said wire mesh structure 1635, in accordance with one embodiment of the present specification. The sleeve 1632 is attached to an anti-migration collar 1634 at the distal end of the wire mesh structure 1635. In some embodiments, the anti-migration collar 1634 includes loops in the wires of the nodes at the distal end of the nodes, as seen with reference to FIG. 4C, and the sleeve 1632 is sutured to the anti-migration collar 1634 at these loops. In the pictured embodiment, a pair of retrieval drawstrings 1637, 1638 are located on the wire mesh structure 1635 proximate its proximal end. A first drawstring 1637 is positioned at the proximal end of the wire mesh structure 1635 and the second drawstring 1638 is positioned distal to the first drawstring 1637 but still proximate the proximal end of the wire mesh structure 1635. The retrieval drawstrings 1637, 1638 pass through the openings between the wires of the wire mesh structure 1635. During retrieval, free ends of the retrieval drawstrings 1637, 1638 are pulled on using a grasper to constrict the wire mesh structure 1635 to a smaller outer diameter so it may be removed from the patient through an endoscope. In one embodiment, the two drawstrings 1637, 1638 are interconnected operably such that constricting one drawstring results in the other drawstring constricting simultaneously.

Figure 16F:
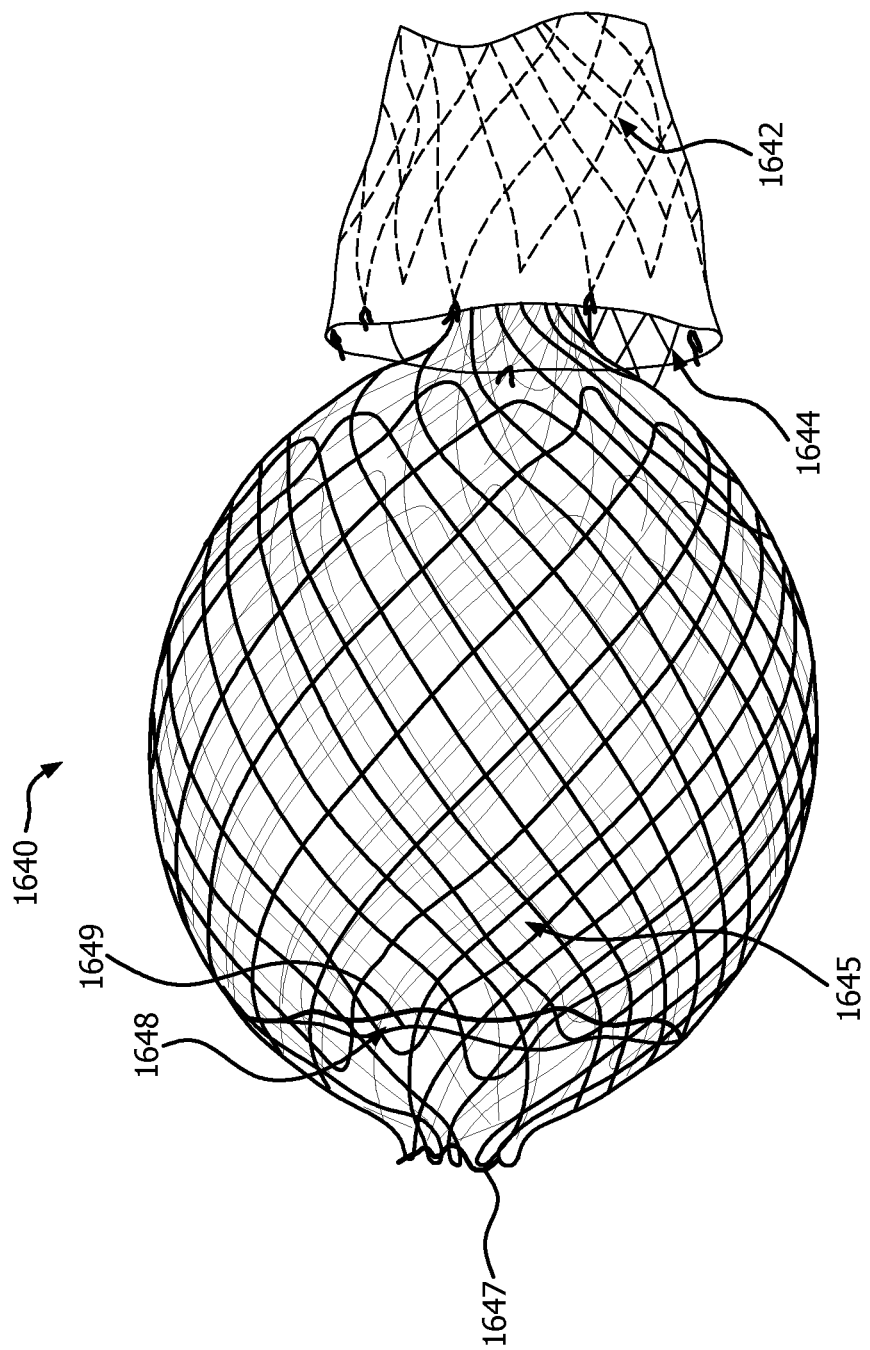
FIG. 16F is an illustration of a wire mesh structure and sleeve of an intragastric device, depicting a single retrieval drawstring on said wire mesh structure, in accordance with one embodiment of the present specification.

FIG. 16F is an illustration of a wire mesh structure 1645 and sleeve 1642 of an intragastric device 1640, depicting a single retrieval drawstring 1648 on said wire mesh structure 1645, in accordance with one embodiment of the present specification. The sleeve 1642 is attached to an anti-migration collar 1644 at the distal end of the wire mesh structure 1645. In some embodiments, the anti-migration collar 1644 includes loops in the wires of the nodes at the distal end of the nodes, as seen with reference to FIG. 4C, and the sleeve 1642 is sutured to the anti-migration collar 1644 at these loops. In the pictured embodiment, a single retrieval drawstring 1648 is located on the wire mesh structure 1645 proximate its proximal end. The retrieval drawstrings 1648 passes through the openings between the wires of the wire mesh structure 1645. During retrieval, free ends of the retrieval drawstring 1648 are pulled on using a grasper to constrict the wire mesh structure 1645 to a smaller outer diameter so it may be removed from the patient through an endoscope. In the pictured embodiment, the single drawstring 1648 is sufficient to constrict two pluralities of nodes 1647, 1649 on the wire mesh structure 1645, a first plurality 1647 at the proximal end of the wire mesh structure 1645 and a second plurality 1649 at the level of the drawstring 1648. In other embodiments, a single drawstring is sufficient for constricting one or more than two pluralities of nodes on the wire mesh structure.

In some embodiments, wherein the sleeve includes metal wire supports, the ends of the wire or wires are designed to be atraumatic to body tissues. In various embodiments, the wire ends are blunted, folded upon the wire, or welded to other wire ends. In other embodiments, the distal end of the sleeve includes a component designed to make said distal end atraumatic to body tissues. FIG. 17A is a cross-sectional illustration of a distal end of a sleeve 1705, depicting one embodiment of a component 1710 designed to configure said distal end to be atraumatic to body tissues. The component 1710 has a cylindrical shape with a proximal end 1711, a distal end 1719, and a lumen 1716 within. The component 1710 is open at both ends 1711, 1719. The lumen 1716 of the component 1710 is in fluid communication with a lumen 1706 of the sleeve 1705 to allow for food to pass through the wire mesh of the device, the sleeve 1705, and the component 1710. The distal end 1719 is rounded into a blunt shape that is atraumatic to body tissues. An outer surface of the component 1710 includes a groove 1713 configured to receive a circular member or O-ring 1714. To attach the component 1710 to the sleeve 1705, the distal end of the sleeve 1705 is coaxially slid onto the proximal end 1711 of the component 1710 such that a portion of the sleeve 1705 is positioned over said groove 1713. The O-ring 1714 is then placed over the sleeve 1705 and into the groove 1713, providing a robust connection of the sleeve 1705 to the component 1710. The distal sleeve end 1707 is then folded in a proximal direction back toward the sleeve 1705 body. In one embodiment, the component 1710 includes a circular flange 1712 which extends outwardly from the outer surface of the component 1710 and then in a proximal direction. The flange 1712 serves to cover any sharp ends present in the folded distal sleeve end 1707 and further protect body tissues from trauma. In various embodiments, the component 1710 has a length in a range of 5 mm to 500 mm, an outside diameter in a range of 3 mm to 30 mm, and an inside diameter in a range of 0.5 to 50 mm.

Figure 17B:
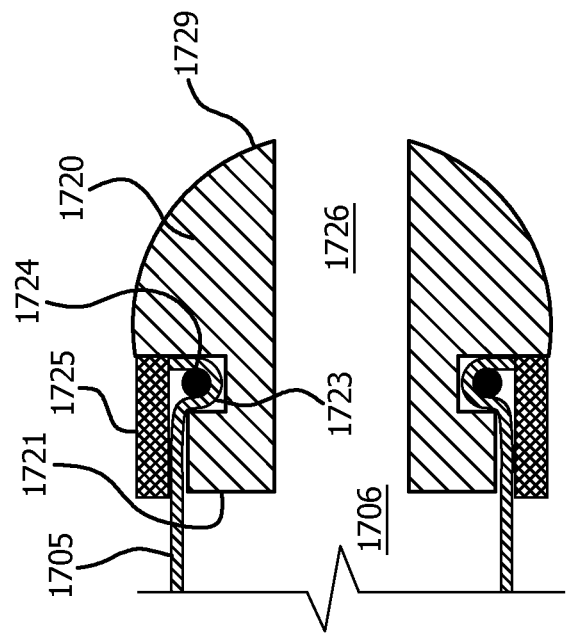
FIG. 17B is a cross-sectional illustration of a distal end of a sleeve, depicting another embodiment of a component designed to configure said distal end to be atraumatic to body tissues.
Figure 17A:
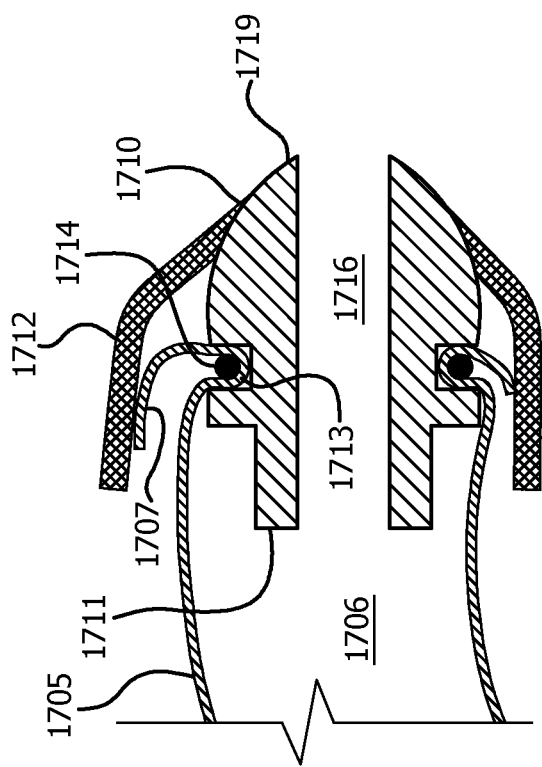
FIG. 17A is a cross-sectional illustration of a distal end of a sleeve, depicting one embodiment of a component designed to configure said distal end to be atraumatic to body tissues.

FIG. 17B is a cross-sectional illustration of a distal end of a sleeve 1705, depicting another embodiment of a component 1720 designed to configure said distal end to be atraumatic to body tissues. The component 1720 has a cylindrical shape with a proximal end 1721, a distal end 1729, and a lumen 1726 within. The component 1720 is open at both ends 1721, 1729. The lumen 1726 of the component 1720 is in fluid communication with a lumen 1706 of the sleeve 1705 to allow for food to pass through the wire mesh of the device, the sleeve 1705, and the component 1720. The distal end 1729 is rounded into a blunt shape that is atraumatic to body tissues. An outer surface of the component 1720 includes a groove 1723 configured to receive a circular member or O-ring 1724. To attach the component 1720 to the sleeve 1705, the distal end of the sleeve 1705 is coaxially slid onto the proximal end 1721 of the component 1720 such that a portion of the sleeve 1705 is positioned over said groove 1723. The O-ring 1724 is placed over the sleeve 1705 and into the groove 1723. The distal sleeve end is then folded in a proximal direction back toward the sleeve 1705 body. A heat shrink tube 1725 is then placed over said distal sleeve end and said O-ring 1724. Heat is applied to the heat shrink tube 1725 to shrink the tube 1725 such that it securely connects the sleeve 1705 to the component 1720. Any sharp ends in the distal sleeve end are contained under the heat shrink tube 1725 and are not exposed to body tissues.

Figure 17C:
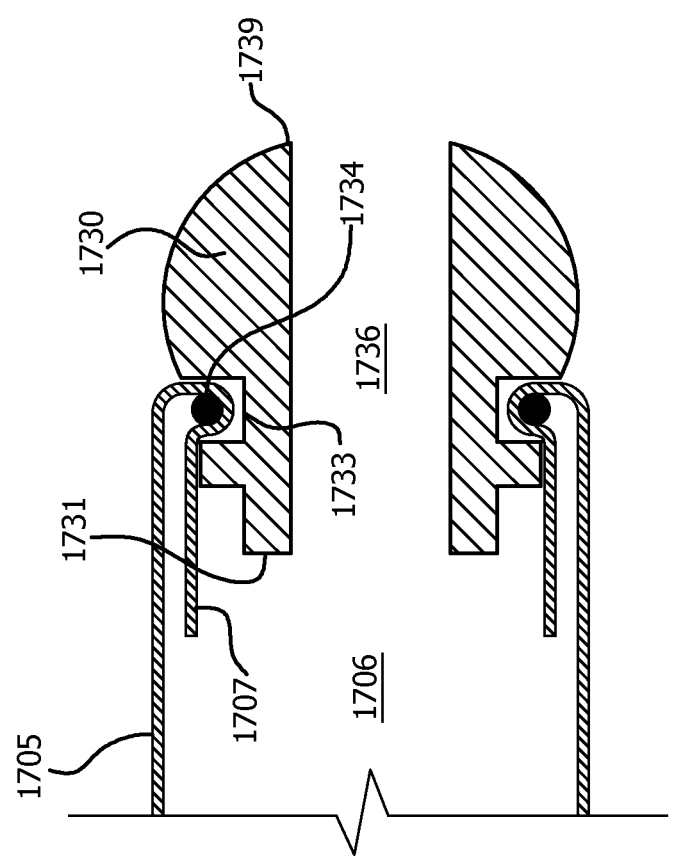
FIG. 17C is a cross-sectional illustration of a distal end of a sleeve, depicting another embodiment of a component designed to configure said distal end to be atraumatic to body tissues.

FIG. 17C is a cross-sectional illustration of a distal end of a sleeve 1705, depicting another embodiment of a component 1730 designed to configure said distal end to be atraumatic to body tissues. The component 1730 has a cylindrical shape with a proximal end 1731, a distal end 1739, and a lumen 1736 within. The component 1730 is open at both ends 1731, 1739. The lumen 1736 of the component 1730 is in fluid communication with a lumen 1706 of the sleeve 1705 to allow for food to pass through the wire mesh of the device, the sleeve 1705, and the component 1730. The distal end 1739 is rounded into a blunt shape that is atraumatic to body tissues. An outer surface of the component 1730 includes a groove 1733 configured to receive a circular member or O-ring 1734. To attach the component 1730 to the sleeve 1705, the sleeve 1705 is first everted to be inside out. The distal end of the sleeve 1705 is then coaxially slid onto the distal end 1739 of the component 1730 such that a portion of the sleeve 1705 is positioned over said groove 1733. The O-ring 1734 is placed over the sleeve 1705 and into the groove 1733. The sleeve 1705 is then folded in a proximal direction back over the O-ring 1734 and proximal end 1731 of the component 1730, providing a robust connection of the sleeve 1705 to the component 1730. This process of connecting the sleeve 1705 to the component 1730 ensures that the distal sleeve end 1707 will become positioned within the sleeve lumen 1706. Any sharp ends in the distal sleeve end 1707 are contained within the sleeve lumen 1706 and are not exposed to body tissues.

Figure 18:
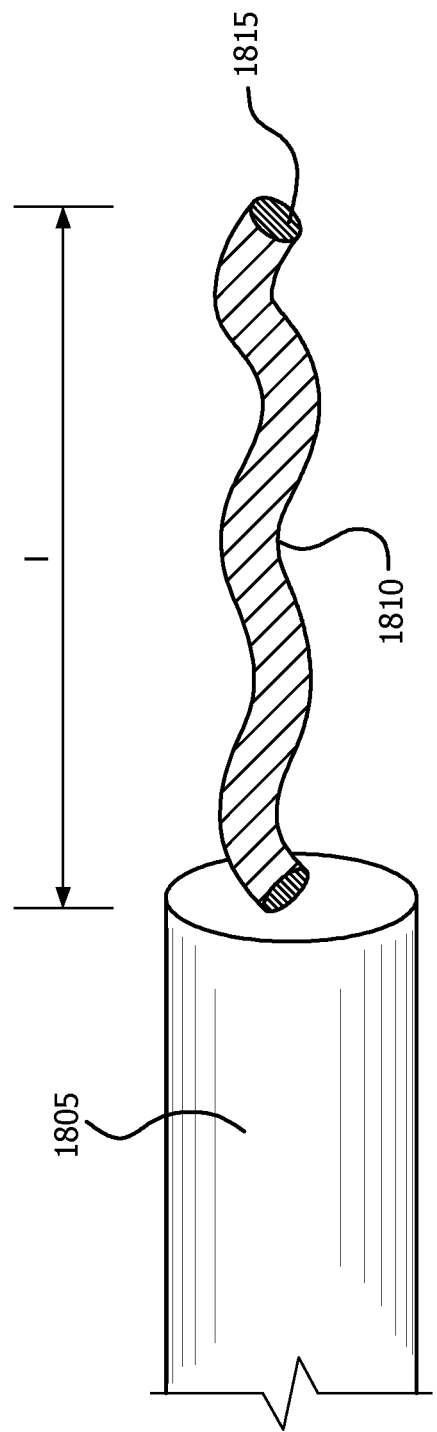
FIG. 18 is an illustration of a distal end of a sleeve with a positioning tail attached thereto, in accordance with one embodiment of the present specification.

FIG. 18 is an illustration of a distal end of a sleeve 1805 with a positioning tail 1810 attached thereto, in accordance with one embodiment of the present specification. The positioning tail 1810 is attached to the distal end of a short sleeve 1805 having a length of 5 mm to 500 mm. The positioning tail 1810 comprises a ribbon of material extending from the distal end of the sleeve 1805 into a patient's duodenum and is used to help maintain proper implant orientation of the sleeve 1805 relative to a patient's pylorus. In various embodiments, the positioning tail 1810 has a length l in a range of 5 mm to 500 mm. In one embodiment, the positioning tail 1810 has a length l of 25 mm. In one embodiment, the distal end of the positioning tail 1810 includes a bead 1815 for weighing down said distal end. In another embodiment, the distal end of the positioning tail includes a plurality of separate free ends similar to a horse tail. In other embodiments, the distal end of the positioning tail includes any mechanism or component designed to provide additional weight or tugging upon said distal end to allow for pulling on said tail to ensure proper sleeve orientation. In one embodiment, the distal end of the positioning tail does not include any additional components.

FIG. 19A is an illustration of a distal end of a sleeve 1905 comprising a plurality of fringes 1907 joined to a ring 1908, in accordance with one embodiment of the present specification. In various embodiments, the distal end of the sleeve 1905 comprises two or more fringes 1907. In one embodiment, the distal end of the sleeve 1905 comprises four fringes 1907. Each fringe 1907 comprises a portion of sleeve material which is separate from adjacent fringes 1907. The fringes 1907 are separated from one another by a space 1906 which allows food passing through the intragastric device to exit from the sleeve 1905. In various embodiments, each fringe 1907 has a length in a range of 5 mm to 500 mm and a width in a range of 1 mm to 15 mm. In some embodiments, the width of each fringe 1907 decreases as the fringe 1907 extends distally. The fringes 1907 are connected to a ring 1908 at the most distal end of the sleeve 1905. The ring 1908 includes a center opening 1909 for passage of food. In some embodiments, the ring 1908 is semi-rigid. In various embodiments, the ring 1908 has an outer diameter in a range of 1 mm to 30 mm and an inner diameter in a range of 1 mm to 30 mm. In various embodiments, the ring 1908 is attached to each fringe 1907 via suturing, gluing, bonding or any other method of attachment. The ring 1908 serves to join the fringes 1907 together and to weigh down the distal end of the sleeve 1905 to assist with proper device orientation. The surfaces of the ring 1908 are blunted to be atraumatic to body tissues. In some embodiments, the fringes 1907 and ring 1908 are parachute shaped.

FIG. 19B is an illustration of a distal end of a sleeve 1910 comprising a plurality of fringes 1912 joined to a ball 1913, in accordance with one embodiment of the present specification. In various embodiments, the distal end of the sleeve 1910 comprises two or more fringes 1912. In one embodiment, the distal end of the sleeve 1910 comprises four fringes 1912. Each fringe 1912 comprises a portion of sleeve material which is separate from adjacent fringes 1912. The fringes 1912 are separated from one another by a space 1911 which allows food passing through the intragastric device to exit from the sleeve 1910. In various embodiments, each fringe 1912 has a length in a range of 5 mm to 500 mm and a width in a range of 1 mm to 15 mm. In some embodiments, the width of each fringe 1912 decreases as the fringe 1912 extends distally. The fringes 1912 are connected to a ball 1913 at the most distal end of the sleeve 1910. In various embodiments, the ball 1913 has a diameter in a range of 2 mm to 30 mm. In various embodiments, the ball 1913 is glued or bonded to each fringe 1907. The ball 1913 serves to join the fringes 1912 together and to weigh down the distal end of the sleeve 1910 to assist with proper device orientation. Since the ball 1913 has a spherical shape, it has no sharp edges and is atraumatic to body tissues. In another embodiment, the most distal ends of the fringes 1912 are tied together into a knot to form the ball 1913 and no additional ball component is required. In some embodiments, the fringes 1912 and ball 1913 are parachute shaped.

In one embodiment, as seen in FIG. 19C, the ball 1913 includes a lumen 1933 to allow for passage of a guide wire. In another embodiment, the ball 1913 has a groove or depression 1932 to receive an inner pusher catheter or plunger of a delivery device. In one embodiment, the circumference of the ball is designed to sit inside an outer catheter of a delivery device.

Figure 19E:
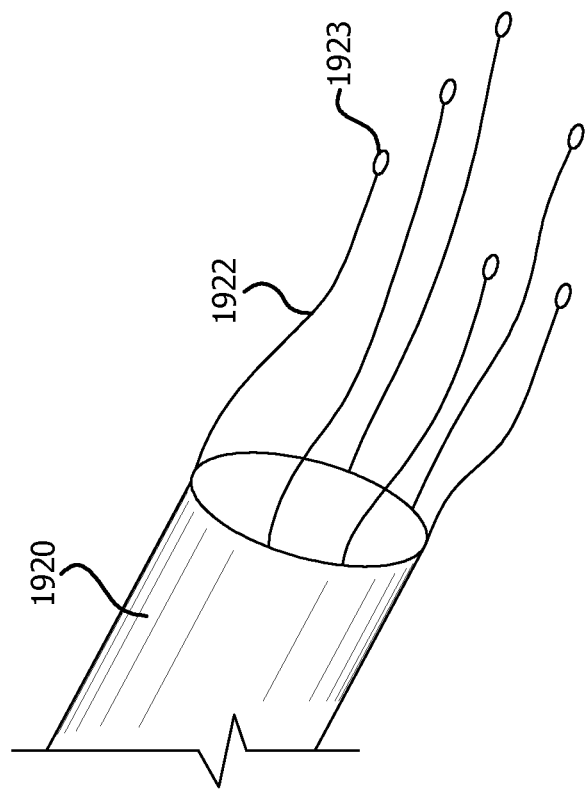
FIG. 19E is an illustration of a distal end of a sleeve having at least one suture with attached suture loop or bead extending therefrom, in accordance with one embodiment of the present specification.
Figure 19D:
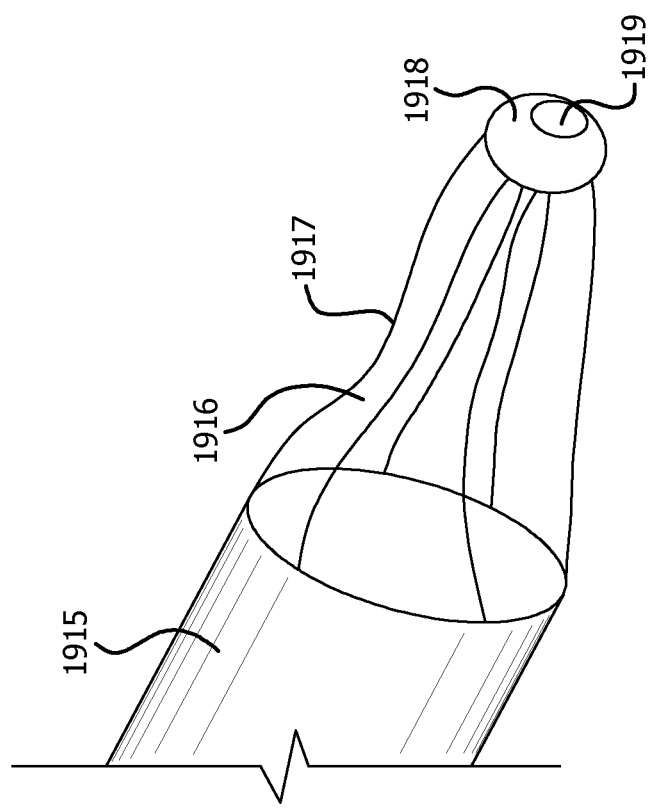
FIG. 19D is an illustration of a distal end of a sleeve having a plurality of sutures extending therefrom and joined to a ball, in accordance with one embodiment of the present specification.

FIG. 19D is an illustration of a distal end of a sleeve 1915 having a plurality of sutures 1917 extending therefrom and joined to a ball 1918, in accordance with one embodiment of the present specification. In various embodiments, the sleeve 1915 includes two or more sutures 1917. In one embodiment, the sleeve 1915 includes six sutures 1917. In various embodiments, the sutures 1917 have a length in a range of 5 mm to 500 mm. In one embodiment, the sutures 1917 are composed of nylon. A proximal end of each suture 1917 is attached to the distal end of the sleeve 1915 and a distal end of each suture 1917 is attached to a ball 1918. In various embodiments, the ball 1918 is glued to each suture 1917. In various embodiments, the ball has a diameter in a range of 3 mm to 30 mm. The ball 1918 is designed to add weight to the distal end of the sleeve 1915 to pull the sleeve 1915 into the proper implant orientation. Since the ball 1918 has a spherical shape, it has no sharp edges and is atraumatic to body tissues. Food exits the distal end of the sleeve 1915 and passes through the spaces 1916 between the sutures 1917. In one embodiment, the ball 1918 includes a center opening 1919 for the passage of guidewire there through. In various embodiments, the ball 1918 is replaced by a ring or similarly designed component to weigh down the sleeve 1915 and ensure proper device orientation. In some embodiments, the sutures 1917 and ball 1918 are parachute shaped.

FIG. 19E is an illustration of a distal end of a sleeve 1920 having at least one suture 1922 with attached suture loop or bead 1923 extending therefrom, in accordance with one embodiment of the present specification. In one embodiment, the sleeve 1920 includes six sutures 1922. In various embodiments, the sutures 1922 have a length in a range of 5 mm to 500 mm. In one embodiment, the sutures 1922 are composed of UHMWPE. A proximal end of each suture 1922 is attached to the distal end of the sleeve 1920 and a distal end of each suture 1922 includes an attached suture loop or bead 1923. The suture loops or beads 1923 are designed to add weight to the distal end of the sleeve 1920 to pull the sleeve 1920 into the proper implant orientation. Since the suture loops or beads 1923 each have a spherical shape, they have no sharp edges and are atraumatic to body tissues.

Figure 20B:
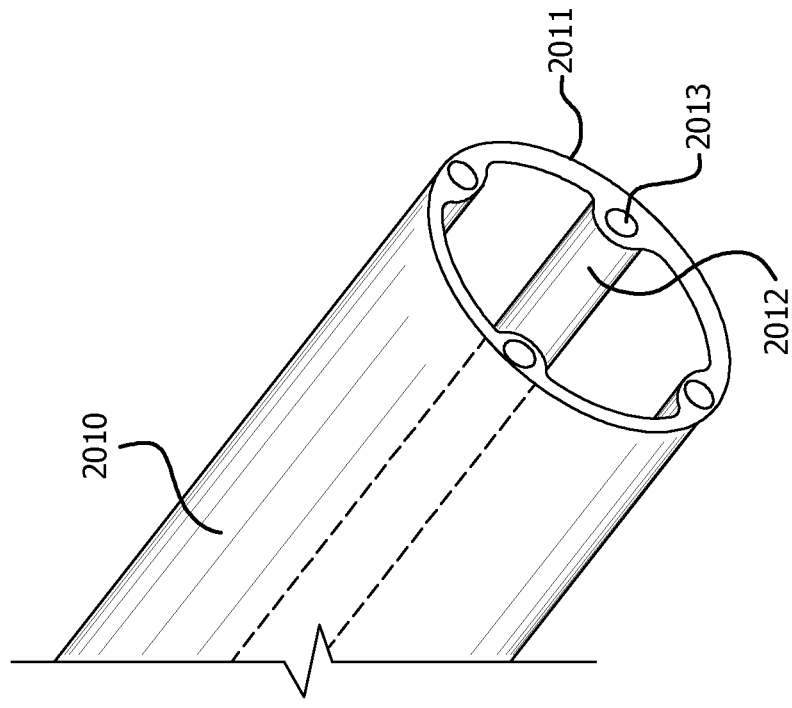
FIG. 20B is an illustration of a distal end of a sleeve depicting at least one channel and support structure within the sleeve wall, in accordance with one embodiment of the present specification.
Figure 20A:
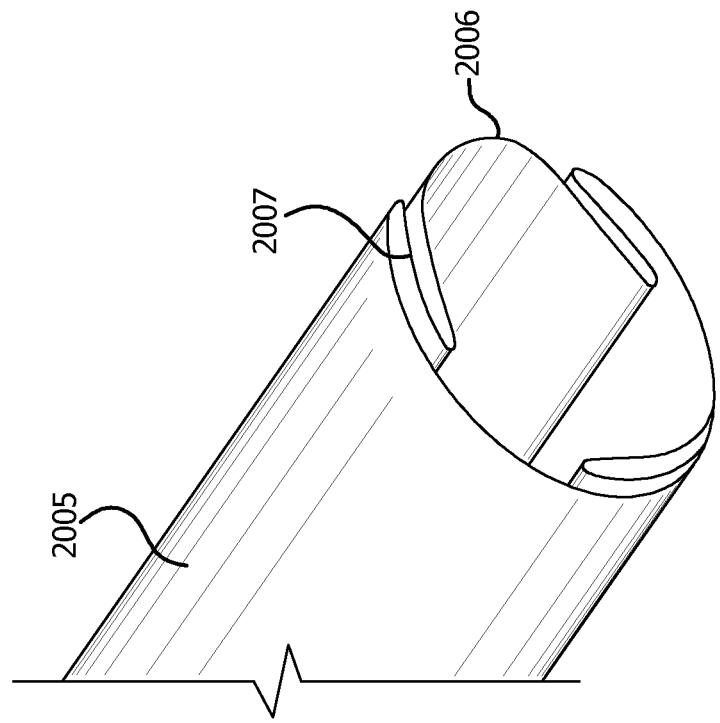
FIG. 20A is an illustration of a distal end of a sleeve depicting at least one fold in the sleeve wall, in accordance with one embodiment of the present specification.

FIG. 20A is an illustration of a distal end of a sleeve 2005 depicting at least one fold 2007 in the sleeve wall 2006, in accordance with one embodiment of the present specification. In one embodiment, the sleeve 2005 includes three folds 2007 in its wall 2006. The folds 2007 are created along a longitudinal axis of the sleeve 2005. In various embodiments, the folds 2007 are positioned equidistant from one another. Referring to FIG. 20A, the sleeve 2005 is folded over itself twice resulting in three layers of sleeve wall 2006 at each fold 2007. The sleeve layers are bonded to each other at each fold 2007. In one embodiment, the sleeve layers are thermally fused together. The folding of the sleeve wall 2006 produces a pleated effect which adds structure and stability to the sleeve 2005. The added structure helps maintain the sleeve 2005 in the proper orientation relative to a patient's pylorus and assists in preventing deformation of the sleeve 2005 by actions of the patient's gastrointestinal tract.

FIG. 20B is an illustration of a distal end of a sleeve 2010 depicting at least one channel 2012 and support structure 2013 within the sleeve wall 2011, in accordance with one embodiment of the present specification. In one embodiment, the sleeve 2010 includes four channels 2012 in its wall 2011 and each channel 2012 includes a support structure 2013 within. In various embodiments, the support structures 2013 comprise tubes or beads. In various embodiments, the support structures 2013 are sized to fit snugly within the channels 2012. The channels 2012 extend along a longitudinal axis of the sleeve 2010. In one embodiment, the channels 2012 extend the entire length of the sleeve 2010. In other embodiments, the channels extend only along a portion of the distal end of the sleeve 2010. In various embodiments, the channels 2012 are positioned equidistant from one another. The inclusion of the channels 2012 and support structures 2013 adds structure and stability to the sleeve 2010. The added structure helps maintain the sleeve 2010 in the proper orientation relative to a patient's pylorus and assists in preventing deformation of the sleeve 2010 by actions of the patient's gastrointestinal tract. In one embodiment, the channel 2012 is a hollow channel which can be filled or inflated with a fluid, such as water or air, to provide rigidity and/or structure to the sleeve 2010.

Figure 20C:
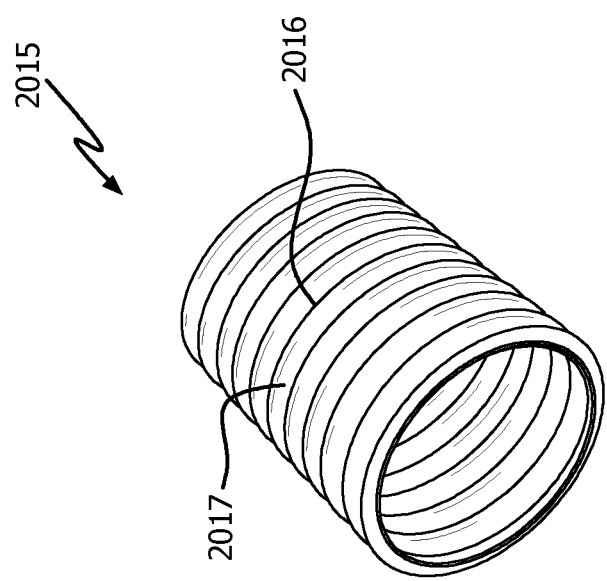
FIG. 20C is an illustration of a portion of a sleeve depicting a corrugated sleeve wall in accordance with one embodiment of the present specification.

FIG. 20C is an illustration of a portion of a sleeve 2015 depicting a corrugated sleeve wall in accordance with one embodiment of the present specification. The sleeve 2015 includes a plurality of alternating annular grooves 2016 and ridges 2017 extending along its length. In one embodiment, the entire sleeve 2015 is corrugated. In other embodiments, only a portion of the distal end of the sleeve 2015 is corrugated. In various embodiments, the corrugated portion of the sleeve 2015 is composed of fluoropolymer or polyethylene (PE). Referring to FIG. 20C, in one embodiment, the corrugated portion of the sleeve 2015 is cylindrical and includes a consistent diameter along its entire length. In another embodiment, the corrugated portion of the sleeve is funnel shaped and includes a diameter that decreases as the sleeve extends distally. In various embodiments, the distal end of the corrugated sleeve 2015 is configured to be soft, rounded, and atraumatic to body tissues. The corrugated structure helps maintain the sleeve 2015 in the proper orientation relative to a patient's pylorus and assists in preventing deformation of the sleeve 2015 by actions of the patient's gastrointestinal tract.

Figure 20D:
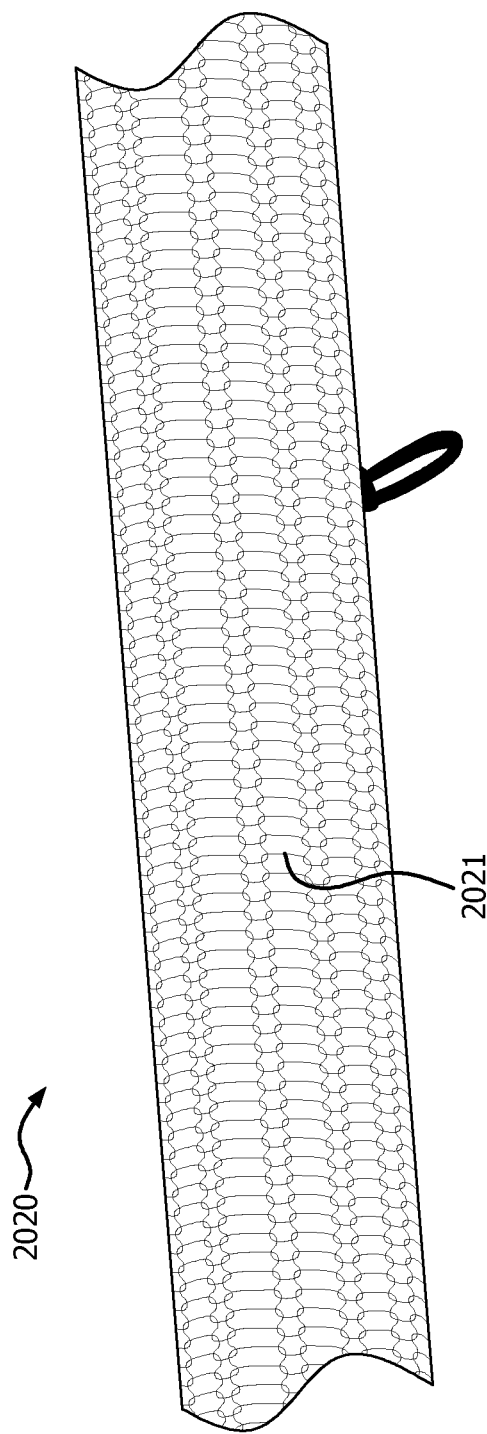
FIG. 20D is an illustration of portion of a sleeve depicting a knitted sleeve wall in accordance with one embodiment of the present specification.

FIG. 20D is an illustration of portion of a sleeve 2020 depicting a knitted sleeve wall in accordance with one embodiment of the present specification. The sleeve 2020 includes a knitted wire pattern 2021 extending along its length. In one embodiment, the entire sleeve 2020 is knitted. In other embodiments, only specific portions, such as the distal end, of the sleeve 2020 are knitted. Referring to FIG. 20D, in one embodiment, the knitted portion of the sleeve 2020 is cylindrical and includes a consistent diameter along its entire length. In various embodiments, the diameter of the sleeve 2020 ranges from 1 cm-10 cm. In one embodiment, the diameter of the sleeve is 25 mm and the length is 500 mm. In another embodiment, the knitted portion of the sleeve is funnel shaped and includes a diameter that decreases as the sleeve extends distally. In various embodiments, the distal end of the knitted sleeve 2020 is configured to be soft, rounded, and atraumatic to body tissues. The knitted structure helps maintain the sleeve 2020 in the proper orientation relative to a patient's pylorus and assists in preventing deformation of the sleeve 2020 by actions of the patient's gastrointestinal tract. The knitted structure provides the sleeve 2020 with structural integrity and prevents the sleeve 2020 from becoming kinked, twisted, or obstructed. In various embodiments, the sleeve 2020 has a radial force high enough to prevent deformation by the peristaltic actions of the gastrointestinal tract but low enough such that the sleeve 2020 can be compressed to allow food to propagate through the sleeve 2020. In addition, the radial force is low enough such that the sleeve is not too rigid which can result in trauma to the gastrointestinal tract, including abrasions. In one embodiment, the knitted structure of the sleeve 2020 functions similarly to a stent, keeping the sleeve 2020 properly positioned within the patient's small intestine.

Figure 20E:
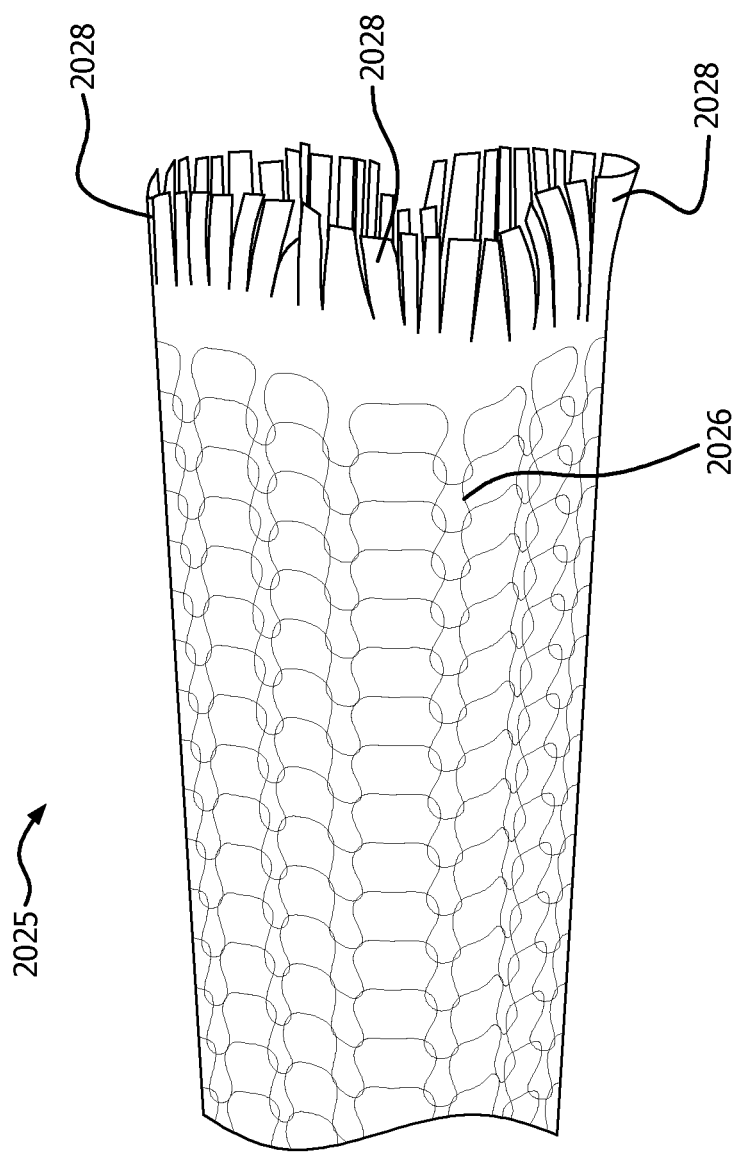
FIG. 20E is an illustration of portion of a sleeve depicting a knitted sleeve wall and a distal sleeve end having frayed edges, in accordance with one embodiment of the present specification.

FIG. 20E is an illustration of portion of a sleeve 2025 depicting a knitted sleeve wall and a distal sleeve end having frayed edges 2028, in accordance with one embodiment of the present specification. The sleeve 2025 includes a knitted wire pattern 2026 extending along its length. The frayed edges 2028 at the distal end of the sleeve 2025 are less traumatic to body tissues.

FIGS. 20F to 20L are illustrations of exemplary sleeve knit patterns 2031, 2032, 2033, 2034, 2035, 2036, 2037 in accordance with various embodiments.

Figure 21A:
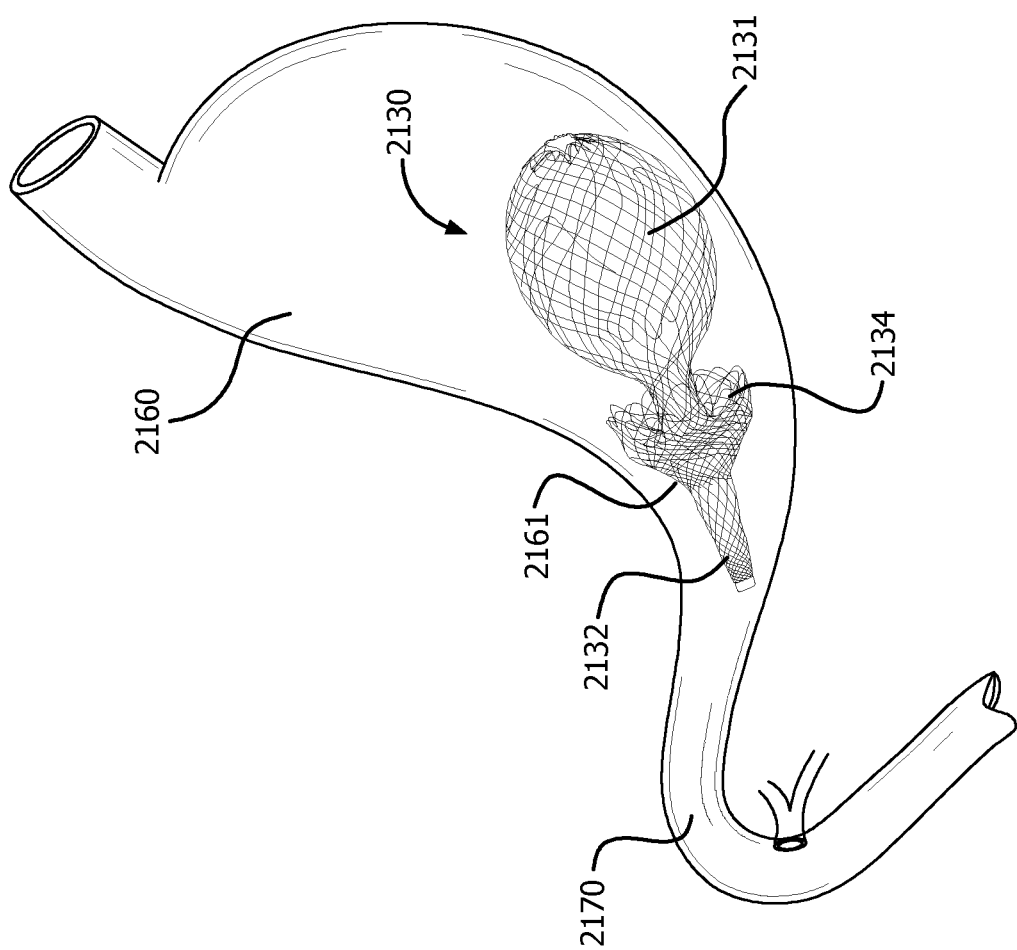
FIG. 21A is an illustration of an intragastric device having an oval shaped wire mesh structure deployed in the gastro-intestinal tract of a patient, in accordance with one embodiment of the present specification.

FIG. 21A is an illustration of an intragastric device 2130 having an oval shaped wire mesh structure 2131 deployed in the gastrointestinal tract of a patient, in accordance with one embodiment of the present specification. In the pictured embodiment, the device 2130 includes a wire mesh structure 2131 having an anti-migration collar 2134 and attached sleeve 2132. The device 2130 is deployed such that the wire mesh structure 2131 resides in the stomach 2160 with the anti-migration collar 2134 positioned just proximal to the pylorus 2161 and the sleeve 2132 extending through the pylorus 2161 and into the duodenum 2170. The distal end of the sleeve 2132 resides in the duodenum 2170. The anti-migration collar prevents migration of the totality of the device 2130 through the pylorus 2161 and into the duodenum 2170. The device 2130 occupies a volume of the stomach 2160, does not move entirely past the pylorus 2161, and provides a bypass for food past the pylorus 2161 and a portion of the duodenum 2170. In various embodiments, the sleeve 2132 is a short sleeve having a length in a range of 5 cm-120 cm. In one embodiment, the sleeve 2132 is a short sleeve having a total length of 60 cm.

In some embodiments, the short sleeve 2132 functions to weigh down wire mesh structure 2131 and orient the wire mesh structure 2131 in the correct direction toward the pylorus 2161. In addition, in one embodiment, the device 2130 having a short sleeve 2132 is capable of moving freely within the patient's stomach 2160 after deployment. The short sleeve 2132 is capable of passing back and forth through the pylorus 2161 atraumatically. During situations when the device 2130 has moved such that the short sleeve 2132 is not positioned within the pylorus 2161 and duodenum 2170 but is rather in the stomach 2160 with the remainder of the device 2130, the short sleeve also functions to impede and regulate the flow of food into the pylorus 2161. This occurs as food enters the device 2130 at the proximal end of the wire mesh structure 2131 and travels through the wire mesh structure 2131 and sleeve 2132, where its progress is slowed as it passes through the funnel shaped sleeve 2132. At no time during its proper function is the device fixedly or permanently anchored to the wall of the gastrointestinal tract. After deployment, for a majority of its functional time, at least a portion of the device or the entire device is free to move relative to the stomach or small intestine. As a result of its included lumen, at no time during its normal function does the device completely or permanently block the passage of gastric contents into the small intestine for any clinically meaningful duration of time. Based on the shape of the sleeve, in various embodiments, the device can increase, decrease, or have no effect on, gastric emptying.

Figure 21B:
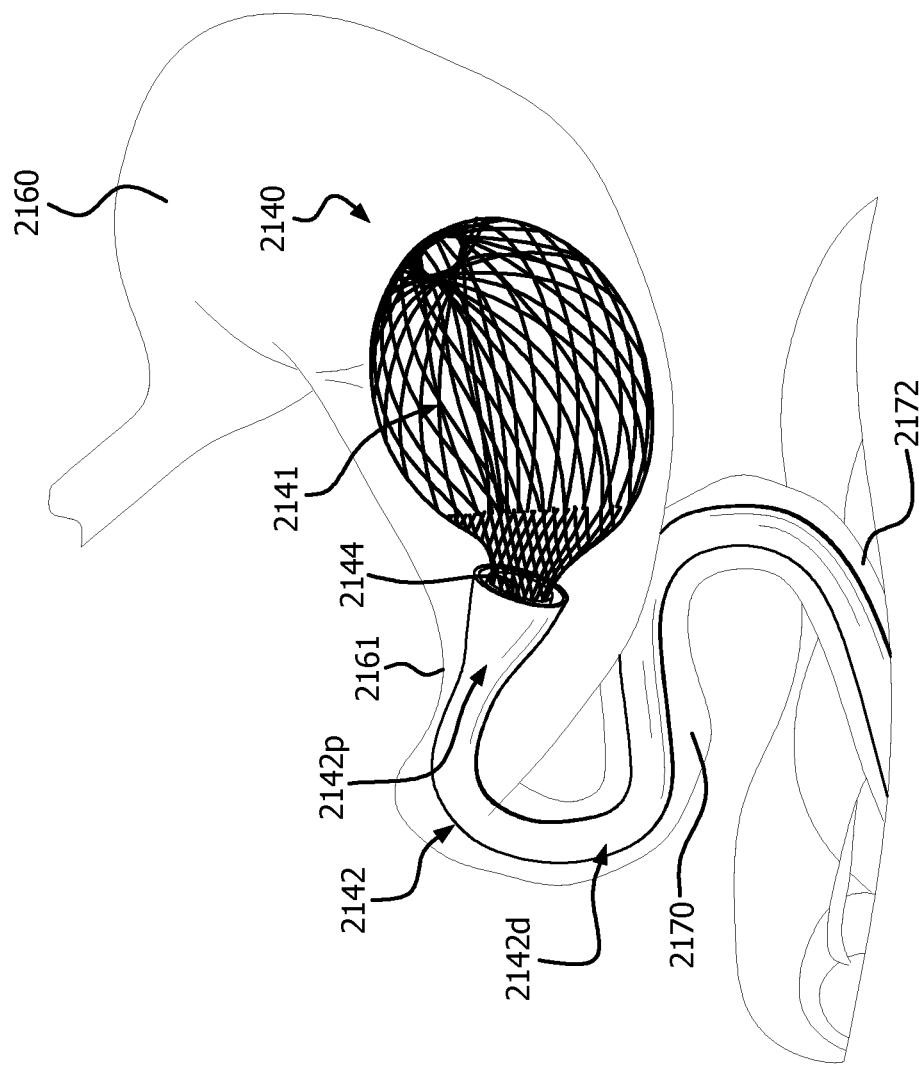
FIG. 21B is an illustration of an intragastric device having an oval shaped wire mesh structure deployed in the gastro-intestinal tract of a patient, in accordance with another embodiment of the present specification.

FIG. 21B is an illustration of an intragastric device 2140 having an oval shaped wire mesh structure 2141 deployed in the gastrointestinal tract of a patient, in accordance with another embodiment of the present specification. The wire mesh structure 2141 is positioned in the patient's stomach 2160 and includes an anti-migration collar 2144 to which is attached a sleeve 2142. The sleeve 2142 includes a proximal, funnel shaped portion $2142p$ which resides in the stomach, just proximal to the pylorus 2161. The sleeve 2142 also includes a distal, cylindrically shaped portion $2142d$ which passes through the pylorus 2161 and the duodenum 2170 and ends in the jejunum 2172, where it releases the gastric contents passing through the intragastric device 2140, effectively bypassing the pylorus 2161 and duodenum 2170. In another embodiment, the sleeve has a shorter length and ends in the duodenum such that gastric contents passing through the intragastric device bypass only the pylorus and a proximal portion of the duodenum. At no time during its proper function is the device fixedly or permanently anchored to the wall of the gastrointestinal tract. After deployment, for a majority of its functional time, at least a portion of the device or the entire device is free to move relative to the stomach or small intestine. As a result of its included lumen, at no time during its normal function does the device completely or permanently block the passage of gastric contents into the small intestine for any clinically meaningful duration of time. Based on the shape of the sleeve, in various embodiments, the device can increase, decrease, or have no effect on, gastric emptying.

FIGS. 21C and 21D are illustrations of several views 2121, 2122, 2123, 2124 of a pylorus 2125 of a patient in an open state and a closed state with and without a sleeve 2126 of an intragastric device passing therethrough, in accordance with some embodiments of the present specification. In view 2121, the pylorus 2125 is closed and there is no sleeve extending therethrough. View 2122 shows a closed pylorus 2125 with a sleeve 2126 extending therethrough. Views 2123 and 2124 show partially open and fully open pylorus 2125 respectively, both with a sleeve 2126 extending therethrough. In various embodiments, the sleeve 2126 comprises a collapsible tubular reinforced membrane that opposes the pyloric orifice inner diameter wall. In various embodiments, the maximum inner diameter of the sleeve 2126 ranges from 25 mm to 40 mm with a wall thickness of approximately 0.2 mm. Any membrane, such as sleeve 2126, passing through the pylorus will have a negligible but finite cross-sectional area. In various embodiments, the cross-sectional area of the sleeve 2126 is approximately 15 $mm^2$, which is equivalent to a plug approximately 4.4 mm in diameter. In other words, the dynamic cross-sectional area of the pyloric orifice will always be reduced by approximately 15 $mm^2$ when a sleeve 2126 is passing therethrough.

Figure 22A:
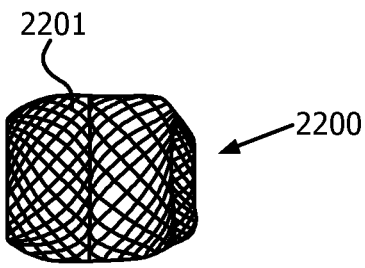
FIG. 22A is an illustration of an expanded wire mesh structure of a first intragastric device in accordance with at least one embodiment.
Figure 22B:
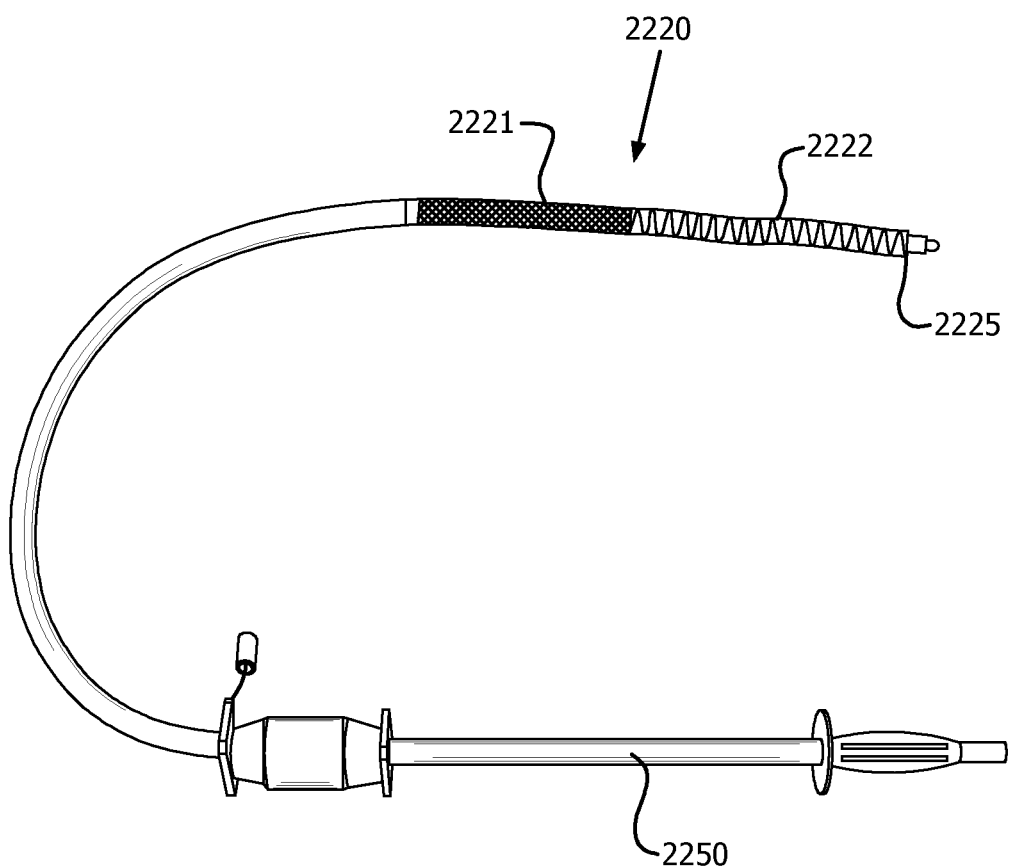
FIG. 22B is a constricted wire mesh structure of a second intragastric device coupled to the distal end of an implantation catheter, in accordance with one embodiment of the present specification.

FIG. 22A is an illustration of an expanded wire mesh structure 2201 of a first intragastric device 2200 in a post-deployment configuration. FIG. 22B is an illustration of a constricted wire mesh structure 2221 of a second intragastric device 2220 coupled to the distal end of an implantation catheter 2250. Looking at both FIGS. 22A and 22B, the second intragastric device 2220 also includes a sleeve 2222 coupled to the distal end of the wire mesh structure 2221. The wire mesh structure 2221 and sleeve 2222 of the second intragastric device 2220 have been compressed and slid coaxially onto the distal end of the implantation catheter 2250. In the pictured embodiment, the wire mesh structure 2221 and sleeve 2222 are maintained in their compressed configuration by a suture line or thread 2225 that has been wrapped about both the wire mesh structure 2221 and sleeve. Once the device 2220 has been positioned in the stomach and duodenum of a patient, the suture line or thread 2225 is unwound and the wire mesh structure 2221 and sleeve 2222 expand to their deployed configuration. As the device 2220 expands, it is released from the catheter 2250. The catheter 2250 is then removed from the patient. In another embodiment, the compressed wire mesh structure and sleeve are held in place over the implantation catheter via an overlaying coaxial sheath. Upon deployment, the sheath is unzipped, pulled away, or torn in a vertical direction to release the device.

Figure 23:
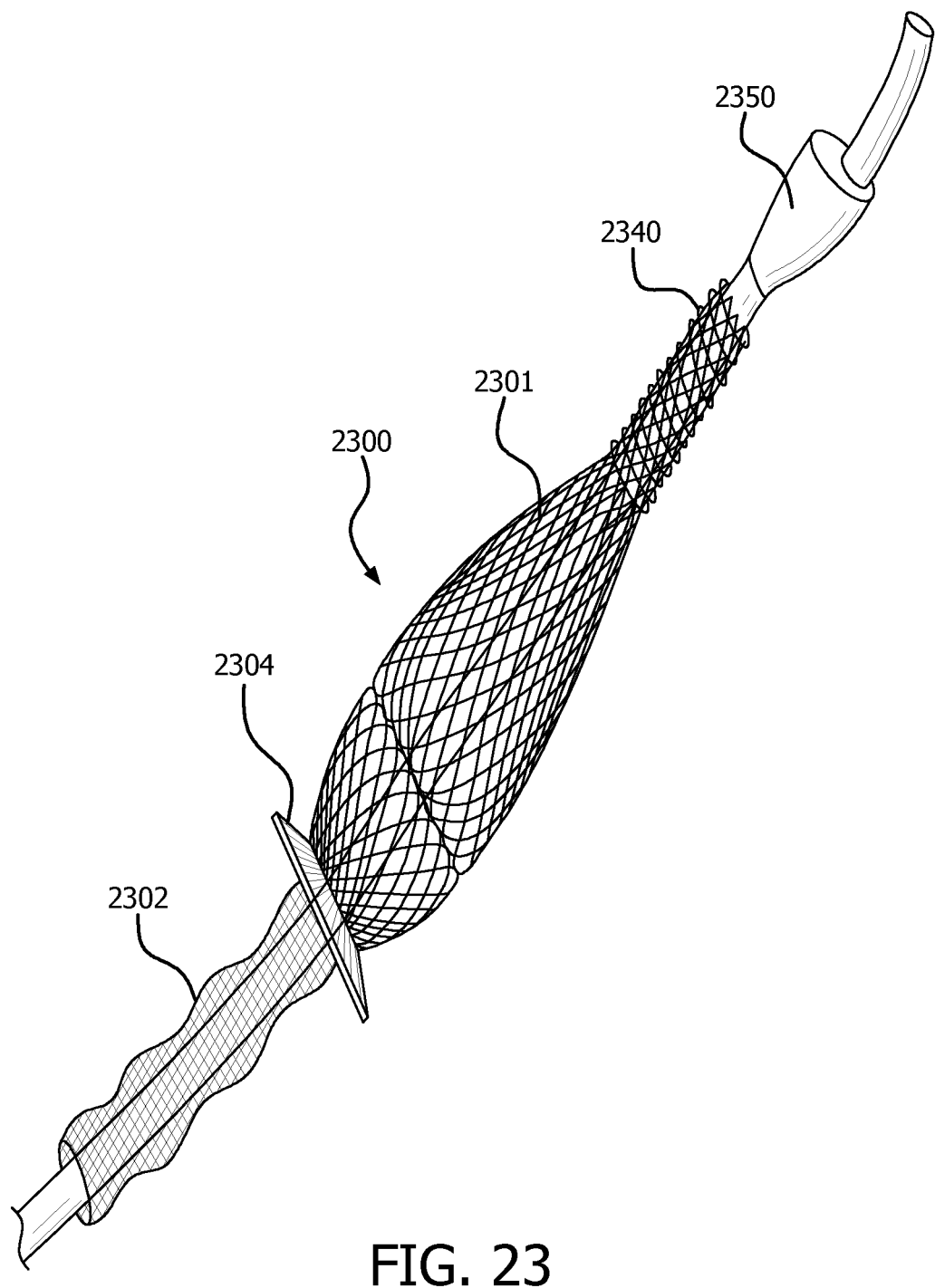
FIG. 23 is an illustration of an intragastric device with a partially constrained wire mesh structure on a delivery catheter, in accordance with one embodiment of the present specification.

FIG. 23 is an illustration of an intragastric device 2300 with a partially constrained wire mesh structure 2301 on a delivery catheter 2350, in accordance with one embodiment of the present specification. The device 2300 also includes a coupled sleeve 2302 and anti-migration component 2304. In the pictured embodiment, the proximal end of the wire mesh structure 2301 is still constricted by a suture or thread 2340. The sleeve 2302, anti-migration component 2304, and a portion of the wire mesh structure 2301 have begun to expand as the constricting suture or thread has already been removed from these components.

Figure 24A:
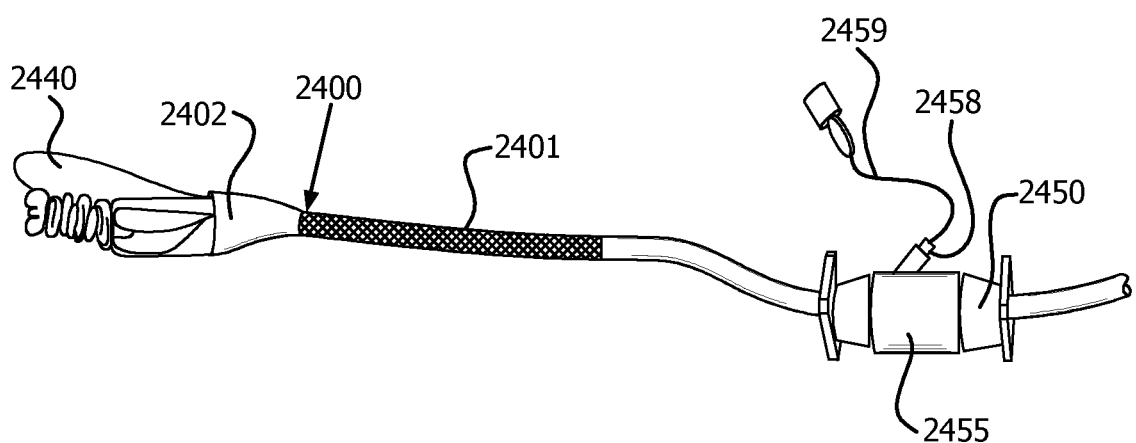
FIG. 24A is an illustration of an exemplary delivery device for an intragastric device, in accordance with one embodiment of the present specification.

FIG. 24A is an illustration of a first exemplary delivery device 2450 for an intragastric device 2400, in accordance with one embodiment of the present specification. An intragastric device 2400, comprising a compressed wire mesh structure 2401 and sleeve 2402, is positioned coaxially about the distal end of the delivery device or catheter 2450. A suture or thread 2440 is wrapped about the intragastric device 2400, maintaining the intragastric device 2400 in its compressed configuration. The catheter 2450 further includes a thread port 2458 from which the suture or thread 2440 used to compress the intragastric device 2400 exits the proximal end of the catheter 2450. A physician pulls on the free end 2459 of the suture or thread 2440 to release the intragastric device 2400. In one embodiment, the catheter 2450 also includes a locking mechanism 2455 for locking the device 2450 in position.

Figure 24B:
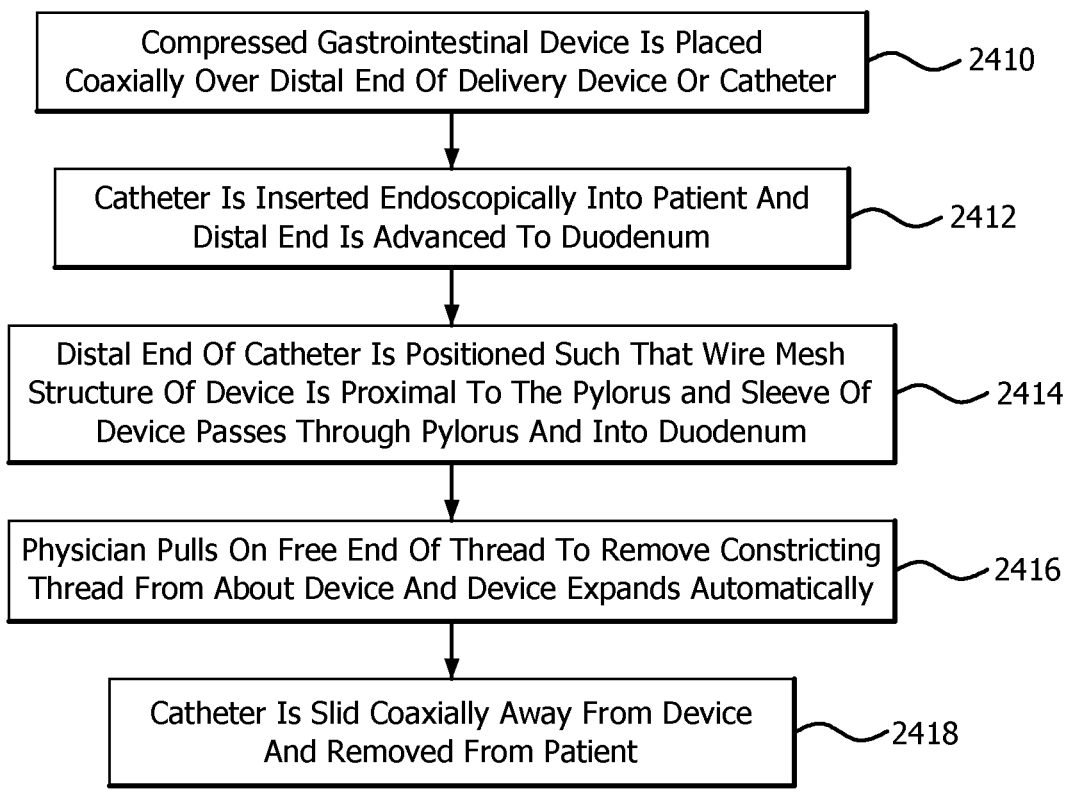
FIG. 24B is a flow chart illustrating the steps involved in delivering an intragastric device using the delivery device of FIG. 24A, in accordance with one embodiment of the present specification.

FIG. 24B is a flow chart illustrating the steps involved in delivering an intragastric device using the delivery device of FIG. 24A, in accordance with one embodiment of the present specification. At step 2410, a compressed intragastric device is placed coaxially over the distal end of the delivery device or catheter. The catheter is then inserted endoscopically into the patient and its distal end is advanced to the duodenum at step 2412. Then, at step 2414, the distal end of the catheter is positioned such that the wire mesh structure of the intragastric device is in the stomach just proximal to the pylorus and the sleeve of the device passes through the pylorus and into the duodenum. At step 2416, the physician pulls on the free end of the thread to remove the constricting thread from about the intragastric device, allowing the intragastric device to expand automatically. Finally, at step 2418, the catheter is slid coaxially away from the intragastric device and removed from the patient.

Figure 25A:
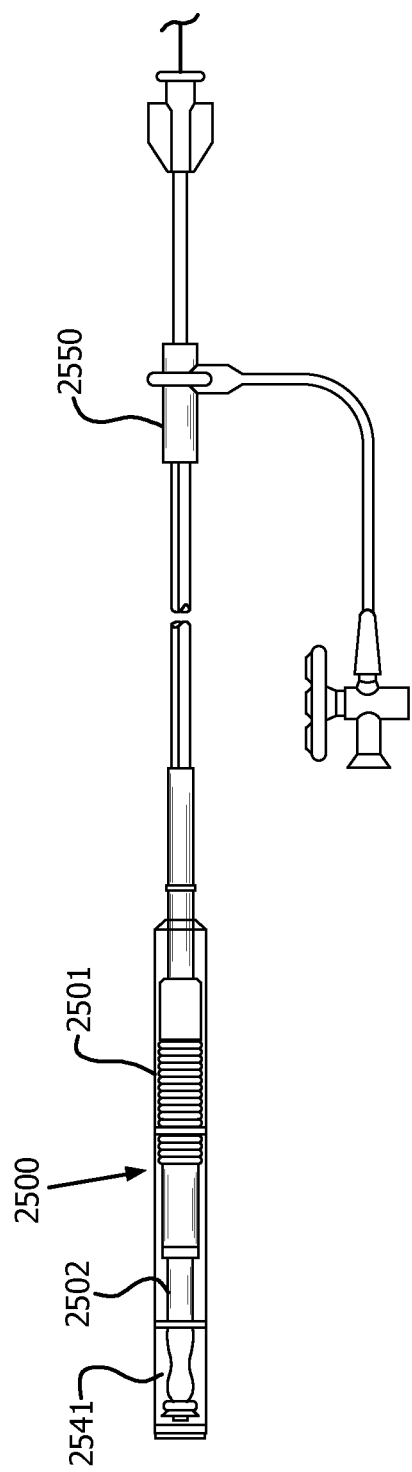
FIG. 25A is an illustration of an exemplary delivery device for an intragastric device, in accordance with one embodiment of the present specification.

FIG. 25A is an illustration of a second exemplary delivery device 2550 for an intragastric device 2500, in accordance with one embodiment of the present specification. An intragastric device 2500, comprising a compressed wire mesh structure 2501 and sleeve 2502, is positioned coaxially about the distal end of the delivery device or catheter 2550. A zippered constraining sheath 2541 is coaxially positioned over the intragastric device 2500, maintaining the intragastric device 2500 in its compressed configuration.

Figure 25B:
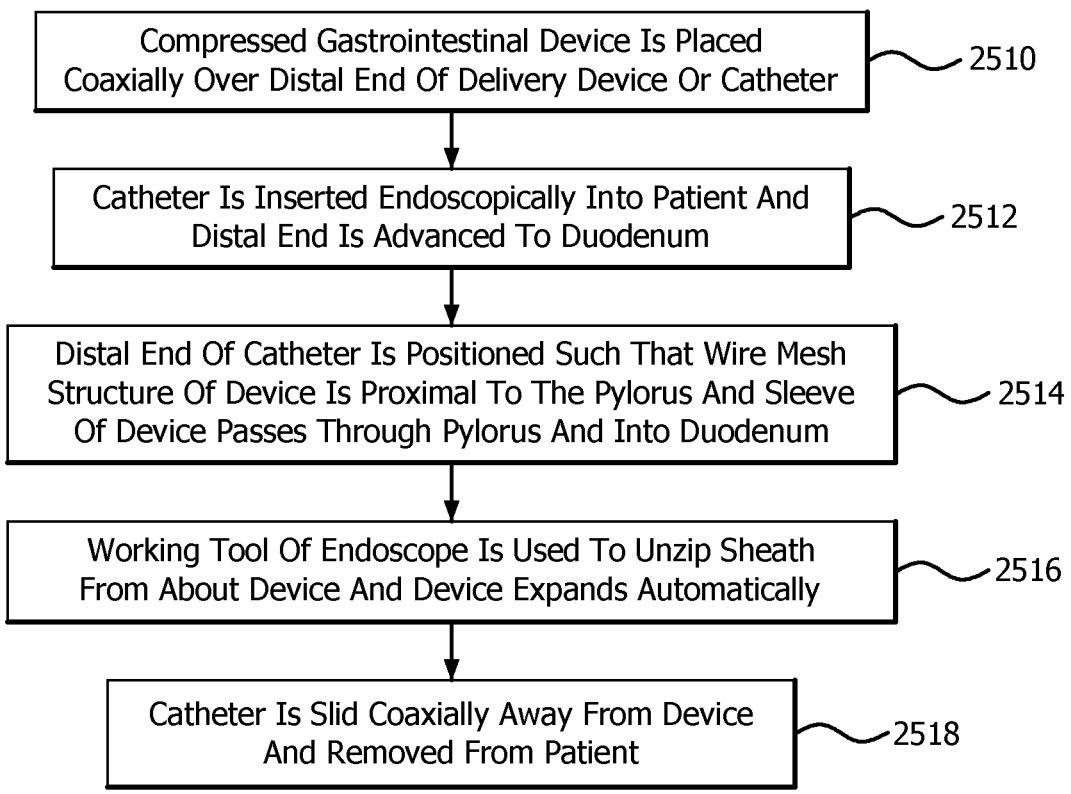
FIG. 25B is a flow chart illustrating the steps involved in delivering an intragastric device using the delivery device of FIG. 25A, in accordance with one embodiment of the present specification.

FIG. 25B is a flow chart illustrating the steps involved in delivering an intragastric device using the delivery device of FIG. 25A, in accordance with one embodiment of the present specification. At step 2510, a compressed intragastric device is placed coaxially over the distal end of the delivery device or catheter. The catheter is then inserted endoscopically into the patient and its distal end is advanced to the duodenum at step 2512. Then, at step 2514, the distal end of the catheter is positioned such that the wire mesh structure of the intragastric device is in the stomach just proximal to the pylorus and the sleeve of the device passes through the pylorus and into the duodenum. At step 2516, a working tool is used to unzip the compressing sheath from about the intragastric device, allowing the intragastric device to expand automatically. Finally, at step 2518, the catheter is slid coaxially away from the intragastric device and removed from the patient.

Figure 25C:
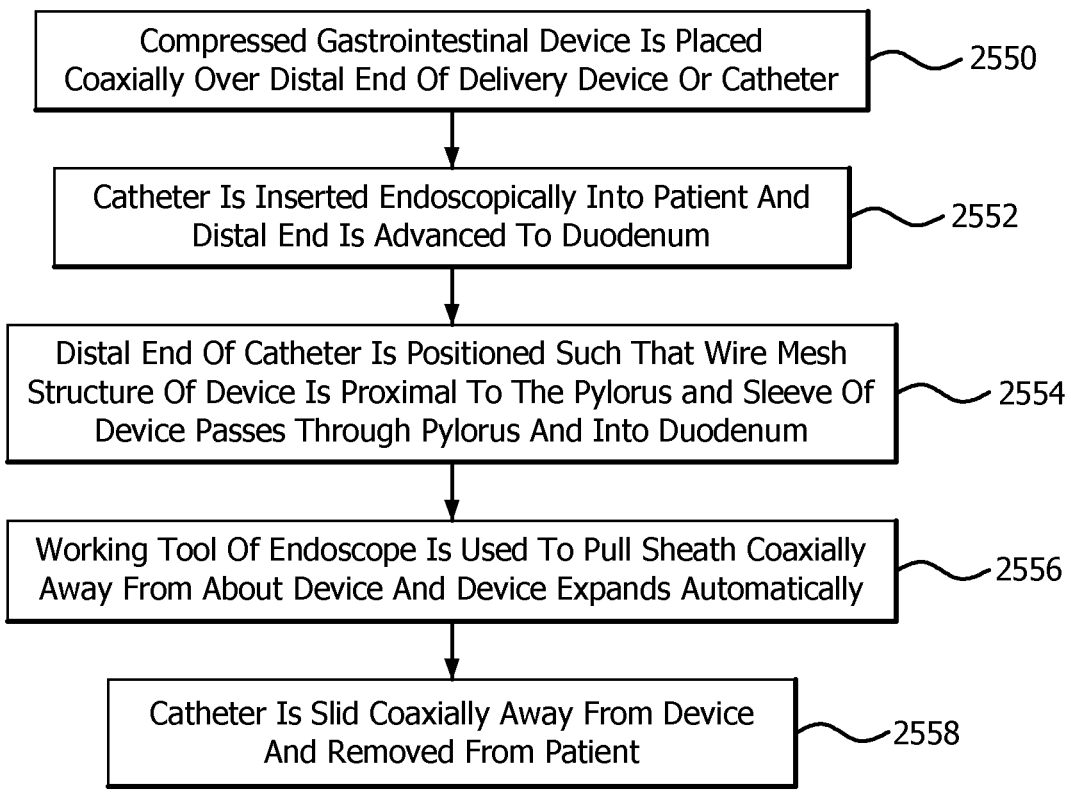
FIG. 25C is a flow chart illustrating the steps involved in delivering an intragastric device using a delivery device comprising a pull away sheath, in accordance with one embodiment of the present specification.

Alternatively, the sheath 2541 is a standard tubular sheath that is pulled off the intragastric device to release the intragastric device in the desired position. FIG. 25C is a flow chart illustrating the steps involved in delivering an intragastric device using a delivery device comprising a pull away sheath, in accordance with one embodiment of the present specification. At step 2550, a compressed intragastric device is placed coaxially over the distal end of the delivery device or catheter. The catheter is then inserted endoscopically into the patient and its distal end is advanced to the duodenum at step 2552. Then, at step 2554, the distal end of the catheter is positioned such that the wire mesh structure of the intragastric device is in the stomach just proximal to the pylorus and the sleeve of the device passes through the pylorus and into the duodenum. At step 2556, a working tool is used to pull the compressing sheath coaxially away from about the intragastric device, allowing the intragastric device to expand automatically. Finally, at step 2558, the catheter is slid coaxially away from the intragastric device and removed from the patient.

Figure 26A:
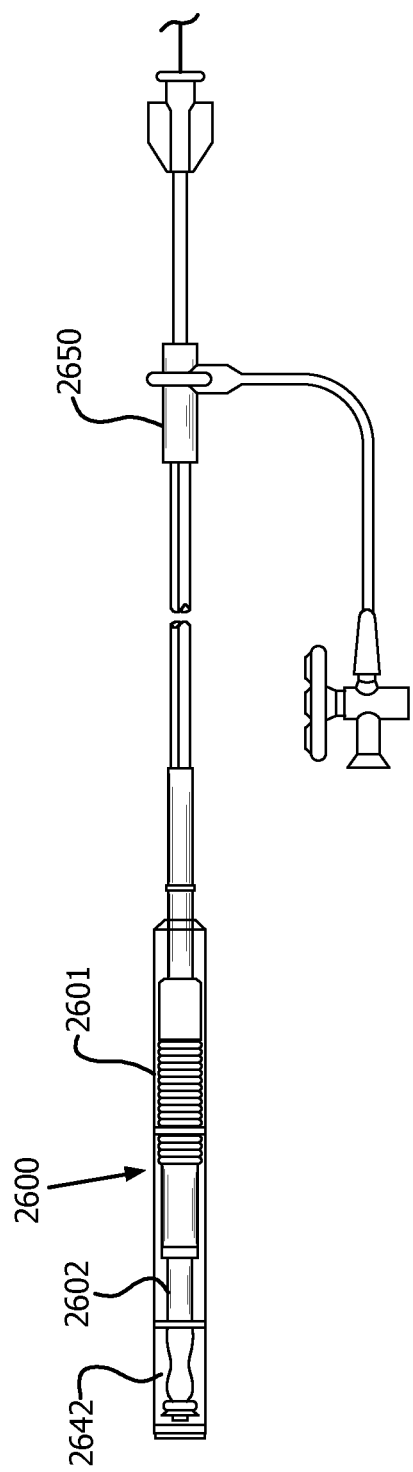
FIG. 26A is an illustration of another exemplary delivery device for an intragastric device, in accordance with one embodiment of the present specification.

FIG. 26A is an illustration of a third exemplary delivery device 2650 for an intragastric device 2600, in accordance with one embodiment of the present specification. An intragastric device 2600, comprising a compressed wire mesh structure 2601 and sleeve 2602, is positioned coaxially about the distal end of the delivery device or catheter 2650. A tear-away constraining sheath 2642 is coaxially positioned over the intragastric device 2600, maintaining the intragastric device 2600 in its compressed configuration.

Figure 26B:
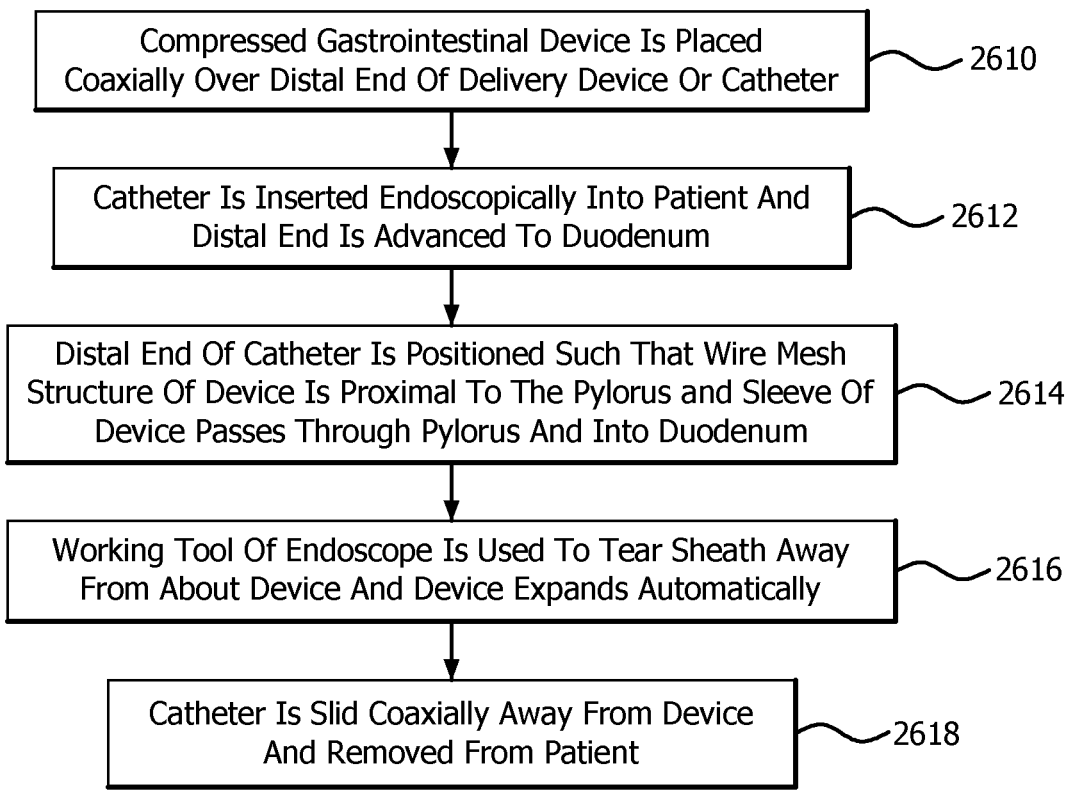
FIG. 26B is a flow chart illustrating the steps involved in delivering an intragastric device using the delivery device of FIG. 26A, in accordance with one embodiment of the present specification.

FIG. 26B is a flow chart illustrating the steps involved in delivering an intragastric device using the delivery device of FIG. 26A, in accordance with one embodiment of the present specification. At step 2610, a compressed intragastric device is placed coaxially over the distal end of the delivery device or catheter. The catheter is then inserted endoscopically into the patient and its distal end is advanced to the duodenum at step 2612. Then, at step 2614, the distal end of the catheter is positioned such that the wire mesh structure of the intragastric device is in the stomach just proximal to the pylorus and the sleeve of the device passes through the pylorus and into the duodenum. At step 2616, a working tool is used to tear away a compressing sheath from about the intragastric device, allowing the intragastric device to expand automatically. Finally, at step 2618, the catheter is slid coaxially away from the intragastric device and removed from the patient.

Figure 26C:
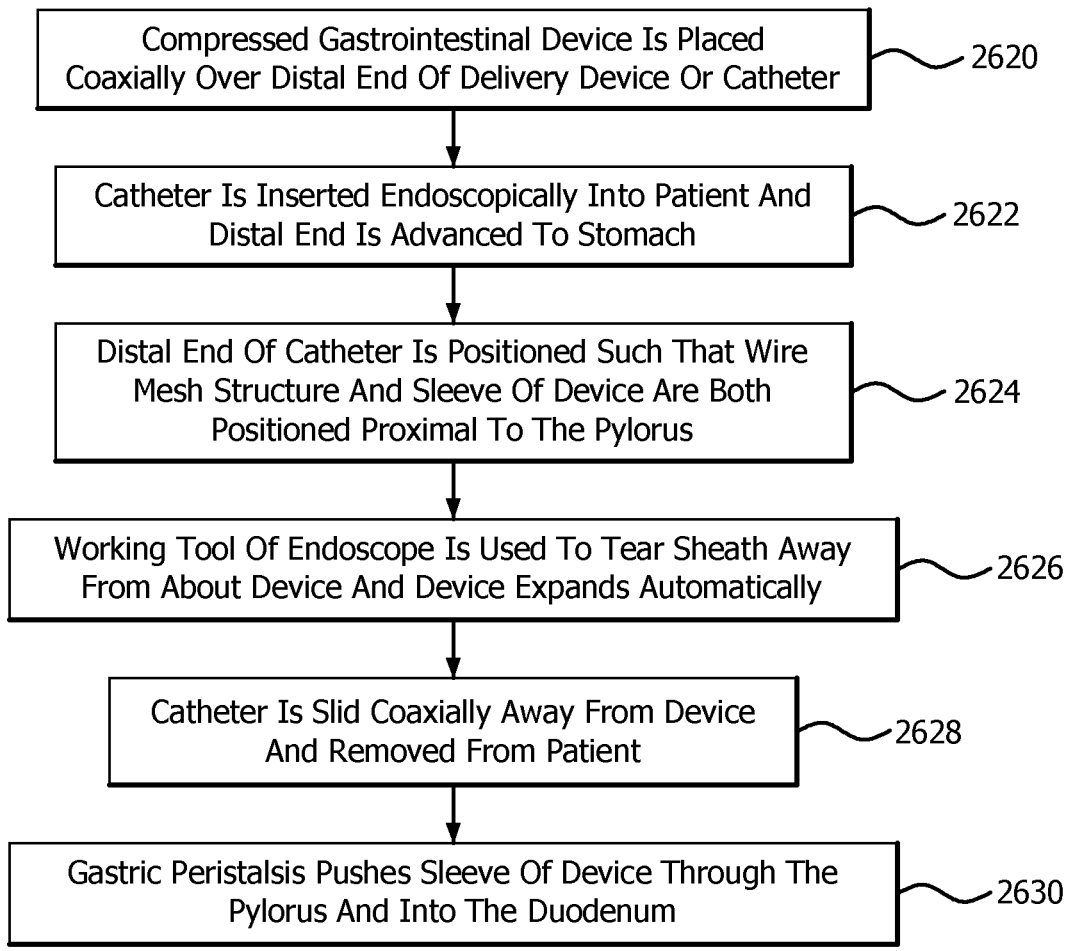
FIG. 26C is a flow chart illustrating the steps involved in delivering an intragastric device using the delivery device of FIG. 26A, in accordance with another embodiment of the present specification.

FIG. 26C is a flow chart illustrating the steps involved in delivering an intragastric device using the delivery device of FIG. 26A, in accordance with another embodiment of the present specification. At step 2620, a compressed intragastric device is placed coaxially over the distal end of the delivery device or catheter. The catheter is then inserted endoscopically into the patient and its distal end is advanced to the stomach at step 2622. Then, at step 2624, the distal end of the catheter is positioned such that the wire mesh structure and the sleeve of the intragastric device are both positioned proximal to the pylorus. At step 2626, a working tool is used to tear away a compressing sheath from about the intragastric device, allowing the intragastric device to expand automatically. At step 2628, the catheter is slid coaxially away from the intragastric device and removed from the patient. Finally, at step 2630, gastric peristalsis pushes the sleeve of the intragastric device through the pylorus and into the duodenum.

Figure 26D:
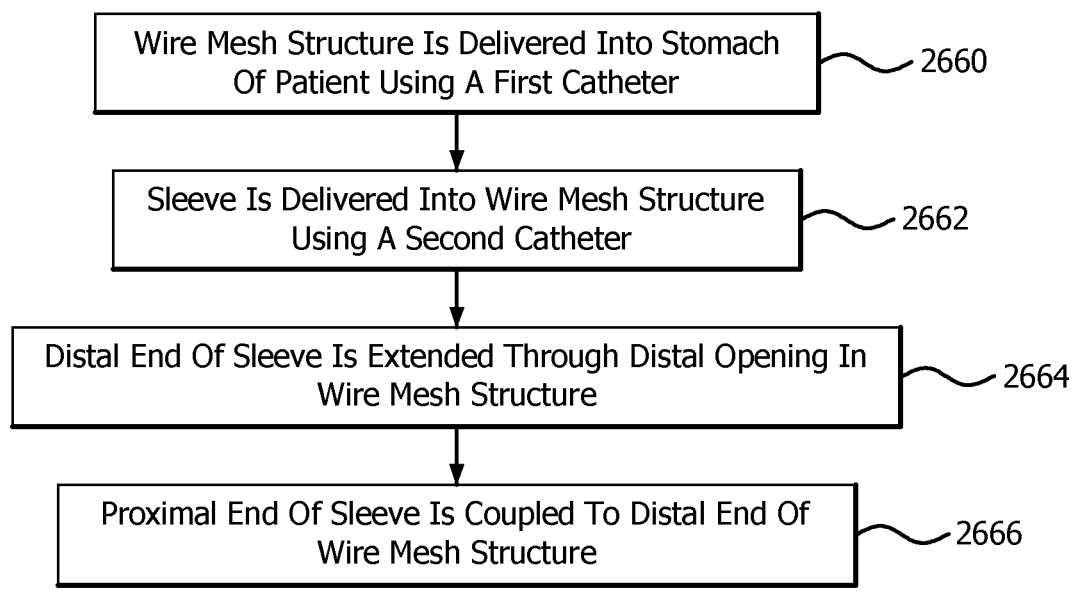
FIG. 26D is a flow chart illustrating the steps involved in delivering a wire mesh structure and sleeve separately and assembling an intragastric device within a patient's gastro-intestinal tract in accordance with at least one embodiment.

FIG. 26D is a flow chart illustrating the steps involved in delivering a wire mesh structure and sleeve separately and assembling an intragastric device within a patient's gastrointestinal tract. At step 2660, the wire mesh structure is delivered into the stomach of a patient by a first catheter. Then, at step 2662, the sleeve is delivered into the wire mesh structure by a second catheter. The distal end of the sleeve is then extended through the distal opening in the wire mesh structure at step 2664. Finally, at step 2666, the proximal end of the sleeve is coupled to the distal end of the wire mesh structure.

Figure 27A:
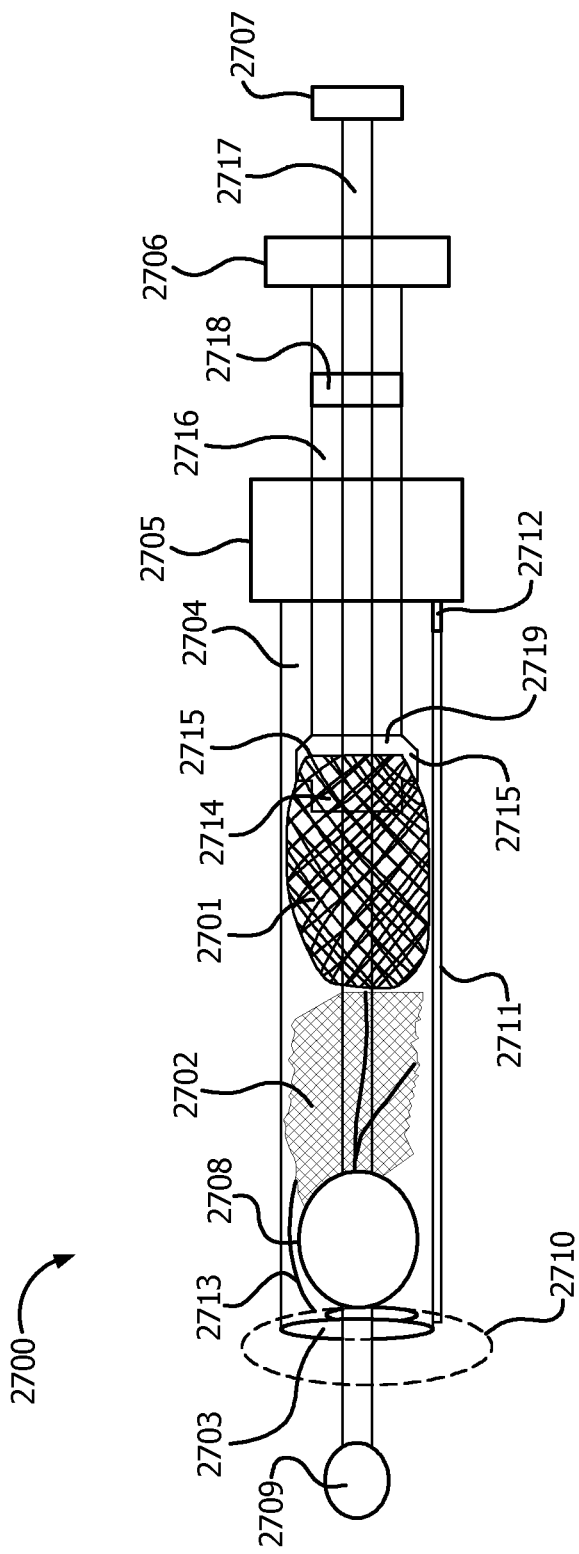
FIG. 27A is an illustration of yet another exemplary delivery device for an intragastric device, in accordance with one embodiment of the present specification.
Figure 27B:
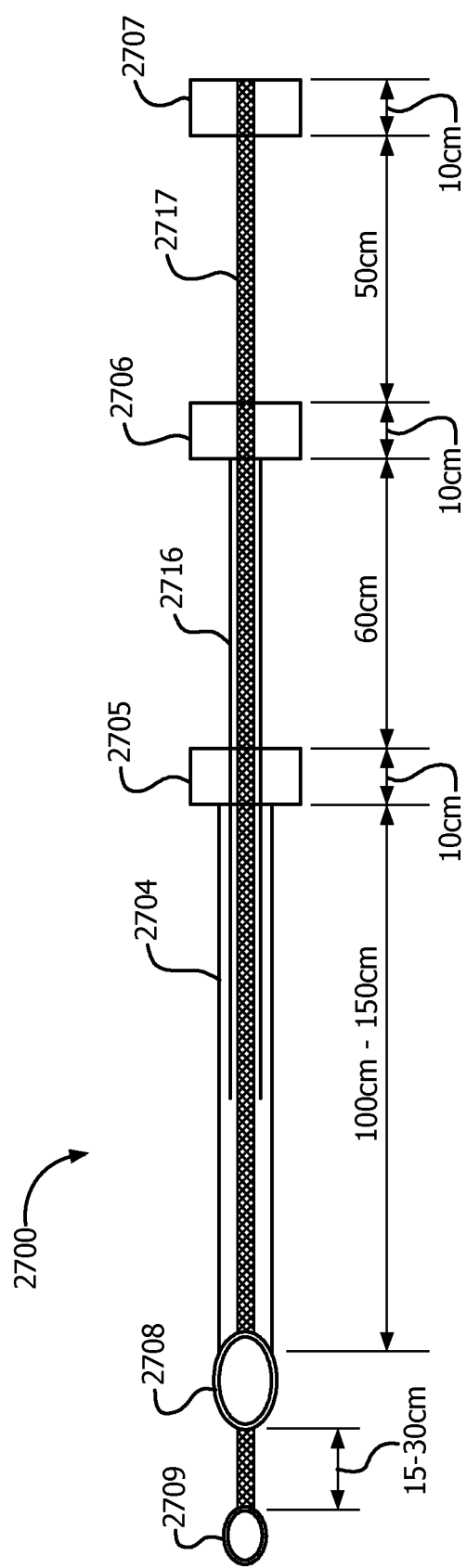
FIG. 27B is another illustration of the delivery device of FIG. 27A, depicting the relative lengths of various components of the delivery device in accordance with at least one embodiment.

FIGS. 27A and 27B are illustrations of a fourth exemplary delivery device 2700 for an intragastric device, in accordance with one embodiment of the present specification. The delivery device 2700 includes a flexible elongate device body, or outer catheter 2704 with a proximal end, a distal end, and a lumen within. The distal end includes an opening 2703 and the proximal end is attached to a first handle 2705. The first handle 2705 is used for positioning the delivery device 2700 in the gastrointestinal tract of a patient. A flexible plunger component 2716 is positioned coaxially, and movable longitudinally, within the lumen of the device body 2704. The plunger 2716 includes a proximal end, a distal end, and also includes a lumen within. The distal tip 2714 of the plunger 2716 includes a mesh retention component 2719 comprising a plurality of fins 2715. The fins 2715 serve to securely hold the wire mesh structure 2701 of an intragastric device and push and pull the wire mesh structure 2701 as the plunger 2716 is moved back and forth within the device body 2704. A second handle 2706 is positioned at the proximal end of the plunger 2716 for moving the plunger 2716 longitudinally within the lumen of the device body 2704. Optionally, in one embodiment, the plunger 2716 includes a stopper 2718 which prevents the plunger 2716 from moving too far in a distal direction. A flexible elongate rod, or inner catheter 2717 is positioned coaxially, and movable longitudinally, within the lumen of the plunger 2716. The rod 2717 includes a proximal end and a distal end. Positioned proximal the distal end of the rod 2717 is a first spherical component or olive 2708 and positioned at the distal end of the rod 2717 is a second spherical component or olive 2709. The first spherical component or olive 2708 has a diameter similar to or greater than that of the second spherical component or olive 2709. Attached to the proximal end of the rod 2717 is a third handle 2707 which is used for moving the rod 2717 longitudinally within the lumen of the plunger 2716. An intragastric device, comprising a wire mesh structure 2701 and a sleeve 2702, is positioned within the delivery device 2700 prior to deployment. The wire mesh structure 2701 is placed with a side loop about the rod 2717 and distal to the tip 2714 of the plunger 2716, with a portion of the wire mesh structure 2701 hooked on the fins 2715 of the tip 2714. In some embodiments, the rod 2717 passes through at least two openings in the wire mesh structure 2701 wherein the openings do not lie along a center longitudinal axis of the wire mesh structure 2701. In one embodiment, the wire mesh structure 2701 is compressed for positioning within the delivery device 2700 such that it has a compressed length of approximately 20 cm. The sleeve 2702, which is attached to the wire mesh structure 2701, is positioned distal to the wire mesh structure 2701 and proximal to the first spherical component or olive 2708. The sleeve 2702 is folded upon itself 2 to 10 times and then wrapped around the rod 2717. In one embodiment, the sleeve 2702 has a length of 80 cm and is folded upon itself 3 times resulting in a compressed length of approximately 30 cm. The sleeve 2702 is not passed coaxially over the rod 2717. Attached to the sleeve 2702 and looped on the rod 2717 in a position distal to the first spherical component or olive 2708 are first and second ends, respectively, of a suture loop 2713. The diameter of the suture loop 2713 about the rod is smaller than the diameter of the first spherical component or olive 2708 but greater than the diameter of the second spherical component or olive 2709. When the rod 2717 is pushed out of the device body 2704, the first spherical component or olive 2708 pushes the suture loop 2713 which pulls the attached sleeve 2702 out of the device body 2704. When the delivery device 2700, along with the rod 2717, are removed from the patient's gastrointestinal tract, the suture loop 2713 slips over the smaller diameter second spherical component or olive 2709, allowing the intragastric device to remain in the patient. In one embodiment, the suture loop 2713 is biodegradable and dissolves over time. In another embodiment, the suture loop 2713 is non-biodegradable. In other embodiments, the suture loop 2713 is a biodegradable hook, ring, cone, or umbrella.

Optionally, in one embodiment, the delivery device 2700 further includes a balloon 2710 at the distal end of the device body 2704. A channel 2711 extends along the length of the device body 2704 and includes an input port 2712 at the proximal end of the device body 2704. The balloon 2710 is inflated using the input port 2712 and channel 2711 to anchor the delivery device within the patient's gastrointestinal tract. Anchoring provides greater traction to the delivery device to allow for pushing and pulling during delivery of the intragastric device.

In some embodiments, the delivery device 2700 further includes a flushing or irrigation mechanism to reduce deployment forces during delivery.

In various embodiments, the delivery device or catheter has variable stiffness along its length. The delivery device is more flexible at its distal end and becomes less flexible along its length toward its proximal end. In some embodiments, the delivery device has three zones of flexibility: a proximal zone, a center zone, and a distal zone. In one embodiment, the proximal zone has a length of 100 cm and a flexibility of 55D, the center zone has a length of 20 cm and a flexibility of 40D, and the distal zone has a length of 30 cm and flexibility of 35D. Optionally, in one embodiment, the distal zone is split into two additional zones, comprising a more distal zone and a less distal zone. Both zones are 15 cm in length and the less distal zone has a flexibility of 35D while the more distal zone has a flexibility of 25D. In one embodiment, the proximal zone is braided and the center and distal zones are coiled.

Figure 27C:
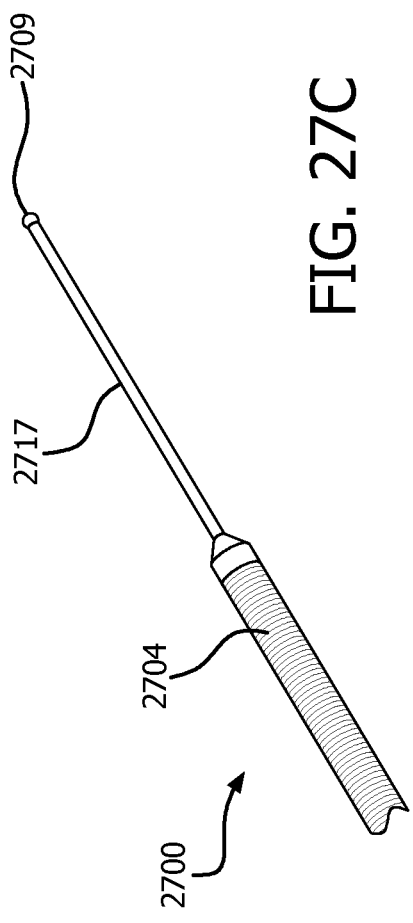
FIG. 27C is an illustration of a distal end of a delivery device depicting a pilot olive for navigation, in accordance with one embodiment of the present specification.

The delivery device includes atraumatic distal ends and the three handle system of the delivery device allows for a shorter overall device body length. In various embodiments, referring to FIG. 27B, the delivery device has the following dimensions: overall length ranging from 275 cm-320 cm; length of said device body or outer catheter 2704 ranging from 100 cm-150 cm; length of said plunger 2716 ranging from 120 cm-150 cm; length of said rod or inner catheter 2717 ranging from 275 cm-320 cm; length of each handle 2705, 2706, 2707 equal to 10 cm; distance between said second spherical component or olive 2709 and said first spherical component or olive 2708 ranging from 15 cm-30 cm; distance between said first handle 2705 and said second handle 2706 when in an initial configuration before delivery equal to 60 cm; and, distance between said second handle 2706 and said third handle 2707 when in an initial configuration before delivery equal to 50 cm. In some embodiments, the outer diameter of the device body or outer catheter 2704 is 10 mm or less. In one embodiment, the delivery device is deployable over a 0.035 inch guidewire. In various embodiments, the plunger 2716 and rod 2717 are sufficiently flexible to allow for atraumatic intestinal navigation. In some embodiments, a solid outer catheter can bend up to 80 degrees and is capable of navigating curves having a radius 30 mm-50 mm. In an embodiment, if a solid outer catheter is coiled into a radius of approximately 50 mm, the sleeve and mesh will kink or cinch in place and not deploy. Therefore, as depicted in FIG. 27C, in some embodiments, the device body or outer catheter 2704 comprises a flexible braided catheter. The flexible braided catheter is capable of bending and coiling beyond the limits described above without causing failure of deployment of the sleeve and wire mesh.

FIG. 27C is an illustration of a distal end of a delivery device 2700 depicting a pilot olive, or first spherical component 2709 for navigation, in accordance with one embodiment of the present specification. The pilot olive 2709 comprises a small sphere with a blunt outer surface attached to the distal end of the rod, or inner catheter 2717 of the delivery device 2700. The pilot olive 2709 guides the device 2700 during delivery and prevents kinking of the device 2700 and trauma to surrounding body tissues. Referring to FIG. 27C, the portion of the inner catheter 2717 extending from the outer catheter 2704 comprises a pilot component. The stiffness of the pilot component is less than the stiffness of the distal portion of the outer catheter 2704. In some embodiments, the pilot component has a variable stiffness with a stiffness close to the stiffness of the distal end of the outer catheter 2704 at its proximal end and a stiffness close to that of a 0.035" guidewire at its distal end.

Figure 27D:
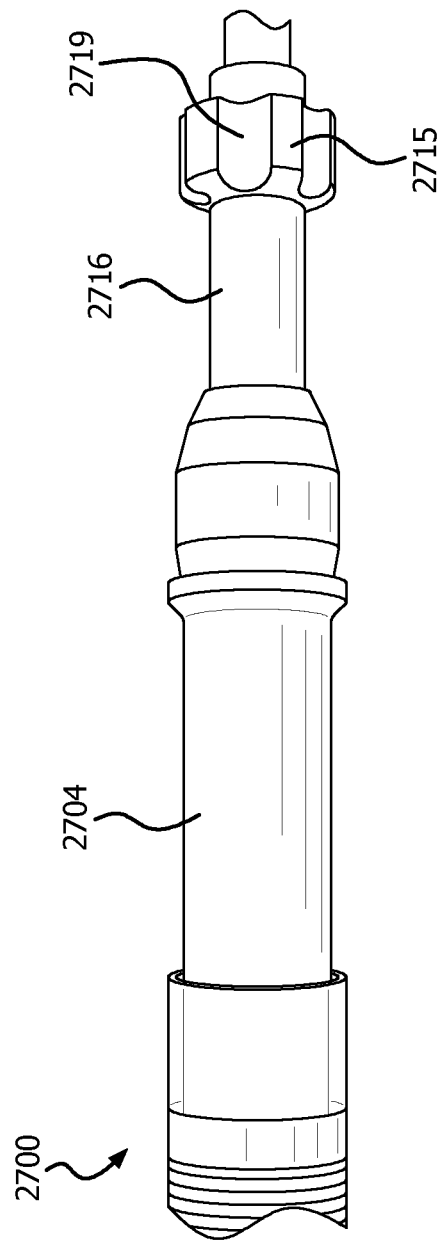
FIG. 27D is an illustration of a portion of a delivery device depicting a mesh retention component, in accordance with one embodiment of the present specification.

FIG. 27D is an illustration of a portion of a delivery device 2700 depicting a mesh retention component 2719, in accordance with one embodiment of the present specification. The mesh retention component 2719 comprises a plurality of fins 2715. The fins 2715 serve to securely hold the wire mesh structure of an intragastric device and push and pull the wire mesh structure as the plunger 2716 is moved back and forth within the device body 2704.

In one embodiment, the sleeve is only partially deployed during delivery. The wire mesh structure functions as an anchor to keep the device positioned. As the patient eats, the sleeve unfurls and becomes fully deployed due to the movements of the gastrointestinal tract.

Figure 27E:
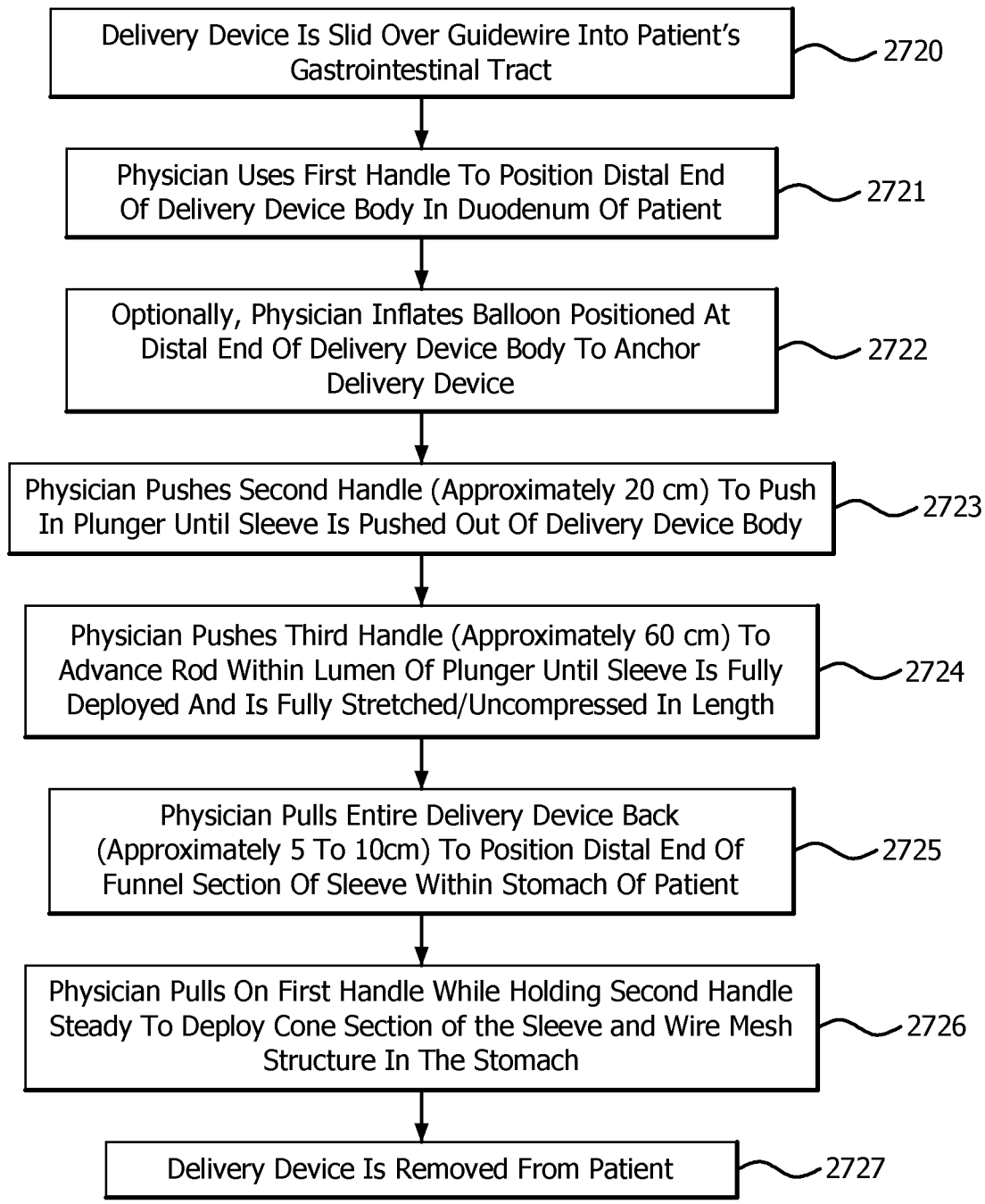
FIG. 27E is a flow chart illustrating the steps involved in delivering an intragastric device using the delivery device of FIG. 27A, in accordance with one embodiment of the present specification.

FIG. 27E is a flow chart illustrating the steps involved in delivering an intragastric device using the delivery device of FIG. 27A, in accordance with one embodiment of the present specification. At step 2720, the delivery device is slid over a guidewire into position within a patient's gastrointestinal tract. At step 2721, a physician uses the first handle to position the distal end of the delivery device body in a duodenum of the patient. Optionally, at step 2722, the physician inflates a balloon at the distal end of the device body to anchor the delivery device in the patient's gastrointestinal tract. The physician then pushes the second handle, pushing in the plunger component, until the sleeve is pushed out of the device body at step 2723. Optionally, the plunger includes a stopper so the physician knows when to stop pushing the second handle. At this point, the sleeve has been advanced approximately 20 cm, past the first spherical component and is positioned just proximal to the second spherical component. The wire mesh structure is positioned just proximal to the first spherical component and the opening at the distal end of the device body. Then, at step 2724, the physician pushes the third handle to advance the rod within the lumen of the plunger approximately 60 cm until the sleeve is fully deployed and is fully stretched or uncompressed. At step 2725, the physician repositions the device by pulling it back approximately 5 to 10 cm so that the distal end of the funnel section of the sleeve is within the stomach. Then, at step 2726, the physician pulls back on the first handle while holding the second handle steady to deploy the funnel section of the sleeve and the wire mesh structure in the stomach. This pulls the device body back while keeping the plunger in place, thus releasing the wire mesh structure. The delivery device is then removed from the patient at step 2727, leaving the intragastric device deployed in the patient's gastrointestinal tract.

Figure 28A:
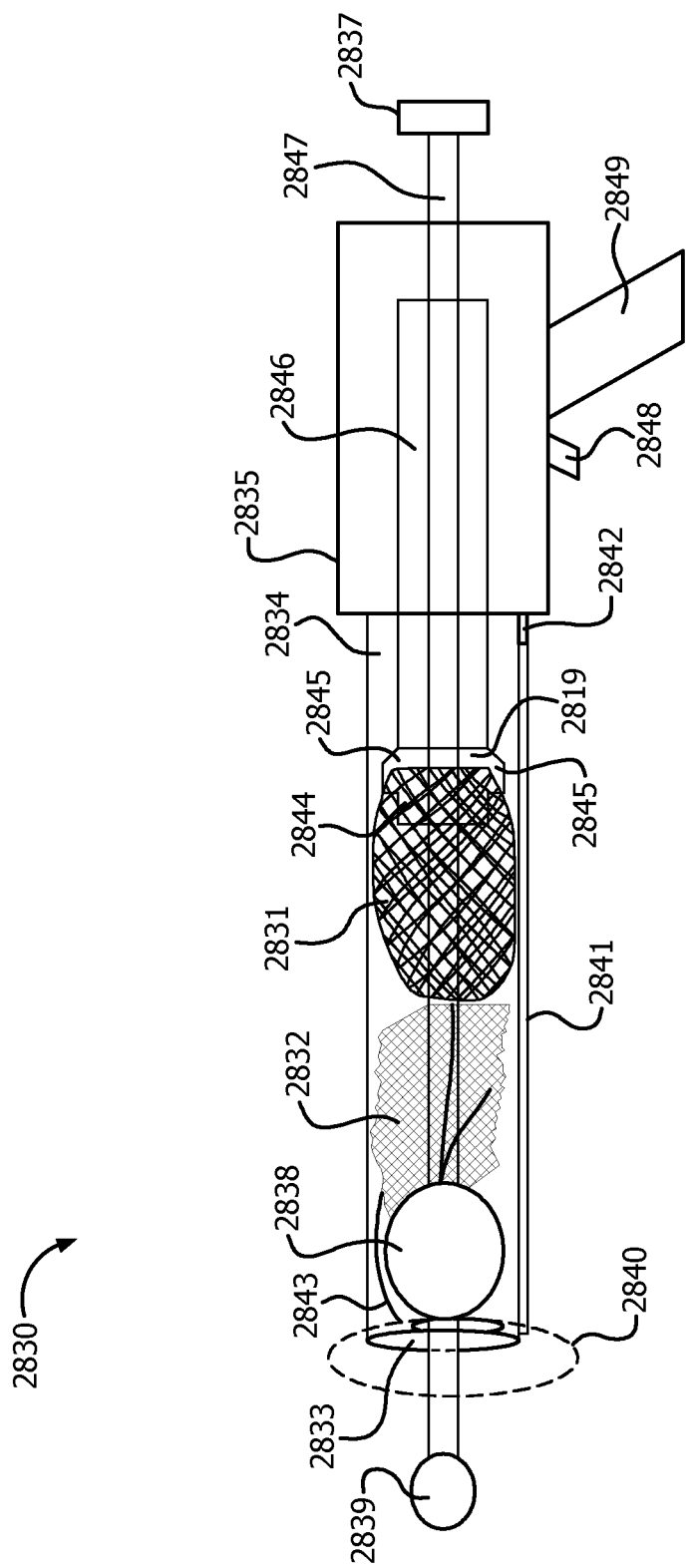
FIG. 28A is an illustration of another exemplary delivery device for an intragastric device, in accordance with one embodiment of the present specification.

FIG. 28A is an illustration of a fifth exemplary delivery device 2830 for an intragastric device, in accordance with one embodiment of the present specification. The delivery device 2830 includes a flexible elongate device body, or outer catheter 2834 with a proximal end, a distal end, and a lumen within. The distal end includes an opening 2833 and the proximal end is attached to an actuating mechanism 2835. The actuating mechanism 2835 includes an actuator handle 2849 and an actuator trigger 2848 and is used to move the components of the delivery device relative to one another. The actuating mechanism is also used for positioning the delivery device 2830 in the gastrointestinal tract of a patient. A flexible plunger component 2846 is positioned coaxially, and movable longitudinally, within the lumen of the device body 2834. The plunger 2846 includes a proximal end, a distal end, and also includes a lumen within. The distal tip 2844 of the plunger 2846 includes a mesh retention component 2819 comprising a plurality of fins 2845. The fins 2845 serve to securely hold the wire mesh structure 2831 of an intragastric device and push and pull the wire mesh structure 2831 as the plunger 2846 is moved back and forth within the device body 2834. The proximal end of the plunger 2846 is positioned within the actuating mechanism wherein pulling the actuation trigger 2848 causes the plunger 2846 to move back and forth longitudinally within the lumen of the device body 2834. A flexible elongate rod, or inner catheter 2847 is positioned within the lumen of the plunger 2846. The rod 2847 includes a proximal end and a distal end. Positioned proximal the distal end of the rod 2847 is a first spherical component or olive 2838 and positioned at the distal end of the rod 2847 is a second spherical component or olive 2839. The olives 2838, 2839 comprise spherical attachments which assist in guiding delivery of the intragastric device. The first spherical component or olive 2838 has a diameter greater than that of the second spherical component or olive 2839. Attached to the proximal end of the rod 2847 is a rod handle 2837 which is used for moving the rod 2847 longitudinally within the lumen of the plunger 2846. An intragastric device, comprising a wire mesh structure 2831 and a sleeve 2832 is positioned within the delivery device 2830 prior to deployment. In various embodiments, the sleeve is compressed axially. In other embodiments, the sleeve is not compressed coaxially. The wire mesh structure 2831 is placed with a side loop about the rod 2847 and distal to the tip 2844 of the plunger 2846, with a portion of the wire mesh structure 2831 hooked on the fins 2845 of the tip 2844. The sleeve 2832, which is attached to the wire mesh structure 2831, is positioned distal to the wire mesh structure 2831 and proximal to the first spherical component or olive 2838. The sleeve 2832 is folded upon itself 2 to 10 times and then wrapped around the rod 2847. The sleeve 2832 is not passed coaxially over the rod 2847. Attached to the sleeve 2832 and looped on the rod 2847 in a position distal to the first spherical component or olive 2838 is a suture loop 2843. The diameter of the suture loop 2843 about the rod 2847 is smaller than the diameter of the first spherical component or olive 2838 but greater than the diameter of the second spherical component or olive 2839. When the rod 2847 is pushed out of the device body 2834, the first spherical component or olive 2838 pushes the suture loop 2843 which pulls the attached sleeve 2832 out of the device body 2834. When the delivery device 2830, along with the rod 2847, are removed from the patient's gastrointestinal tract, the suture loop 2843 slips over the smaller diameter second spherical component or olive 2839, allowing the intragastric device to remain in the patient. In one embodiment, the suture loop 2843 is biodegradable and dissolves over time. In other embodiments, the suture loop 2843 is a biodegradable hook, ring, cone, or umbrella.

Optionally, in one embodiment, the delivery device 2830 further includes a balloon 2840 at the distal end of the device body 2834. A channel 2841 extends along the length of the device body 2834 and includes an input port 2842 at the proximal end of the device body 2834. The balloon 2840 is inflated using the input port 2842 and channel 2841 to anchor the delivery device within the patient's gastrointestinal tract. Anchoring provides greater traction to the delivery device to allow for pushing and pulling during delivery of the intragastric device.

Figure 28B:
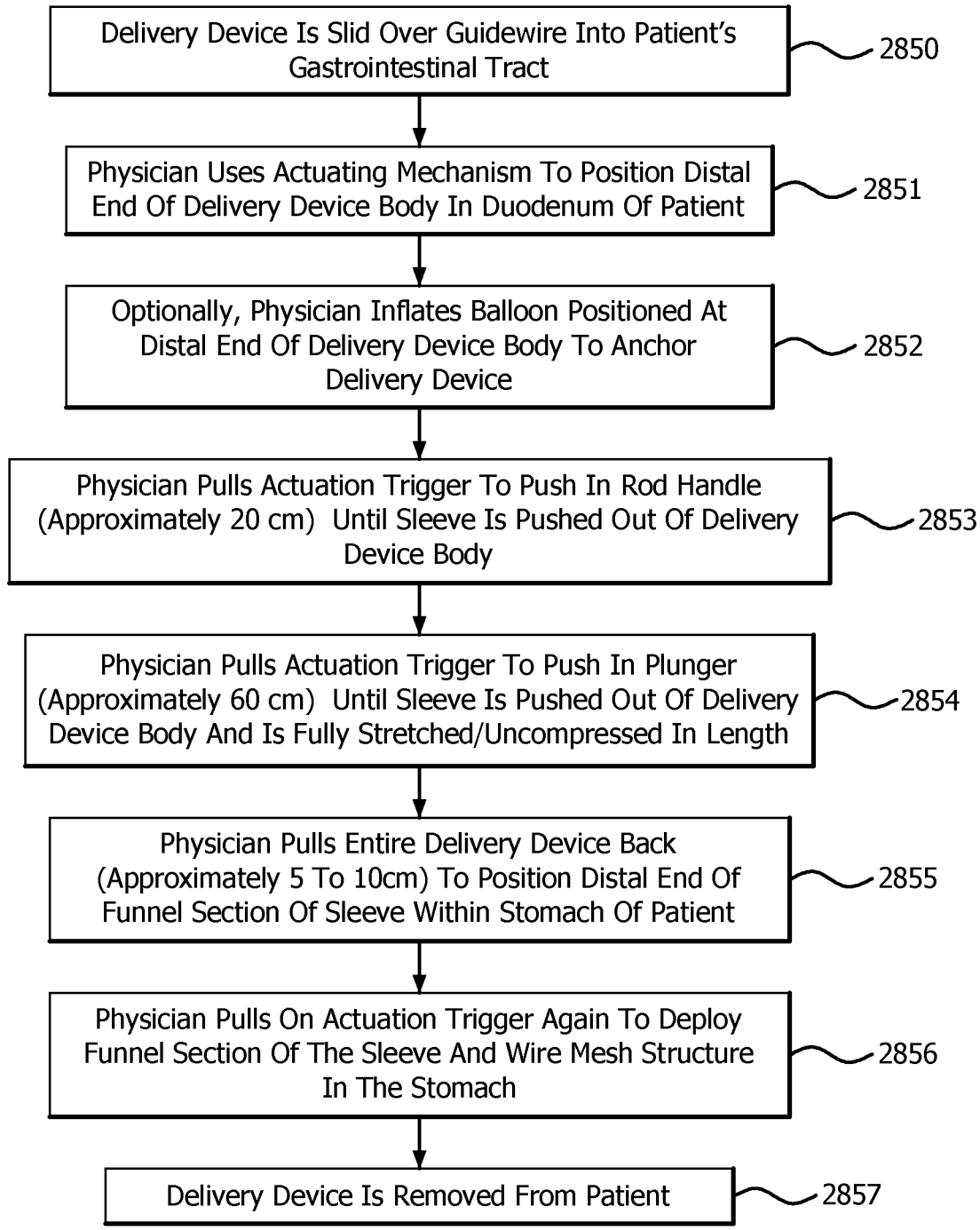
FIG. 28B is a flow chart illustrating the steps involved in delivering an intragastric device using the delivery device of FIG. 28A, in accordance with one embodiment of the present specification.

FIG. 28B is a flow chart illustrating the steps involved in delivering an intragastric device using the delivery device of FIG. 28A, in accordance with one embodiment of the present specification. At step 2850, the delivery device is slid over a guidewire into position within a patient's gastrointestinal tract. At step 2851, a physician uses the actuating mechanism to position the distal end of the delivery device body in a duodenum of the patient. Optionally, at step 2852, the physician inflates a balloon at the distal end of the device body to anchor the delivery device in the patient's gastrointestinal tract. The physician then pulls on the actuation trigger until it locks a first time, pushing in rod handle, until the sleeve is pushed out of the device body at step 2853. Optionally, the plunger includes a stopper so the physician knows when to stop pushing the second handle. At this point, the sleeve has been advanced approximately 20 cm, past the first spherical component and is positioned just proximal to the second spherical component. The wire mesh structure is positioned just proximal to the first spherical component and the opening at the distal end of the device body. Optionally, at step 2854, the physician pulls on the trigger to advance the plunger approximately 60 cm until the sleeve is fully deployed and is fully stretched or uncompressed. At step 2855, the physician repositions the device by pulling it back approximately 5 to 10 cm so that the distal end of the funnel section of the sleeve is within the stomach. Then, at step 2856, the physician pulls on the actuation trigger again until it locks a second time. This pulls the device body back while keeping the plunger in place, thus releasing the funnel section of the sleeve and the wire mesh structure. The delivery device is then removed from the patient at step 2857, leaving the intragastric device deployed in the patient's gastrointestinal tract.

Figure 29A:
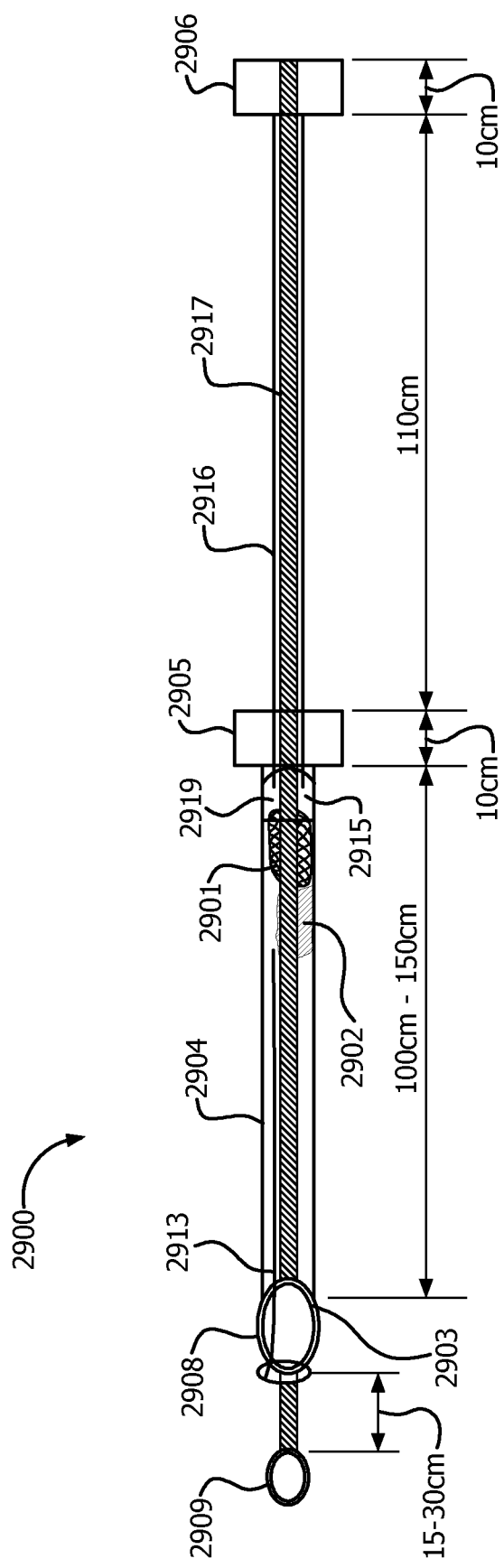
FIG. 29A is an illustration of another exemplary delivery device for an intragastric device, in accordance with one embodiment of the present specification.

FIG. 29A is an illustration of yet another exemplary delivery device 2900 for an intragastric device, in accordance with one embodiment of the present specification. The delivery device 2900 of FIG. 29A differs from the delivery device 2700 depicted in FIG. 27A in that it includes only two handles 2905, 2906 and a device body or outer catheter 2904 and rod or inner catheter 2917. The delivery device 2900 of FIG. 29A does not include a separate plunger with its own handle. Instead, a plunger 2916 is integrated with the second handle 2906 and coaxially envelopes a proximal portion of the inner catheter 2917. The delivery device 2900 includes a flexible elongate device body, or outer catheter 2904 with a proximal end, a distal end, and a lumen within. The distal end includes an opening 2903 and the proximal end is attached to a first handle 2905. The first handle 2905 is used for positioning the delivery device 2900 in the gastrointestinal tract of a patient. In one embodiment, the first handle 2905 includes a Y-connector. A flexible elongate rod, or inner catheter 2917 is positioned coaxially, and movable longitudinally, within the lumen of the outer catheter 2904. The rod 2917 includes a proximal end attached to a second handle 2906 and a distal end. A flexible plunger component 2916 is positioned coaxially over a proximal portion of, and moves longitudinally with, the inner catheter 2917. The plunger 2916 includes a proximal end also attached to second handle 2906 and a distal end. The distal tip of the plunger 2916 includes a mesh retention component 2919 comprising a plurality of fins 2915. The fins 2915 serve to securely hold the wire mesh structure 2901 of an intragastric device and push and pull the wire mesh structure 2901 as the plunger 2916 and inner catheter 2917 are moved back and forth within the outer catheter 2904. The second handle 2906 is positioned at the proximal end of the plunger 2916 and inner catheter 2917 for moving the plunger 2916 and inner catheter 2917 longitudinally within the lumen of the outer catheter 2904. Optionally, in one embodiment, the plunger includes a stopper which prevents the plunger and inner catheter from moving too far in a distal direction. Positioned proximal the distal end of the inner catheter 2917 is a first spherical component or olive 2908 and positioned at the distal end of the inner catheter 2917 is a second spherical component or olive 2909. The first spherical component or olive 2908 has a diameter greater than that of the second spherical component or olive 2909. An intragastric device, comprising a wire mesh structure 2901 and a sleeve 2902, is positioned within the delivery device 2900 prior to deployment. The wire mesh structure 2901 is placed with a side loop about the rod 2917 and distal to the tip of the plunger 2916, with a portion of the wire mesh structure 2901 hooked on the fins 2915 of the retention component 2919. In some embodiments, the rod 2917 passes through at least two openings in the wire mesh structure 2901 wherein the openings do not lie along a center longitudinal axis of the wire mesh structure 2901. In one embodiment, the wire mesh structure 2901 is compressed for positioning within the delivery device 2900 such that it has a compressed length of approximately 30 cm. The sleeve 2902, which is attached to the wire mesh structure 2901, is positioned distal to the wire mesh structure 2901 and proximal to the first spherical component or olive 2908. The sleeve 2902 is folded upon itself 2 to 10 times and then wrapped around the inner catheter 2917. In one embodiment, the sleeve 2902 has a length of 80 cm and is folded upon itself 3 times resulting in a compressed length of approximately 30 cm. The sleeve 2902 is not passed coaxially over the inner catheter 2917. Attached to the sleeve 2902 and looped on the inner catheter 2917 in a position distal to the first spherical component or olive 2908 are first and second ends, respectively, of a suture loop 2913. The diameter of the suture loop 2913 about the rod is smaller than the diameter of the first spherical component or olive 2908 but greater than the diameter of the second spherical component or olive 2909. When the inner catheter 2917 is pushed out of the outer catheter 2904, the first spherical component or olive 2908 pushes the suture loop 2913 which pulls the attached sleeve 2902 out of the outer catheter 2904. When the delivery device 2900, along with the inner catheter 2917, are removed from the patient's gastrointestinal tract, the suture loop 2913 slips over the smaller diameter second spherical component or olive 2909, allowing the intragastric device to remain in the patient. In one embodiment, the suture loop 2913 is biodegradable and dissolves over time. In other embodiments, the suture loop 2913 is a biodegradable hook, ring, cone, or umbrella.

Optionally, in one embodiment, the delivery device 2900 further includes a balloon at the distal end of the device body. A channel extends along the length of the device body and includes an input port at the proximal end of the device body. The balloon is inflated using the input port and channel to anchor the delivery device within the patient's gastrointestinal tract. Anchoring provides greater traction to the delivery device to allow for pushing and pulling during delivery of the intragastric device.

In some embodiments, the delivery device 2900 further includes a flushing or irrigation mechanism to reduce deployment forces during delivery.

In various embodiments, the delivery device or catheter has variable stiffness along its length. The delivery device is more flexible at its distal end and becomes less flexible along its length toward its proximal end. In some embodiments, the delivery device has three zones of flexibility: a proximal zone, a center zone, and a distal zone. In one embodiment, the proximal zone has a length of 100 cm and a flexibility of 55D, the center zone has a length of 20 cm and a flexibility of 40D, and the distal zone has a length of 30 cm and flexibility of 35D. Optionally, in one embodiment, the distal zone is split into two additional zones, comprising a more distal zone and a less distal zone. Both zones are 15 cm in length and the less distal zone has a flexibility of 35D while the more distal zone has a flexibility of 25D. In one embodiment, the proximal zone is braided and the center and distal zones are coiled.

The delivery device includes atraumatic distal ends and the two handle system of the delivery device allows for a shorter overall device body length. In various embodiments, the delivery device has the following dimensions: overall length ranging from 265 cm-310 cm; length of said device body or outer catheter 2904 ranging from 100 cm-150 cm; length of said plunger 2916 ranging from 120 cm-150 cm; length of said rod or inner catheter 2917 ranging from 265 cm-310 cm; length of each handle 2905, 2906, 2907 equal to 10 cm; distance between said second spherical component or olive 2909 and said first spherical component or olive 2908 ranging from 15 cm-30 cm; and, distance between said first handle 2905 and said second handle 2906 when in an initial configuration before delivery equal to 110 cm. In some embodiments, the outer diameter of the device body or outer catheter 2904 is 10 mm or less. In one embodiment, the delivery device is deployable over a 0.035 inch guidewire. In various embodiments, the plunger 2916 and inner catheter 2917 are sufficiently flexible to allow for atraumatic intestinal navigation. In some embodiments, a solid outer catheter can bend up to 80 degrees and is capable of navigating curves having a radius 30 mm-50 mm. In an embodiment, if a solid outer catheter is coiled into a radius of approximately 50 mm, the sleeve and mesh will kink or cinch in place and not deploy. Therefore, in some embodiments, the outer catheter 2904 comprises a flexible braided catheter. The flexible braided catheter is capable of bending and coiling beyond the limits described above without causing failure of deployment of the sleeve and wire mesh.

In one embodiment, the sleeve is only partially deployed during delivery. The wire mesh structure functions as an anchor to keep the device positioned. As the patient eats, the sleeve unfurls and becomes fully deployed due to the movements of the gastrointestinal tract.

In some embodiments, the outer catheter has a variable stiffness along its length and the inner catheter, coaxially positioned inside the outer catheter, includes an atraumatic distal end and a lumen for receiving a guiding device. Prior to delivery, an intragastric device is positioned in a space between the inner catheter and the outer catheter. The inner catheter further includes a flexible extension having a length of at least 5 cm at its distal end which extends beyond a distal end of the outer catheter. In some embodiments, the guiding device is a guidewire. In other embodiments, the guiding device is an endoscope for over the scope delivery. In some embodiments, the atraumatic distal end of the inner catheter is a ball-tip. In some embodiments, the inner catheter has a variable stiffness along its length. In some embodiments, said flexible extension includes a proximal end and a distal end and has a variable stiffness along its length wherein the stiffness varies between a stiffness of a guidewire at said distal end to a stiffness of said inner catheter at said proximal end. In other embodiments, the stiffness of the flexible extension is constant along its length.

FIG. 29B is a cross sectional illustration of a pre-deployment coaxial arrangement of a sleeve 2935 of an intragastric device within a delivery device 2930, in accordance with one embodiment of the present specification. The delivery device 2930 comprises an inner catheter 2933 positioned coaxially within a lumen 2936 of an outer catheter 2937. The inner catheter 2933 includes a guide wire port 2932 for insertion of a guide wire to assist in guiding delivery. In various embodiments, the guide wire is a super stiff guide wire having a diameter in a range of 0.035 to 0.038 inches. In the arrangement depicted in FIG. 29B, the sleeve 2935 is depicted around the inner catheter 2933 such that the inner catheter 2933 is positioned within a lumen 2934 of the sleeve 2935.

FIG. 29C is a cross sectional illustration of a pre-deployment coaxial arrangement of a sleeve of 2935 an intragastric device within a delivery device 2930, in accordance with another embodiment of the present specification. The delivery device 2930 comprises an inner catheter 2933 positioned coaxially within a lumen 2936 of an outer catheter 2937. The inner catheter 2933 includes a guide wire port 2932 for insertion of a guide wire to assist in guiding delivery. In the arrangement depicted in FIG. 29C, the sleeve 2935 is depicted adjacent the inner catheter 2933 such that the inner catheter 2933 is positioned outside of a lumen 2934 of the sleeve 2935.

FIG. 29D is a cross sectional illustration of a pre-deployment coaxial arrangement of a sleeve 2933 of an intragastric device within a delivery device 2930 depicted over an endoscope 2939, in accordance with one embodiment of the present specification. The delivery device 2930 comprises an inner catheter 2933 positioned coaxially within a lumen 2936 of an outer catheter 2937. The inner catheter 2933 includes an endoscope port 2938, within which is positioned an endoscope 2939, to assist in guiding delivery. In the arrangement depicted in FIG. 29D, the sleeve 2935 is depicted around the inner catheter 2933 such that the inner catheter 2933 is positioned within a lumen 2934 of the sleeve 2935.

In some embodiments, a system for delivering an intragastric device to a gastrointestinal tract of a patient comprises: a porous mesh structure having a first lumen; a sleeve attached to said porous mesh structure and having a second lumen; and, a coaxial catheter system comprising an outer catheter and an inner catheter, wherein, prior to delivery, said porous mesh structure and said sleeve are constrained into a space between said outer and inner catheters wherein the outer catheter covers a substantial portion of the intragastric device and the inner catheter passes within a majority of the first lumen of the mesh but outside of a majority of the second lumen of the sleeve. In some embodiments, the inner catheter is operationally attached to the sleeve at a distal end of the inner catheter such that, when actuated, the inner catheter pushes the sleeve out of the coaxial catheter system and is then detached from the sleeve to deliver the intragastric device in the gastrointestinal tract.

Figure 29E:
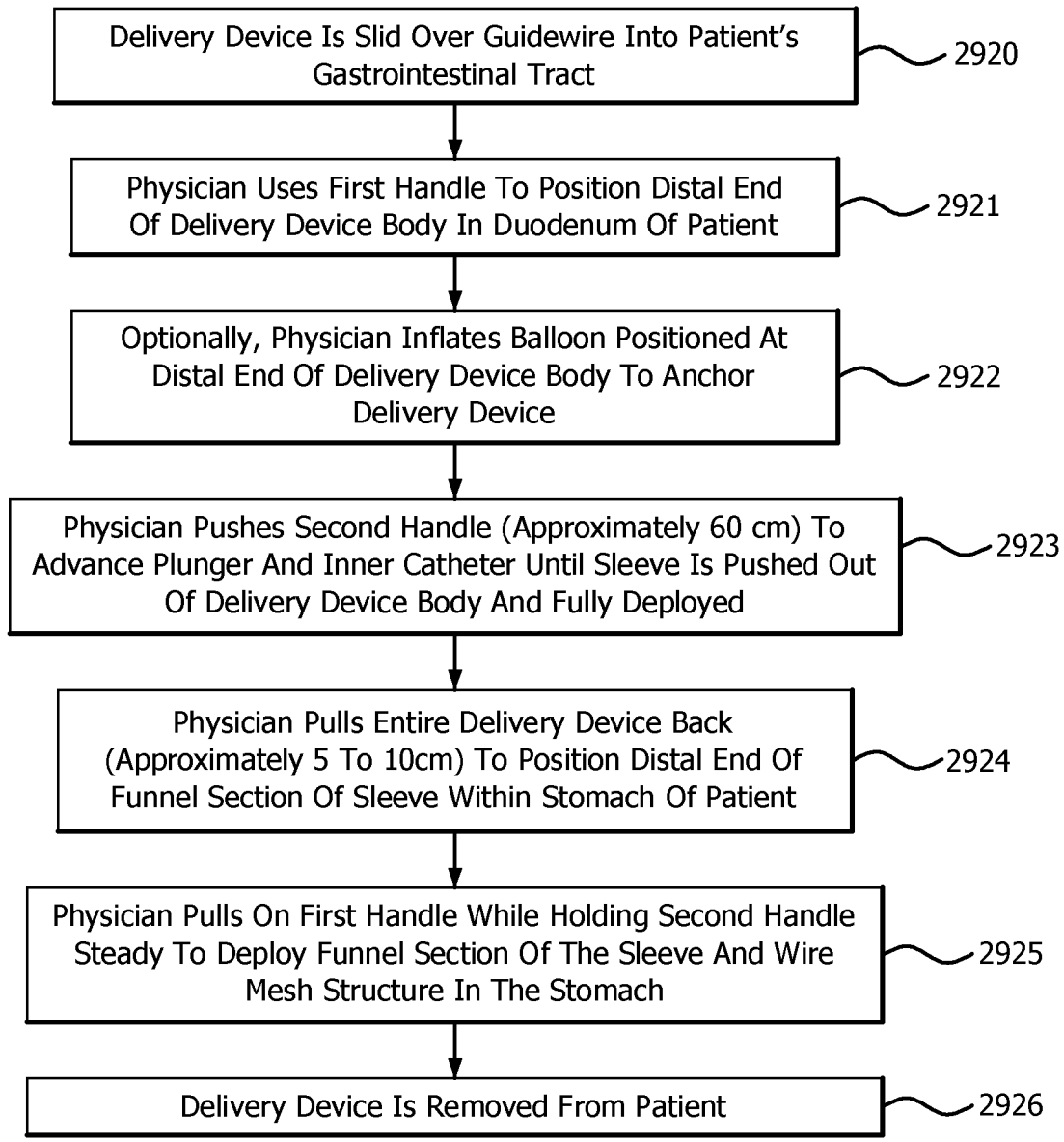
FIG. 29E is a flow chart illustrating the steps involved in delivering an intragastric device using the delivery device of FIG. 29A, in accordance with one embodiment of the present specification.

FIG. 29E is a flow chart illustrating the steps involved in delivering an intragastric device using the delivery device of FIG. 29A, in accordance with one embodiment of the present specification. At step 2920, the delivery device is slid over a guidewire into position within a patient's gastrointestinal tract. At step 2921, a physician uses the first handle to position the distal end of the delivery device body in a duodenum of the patient. Optionally, at step 2922, the physician inflates a balloon at the distal end of the device body to anchor the delivery device in the patient's gastrointestinal tract. The physician then pushes the second handle (approximately 60 cm) to advance the plunger and inner catheter until the sleeve is pushed out of the delivery device body and fully deployed at step 2923. Optionally, the plunger includes a stopper so the physician knows when to stop pushing the second handle. At step 2924, the physician repositions the device by pulling it back approximately 5 to 10 cm so that the distal end of the funnel section of the sleeve is within the stomach. Then, at step 2925, the physician pulls back on the first handle while holding the second handle steady to deploy the funnel section of the sleeve and the wire mesh structure in the stomach. This pulls the device body back while keeping the plunger and inner catheter in place, thus releasing the wire mesh structure. The delivery device is then removed from the patient at step 2926, leaving the intragastric device deployed in the patient's gastrointestinal tract.

Figure 30A:
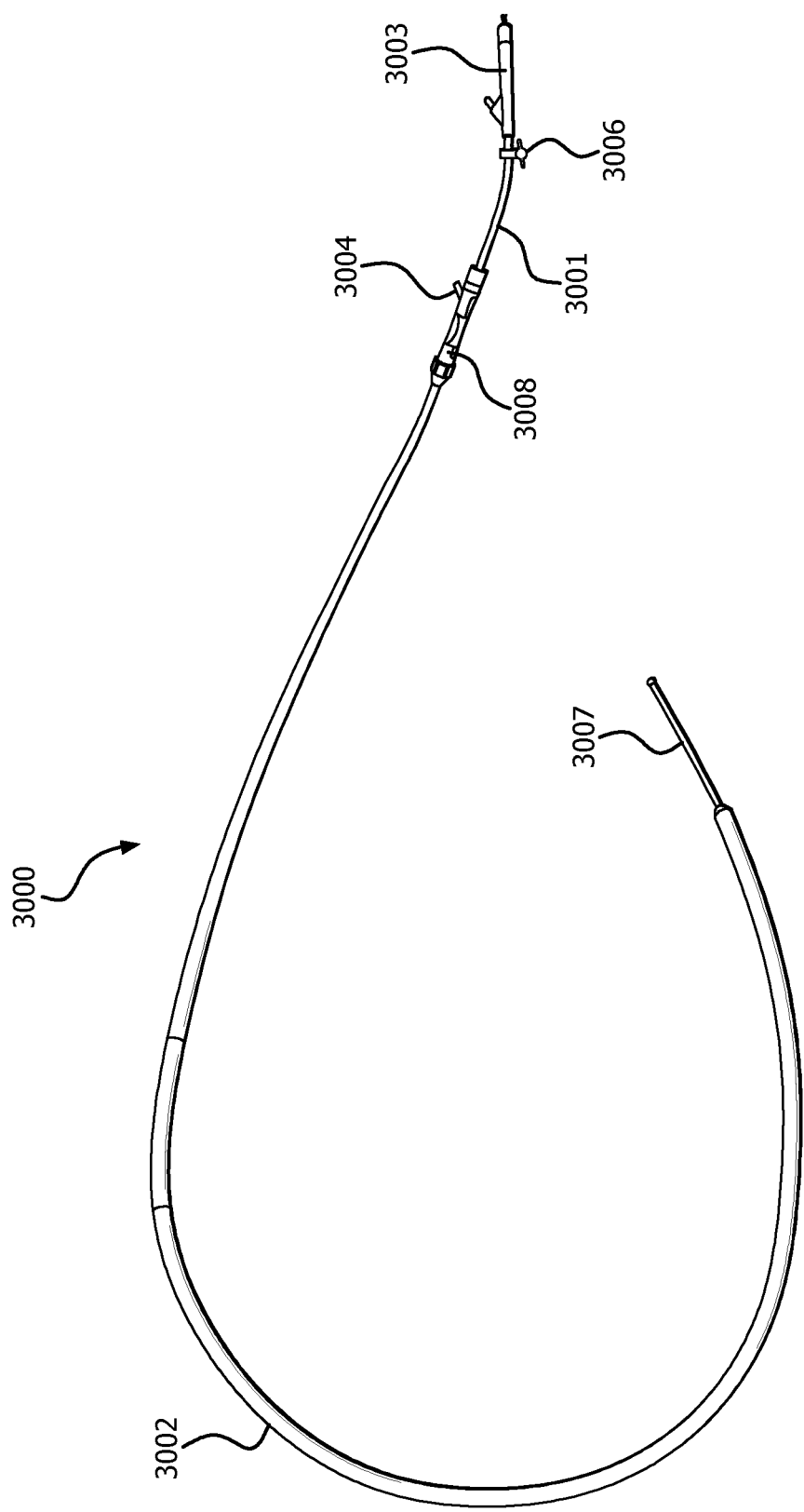
FIG. 30A is an illustration of a seventh exemplary delivery device for an intragastric device, in accordance with one embodiment of the present specification.

FIG. 30A is an illustration of a seventh exemplary delivery device 3000 for an intragastric device, in accordance with one embodiment of the present specification. The delivery device 3000 comprises a coaxial delivery system having flexible outer catheter 3002 and flexible inner catheter 3001 shafts on which an intragastric device is preloaded. The outer catheter 3002 includes a proximal end and a distal end and a lumen within. The inner catheter 3001 is positioned within the lumen of the outer catheter 3002 and also includes a proximal end and a distal end and a lumen within. The lumen of the inner catheter 3001 is configured to receive a guide wire. In various embodiments, the delivery device 3000 is approximately 3 meters in length and is used to deliver an intragastric device trans-orally into the stomach and duodenum or jejunum of a patient. The delivery device 3000 has a variable stiffness along its length providing sufficient flexibility to track through the small intestinal loops while also having sufficient pushability to prevent gastric looping. In various embodiments, the outer catheter 3002 has a length of approximately 1.5 meters. In some embodiments, a distal portion of the outer catheter 3002 includes a lubricious hydrophilic coating which can be activated just prior to delivery to ease navigation. In one embodiment, the coating covers approximately the distal 0.65 meters of the outer catheter 3002. The proximal end of the device 3000 includes a proximal portion of the inner catheter 3001 not covered by the outer catheter 3002. A pair of stopping mechanisms 3004, 3006 are positioned on the inner catheter 3001 as further described with reference to FIGS. 30E and 30G. A first handle 3003, having a proximal end, a distal end, and lumen configured to receive a guide wire, is attached to the proximal end of the inner catheter 3001. A second handle 3008, having a proximal end, a distal end, and a lumen configured to receive said inner catheter 3001, is attached to the proximal end of the outer catheter 3002 and is positioned coaxially about, and slidably over, the inner catheter 3001. Movement of the second handle 3008 proximally and distally relative to the first handle 3003 results in sliding of the outer catheter 3002 over the inner catheter 3001 proximally and distally.

Extending distally from the distal end of the inner catheter 3001 is a pilot component 3007. The pilot component comprises an elongate ultra-flexible rod having a proximal end and a distal end. The proximal end of the pilot component includes a proximal spherical component, or olive as described with reference to FIGS. 30D and 30E below. The distal end of the pilot component 3007 includes a distal spherical component, or olive, as described further with reference to FIGS. 30D and 30F below. In some embodiments, the pilot component 3007 is also covered with a lubricious hydrophilic coating.

Figure 30B:
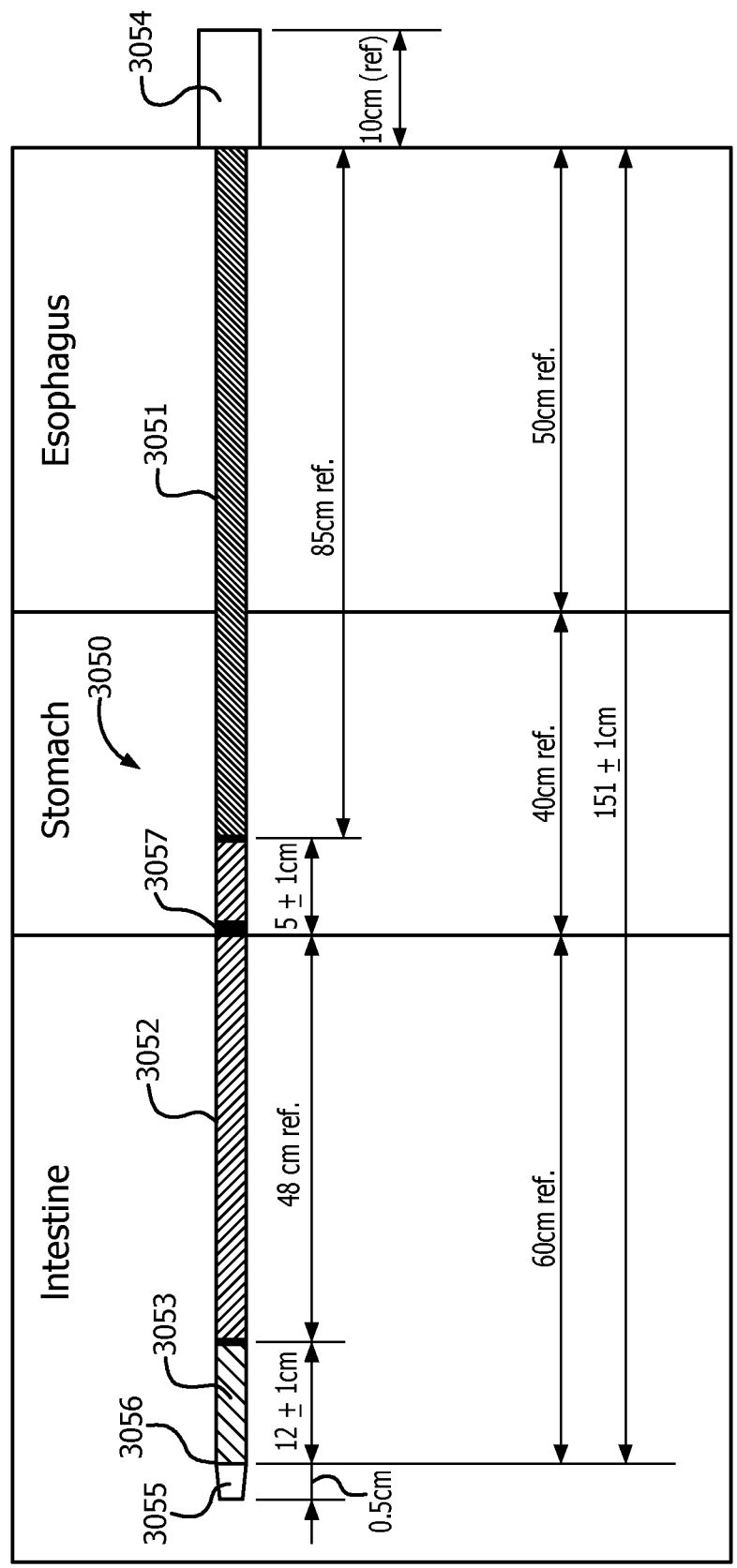

FIG. 30B is an illustration of one exemplary embodiment of an outer catheter 3050 for use in the delivery device of FIG. 30A. The outer catheter 3050 includes three segments of varying stiffness, each having a proximal end, a distal end, and a lumen: a proximal segment 3051, a center segment 3052, and a distal segment 3053. Attached to the proximal end of the proximal segment 3051 is the second handle 3054. Attached to the distal end of the distal segment 3053 is a soft tip 3055. Both the second handle 3054 and soft tip 3055 include lumens for receiving an inner catheter. In one embodiment, the outer catheter 3050 includes a first radiopaque marker 3056 at the junction of the soft tip 3055 with the distal segment 3053 and a second radiopaque marker 3057 on the center segment 3052, approximately 4-6 cm from the junction of the center segment 3052 with the proximal segment 3051. In various embodiments, the proximal segment 3051 has a length of approximately 85 cm and a stiffness which is 120% of the stiffness of the center segment 3052. In various embodiments, the center segment 3052 has a length in a range of approximately 52-54 cm. In various embodiments, the distal segment 3053 has a length in a range of approximately 11-13 cm and a stiffness which is 80% of the stiffness of the center segment 3052. In various embodiments, the outer catheter 3050 has an overall length in a range of 150-152 cm, not including the second handle 3054 or soft tip 3055. In one embodiment, the second handle 3054 has a length of 10 cm. In one embodiment, the soft tip 3055 has a length of 0.5 cm. During delivery, the second handle 3054 is positioned outside the patient's body. In some embodiments, during delivery, approximately the proximal 50 cm of the proximal segment 3051 is positioned in the esophagus. In some embodiments, during delivery, approximately the distal 35 cm of the proximal segment 3051 and the proximal 4-6 cm of the center segment 3052 are positioned in the stomach. In some embodiments, during delivery, approximately the distal 48 cm of the center segment 3052 and the entirety of the distal segment 3053 and soft tip 3055 are positioned in the intestine.

Figure 30C:
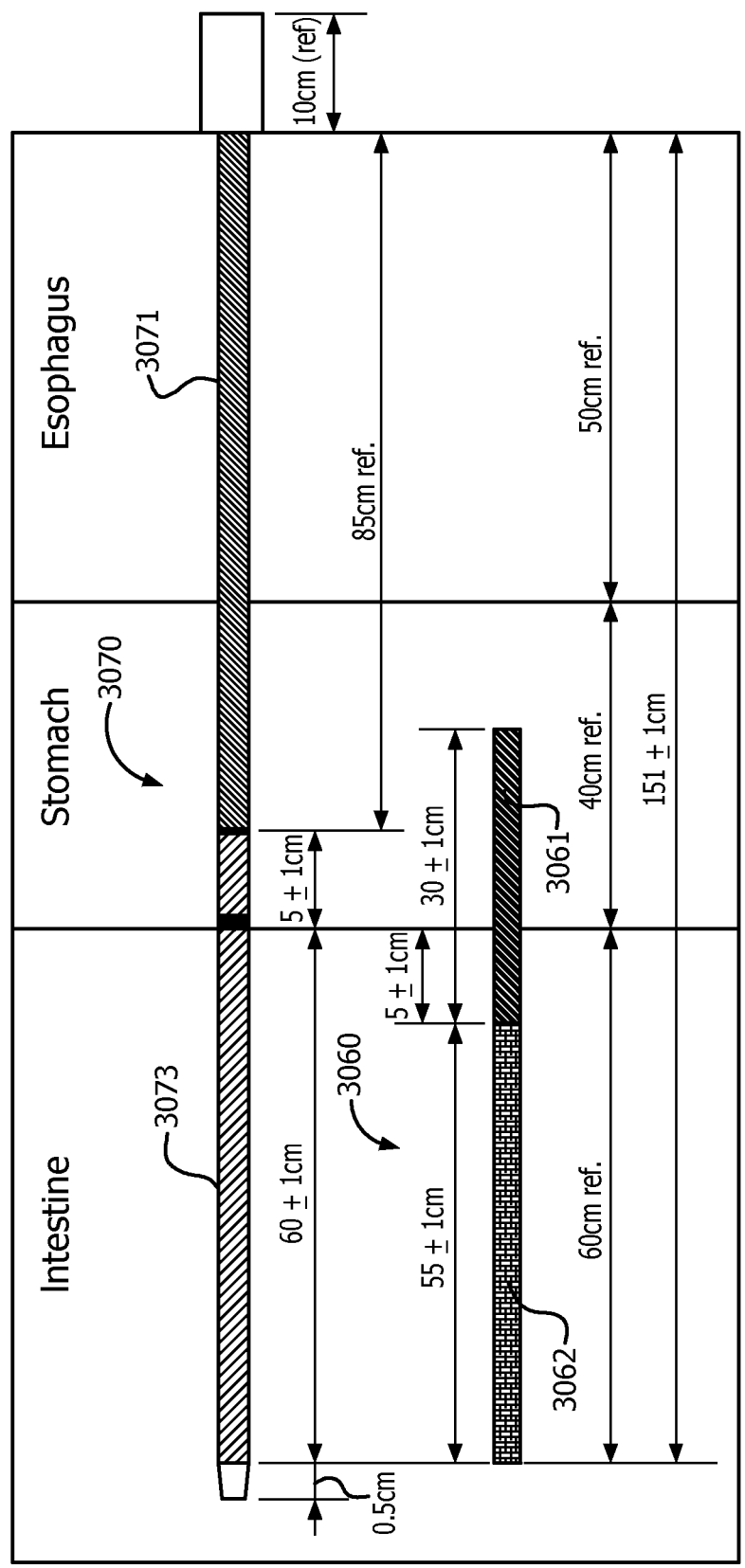

FIG. 30C is an illustration of another embodiment of an outer catheter 3070 depicting the dimensions a compressed sleeve 3062 and compressed wire mesh structure 3061 of an intragastric device 3060 relative to the dimensions of the outer catheter 3070. The outer catheter 3070 of FIG. 30C includes only a proximal segment 3071 and a distal segment 3073. The distal segment 3073 has a length in a range of 63-67 cm, with 59-61 cm positioned in the intestine and 4-6 cm positioned in the stomach. The compressed sleeve 3062 has a length in a range of 54-56 cm, is contained fully within the distal segment 3073, and is positioned entirely within the intestine. The compressed wire mesh structure 3061 has a length in a range of approximately 29-31 cm. Approximately 9-11 cm of wire mesh structure 3061 is contained within the proximal end of the distal segment 3073 and 19-21 cm of the wire mesh structure 3061 is contained within the distal end of the proximal segment 3071. Approximately 4-6 cm of the wire mesh structure 3061 is positioned in the intestine and 24-26 cm of the wire mesh structure is positioned in the stomach.

Figure 30D:
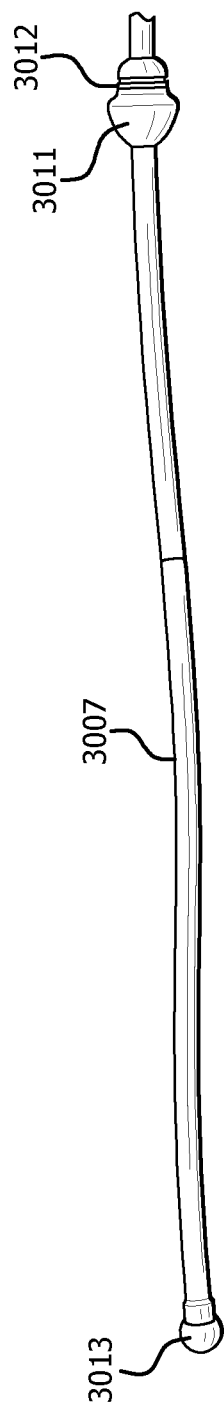

FIG. 30D is a close up illustration of the distal end of the delivery device 3000 of FIG. 30A, depicting the pilot component 3007 and proximal 3011 and distal 3013 spherical components. The proximal spherical component 3011 is shaped to be atraumatic and includes a radiopaque marker 3012 for radiographic visualization during delivery. The distal spherical component 3013 is configured in a ball-tip shape and is also designed to be atraumatic to body tissues. The design of the pilot component 3007 and proximal 3011 and distal 3013 spherical components is configured to facilitate atraumatic and easy 'over-the-guide wire' tracking through the intestinal loops. The stiffness of the pilot component 3007 is less than the stiffness of the distal portion of the outer catheter. In some embodiments, the pilot component 3007 has a variable stiffness with a stiffness close to the stiffness of the distal end of the outer catheter at its proximal end and a stiffness close to that of a 0.035" guidewire at its distal end.

FIG. 30E is an illustration of the proximal end of the delivery device of FIG. 30A, depicting the outer catheter 3002 retracted to a first stopping mechanism 3004. During delivery of an intragastric device which has been preloaded on the delivery device, a user steadies the first handle 3003 to hold inner catheter 3001 in place while using the second handle 3008 to retract, or slide proximally, the outer catheter 3002 over the inner catheter 3001. The outer catheter 3002 is retracted until a proximal end of the second handle 3008 contacts a first stopping mechanism 3004. A second stopping mechanism 3006 is also positioned on the inner catheter 3001, proximal to the first stopping mechanism 3004. In some embodiments, the stopping mechanisms 3004, 3006 comprise plastic rings firmly secured to the inner catheter using wing nuts 3004a, 3006a. In some embodiments, the first handle 3003 includes a first port 3013 for injection of a fluid, such as saline or water, for flushing the lumen of the inner catheter 3001. In some embodiments, the second handle 3008 includes a second port 3018 for injection of a fluid, such as saline or water, for flushing the lumen of the outer catheter 3002.

FIG. 30F is an illustration of one embodiment of a sleeve 3022 of an intragastric device partially deployed corresponding to the outer catheter 3002 position depicted in FIG. 30E. Referring to FIGS. 30E and 30F simultaneously, when the outer catheter 3002 has been retracted such that the proximal end of the second handle 3008 is in contact with the first stopping mechanism 3004, the sleeve 3022 has been partially deployed as depicted in FIG. 30F. The portion of the sleeve 3022 deployed is the cylindrical distal portion 1622d as described with reference to FIG. 16D. This is the portion of the sleeve 3022 which resides in the small intestine of the patient. The outer catheter 3002 has been retracted to the junction point 1622j of the sleeve described in FIG. 16D. As pictured in FIG. 30F, in some embodiments, the sleeve 3022 is wrapped coaxially around the inner catheter 3001 of the delivery device. In other words, the inner catheter 3001 does not pass through the lumen of the sleeve 3022. In one embodiment, the distal end of the outer catheter 3002 includes a radiopaque marker 3009 to ensure proper placement of the delivery device under radiographic visualization.

FIG. 30G is an illustration of the proximal end of the delivery device of FIG. 30A, depicting the outer catheter 3002 retracted to a second stopping mechanism 3006. The first stopping mechanism has been removed to allow further retraction of the outer catheter 3002. Continuing with delivery of an intragastric device, the user steadies the first handle 3003 to hold inner catheter 3001 in place while using the second handle 3008 to further retract the outer catheter 3002 over the inner catheter 3001. The outer catheter 3002 is retracted until a proximal end of the second handle 3008 contacts the second stopping mechanism 3006.

FIG. 30H is an illustration of one embodiment of a wire mesh structure 3021 of an intragastric device partially deployed corresponding to the outer catheter 3002 position depicted in FIG. 30G. Referring to FIGS. 30G and 30H simultaneously, when the outer catheter 3002 has been retracted such that the proximal end of the second handle 3008 is in contact with the second stopping mechanism 3006, the wire mesh structure 3021 has been partially deployed as depicted in FIG. 30H. The anti-migration collar 3024 of the wire mesh structure 3021 has been deployed and, as a result of its shape memory properties, has everted to its post-deployment configuration from its pre-deployment configuration as depicted in FIG. 11D. The proximal end of the now fully deployed sleeve 3022 is depicted attached to the anti-migration collar 3024. As pictured in FIG. 30H, in some embodiments, the inner catheter 3001 is passed through spaces between the wires of wire mesh structure 3021 along a side of said structure 3021. In other words, the inner catheter 3001 does not pass through the center of the wire mesh structure 3021.

Figure 30I:
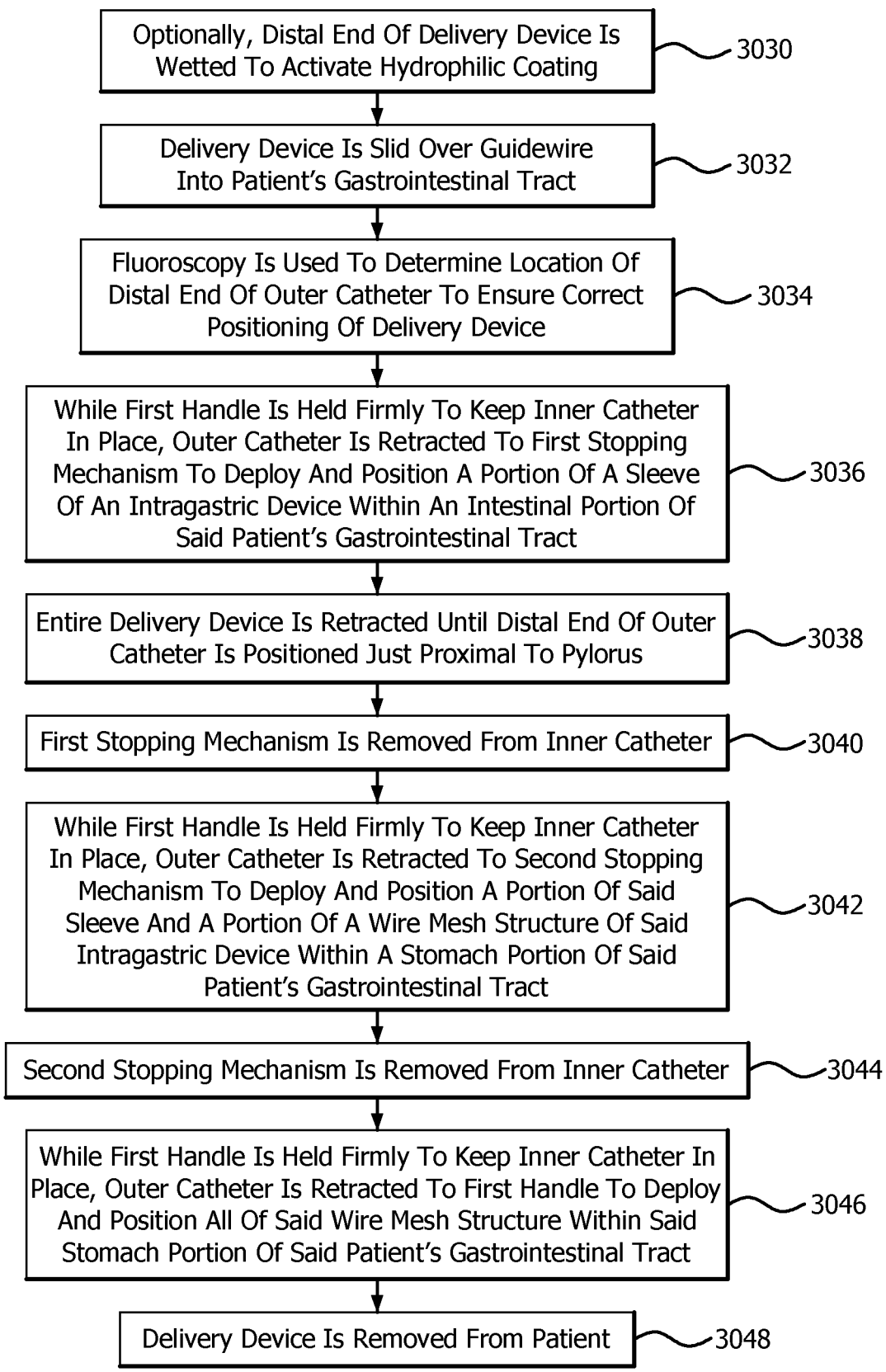

FIG. 30I is a flow chart illustrating the steps involved in delivering an intragastric device using the delivery device of FIG. 30A, in accordance with one embodiment of the present specification. At step 3030, optionally, the distal end of the delivery device is wetted to activate a lubricious hydrophilic coating, which will ease insertion and navigation of the delivery device. The delivery device is then slid over a guide wire and into a patient's gastrointestinal tract at step 3032. Fluoroscopy is used at step 3034 to determine the location of the distal end of the outer catheter to ensure correct positioning of the delivery device. While the first handle is held firmly to keep the inner catheter in place, the outer catheter is retracted to the first stopping mechanism to deploy and position a portion of the sleeve of a pre-loaded intragastric device within an intestinal portion of the patient's gastrointestinal tract at step 3036. Then, at step 3038, the entire delivery device is retracted until the distal end of the outer catheter is positioned just proximal to the pylorus. The first stopping mechanism is removed from the inner catheter at step 3040. While the first handle is held firmly to keep the inner catheter in place, the outer catheter is retracted to the second stopping mechanism to deploy and position a portion of the sleeve and a portion of the wire mesh structure of the intragastric device within a stomach portion of the patient's gastrointestinal tract at step 3042. At step 3044, the second stopping mechanism is removed from the inner catheter. While the first handle is held firmly to keep the inner catheter in place, the outer catheter is retracted to the first handle to deploy and position all of the wire mesh structure within the stomach portion of the patient's gastrointestinal tract at step 3046. The delivery device is then removed from the patient at step 3048.

FIG. 31A is an illustration of a wire mesh structure 3101 of an intragastric device 3100 being loaded onto a delivery device, in accordance with one embodiment of the present specification. Referring to FIG. 31A, a portion of the inner catheter 3131 and pilot component 3137 of the delivery device are depicted. The delivery device includes a proximal spherical component 3135 at the transition from inner catheter 3101 to pilot component 3137. The wire mesh structure 3101 includes a sleeve 3102 attached to its anti-migration collar 3104. When loading the intragastric device 3100 onto the delivery device, the pilot component 3137 is passed through an off-center opening between the wires of the wire mesh structure 3101 such that the proximal spherical component 3135 is positioned just distal to the wire mesh structure 3101 and the inner catheter 3131 lies within the internal volume of the wire mesh structure 3101.

FIG. 31B is an illustration of the wire mesh structure 3101 of FIG. 31A further loaded onto the delivery device. The proximal end of the wire mesh structure 3101 has been compressed and is now contained within the distal end of the outer catheter 3132 of the delivery device. The proximal spherical component is no longer visible as the wire mesh structure 3101 has been advanced proximally along the inner catheter 3131. Referring to FIG. 31B, the inner catheter is depicted exiting the wire mesh structure 3101 through an opening offset from center of the wire mesh structure 3101. The sleeve is then wrapped coaxially about the inner catheter as described with reference to FIG. 31C. In another embodiment, the inner catheter (and attached pilot component) continues within the wire mesh structure and exits through an opening in a side of the proximal, funnel shaped portion of the sleeve. In another embodiment, the inner catheter continues within the wire mesh structure and exits through an opening in a side of the distal, cylindrically shaped portion of the sleeve. In yet another embodiment, the inner catheter continues within the wire mesh structure, passes through the entire sleeve, and exits through the opening in the distal end of the sleeve.

FIG. 31C is an illustration of the wire mesh structure 3101 of FIG. 31A loaded onto the delivery device such that only the anti-migration collar 3104 remains to be loaded. FIG. 31D is an illustration of the wire mesh structure of FIG. 31A fully loaded onto the delivery device. Referring to FIG. 31D, the wire mesh structure is no longer visible as it is fully contained within the distal end of the outer catheter 3132. The sleeve 3102 is depicted wrapped coaxially about the inner catheter 3131.

FIG. 31E is an illustration of a sleeve 3102 of the intragastric device of FIG. 31A partially loaded onto the delivery device. A portion of the sleeve 3102, wrapped coaxially about the inner catheter 3131, is visible extending from the distal end of the outer catheter 3132. FIG. 31F is an illustration of the intragastric device of FIG. 31A fully loaded onto the delivery device. The proximal spherical component 3135 is positioned at the distal end of the outer catheter 3132. In one embodiment, a plurality of sutures 3105 extending from the distal end of the sleeve are tied about the proximal spherical component 3135 to maintain the intragastric device in place until ready for delivery. Prior to delivery, the sutures 3105 are undone so the intragastric device may be deployed.

FIG. 32A is an illustration of a retrieval device 3200 for removing an intragastric device in accordance with another embodiment of the present specification. The retrieval device 3200 includes a flexible outer tube 3202 comprising an elongate body having a proximal end, a distal end, and a lumen within. A first handle 3212 is attached to the proximal end and an opening 3222 is positioned at the distal end of the outer tube 3202. A flexible inner member 3204 comprising an elongate body with a proximal end and a distal end is disposed within the lumen of the outer tube 3202. In one embodiment, the inner member 3204 comprises a flexible metal wire. A second handle 3214 is attached to the proximal end and a retrieval mechanism 3224 is formed from the distal end of the inner member 3204. In one embodiment, the retrieval mechanism 3224 comprises a hook. In one embodiment, the hook is lockable.

FIG. 32B is a flow chart illustrating the steps involved in removing an intragastric device from a patient using the retrieval device of FIG. 32A, in accordance with one embodiment of the present specification. At step 3232, a physician inserts the outer tube of the retrieval device into a working channel of an endoscope inserted into a patient. At this point, the retrieval mechanism at the distal end of the inner member is contained within the distal end of the outer tube. At step 3234, the physician holds the first handle securely to position the retrieval device within the gastrointestinal tract of the patient. Then, at step 3236, the physician pushes on the second handle to extend the retrieval mechanism through the opening and beyond the distal end of the outer tube. The physician manipulates the second handle to grasp a proximal end of the intragastric device with the retrieval mechanism at step 3238. In one embodiment, the proximal end of the intragastric device includes a set of staggered nodes, as depicted as nodes 1615 with reference to FIG. 16B, to ease grasping with the retrieval mechanism. Once the intragastric device has been secured by the retrieval mechanism, the physician pulls on the second handle to pull the retrieval mechanism and at least a portion of the attached intragastric device into the distal end of the outer tube at step 3240. The intragastric device is composed of a shape memory metal so that it is easily compressible to a size capable of fitting into said outer tube. Optionally, at step 3242, the physician actuates a locking mechanism on the retrieval device to prevent the retrieval mechanism and attached intragastric device from slipping out of the distal end of the outer tube. Finally, at step 3244, the physician removes the retrieval device and attached intragastric device from the patient.

FIG. 33A is an illustration of an embodiment of an intragastric device 3300 in an exemplary post-deployment configuration having a dumbbell shape. The device 3300 includes a first, upper wire mesh 3361 at its proximal end and a second, lower wire mesh 3362 at its distal end. The internal volumes of the two wire meshes 3361, 3362 are in fluid communication with one another. In various embodiments, the size of the second wire mesh 3362 is equal to or smaller than the size of the upper wire mesh 3361. The device 3300 further includes a first opening 3363 at the proximal end of the upper wire mesh 3361 and a second, larger opening 3364 at the distal end of the lower wire mesh 3362. Food enters the device 3300 at the first opening 3363, travels through the internal volume of the upper wire mesh 3361, into and through the internal volume of the lower wire mesh 3362, and exits through the second opening 3364. In one embodiment, the wire mesh of the lower wire mesh portion 3362 is an extension of the wire mesh of the upper wire mesh portion 3361. In another embodiment, the two wire mesh portions 3361, 3362 are comprised of separate wire mesh structures which are then attached prior to deployment. In the pictured embodiment, the device 3300 includes a membrane 3367 covering the entire outer surface of the device 3300 with the exception of the two openings 3363, 3364.

FIG. 33B is an illustration of an embodiment of an intragastric device 3320 having a double-wire mesh structure wherein the lower wire mesh is formed from an everted anti-migration component 3324. The device 3320 has a dumbbell shaped structure similar to the double-mesh device structure embodiments discussed in the present specification and functions similarly to those devices. The upper wire mesh 3322 is similar to the wire mesh structure 210 of FIG. 2B and the lower mesh structure is similar to the anti-migration collar 214 of FIG. 2B except that the lower mesh structure 3324 is larger and everts or curves completely in a proximal direction to form said lower mesh structure 3324 as depicted in FIG. 33B. The first wire mesh structure 3322 comprises a plurality of free ends extending from its lower portion, or base. One portion of said plurality of free ends are curved upon themselves to create the everted portion 3324 on the right side while a second portion of said plurality of free ends are curved upon themselves to create the everted portion 3324 on the left side. It should be appreciate that this eversion can occur around the entire periphery of the first wire structure thereby creating a torus, which may be elongated, elliptical, or egg shape.

In various embodiments, the device 3300 has a total length ranging between 50 and 500 mm. In a preferred embodiment, the device 3300 has a total length of 180 mm. In various embodiments, the upper wire mesh 3361 has a length ranging between 30 and 250 mm. In a preferred embodiment, the upper wire mesh 3361 has a length of 140 mm. In various embodiments, the lower wire mesh 3362 has a length ranging between 1 and 250 mm. In a preferred embodiment, the lower wire mesh 3362 has a length of 10 mm. In various embodiments, the upper wire mesh 3361 has a width ranging between 30 and 300 mm. In a preferred embodiment, the upper wire mesh 3361 has a width of 120 mm. In various embodiments, the lower wire mesh 3362 has a width ranging between 10 and 300 mm. In a preferred embodiment, the lower wire mesh 3362 has a width of 60 mm. In various embodiments, the first opening 3363 has a diameter ranging between 5 and 50 mm. In a preferred embodiment, the first opening 3363 has a diameter of 20 mm. In various embodiments, the second opening 3364 has a diameter ranging from 10 to 75 mm. In a preferred embodiment, the second opening 3364 has a diameter of 30 mm.

FIG. 34A is an illustration of another exemplary double-wire mesh intragastric device 3400*a* in a post-deployment configuration in accordance with one embodiment of the present specification. The pictured embodiment includes a first wire mesh structure 3401 positioned on top of a second wire mesh structure 3411 and a sleeve 3402 coupled to the distal end of the second wire mesh structure 3411. A first anti-migration component 3404 at the base of the first wire mesh structure 3401 rests inside the second wire mesh structure 3411 and functions to couple the two wire mesh structures 3401, 3411 together. The first anti-migration component 3404 also helps to prevent the second wire mesh structure 3411 from being compressed by gastric contractions and keeps the device 3400*a* out of the pylorus. A second anti-migration component 3414, at the base of the second wire mesh structure 3411, acts to prevent the entirety of the device 3400*a* from being passed through the pylorus. Food first passes through openings in the top of the combined intragastric device 3400*a* and is sequestered in the first wire mesh structure 3401. The food then slowly passes into, and is sequestered in, the second wire mesh structure 3411. Finally, the food slowly releases through the openings in the bottom of the combined intragastric device 3400*a* into a sleeve 3402 attached to distal end of the second wire mesh structure 3411 that bypasses the pylorus to release the food into the small intestine. In one embodiment, there is no attached sleeve 3402 and the food is released through the openings in the bottom of the combined intragastric device 3400*a* back into the stomach. The combined wire mesh structures 3401, 3411 work together to occupy an increased volume in a patient's stomach and further delay the passage of food through the gastrointestinal tract. The combined two wire mesh structures 3401, 3411 also act to induce satiety even more quickly and induce a longer lasting satiety than a single mesh structure device. The two wire-mesh structures are able to move relative to each other as compared to a single structure, allowing them to adjust better to the shape of the stomach, resulting in better tolerability and/or less complications.

FIG. 34B is an illustration of another exemplary double-wire mesh intragastric device 3400*b* in a post-deployment configuration in accordance with one embodiment of the present specification. The pictured embodiment includes a first wire mesh structure 3421 positioned on top of a second wire mesh structure 3431. The two wire mesh structures 3421, 3431 work together to occupy an increased volume in a patient's stomach and further delay the passage of food through the gastrointestinal tract. The two wire-mesh structures are able to move relative to each other as compared to a single structure, allowing them to adjust better to the shape of the stomach, resulting in better tolerability and/or less complications.

FIG. 34C is an illustration of another exemplary double-wire mesh intragastric device 3400*c* in a post-deployment configuration in accordance with one embodiment of the present specification. The pictured embodiment includes a first wire mesh structure 3451 positioned on top of a second wire mesh structure 3461. An anti-migration component 3464 at the base of the second wire mesh structure 3461 acts to prevent the entirety of the device 3400*c* from being passed through the pylorus. The two wire mesh structures 3451, 3461 work together to occupy an increased volume in a patient's stomach and further delay the passage of food through the gastrointestinal tract. The two wire-mesh structures are able to move relative to each other as compared to a single structure, allowing them to adjust better to the shape of the stomach, resulting in better tolerability and/or less complications.

FIG. 34D is an illustration of another exemplary double-wire mesh intragastric device 3400*d* in a post-deployment configuration in accordance with one embodiment of the present specification. The pictured embodiment includes a first wire mesh structure 3471 positioned on top of a second wire mesh structure 3481. A first anti-migration component 3474 at the base of the first wire mesh structure 3471 rests inside the second wire mesh structure 3481 and functions to couple the two wire mesh structures 3471, 3481 together. The first anti-migration component 3474 also helps to prevent the second wire mesh structure 3481 from being compressed by gastric contractions and keeps the device 3400*d* out of the pylorus. A second anti-migration component 3484 at the base of the second wire mesh structure 3481 acts to prevent the entirety of the device 3400d from being passed through the pylorus. The two wire mesh structures 3471, 3481 work together to occupy an increased volume in a patient's stomach and further delay the passage of food through the gastrointestinal tract.

FIG. 34E is an illustration of another exemplary double-wire mesh intragastric device 3400e in a post-deployment configuration in accordance with one embodiment of the present specification. The pictured embodiment includes a first wire mesh structure 3493 positioned on top of a second wire mesh structure 3495. An anti-migration component 3497 at the base of the first wire mesh structure 3493 rests inside the second wire mesh structure 3495 and functions to couple the two wire mesh structures 3493, 3495 together. The anti-migration component 3497 also helps to prevent the second wire mesh structure 3495 from being compressed by gastric contractions and keeps the device 3400e out of the pylorus. The two wire mesh structures 3493, 3495 work together to occupy an increased volume in a patient's stomach and further delay the passage of food through the gastrointestinal tract.

In various embodiments, any of the double-wire mesh intragastric devices of FIGS. 34B to 34E further includes a sleeve attached to the distal end of the second wire mesh structure. In various embodiments, the anti-migration components, or collars, of the devices of the present specification have a length ranging from 1 mm to 100 mm and an outer diameter of 25 mm to 75 mm for a ratio of length to outer diameter ranging from 0.01 to 4. In one embodiment, the anti-migration component, or collar, has a length equal to 15 mm and an outer diameter of 60 mm for a ratio of length to outer diameter of 0.25. In various embodiments, the wire meshes of the intragastric devices of the present specification are configured to be fatigue resistant for a period of at least six months, wherein fatigue resistant is defined as break resistant under intended use.

FIG. 34F is an illustration of another exemplary double-wire mesh intragastric device 3400f in a post-deployment configuration in accordance with one embodiment of the present specification. The pictured embodiment includes a first wire mesh structure 3491 positioned on top of a second wire mesh structure 3499 and a sleeve 3492 coupled to the distal end of the second wire mesh structure 3499. An anti-migration component 3494 at the base of the second wire mesh structure 3499 acts to prevent the entirety of the device 3400f from being passed through the pylorus. The two wire mesh structures 3491, 3499 work together to occupy an increased volume in a patient's stomach and further delay the passage of food through the gastrointestinal tract.

FIGS. 34G and 34H are illustrations of exemplary double-wire mesh intragastric devices 3400g in a post-deployment configuration in accordance with one embodiment of the present specification. The pictured embodiment includes a first wire mesh structure 3403 positioned on top of a second wire mesh structure 3405 and a sleeve 3407 coupled to the distal end of the second wire mesh structure 3405. A first anti-migration feature 3409 at the base of the first wire mesh structure 3403 functions to couple the two wire mesh structures 3403, 3405 together. The first anti-migration feature 3409 also helps to prevent the second wire mesh structure 3403 from being compressed by gastric contractions when the first wire mesh structure 3405 is being compressed and keeps the device 3400f from passing through the pylorus in its entirety. A second anti-migration component 3413, at the base of the second wire mesh structure 3405, acts to prevent the entirety of the device 3400g from being passed through the pylorus. The combined wire mesh structures 3403, 3405 work together to occupy an increased volume in a patient's stomach and further delay the passage of food through the gastrointestinal tract. In an embodiment, the device 3400g is covered with a protective covering such as a silicon or a PTFE sheath. In some embodiments, the first and second wire mesh structures 3403, 3405 are made of hand braided Nitinol wires having a thickness in a range of 0.1 mm to 1.0 mm and, more preferably, approximately 0.4 mm, and the sleeve 3407 is made of machine braided Nitinol wires having a thickness in a range of 0.05 mm to 0.7 mm and, more preferably, approximately 0.127 mm.

In an embodiment, the device 3400g has a total length of approximately 100 to 850 mm. In an embodiment, the first wire mesh 3403 has a central diameter of approximately 90 mm. In an embodiment, the lengths of each of the first wire mesh 3403 and the second wire mesh 3405 are approximately 70 mm and a total length measured from the proximal end of the first wire mesh 3403, including the first anti-migration component 3409, to the distal end of the second mesh 3405 is approximately 145 mm. In various embodiments, the diameter of an opening 3425 in the proximal end is approximately 5 mm to 25 mm and the diameter of an opening 3423 in the distal end of the sleeve 3407 ranges from 5 mm to 35 mm. Also, in an embodiment, the width of the first anti-migration component 3409 at the base of the first wire mesh structure 3403 is approximately 5 mm. In an embodiment, the diameter of the sleeve 3407 is approximately 25 mm. Further, in an embodiment, an overall length of the sleeve is approximately 505 mm, wherein the length from proximal point 3415 to midpoint 3417 is approximately 137 mm, and the length from distal point 3419 to distal end 3423 is approximately 57 mm.

FIG. 34I illustrates an intragastric device 3400h having two wire meshes coupled with an anti-migration feature, in accordance with an embodiment of the present specification. As shown, the device 3400h comprises a first wire mesh structure 3462 positioned on top of a second wire mesh structure 3472 and an anti-migration collar 3473 coupled to the distal end of the second wire mesh structure 3472. A first anti-migration feature 3463 at the base of the first wire mesh structure 3462 functions to couple the two wire mesh structures 3462, 3472 together. The first anti-migration feature 3463 also helps to prevent the first wire mesh structure 3462 from being compressed by antral contractions while the second wire mesh structure 3472 is being compressed by the antral contractions and keeps the device 3400h out of the pylorus. The anti-migration collar 3473, at the base of the second wire mesh structure 3472, acts to prevent the entirety of the device 3400g from being passed through the pylorus.

In various embodiments, the total length of device 3400h ranges from 30 mm to 300 mm. In an embodiment, the first wire mesh 3462 has a central diameter of approximately 90 mm, range 20 to 200. In an embodiment, the lengths of each of the first wire mesh 3462 and the second wire mesh 3472 are in a range of 20 mm to 100 mm and, more preferably, approximately 70 mm, and a total length measured from the proximal end of the first wire mesh 3462, including the first anti-migration feature 3463, to the distal end of the second mesh 3472 in a range of 30 mm to 200 mm, and more preferably, approximately 145 mm. In an embodiment shown in FIG. 34J, the diameter of an opening 3465 in the proximal end is approximately 5 mm to 35 mm and the diameter of an opening 3475 in the distal end ranges from 5 mm to 60 mm. Also, in an embodiment, the width of the first anti-migration component 3463 at the base of the first wire mesh structure 3462 is approximately 5 mm. In some embodiments, the length of the anti-migration collar 3473 ranges from 5 mm to 100 mm. In embodiments, an inner diameter 3476 of anti-migration collar 3473 ranges from approximately 10 mm to 30 mm while an outer diameter 3477 ranges from 25 mm to 77 mm.

In embodiments, (as explained with reference to FIGS. 3E and 3F), the wire mesh device 3400*h* comprises a plurality of loops (FIGS. 34L and 34M) formed in the wires of the first and second wire mesh structures 3462, 3472 at their proximal and distal ends as well as the distal end of anti-migration collar 3473. In an embodiment, a thickness of the wire forming the loops, such as wire loop 3466, is approximately 0.4 mm and a diameter of a circular portion 3467 of wire loop 3466 is approximately 2 mm. In an embodiment, the distal end of anti-migration collar 3473 comprises 9 loops, such as the wire loop 3466 shown in FIGS. 34L and 34M. In various embodiments, first anti-migration component 3463 is attached to the first and second wire mesh structure 3462, 3472 by means of soft PTFE wires 3468 having a diameter of approximately 0.20 mm. Also, in embodiments, anti-migration collar 3473 is also attached to the wire mesh 3472 by means of soft PTFE wires 3438 having a diameter of approximately 0.20 mm.

FIG. 35 is an illustration of one single intragastric device 3530 being passed over a guidewire 3535 and attached to a previously deployed single intragastric device 3520 in a stomach 3512. A catheter 3521 is depicted passing through the esophagus 3511 and into the stomach 3512. The catheter 3521 is deploying the second single intragastric device 3530 and assisting in its attachment to the previously deployed intragastric device 3520. Operationally, the catheter 3521 will be passed into an opening of the existing intragastric device 3520, preferably the opening used by the original catheter to deploy the device. The second device 3530 is then deployed with a portion of the second device, such as a neck, protrusion, or other member, fixedly attached to the first device 3520, thereby anchoring the two devices together. In another embodiment, the two devices are pre-attached outside the body and are than deployed inside a human subject as a single unit.

FIG. 36 is an illustration of a fully deployed combined intragastric device 3600 in a stomach 3612. The two single intragastric devices 3620, 3630 are depicted attached one on top of the other, occupying a greater stomach 3612 volume than one single intragastric device 3620.

FIGS. 37A and 37B are side and oblique perspective views, respectively, of another exemplary combined or dual-wire mesh intragastric device 3700 in a post-deployment configuration, in accordance with an embodiment of the present specification. The pictured embodiment includes a first wire mesh structure 3701 flexibly connected, attached or coupled to a second wire mesh structure 3702 to form a substantially dumbbell or barbell shaped intragastric device 3700. In a pre-deployment configuration, corresponding to a fully compressed or constrained state, the first wire mesh structure 3701 has a first volume and, in a post-deployment configuration, corresponding to a fully expanded or relaxed state, the first wire mesh structure 3701 has a second volume. In various embodiments, the first volume is less than the second volume. In a pre-deployment configuration, corresponding to a fully compressed or constrained state, the second wire mesh structure 3702 has a third volume and, in a post-deployment configuration, corresponding to a fully expanded or relaxed state, the second wire mesh structure 3702 has a fourth volume. In various embodiments, the third volume is less than the fourth volume.

In accordance with embodiments, the first wire mesh structure 3701 has a first shape and size or dimension in a pre-deployment configuration and a second shape and size or dimension in a post-deployment configuration. In accordance with embodiments, the second wire mesh structure 3702 has a third shape and size or dimension in a pre-deployment configuration and a fourth shape and size or dimension in a post-deployment configuration. In some embodiments, the post-deployment shapes and dimensions are similar for the first and second wire mesh structures 3701, 3702. In other embodiments, the post-deployment shapes and dimensions are dissimilar for the first and second wire mesh structures 3701, 3702. In various embodiments, the post-deployment shapes are substantially spherical, oval, obloid, kidney bean, ovoid or inverted egg shapes.

In various embodiments of the present specification, the first wire mesh structure and/or the second wire mesh structure 3702 has a variable post-deployment volume such that one or both can be expanded to different sizes. During deployment, variable levels of deployment size are used to check the position of the device and any deployment issues. For example, in some embodiments, the device is slowly deployed in steps of deployment and is checked for appropriate deployment and positioning at the different steps. After full deployment, in some embodiments, the size is fixed. In some embodiments, the two wire mesh structures are weaved separately or the wire mesh design in a single weave is different, allowing for different stiffness, compression, and sizing of the two wire mesh structures.

In a preferred embodiment, the post-deployment shapes are substantially spherical or elliptical with similar dimensions.

In various embodiments, the present specification provides a wire mesh device as a prosthetic that is sized small enough such that the device may be easily delivered via a catheter into a patient's body but is also large enough such that it does not pass through the patient's antrum/pylorus and cause damage. In addition, the device is adequately sized to be effective in sequestering food and delaying gastric emptying. For example, in various embodiments, a device having a combined post-deployment volume of less than 50 ml is not effective in sequestering food and delaying gastric emptying and could be passed through the pylorus, while a device having a post-deployment volume of greater than 3,500 ml is too large and would adversely affect digestive processes. Further, the wire mesh devices are not anchored or permanently attached to any stomach structure, are free floating, and serve to position the optional sleeve in the patient's intestine, without a physician having to physically attach or anchor the sleeve to the patient's GI tract. This allows both the mesh and sleeve structure to move relative to the GI tract wall. In various embodiments, the devices are free to move about the stomach such that a patient's pylorus is blocked less than 100% of time and said blocking comprises less than 100% of an opening defined by the pylorus. In various embodiments, the devices block the pylorus over 50% of the time, more preferably over 90% of the time, and most preferably over 95% of the time.

In various embodiments, the wire mesh structures, both single and double wire mesh configurations, of the intragastric devices of the present specification, provide several benefits over conventional gastrointestinal space-occupying balloons. While traditional balloons can be deformed by gastric pressure, the volume of the balloons is substantially constant. High stomach wall pressure is reciprocated by fixed volume balloons and water filled balloons can create pressure ulcers due to gravity and/or inertia. Air filled balloons can create a gassy feeling in the patient. Since the volume of the wire mesh devices of the present specification is variable, the wire mesh devices avoid these problems. Additionally, over stretching trauma of the stomach wall can occur with traditional balloons as food cannot enter the balloon. Food is intended to pass through the wire mesh devices of the present specification and therefore over stretching is not a concern. The intragastric devices of the present specification also allow for delayed gastric emptying as food is retained in the wire mesh structure, a benefit that is not provided by traditional balloons. The constant low outward pressure of the wire mesh structures also induces satiety while the variable volume and shape provide natural comfort.

Table 1 lists ranges of post-deployment diameter, height, volume and pre-deployment compressed length of various intragastric double-mesh devices, in accordance with some embodiments of the present specification. In some embodiments, a double-mesh intragastric device has a post-deployment diameter, at its widest point, ranging from 20 to 200 mm. More preferably, in some embodiments, a double-mesh intragastric device has a post-deployment diameter, at its widest point, ranging from 50 to 150 mm, and, still more preferably, ranging from 80 to 100 mm. In one embodiment, a double-mesh intragastric device has a post-deployment diameter of 90 mm. In some embodiments, a double-mesh intragastric device has a post-deployment height ranging from 45 to 400 mm. More preferably, in some embodiments, a double-mesh intragastric device has a post-deployment height ranging from 105 to 300 mm, and, still more preferably, a post-deployment height of 145 mm. In some embodiments, a first wire mesh structure has a first length equal to or less than 75 cm, and more preferably, approximately 15 cm. In some embodiments, a first wire mesh structure has a pre-deployment volume equal to or less than 5 ml, and more preferably, equal to or less than 110 ml and a post-deployment volume equal to or greater than 5 ml, and more preferably, equal to or greater than 125 ml. In some embodiments, a second wire mesh structure has a second length equal to or less than 70 cm. In some embodiments, a second wire mesh structure has a pre-deployment volume equal to or less than 5 ml, and more preferably, equal to or less than 100 ml and a post-deployment volume equal to or greater than 5 ml, and more preferably, equal to or greater than 110 ml. In some embodiments, the first wire mesh structure has a post deployment volume greater than 5 ml and less than 5000 ml. In some embodiments, the second wire mesh structure has a post deployment volume greater than 20 ml and less than 4000 ml. In some embodiments, a double-mesh intragastric device has a post-deployment volume (both meshes together) ranging from 8 to 8381 ml. More preferably, in some embodiments, a double-mesh intragastric device has a post-deployment volume (both meshes together) ranging from 131 to 3536 ml, and, still more preferably, ranging from 442 to 826 ml. In one embodiment, a double-mesh intragastric device has a post-deployment volume (both meshes together) of 657 ml. In some embodiments, a double-mesh intragastric device has a pre-deployment compressed length ranging from 63 to 629 mm. Pre-deployment compressed length refers to the total length of the device when compressed into a catheter for deployment into a subject's body. More preferably, in some embodiments, a double-mesh intragastric device has a pre-deployment compressed length ranging from 157 to 471 mm, and, still more preferably, ranging from 236 to 290 mm. In one embodiment, a double-mesh intragastric device has a pre-deployment compressed length of 269 mm.

TABLE 1

| Diameter (mm) | Height (mm) | Volume (ml) two meshes | Compressed Length (mm) |
| --- | --- | --- | --- |
| 200 | 400 | 8381 | 629 |
| 150 | 300 | 3536 | 471 |
| 100 | 145 | 826 | 290 |
| 90 | 145 | 657 | 269 |
| 80 | 145 | 442 | 236 |
| 50 | 105 | 131 | 157 |
| 20 | 45 | 8 | 63 |

Each of the first and second wire mesh structure 3701, 3702 has a top or upper half surface or hemisphere, a bottom or lower half surface or hemisphere and an interior volume defined by the respective post-deployment shapes and sizes or dimensions of the wire mesh structures 3701, 3702. The first wire mesh structure 3701 includes at least one first opening (or first surface area of openings) 3705 proximate the top or upper half surface or hemisphere and at least one second opening (or second surface area of openings) 3706 proximate the bottom or lower half surface or hemisphere such that food enters the structure 3701 through the at least one first opening 3705, passes through the interior, and exits the structure 3701 through the at least one second opening 3706. The second wire mesh structure 3702 includes at least one third opening (or third surface area of openings) 3707 proximate the top or upper hemisphere and at least one fourth opening (or fourth surface area of openings) 3708 proximate the bottom or lower hemisphere such that food enters the structure 3702 through the at least one third opening 3707, passes through the interior, and exits the structure 3702 through the at least one fourth opening 3708. In various embodiments, the post-deployment shape of the first wire mesh structure includes a first plurality of curved surfaces defined by an arc which is determined by a radius in a range of 0.2 cm to 20 cm and a central angle in a range of 5 to 175 degrees. In various embodiments, the post-deployment shape of the second wire mesh structure includes a second plurality of curved surfaces defined by an arc which is determined by a radius in a range of 0.1 cm to 15 cm and a central angle in a range of 1 to 179 degrees.

In accordance with some embodiments, the first and second wire mesh structures 3701, 3702 are porous structures. In other embodiments, the first and second wire mesh structures 3701, 3702 are substantially covered with a membrane to further impede the passage of food out of the intragastric device 3700. In various embodiments, the membrane covers 10% to 99% of the device 3700 leaving only the at least one first, second, third and fourth openings 3705, 3706, 3707, 3708 uncovered. This directs the food to enter the device 3700 through the at least one first opening 3705 and leave the device 3700 through the at least one fourth opening 3708.

The first wire mesh structure 3701 includes a first plurality of free ends or nodes positioned at the at least one first opening 3705 and a second plurality of free ends or nodes positioned at the at least one second opening 3706. The second wire mesh structure 3702 includes a third plurality of free ends or nodes positioned at the at least one third opening 3707 and a fourth plurality of free ends or nodes positioned at the at least one fourth opening 3708. The pluralities of nodes comprise bends or curves in the wires of the wire mesh structures 3701, 3702 which are unsupported or not connected to other portions of the wire mesh. In other words, the pluralities of nodes are loops or bends comprising the free ends at each end of the wire mesh structures 3701, 3702. In accordance with various embodiments, the first, second, third and fourth pluralities of nodes include hoops. In one embodiment, hoops are formed from twisting the free ends of the pluralities of nodes into a hoop shape. In another embodiment, the hoops comprise separate wire hoops that are sutured to the free ends of the pluralities of nodes.

In various embodiments, a connection is formed between a portion of a plurality of free ends of the first wire mesh structure defining said second surface area of openings 3706 and a portion of a plurality of free ends of the second wire mesh structure defining said third surface area of openings 3707. In some embodiments, the connection comprises a first flexible suture attached, at one end, to a first point on said second surface area of openings 3706 and, at a second end, to a second point on said third surface area of openings 3707. In various embodiments, a length of the connection is in a range of 0 mm to 200 mm wherein a lower bound ranges from 0 mm to 2 mm and every increment therein. In some embodiments, the connection comprises a second flexible suture attached, at one end, to a third point on said second surface area of openings 3706 and, at a second end, to a fourth point on said third surface area of openings 3707 wherein said third point is different from the first point and said fourth point is different from the second point. In various embodiments, a length of the connection, including the second flexible suture, is in a range of 0 mm to 300 mm wherein a lower bound ranges from 0 mm to 2 mm and every increment therein. In some embodiments, the connection comprises a third flexible suture attached, at one end, to a fifth point on said second surface area of openings 3706 and, at a second end, to a sixth point on said third surface area of openings 3707, wherein said fifth point is different from the first point and the third point and wherein said sixth point is different from the second point and the fourth point. In various embodiments, a length of the connection, including the third flexible suture, is in a range of 0 mm to 300 mm wherein a lower bound ranges from 0 mm to 2 mm and every increment therein. In some embodiments, the connection comprises a fourth flexible suture attached, at one end, to a seventh point on said second surface area of openings 3706 and, at a second end, to an eighth point on said third surface area of openings 3707, wherein said seventh point is different from said the first point, the third point, and the fifth point and wherein said eighth point is different from the second point, the fourth point, and the sixth point. In various embodiments, a length of the connection, including the second flexible suture, is in a range of 0 mm to 300 mm wherein a lower bound ranges from 0 mm to 2 mm and every increment therein.

As shown in FIG. 37C, in accordance with an aspect of the present specification, a portion of the second pluralities of nodes 3701n of the first wire mesh structure 3701 are flexibly connected, coupled or attached to a portion of the third pluralities of nodes 3702n of the second wire mesh structure 3702 using a plurality of sufficiently loose sutures or suture knots 3710. Though sutures are depicted in FIG. 37C, in other embodiments, the flexible connection between the first wire mesh structure and the second wire mesh structure can comprise any flexible member, such as a flexible metal wire or plastic component. In these other embodiments, a suture is not required. In some embodiments, the plurality of sutures 3710 includes at least two standalone flexible connection or suture points wherein at least two nodes of the second pluralities of nodes 3701n of the first wire mesh structure 3701 are flexibly coupled to at least two nodes of the third pluralities of nodes 3702n of the second wire mesh structure 3702. In a preferred embodiment, the plurality of sutures 3710 includes three or four standalone flexible connection or suture points. In various embodiments, a length of the connection between the openings on the lower surface of the first wire mesh structure and the openings on the upper surface of the second wire mesh structure is in a range of 0 mm-300 mm. In various embodiments, the connection of the first wire mesh structure to the second wire mesh structure has a length such that the first wire mesh structure can be compressed up to a range of 1% to 99%, and more preferably, 40% to 99%, and all increments therein, of its equatorial diameter without leading to a compression of the second wire mesh structure. In various embodiments, the plurality of sutures 3710 are distributed equidistantly along the peripheries of the second and third openings 3706, 3707. FIG. 37E shows two connection or suture points 3711 utilized to flexibly connect the first and second wire mesh structures 3701, 3702. In an embodiment, the two connection or suture points 3711 are separated from one another by 180 degrees.

In an alternate embodiment, the first and second wire mesh structures 3701, 3702 are flexibly coupled by interweaving or meshing (instead of using a plurality of sutures or suture knots) a portion of the second pluralities of nodes 3701n of the first wire mesh structure 3701 to a portion of the third pluralities of nodes 3702n of the second wire mesh structure 3702.

In an optional embodiment, as shown in FIG. 37D, a sleeve 3725, having a proximal end, a distal end, and a lumen, is coupled at its proximal end to the lower portion of the second wire mesh structure 3702. The sleeve 3725 includes, at its proximal end, a first opening 3741 in fluid communication with the fourth opening or fourth surface area of openings (3708 of FIG. 37A) of the second wire mesh structure 3702 and a second opening 3742 at said distal end. In some embodiments, the sleeve 3725 is coupled, via a plurality of sutures, to the fourth plurality of nodes 3702p of the second wire mesh structure 3702. The optionally coupled sleeve 3725, when deployed, extends from the patient's stomach into the duodenum where it empties, or, in other embodiments, through the duodenum and into the jejunum. In one embodiment, the sleeve 3725 functions to transit sequestered food/chyme from the intragastric device 3700 directly to the mid-duodenum or mid-jejunum.

Referring now to FIGS. 37A through 37C, it should be appreciated that, in various embodiments, the first and second wire mesh structures 3701, 3702 are woven and constructed separately and flexibly attached or sutured, thereafter, either inside (as described earlier with reference to FIGS. 35, 36) or outside a patient's body. It should also be appreciated that the coupling sutures can be cut for removal of the two structures 3701, 3702 separately, from the patients' stomach.

In various embodiments, each of the connection or suture points comprises a figure eight knot, optionally, additionally secured with glue and a heat shrink tube. In one embodiment, each knot comprises 30 lb. break-strength ultra-high-molecular-weight-polyethylene (UHMWPE) braided suture line to provide a reliable connection between the first and second wire mesh structures 3701, 3702.

In accordance with various aspects of the present specification, the flexible connection or attachment of the first and second wire mesh structures 3701, 3702, using the plurality of sutures 3710, and the resultant intragastric device 3700 provides various benefits and functionalities (discussed below).

The flexible connection or attachment enables a fluid communication between the first and second wire mesh structures 3701, 3702. That is, food first passes through the at least one first opening 3705 in the top of the combined intragastric device 3700 and is sequestered in the first wire mesh structure 3701. The food then slowly passes into, and is sequestered in, the second wire mesh structure 3702. Finally, the food slowly releases through the at least one fourth opening 3708 in the bottom of the combined intragastric device 3700 and back into the stomach. The connected wire mesh structures 3701, 3702 work together to occupy an increased volume in a patient's stomach and further delay the passage of food through the gastrointestinal tract. The connected two wire mesh structures 3701, 3702 also act to induce satiety even more quickly and induce a longer lasting satiety than a single mesh structure device.

The flexible connection or attachment enables the first and second wire mesh structures 3701, 3702 to pivot, bend or move in substantially all directions relative to each other. Referring to FIG. 37F, the first wire mesh structure 3701 has a first longitudinal axis 3715 passing through a center of the first structure 3701, a center of a first surface area of openings 3721 at the proximal end of the first structure 3701, and a center of a second surface area of openings 3722 at the distal end of the first structure while the second wire mesh structure 3702 has a second longitudinal axis 3716 passing through a center of the second structure 3702, a center of a third surface area of openings 3731 at a proximal end of the second structure 3702, and a center of a fourth surface area of openings 3732 at a distal end of the second structure. A degree of movement of the two structures 3701, 3702, relative to each other, is illustrated and defined by an angular displacement 3717 between the first and second longitudinal axes 3715, 3716. In various embodiments, the flexible connection points 3711 enable the first and second wire mesh structures 3701, 3702 to have a degree of movement (or angular displacement 3717 between the first and second longitudinal axes 3715, 3716) of up to 90 degrees relative to each other in all directions. In some embodiments, the connection of the first wire mesh structure to the second wire mesh structure has a length such that, upon more than 90% compression of the first wire mesh structure, the second wire mesh structure has an angular displacement relative to the first wire mesh structure of 10% or less.

During a process of deployment, the flexible connection or attachment enables one wire mesh structure, for example the first wire mesh structure 3701, to open almost completely without the need to deploy the other wire mesh structure, for example the second wire mesh structure 3702. FIG. 38A illustrates a process of deployment of a combined intragastric device 3800. As shown, the device 3800 further includes a catheter or over-tube 3820 wherein a first wire mesh structure 3801 is nearly or almost completely deployed while a second wire mesh structure 3802, connected or attached to the first wire mesh structure 3801 via a plurality of sutures 3810, is still constrained serially within the catheter or over-tube 3820. In some embodiments, the catheter 3820 comprises a housing and a lumen extending through the housing. In some embodiments, the lumen has a diameter equal to or less than 2 cm, and more preferably, approximately 0.9 cm. On compression of one wire mesh structure, for example the second wire mesh structure 3702, into a tubular structure (such as an over-tube or catheter) during a process of withdrawal or removal, the flexible connection or attachment enables alignment of the other wire mesh structure, for example the first wire mesh structure 3701, to be compressed into the tubular structure. FIGS. 38B through 38D illustrate a process of withdrawal or removal of the combined intragastric device 3800. As shown in FIG. 38B, the second wire mesh structure 3802 is partially compressed as it is being withdrawn into the catheter 3820 using a grasper 3822 through an endoscope 3825 (for example), while the first wire mesh structure 3801 remains unconstrained or in a deployed configuration. As the second wire mesh structure 3802 is fully compressed due to its full withdrawal into the catheter 3820, as shown in FIG. 38C, the plurality of sutures 3810 enable alignment or orientation of the first wire mesh structure 3801 for compression into the catheter 3820 for removal. Finally, as shown in FIG. 38D, the aligned or oriented first wire mesh structure 3801 begins getting constrained or compressed into the catheter 3820 for removal, as the fully compressed second wire mesh structure 3802 is further withdrawn into the catheter 3820 using the endoscope 3825.

Thus, the flexible connection or attachment enables one wire mesh structure to be compressed or withdrawn and released or deployed independent of the other wire mesh structure.

Referring now to FIGS. 37A through 37F, it should be noted that the plurality of sutures 3710 need to be long enough to enable the pivoting, bending or relative degree of movement of the two wire mesh structures 3701, 3702 but short enough to communicate compression forces from one wire mesh structure (as it is being withdrawn or deployed) to the other wire mesh structure. In some embodiments, one wire mesh structure can be compressed up to 99% of its equatorial diameter (in embodiments where the first and second wire mesh structures 3701, 3702 are substantially spherical) without radially compressing the other wire mesh structure—but beyond that, the compression is communicated. This has an anti-migration advantage in that the intragastric device 3700 is unlikely to pass through a fully relaxed pylorus even if one of the two wire mesh structures is substantially compressed while in a post-deployment configuration. In various embodiments, a length of a connection or suture point, from a node of the second pluralities of nodes to a node of the third pluralities of nodes, is in a range of 1 mm and twice the diameter of the third opening 3707 of the second wire mesh 3702 (FIGS. 37A, 37B).

The combined or dual-wire mesh intragastric device 3700 of the present specification provides various benefits or advantages compared to deploying a single large device. Firstly, the combined intragastric device 3700 offers better protection against migration of the device 3700 through a relaxed pylorus of a patient. If a single large device gets compressed it can migrate relatively easily through the relaxed pylorus. However, it is unlikely for both the wire mesh structures 3701, 3702 of the intragastric device 3700 to be compressed accidentally thereby offering mitigation against migration risk.

Secondly, a single large device will be relatively inflexible, thereby putting excessive pressure against the patient's stomach lining, at least for some of the time. In contrast, the intragastric device 3700 has a sufficiently large post-deployment structure or occupied volume while still minimizing excessive pressure against the stomach wall (and prevent abrasions on the stomach wall or lining) because the intragastric device 3700 will bend and move (owing to the flexible connection or attachment of the two connected wire mesh structures 3701, 3702), thereby better suiting the stomach contours. Thus, the intragastric device 3700 of the present specification, when deployed, offers improved balance or optimization between a need to occupy a large stomach volume and a need to minimize pressure on the stomach. In various embodiments, the intragastric device 3700, when deployed, occupies 25% to 95% of the gastric volume or the patient's stomach volume.

It should be appreciated that the present disclosure is intended to provide a teaching of several exemplary embodiments of the present invention and is should not be limited to the specific structures disclosed herein. Other variations of the disclosed embodiments, which would be understood by those of ordinary skill, are covered by the present application and are within the scope of the invention, as further defined by the claims.

We claim:

1. An intragastric device configured for deployment in a stomach of a person, said device comprising:
    a first wire mesh structure having a pre-deployment shape that is compressed within a lumen of a catheter and a post-deployment shape that is expanded within the stomach of the person, wherein said pre-deployment shape has a first volume that is equal or less than 110 ml and a first length that is equal to or less than 75 cm and wherein said post-deployment shape has a porous, enclosed second volume, defined by a first plurality of curved surfaces, that is equal to or greater than 125 ml, said first wire mesh structure further comprising an upper portion and a lower portion wherein the upper portion has a first surface area of openings configured to permit material to enter from outside the second volume to inside the second volume and wherein the lower portion has a first set of nodes defining a second surface area of openings;
    a second wire mesh structure having a pre-deployment shape that is compressed within said lumen of the catheter and a post-deployment shape that is expanded within the stomach of the person, wherein said pre-deployment shape has a third volume that is equal or less than 100 ml and a second length that is equal to or less than 70 cm and wherein said post-deployment shape has a porous, enclosed fourth volume, defined by a second plurality of curved surfaces, that is equal to or greater than 110 ml, said first wire mesh structure further comprising an upper portion and a lower portion wherein the upper portion has a second set of nodes defining a third surface area of openings configured to permit material to enter from outside the fourth volume to inside the fourth volume and wherein the lower portion has a fourth surface area of openings; and
    a plurality of flexible members loosely extending between said first and second wire mesh structures to flexibly couple the first and second sets of nodes to allow for free relative movement in distance between said wire mesh structures, each flexible member comprising either a plastic component or a suture, wherein said plurality of flexible members include:
        a first flexible member attached, at one end, to a first point in the first set of nodes and, at a second end, to a second point in the second set of nodes and
        a second flexible member attached, at one end, to a third point in the first set of nodes and, at a second end, to a fourth point in the second set of nodes, wherein said first point is different from the third point, wherein said second point is different from the fourth point, and wherein each node in the first and second sets of nodes is a free end of the first or second wire mesh structure that is unsupported by any other portion of the first or second wire mesh structure.

2. The intragastric device of claim 1, wherein a length of said first flexible member, from the first point on the second surface area of openings to the second point on said third surface area of openings, is in a range of 0.01 mm and 300 mm.

3. The intragastric device of claim 2, wherein a length of said second flexible member, from the third point on the second surface area of openings to the fourth point on said third surface area of openings, is in a range of 0.01 mm and 100 mm.

4. The intragastric device of claim 1, wherein the first flexible member and the second flexible member are separated by 180 degrees.

5. The intragastric device of claim 1, wherein said plurality of flexible members include a third flexible member attached, at one end, to a fifth point on said second surface area of openings and, at a second end, to a sixth point on said third surface area of openings, wherein said fifth point is different from the first point and the third point and wherein said sixth point is different from the second point and the fourth point.

6. The intragastric device of claim 5, wherein a length of said third flexible member, from the fifth point on the second surface area of openings to the sixth point on said third surface area of openings, is in a range of 0.01 mm and 300 mm.

7. The intragastric device of claim 5, wherein said plurality of flexible members include a fourth flexible member attached, at one end, to a seventh point on said second surface area of openings and, at a second end, to an eighth point on said third surface area of openings, wherein said seventh point is different from the first point, the third point, and the fifth point and wherein said eighth point is different from the second point, the fourth point and the sixth point.

8. The intragastric device of claim 7, wherein a length of said fourth flexible member, from seventh point on the second surface area of openings to the eighth point on said third surface area of openings, is in a range of 0.01 mm and 100 mm.

9. The intragastric device of claim 1, wherein said first and second wire mesh structures have a degree of movement in all directions relative to each other, said degree of movement being defined by an angular displacement between a first longitudinal axis passing through a center of said first wire mesh structure, a center of the first surface area of openings, and a center of the second surface area of openings and a second longitudinal axis passing through a center of said second wire mesh structure, a center of the third surface area of openings, and a center of the fourth surface area of openings.

10. The intragastric device of claim 9, wherein said angular displacement is equal to, or less than, 90 degrees.

11. The intragastric device of claim 1, wherein said plurality of flexible members include a flexible suture attached, at one end, to a fifth point on said second surface area of openings and, at a second end, to a sixth point on said third surface area of openings, wherein said fifth point is different from the first point and the third point and wherein said sixth point is different from the second point and the fourth point.

12. The intragastric device of claim 1, wherein the first wire mesh structure and the second wire mesh structure are positioned serially within the lumen of the catheter.

13. The intragastric device of claim 1, wherein at least one of the first plurality of curved surfaces is defined by an arc and wherein said arc is determined by a radius in a range of 0.2 cm to 20 cm and a central angle in a range of 5 to 175 degrees.

14. The intragastric device of claim 13, wherein at least one of the second plurality of curved surfaces is defined by an arc and wherein said arc is determined by a radius in a range of 0.1 cm to 15 cm and a central angle in a range of 1 to 179 degrees.

15. The intragastric device of claim 1, wherein said connection is formed between a portion of a plurality of free ends of the first wire mesh structure defining said second surface area of openings and a portion of a plurality of free ends of the second wire mesh structure defining said third surface area of openings.

16. The intragastric device of claim 1, wherein the first wire mesh structure has at least one of a spherical and elliptical shape.

17. The intragastric device of claim 16, wherein the second wire mesh structure has at least one of a spherical and elliptical shape.

18. The intragastric device of claim 1, wherein said plurality of flexible members include a first flexible suture attached, at one end, to a first point on said second surface area of openings and, at a second end, to a second point on said third surface area of openings.

19. An intragastric device configured for deployment in a stomach of a person, said device comprising:
- a first structure that is compressible to a pre-deployment shape having a first volume and expandable to a post-deployment shape having a second volume that is porous, enclosed, and defined by a first plurality of curved surfaces and that is greater than the first volume, the first structure having an upper portion and a lower portion, the upper portion having a first surface area of openings configured to permit material to enter from outside the second volume to inside the second volume and the lower portion having a first set of nodes defining a second surface area of openings;
- a second structure having a pre-deployment shape that is compressible to a pre-deployment shape having a third volume and expandable to a post-deployment shape having a fourth volume that is a porous, enclosed and defined by a second plurality of curved surfaces and that is greater than the third volume, the second structure further comprising an upper portion and a lower portion wherein the upper portion of the second structure has a second set of nodes defining a third surface area of openings configured to permit material to enter from outside the fourth volume to inside the fourth volume and the lower portion of the second structure has a fourth surface area of openings; and
- a plurality of flexible members loosely extending between and coupling the first and second sets of nodes to allow for free relative movement in distance between said first and second structures, the plurality of flexible members being sufficiently loose between the first and second structures to permit compression of the first structure to 95% of its diameter without leading to a compression of said second structure, wherein each node in the first and second sets of nodes is a free end of the first or second structure that is unsupported by any other portion of the first or second structure.

20. An intragastric device configured for deployment in a stomach of a person, said device comprising:
- a first wire mesh structure having a pre-deployment shape with a first volume that is compressed within a lumen of a catheter and a post-deployment shape with a second volume greater than the first volume that is expanded within the stomach of the person, said first wire mesh structure further comprising an upper portion and a lower portion wherein the upper portion has a first surface area of openings configured to permit material to enter from outside the second volume to inside the second volume and wherein the lower portion has a first set of nodes defining a second surface area of openings;
- a second wire mesh structure having a pre-deployment shape with a third volume that is compressed within said lumen of the catheter and a post-deployment shape with a fourth volume greater than the third volume that is expanded within the stomach of the person, said first wire mesh structure further comprising an upper portion and a lower portion wherein the upper portion has a second set of nodes defining a third surface area of openings configured to permit material to enter from outside the fourth volume to inside the fourth volume and wherein the lower portion has a fourth surface area of openings; and
- a plurality of flexible members, comprising a plurality of sutures, to flexibly couple the first and second sets of nodes, wherein said plurality of flexible members include:
- a first flexible member attached, at one end, to a first point in the first set of nodes and, at a second end, to a second point in the second set of nodes and
- a second flexible member attached, at one end, to a third point in the first set of nodes and, at a second end, to a fourth point in the second set of nodes, wherein said first point is different from the third point and wherein said second point is different from the fourth point, and wherein each node in the first and second sets of nodes is a free end of the first or second wire mesh structure that is unsupported by any other portion of the first or second wire mesh structure.

* * * * *